US006759385B1

(12) United States Patent
Conti-Fine

(10) Patent No.: US 6,759,385 B1
(45) Date of Patent: Jul. 6, 2004

(54) METHODS TO TREAT UNDESIRABLE IMMUNE RESPONSES

(75) Inventor: Bianca M. Conti-Fine, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 179 days.

(21) Appl. No.: 09/595,990

(22) Filed: Jun. 16, 2000

Related U.S. Application Data

(63) Continuation of application No. PCT/US98/26787, filed on Dec. 16, 1998, which is a continuation-in-part of application No. 08/991,143, filed on Dec. 16, 1997.

(51) Int. Cl.[7] .............................................. A61K 38/00

(52) U.S. Cl. ....................... 514/2; 530/300; 424/184.1; 424/185.1

(58) Field of Search ................................ 514/2–20, 44; 530/300; 424/184.1, 185.1

(56) References Cited

U.S. PATENT DOCUMENTS

| | | | |
|---|---|---|---|
| 4,649,132 A | 3/1987 | Zimmerman et al. ......... 514/12 |
| 4,822,606 A | 4/1989 | Snyderman et al. .......... 424/88 |
| 4,962,091 A | 10/1990 | Eppstein et al. ............... 514/2 |
| 5,114,721 A | 5/1992 | Cohen et al. ............... 424/534 |
| 5,158,884 A | 10/1992 | Conti-Tronconi et al. ....................... 435/240.2 |
| 5,298,490 A | 3/1994 | Heavner et al. ............... 514/17 |
| 5,571,499 A | 11/1996 | Hafler et al. .................. 414/43 |
| 5,571,500 A | 11/1996 | Hafler et al. .................. 424/43 |
| 5,578,496 A | 11/1996 | Atassi et al. ................ 436/506 |
| 5,585,362 A | 12/1996 | Wilson et al. ................ 514/44 |
| 5,614,396 A | 3/1997 | Bradley et al. .......... 435/172.3 |
| 5,641,473 A | 6/1997 | Hafler et al. .................. 424/43 |
| 5,641,474 A | 6/1997 | Hafler et al. .................. 424/43 |
| 5,681,571 A | 10/1997 | Holmgren et al. ........ 424/236.1 |
| 5,783,567 A | 7/1998 | Hedley et al. ................ 514/44 |
| 5,785,973 A | 7/1998 | Bixler et al. ........... 424/196.11 |
| 5,817,308 A | 10/1998 | Scott et al. .............. 424/93.21 |
| 6,077,509 A * | 6/2000 | Weiner et al. ............ 424/184.1 |
| 6,268,491 B1 | 7/2001 | Garman et al. ............ 536/23.5 |

FOREIGN PATENT DOCUMENTS

| | | |
|---|---|---|
| EP | 0378881 | 1/1989 |
| WO | 88/10120 | 12/1988 |
| WO | 92/06117 | 4/1992 |
| WO | 94/00148 | 6/1992 |
| WO | 94/25060 | 4/1993 |
| WO | 95/26365 | 10/1995 |
| WO | 97/19698 | 11/1995 |

OTHER PUBLICATIONS

Pruthi et a. Autoimmune factor VIII inhibitors. Current Opinion in Hematology 1999; 6:314–322.*

Daniel, Dylan.,et al., "Protection of nonobese diabetic mice from diabetes by intransal or subcutaneous administration of insulin peptide B–(9–23)", *Proc. Natl. Acad. Sci. Immunology* vol. 93, (1996), pp. 956–960.

Bellone, M., et al., "Experimental Myasthenia Gravis in Congienic Mice. Sequence Mapping and H–2 Restriction of T Helper Epitopes of the alpha Subunits of *Torpedo californica* and Murine Acetylcholine Receptors", *European Journal of Immunology, 21*, pp. 2303–2310, (1991).

Briner, T.J., et al., "Peripheral T–cell Tolerance Induced in Naive and Primed Mice by Subcutaneous Injection of Peptides from the Major Cat Allergen Fel d I", *Proc. Natl. Acad. Sci. USA, 90*, 7608–7612, (1993).

Collier, R.J., et al., "Structure and Activity of Diptheria Toxin", *ADP–Ribosylation Reactions: Biology and Medicine*, Chapter 34, O. Hayaishi, et al., Editors, Academic Press, Inc., NY, pp. 575–592, (1982).

Conti–Fine, B.M., "T–Cell Recognition of the Acetylcholine Receptor in Myasthenia Gravis", *IXth International Conference on Myasthenia Gravis and Related Disorders*, Abstract, Conference held at Loews Santa Monica Beach Hotel, Santa Monica, CA, 4 p., (May 7–10, 1997).

Conti–Fine, B.M., et al., *Myasthenia Gravis: The Immunobiology of an Autoimmune Disease*, Chapters 6, 8, 9, & 10, Neuroscience Intelligence Unit, Chapman & Hall, R.G. Landes Co., Austin, TX, pp. 89–104, 121–206, (1997).

Conti–Fine, B.M., et al., "Antibodies as Tools to Study the Structure of Membrane Proteins: The Case of the Nicotinic Acetylcholine Receptor", *Annual Review of Biophysics and Biomolecular Structure, 25*, 197–229, (1996).

Counsell, C.M., et al., "Allergens, IgE, Mediators, Inflammatory Mechanisms. Definition of the Human T–cell Epitopes of Fel d 1, the Major Allergen of the Domestic Cat", *J. Allergy Clin. Immunol.*, 98(5), 884–894, (1996).

Good, M.F., et al., "Peptide Immunization Can Elicit Malaria Protein–Specific Memory Helper but Not Proliferative T Cells", *Peptide Research*, 3(3), 110–115, (1990).

Hetzel, et al., "Peptide–Mediated Immunoregulation", *Int. Arch. Allergy Immunol.*, 107, 275–277, (1995).

(List continued on next page.)

Primary Examiner—Dave T. Nguyen
Assistant Examiner—Jon Eric Angell
(74) Attorney, Agent, or Firm—Schwegman, Lundberg, Woessner & Kluth, P.A.

(57) ABSTRACT

Isolated and purified peptides and variants thereof, useful to prevent or treat antibody-mediated diseases, or indications caused by an undesirable antibody response to a given antigen, are provided. Also provided are peptides and methods useful to prevent or treat indications associated with the use of viral vectors in gene replacement therapy. Further, a method to inhibit or prevent aberrant immune responses to exogenous, non-infectious antigen is provided.

17 Claims, 67 Drawing Sheets

OTHER PUBLICATIONS

Higgins, J.A., et al., "Peptide–induced nonresponsiveness of HLA–DP restricted human T cells reactive with Dermatophagoides spp. (house dust mite)", *The Journal of Allergy and Clinical Immunology*, 90 (5), pp. 749–756,m (Nov. 1992).

Hoyer, L.W., "Future Approaches to Factor VIII Inhibitor Therapy", *Am. J. of Medicine*, vol. 91, No. 5A, 40s–44s, (Nov. 4, 1991).

Hoyne, G.F., et al., "Inhibition of T Cell and Antibody Responses to House Dust Mice Allergen by Inhalation of the Dominant T Cell Epitope in Naive and Sensitized Mice", *J. Exp. Med.*, 178, 1783–1788, (1993).

Karachunski, P.I., et al., "Subcutaneous administration of T–epitope sequences fo the acetylcholine receptor prevents experimental myasthenia gravis", *J. Neuroimmunol.*, vol. 93, No. 1–2, 108–121, (Jan. 1, 1999).

Karin, N., et al., "Reversal of Experimental Autoimmune Encephalomyelitis by a Soluble Peptide Variant of a Myelin Basic Protein Epitope: T Cell Receptor Antagonism and Reduction of Interferon gamma and Tumor Necrosis Factor alpha Production", *Journal of Experimental Medicine*, 180, 227–2237, (Dec., 1994).

Karpati, G., et al., "The Scope of Gene Therapy in Humans: Scientific, Safety and Ethical Considerations", *Neuromuscular Disorders*, 7, 273–276, (1997).

Karpus, W.J., et al., "Inhibition of Relapsing Experimental Autoimmune Encephalomyelitis in SJL Mice Feeding the Immunodominant PLP139–151 Peptide", *Journal of Neuroscience Research*, 45, pp. 410–423, (1996).

Kurup, V.P., et al., "*Aspergillus fumigatus* Peptides Diferentially Express Th1 and Th2 Cytokines", *Peptides*, vol. 17, No. 2, 183–190, (1996).

Lennon, V.A., et al., "Definition of Myasthenogenic Sites of the Human Acetylcholine Receptor Using Synthetic Peptides", *Annals of the New York Academy of Sciences*, 505, 439–450, (1987).

Lennon, V.A., et al., "Region of Peptide 125–147 of Acetylcholine Receptor a Subunit is Exposed at Neuromuscular Junction and Induces Experimental Autoimmune Myasthenia Gravis, T–cell Immunity, and Modulating Antibodies", *Proc. Natl. Acad. Sci. USA*, 82, 8805–8809, (1985).

Lider, O., et al., "Suppression of Experimental Autoimmune Encephalomyelitis by Oral Administration of Myelin Basic Protein", *The Journal of Immunology*, 142, 748–752, (Feb. 1, 1989).

Ma, C.G., et al., "Suppression of Experimental Autoimmune Myasthenia Gravis by Nasal Administration of Acetylcholine Receptor", *Journal of Neuroimmunology*, 58, 51–60 (1995).

Martino, G., et al., "The human–severe combined immunodeficiency myasthenic mouse model: a new approach for the study of myasthenia gravis", *Database Medline online! US Natl library of medicine (NLM), Bethesda, MD*, Database accession No. 93297902 XP002115152 abstract & annals of Neurology, 34 (1), 48–56, (Jul. 1993).

Metzler, B., et al., "Inhibition of Experimental Autoimmune Encephalomyelitis by Inhalation but not Oral Administration of the Encephalogenic Peptide: Influence of MHC Binding Affinity", *International Immunology*, 5 (9), pp. 1159–1165, (1993).

Moiola, L., et al., "Myasthenia Gravis", *J. Immunol.*, 152 (9), 4686–4698, (1994).

Neutra, M.R., et al., "Antigen Sampling Across Epithelial Barriers and Induction of Mucosal Immune Responses", *Annual Review of Immunology*, 14, pp. 275–300, (1996).

Norman, P.S., et al., "Treatment of Cat Allergy with T–cell Reactive Peptides", *Am. J. Respir. Crit. Care med.*, 154, 1623–1628, (1996).

O'Sullivan, D., et al., "Characterization of the Specificty of Peptide Binding to Four DR Haplotypes", *The Journal of Immunology*, 145, pp. 1799–1808, (Sep. 15, 1990).

Phillips, G., et al., "American Society for Blood and Marrow Transplantation Guidelines for Clinical Centers", *Biology of Blood and Marrow Transplantation*, 1, 54–55 (1995).

Protti, M.P., et al., "Myasthenia Gravis: Recognition of a Human Autoantigen at the Molecular Level", *Immunol. Today*, 14, pp. 363–368, (1993).

Schwartz, R.S., et al., "Autoimmunity and Autoimmune Diseases", *Fundamental Immunology, Second Edition*, Raven Press, New York, 819–859, (1989).

Shaw, D.M., et al., "Influence of the T–Helper Epitope on the Titre and Affinity of Antibodies to B–Cell Epitopes after Co–Immunization", *Molecular Immunology*, 30(11), 961–968, (1993).

Shenoy, M., et al., "Suppression of Experimental Autoimmune Myasthenia Gravis by Epitope–Specific Neonatal Tolerance to Synthetic Region alpha146–162 of Acetylcholine Receptor", *Clinical Immunology and Immunopathology*, 66, 230–238, (Mar. 1993).

Shenoy, M., et al., "The Pathogenic Role of Acetylcholine Receptor alpha Chain Epitope within alpha146–162 in the Development of Experimental Autoimmune Myasthenia Gravis in C57BL6 Mice", *Clinical Immunlogy and Immunopathology*, 73, 338–343, (Dec. 1994).

Tisch, R., et al., "Antigen–specific Immunotherapy: Is It a Real Possibility to Combat T–cell–mediated Autoimmunity?", *Proc. Natl. Acad. Sci. USA*, 91, 437–438, (Jan., 1994).

Wang, Z.Y., et al., "Th1 Epitope Repertoire on the alpha Subunit of Human Muscle Acetylcholine Receptor in Myasthenia Gravis", *Neurology*, 48, 1643–1653, (1997).

Weiner, H.L., et al., "Oral Tolerance: Immunologic Mechanisms and Treatment of Animal and Human Organ–Specific Autoimmune Diseases by Oral Administration of Autoantigens", *Annual Review of Immunology*, 12, 809–837, (1994).

Wraith, D.C., et al., "Antigen Recognition in Autoimmune Encephalomyelitis and the Potential for Peptide–Mediated Immunotherapy", *Cell*, 59, 247–255, (1989).

Yeh, T.M., et al., "T Cells Reactive with a Small Synthetic Peptide of the Acetylcholine Receptor Can Provide Help for a Clonotypically Heterogeneous Antibody Responses and Subsequently Impaired Muscle Function", *The Journal of Immunology*, 144, 1654–1660, (Mar. 1, 1990).

Yu, M., et al., "A Predictable Sequential Determinant Spreading Cascade Invariably Accompanies Progression of Experimental Autoimmune Encephalomyelitis: A Basis for Peptide–Specific Therapy After Onset of Clinical Disease", *J. Exp. Med*, 183, 1777–1788, (Apr. 1996).

\* cited by examiner

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 9

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 10

FIG. 16A
BL from healthy subject
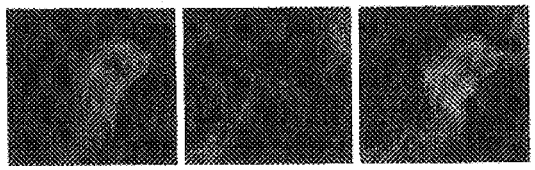
BL from MG patient
α-BTX    Human IgG    Merge
FIG. 16C
FIG. 16B
CD4+ depleted BL from MG patient
plus CD4+ cells specific for TTD
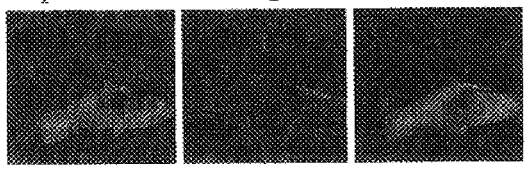
CD4+ depleted BL from MG patient
plus CD4+ cells specific for α304-322
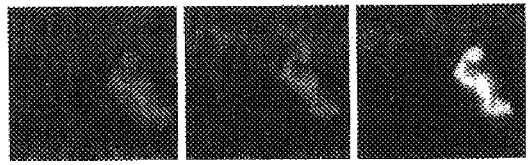
α-BTX    Human IgG    Merge
FIG. 16D

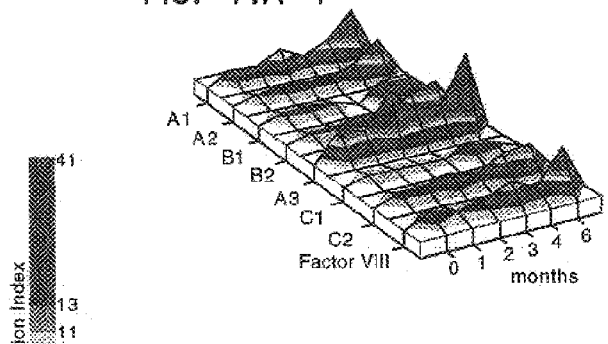
FIG. 41A-1 Patient 1
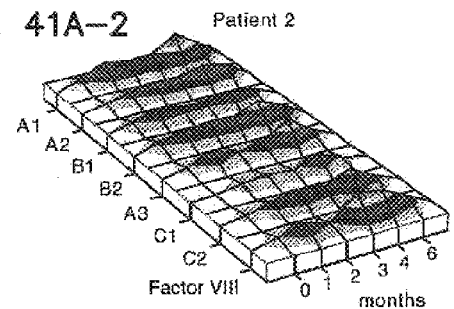
FIG. 41A-2 Patient 2
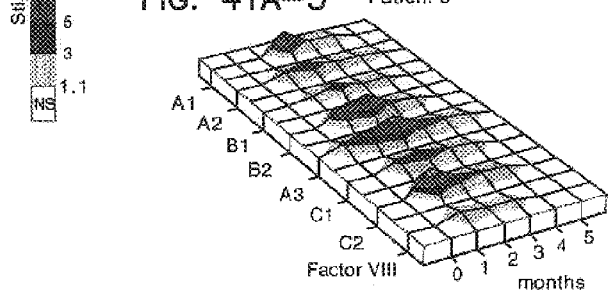
FIG. 41A-3 Patient 3
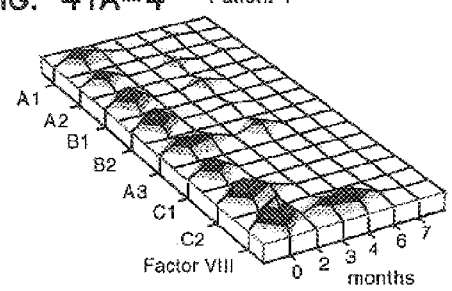
FIG. 41A-4 Patient 4

HEMOPHILIA A WITH INHIBITORS
FIG. 41B-1
Patient 5
FIG. 41B-2
Patient 6
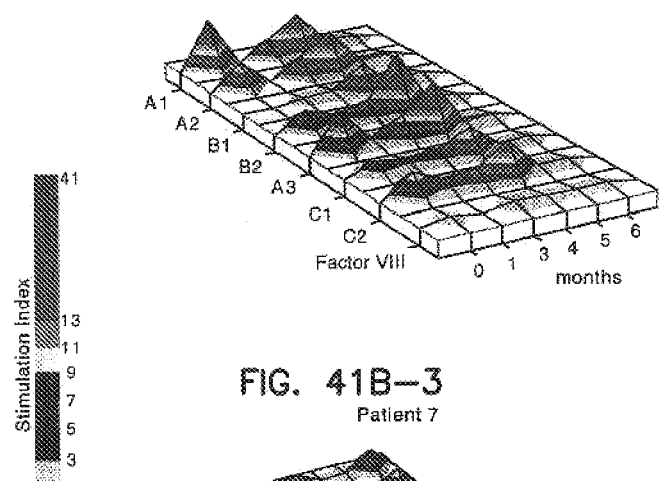
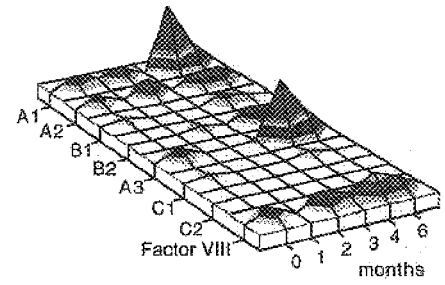
FIG. 41B-3
Patient 7
FIG. 41B-4
Patient 8
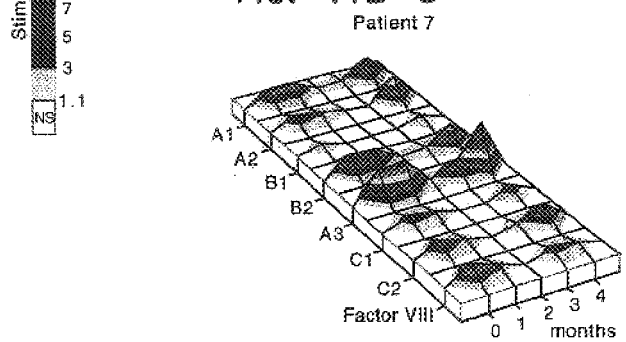
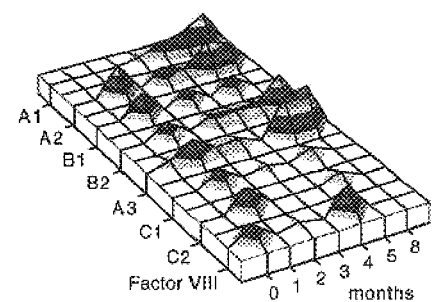

HEMOPHILIA A WITHOUT INHIBITORS
FIG. 41C-1  Patient 9
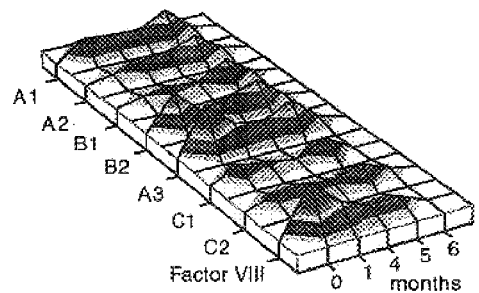
Patient 10
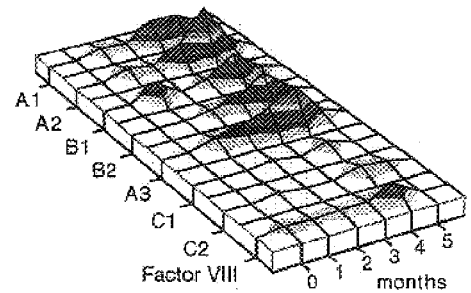
FIG. 41C-2
FIG. 41C-3
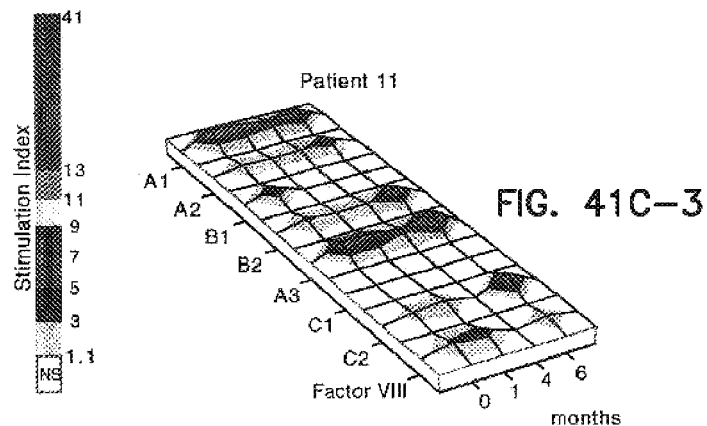

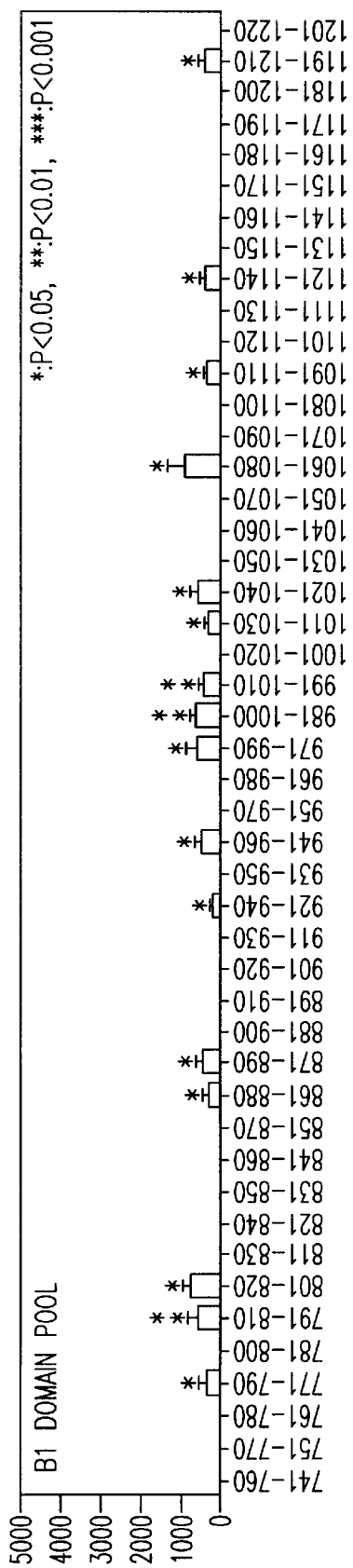
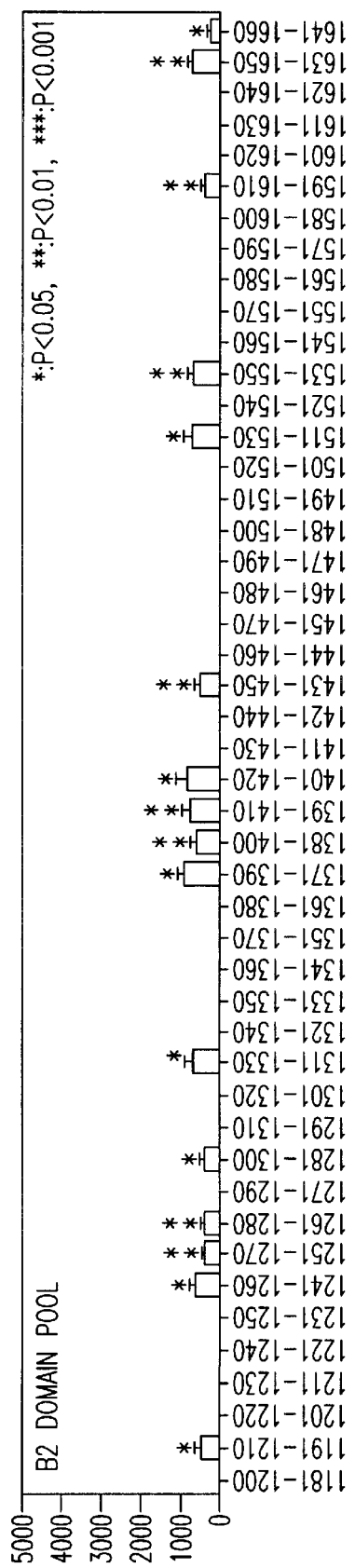
FIG. 48D
FIG. 48E

METHODS TO TREAT UNDESIRABLE IMMUNE RESPONSES

CROSS-REFERENCE TO RELATED APPLICATIONS

This application is a continuation of International Patent Application No. PCT/US98/26787, filed on Dec. 16, 1998, which in turn is a continuation in part of pending U.S. patent application No. 08/991, 143 filed on Dec. 16, 1997, all of which are incorporated herein by reference.

STATEMENT OF GOVERNMENT RIGHTS

The present invention was made with the support of the United States Government (National Institute of Neurological and Communicative Disorders and Strokes, Grant NS 23919). The Government may have certain rights in the invention.

BACKGROUND OF THE INVENTION

Ideal treatments for a pathological condition or disease caused by an undesirable immune response would specifically affect antigen-specific T and B cells. Antigen specific tolerization of T cells can be obtained by delivery of the antigen through routes, such as oral, intraperitoneal and nasal administration, that downregulate, rather than activate, CD4+ responses (Matzinger, 1994; Nossal, 1995). Tolerization of T cells by those routes has proven effective for the prevention and/or treatment of CD4+ T cell mediated autoimmune diseases, e.g., experimental autoimmune encephalomyelitis (EAE) (Metzler et al., 1993; Miller et al., 1994; Genain et al., 1996; Al-Sabbagh et al., 1996), collagen-induced arthritis (Al-Sabbagh et al., 1996), and experimental uveitis (Dick et al., 1993). Moreover, the administration of the antigen by these methods reduced or inhibited the immune response specific for the particular antigen administered. For example, aerosol administration of myelin basic protein (MBP) to MBP-immunized rats that had developed relapsing EAE decreased the intensity of the immune response to MBP and the severity of the attacks (Al-Sabbagh et al., 1996). Spleen T cells from rats that had inhaled MBP transferred protection to naive animals (Al-Sabbagh et al., 1996).

It is unclear whether similar approaches could be used for antibody (Ab)-mediated diseases for two reasons. First, while effective at reducing antigen-specific CD4+ responses, administration of antigen through routes that downregulate CD4+ responses may directly stimulate B cells specific for the administered antigen (Kuper et al., 1992; Liu et al., 1993; Husby et al., 1994; Neutra et al., 1996). This stimulation may have disastrous consequences, as has been shown in marmoset EAE (Genain et al., 1996), where intraperitoneal administration of myelin resulted in CD4+ tolerance to myelin, but also in an acute, fatal form of EAE. The fatal form of EAE was characterized by antibody specific for the myelin oligodendrocyte glycoprotein. Second, administration of antigen through routes that stimulate Th2 cells and downregulate pro-inflammatory Thi cells can stimulate antibody synthesis (Neutra et al., 1996; Abbas et al., 1996), and cause exacerbation rather than improvement of antibody-mediated autoimmune diseases.

Short T epitope sequences may be safer for inducing T cell tolerance than the whole antigen molecule, since peptide-specific antibodies very seldom crossreact with the cognate native antigen (Conti-Fine et al., 1996). Peptides have been used with dubious success for oral tolerization in EAE (Karpus et al., 1996; Metzler et al., 1993), although peptides are not ideal for oral tolerization because they are easily digested by gastrointestinal proteases.

Thus, there is a need for an improved method to treat or inhibit antibody-mediated diseases.

SUMMARY OF THE INVENTION

The present invention provides a therapeutic method comprising the administration of an "epitope" peptide comprising a universal and/or immunodominant epitope sequence derived from a particular antigen that is associated with an antibody-mediated disease in a mammal. The method is effective to specifically tolerize, or down regulate the priming and/or activity of, the antigen-specific T cells of said mammal. The sequence of the epitope peptide does not include the entire sequence of the antigen from which it is derived.

Many autoimmune diseases and other pathological conditions are directly caused by antibodies. Such antibodies are directed against proteins or other antigenic components of the host in diseases such as autoimmune diseases, or against exogenous substances in, for example, allergic diseases. The antibodies may also be directed against therapeutic agents, i.e., proteins or other antigenic substances given to the host for therapeutic purposes, such as the administration of factor VIII to treat bleeding in hemophilia A patients. These therapeutic agents may be administered exogenously, or may be synthesized by the host as a result of gene therapy.

Antibody synthesis is controlled by T cells. In mammals there are limited sets of epitopes for each antigen that dominate the T cell response, referred to as immunodominant T cell epitope sequences (hereinafter “immunodominant epitope sequences”). Moreover, in humans, CD4+ cells recognize universal, immunodominant epitope sequences. As T cell epitopes may comprise as few as 7 amino acid residues corresponding to an amino acid sequence present in a particular antigen, peptides having at least about 7 amino acid residues may be useful to tolerize, or down regulate the priming and/or activity of, T cells (e.g., CD4+ cells) specific for the peptide and its corresponding antigen. Thus, immunodominant and/or universal epitope peptides may be administered so as to regulate a mammal’s T cell and antibody response.

To determine whether the delivery of a given peptide is useful to inhibit or treat a particular indication or disease in humans, the immunodominant and/or universal epitopes for a relevant antigen are identified. These epitopes are then identified, synthesized and administered to non-human mammals, preferably ones that are models for a particular human indication or disease, to determine whether the epitope peptide is useful to down regulate the T cell and antibody response to a particular antigen. For example, rodents immunized with Torpedo fish ACHR (TAChR) and, thus, susceptible to experimental myasthenia gravis (EMG) are useful to determine whether the administration of acetylcholine receptor (AChR)-derived epitope peptides can result in T cell tolerization. As described hereinbelow, EMG was induced in C57B1/6 (B6) mice by immunization with purified TAChR. The immunized animals have sensitized CD4+ and B cells, and produce high affinity IgG antibodies which cross-react with mouse muscle ACHR. The immunized B6 mice have anti-TAChR CD4+ T cells that recognize primarily epitopes within residues 146–169, 181–200 and 360–378 of the TAChR α subunit. Surprisingly, nasal administration of synthetic sequences of the TAChR α subunit representing epitopes recognized by anti-TAChR CD4+ T helper cells, given before and during immunization with TAChR, resulted in 1) decreased CD4+ responsiveness to those epitopes and to TAChR; 2) reduced synthesis of anti-TAChR antibodies; and 3) an absence of EMG.

In contrast to B6 mice, nasal administration of synthetic ACHR CD4+ epitopes did not prevent EMG in IL-4 knock out (KO) mice (Example III). Thus, the protective effects of nasal tolerization require presence of Th2 cells, although this procedure also results in the deletion of Th1 cells specific for the administered epitopes.

Moreover, the results obtained with nasal administration of AChR CD4+ epitopes were confirmed using another route of administration, i.e., subcutaneous administration (Example IV). Subcutaneous administration to B6 mice of a pool of solutions of synthetic TAChR $CD4^+$ epitopes (α150-169, α181-200 and α360-378), or of peptide α150-169 alone, given before and during immunization with TAChR, strongly reduced the synthesis of anti-TAChR Ab and prevented EMG. The peptide treatment reduced the $CD4^+$ responses in vitro to the administered peptide epitopes, not to the TAChR molecule.

Secretion of cytokines by spleen $CD4^+$ cells from TAChR-immunized mice, challenged with TAChR in vitro, indicated that in sham-tolerized mice only Th1 cells responded to the TAChR, while in peptide-treated mice the $CD4^+$ cells that responded to TAChR were, or included, Th2 cells. Peptide-treated mice made anti-peptide Ab, that included a large fraction of Th2-driven IgG1. The subcutaneous treatment had some inhibitory effect on anti-AChR Th2 cells, since the serum anti-TAChR Ab IgG1 were modestly reduced after large doses of tolerizing peptide(s).

To determine directly whether $CD4^+$ cells have an important pathogenic role in antibody-mediated autoimmune diseases, e.g., MG, SCID mice were engrafted with lymphocytes from MG patients (Example II). Mice transplanted with lymphocytes from MG patients frequently developed myasthenic weakness, and they had human anti-AChR Ab in their serum and bound to muscle AChR. Mice transplanted with lymphocytes from controls did not develop myasthenic weakness, or anti-AChR Ab. Thus, $CD4^+$ cells are necessary for MG pathogenesis, and $CD4^+$ cells specific for universal AChR epitopes help the synthesis of pathogenic antibody.

Likewise, hemophilia A mice (factor VIII knockout mice), which do not produce factor VIII but produce anti-factor VIII antibodies after exogenous administration of factor VIII, are useful to test whether factor VIII T cell epitope peptides can down regulate the anti-factor VIII immune response in these mice.

With respect to universal, immunodominant CD4+ epitopes in humans, it has been shown that diphtheria toxin (DTX) and tetanus toxin (TTX) have such epitopes, see U.S. application Ser. No. 08/564,972; Raju et al., 1995; Raju et al.,1996; Diethelem et al., 1997), respectively. As described hereinbelow, universal, immunodominant CD4+ epitope sequences exist on human ACHR, the endogenous protein that is associated with the sensitization of CD4+ cells and production of high affinity IgG in myasthenia gravis (MG) patients. Moreover, the universal, immunodominant epitope sequences recognized by CD4+ T cells of MG patients can lead to the synthesis of pathogenic anti-AChR antibodies (Conti-Fine et al., 1997). Also as described hereinbelow, the majority of humans sensitized to factor VIII have CD4+ cells that recognize certain universal epitopes of factor VIII.

In particular, respiratory, e.g., nasal (upper) or lower respiratory tract, administration is a promising tolerizing route when using an epitope peptide, since the peptide does not need to overcome the proteolytic barriers present in the digestive system, and crosses the epithelia more readily than larger polypeptide molecules. Thus, synthetic CD4+ epitope sequences may be more effective than the whole or native antigen for tolerance induction. Moreover, the peptides of the invention can be prepared in large quantities and in high purity by chemical syntheses and thus are much less expensive and more readily obtained than a preparation comprising isolated autoantigen. Further, the delivery of epitope peptides to other mucosal surfaces, e.g., in the intestine, the mouth, the genital tract, and the eye, may also be employed in the practice of the methods of the invention, although the invention is not limited to administration by mucosal routes.

The administration of peptides to mucosal surfaces can result in a state of peripheral tolerance, a situation characterized by the fact that immune responses in non-mucosal tissues do not develop even if the peptide initially contacted with the mucosa is reintroduced, or its corresponding antigen is introduced or interacts with the immune system (e.g., in autoimmune diseases), in the organism by a non-mucosal route. Since this phenomenon is exquisitely specific for the peptide, and thus does not influence the development of systemic immune responses against other antigens, its use is particular envisioned for preventing and treating illnesses associated or resulting from the development of exaggerated immunological reactions against specific antigens encountered in nonmucosal tissues. For example, one embodiment of the invention is a method in which a mammal is contacted with a peptide of the invention via nasal inhalation in an amount that results in the T cells of said mammal having diminished capability to develop a systemic and/or peripheral immune response when they are subsequently contacted with an antigen comprising an immunodominant and/or universal portion of said peptide.

Thus, the invention provides a method of preventing or inhibiting an indication or disease associated with aberrant, e.g., excessive, pathogenic or otherwise undesirable antibody production. The method comprises administering to a mammal afflicted with, or at risk of, the indication or disease an amount of a peptide, a variant thereof or a combination thereof, that is formally a fragment of a native antigen, and having an immunodominant and/or universal epitope sequence of said antigen which is effective to prevent or inhibit at least one symptom of the indication or disease. Preferably, for humans, the peptide comprises a universal, immunodominant epitope sequence. It is preferred that the peptide is administered to a mucosal surface. A preferred mucosal surface to which the peptides of the invention are administered is the respiratory tract.

Also provided is a method in which the administration of a peptide of the invention to a mammal results in the suppression, tolerization, or down regulation of the priming and/or activity, of T cells of a mammal at risk or, or having, an indication or disease associated with aberrant, pathogenic or otherwise undesirable antibody production. Further provided is a method in which the administration of a peptide of the invention results in the decrease in the amount or activity of antibodies which are characteristic of the particular disease or indication. Preferably, the administration of a peptide of the invention to a mammal results in T cell tolerization, the down regulation of priming or activity of T cells, a reduction in the amount or affinity of pathogenic antibodies, the inhibition of at least one symptom of the indication or disease, or any combination thereof.

The invention also provides a method to prevent or inhibit an indication or disease characterized by the presence of an antibody specific for an endogenous antigen. The method comprises administering to a mammal in need thereof an effective amount of a peptide, a variant thereof, or a combination thereof, wherein the peptide represents a fragment of said antigen and comprises an immunodominant and/or universal epitope sequence of said antigen. The administration is effective to reduce or eliminate at least one symptom of the indication or disease, tolerize or down regulate the priming or activity of T cells specific for the epitope and the antigen comprising said epitope, and/or decrease the amount or affinity of the antibody for the endogenous antigen. Indications and diseases characterized by the presence of an antibody which binds an endogenous antigen include antibody-mediated autoimmune diseases such as myasthenia gravis, systemic lupus erythematosus, pemphigus, thrombic thrombocytopenic purpura and the like.

Preferably, the peptide is nasally administered to a human in an amount effective to suppress or tolerize, or down regulate the priming or activity of, the CD4+ cells of said human which induce the production of pathogenic antibodies. A preferred peptide to prevent or treat myasthenia gravis is a peptide that comprises a universal and/or immunodominant epitope sequence of human AChR. Likewise, preferred peptides that are useful to prevent or treat the undesirable immune responses to factor VIII that may develop in hemophilia A patients after treatment with factor VIII, or to factor IX that may develop in hemophilia B patients after treatment with factor IX, would be universal and/or immunodominant CD4+ epitope sequences of factor VIII and factor IX, respectively.

Yet another embodiment of the invention is a method to prevent or inhibit an indication or disease characterized by the presence of an antibody specific for an exogenous antigen, wherein the antigen is not associated with an infectious agent, e.g., a virus, bacteria or fungus, with the exception of viruses employed to transfer genes for gene therapy, and fungal components that cause allergic responses. The method comprises administering to a mammal in need thereof an amount of a peptide, a variant thereof, or a combination thereof, effective to reduce or eliminate at least one symptom of the indication or disease, tolerize or down regulate the priming or activity of, T cells specific for the epitope and/or decrease the amount or affinity of the antibody specific for the exogenous antigen. The administered peptide is a fragment of said antigen and comprises an immunodominant and/or universal epitope sequence of the exogenous antigen. For example, allergies are characterized by an exaggerated immune response to certain environmental factors. Thus, to prevent or inhibit an exaggerated antibody-mediated immune response to a proteinaceous allergen, an effective amount of a peptide comprising an immunodominant and/or universal epitope sequence of the allergen, is administered to the mammal.

Further provided is a method to tolerize a mammal to an antigen associated with aberrant or pathogenic, or otherwise undesirable, antibody production in the mammal. The method comprises administering to the mammal an amount of at least one peptide, a variant thereof or a combination thereof, having a universal and/or immunodominant epitope sequence effective to tolerize, or down regulate the priming or activity of T cells of, the mammal to an antigen comprising said epitope, wherein said peptide is a fragment or subunit of said antigen.

Yet another embodiment of the invention is a method to identify an immunodominant epitope sequence in a mammal. The method comprises contacting at plurality of samples with a panel of peptides. Each sample comprises T cells and antigen presenting cells obtained from an individual mammal. The panel of peptides together correspond to the entire sequence of a particular antigen. Preferably, the peptides comprise overlapping sequences, i.e., each peptide comprises a sequence which overlaps with a portion of the sequence of at least one other peptide, such as the two adjacent peptides. Each sample is contacted with one of the peptides. Preferably, the mammals have been previously exposed to the antigen. Then it is determined whether the T cells from the mammal proliferate in response to one of the peptides relative to a sample contacted with an unrelated peptide that does not comprise an immunodominant epitope sequence and/or a sample which is not contacted with a peptide.

Another embodiment of the invention is a method to identify a universal epitope sequence useful to tolerize, or down regulate the priming or activity of, T cells of a mammal, e.g., a human. The method comprises contacting at least two samples with a preselected peptide, a variant thereof or combination thereof One sample comprises T cells obtained from a first individual mammal. The second sample comprises T cells from a second mammal, wherein the genotype of the second mammal differs at the immune response loci from the genotype of the firsi mammal, and wherein the mammals are of the same species. The samples to be tested preferably comprise T cells of a mammal that are sensitized to an antigen comprising said peptide. Preferably, the T cells are obtained from a mammal having, or at risk of, an indication or disease associated with aberrant or pathogenic, or otherwise undesirable, antibodies to the antigen. Then it is determined whether or not the T cells from each mammal proliferate relative to (negative) control T cells which were not exposed to a peptide or any other antigenic stimulus, and/or relative to T cells exposed to a (negative) control peptide, i.e., one not having a universal epitope sequence. A peptide having a universal epitope sequence will induce the proliferation of T cells from samples from a majority of mammals of the same species, mammals which differ at the immune response loci.

Thus, the invention also provides a tolerogen comprising at least one isolated and purified epitope peptide having a universal and/or immunodominant epitope sequence and a physiologically compatible carrier, the administration of which to a sensitized mammal results in the suppression or reduction of the immune response of that mammal to an antigen which comprises at least an immunogenic portion of the peptide. Alternatively, the administration of at least one isolated and purified epitope peptide having a universal and/or immunodominant epitope sequence and a physiologically compatible carrier, to a non-sensitized mammal results in the blocking of or a reduction in the priming to an antigen which comprises at least an immunogenic portion of the peptide, when such antigen is administered to the mammal in a manner that normally results in an immune response. It is preferred that the peptide contains a contiguous sequence of at least about 7 amino acids having identity with the amino acid sequence of the antigen, and that the peptide is no more than about 40 amino acid residues in length, i.e., it represents a subunit of said antigen. It is also preferred that the tolerogen is nasally administered.

A further embodiment of the invention is a method to inhibit or suppress an antibody-mediated disease that is associated with the administration of an endogenous protein or the use of gene therapy to replace such a protein. An endogenous protein that is administered so as to supplement or replace a deficiency in that protein includes, but is not limited to, insulin or fragments thereof, gamma globulins or fragments thereof, factor VIII or fragments thereof, factor IX or fragments thereof, cystic fibrosis transmembrane regulator or fragments thereof, growth hormone or fragments thereof, a transplantation antigen or fragments thereof and the like. Moreover, the endogenous protein may be recombinantly produced (referred to as "recombinant" protein or polypeptide). Replacement gene therapy includes the use of viral vectors to introduce and express a therapeutic gene, e.g., an endogenous protein. Because the endogenous protein or exogenous viral protein is "foreign" to the host, the host may have an immune response to these proteins. To suppress this response, a mammal at risk of, or having, a disease characterized by a decreased amount of, or a lack of, an endogenous protein or polypeptide, e.g., hemophilia A or B, adenosine deamidase deficiency, cystic fibrosis or diabetes, is administered a peptide, a variant thereof or a combination thereof in an amount effective to suppress or tolerize, or down regulate the priming and/or activity of, T cells specific for the endogenous protein. Similarly, to suppress an immune response to a viral protein present in a delivery vehicle for gene therapy, a mammal in need of gene therapy or subjected to gene therapy is administered a peptide, a variant thereof or a combination thereof in an amount effective to suppress or tolerize, or down regulate the priming and/or activity of, T cells specific for the viral protein. Preferably, the epitope peptide is a subunit of the endogenous protein and comprises immunodominant and/or universal epitope sequences derived from the endogenous protein, e.g., peptides of factor VIII for hemophilia A, or an epitope peptide derived from the viral protein of the viral vector employed for gene therapy, e.g., peptides of a retrovirus or adenovirus glycoprotein or capsid protein.

Also provided is a therapeutic method, comprising: nasally administering to a mammal subjected to gene therapy which employs a recombinant virus as a delivery vehicle, an amount of an epitope peptide, a variant thereof or a combination thereof effective to suppress an immune response to the virus-specific proteins present in the delivery vehicle, wherein the peptide comprises an immunodominant and/or universal epitope sequence of the virus protein.

Further provided is therapeutic method, comprising: nasally administering to a mammal having an indication or disease characterized by a decreased amount or a lack of an endogenous protein, wherein the mammal is subjected to exogenous introduction of the protein or the corresponding recombinant polypeptide, an amount of an epitope peptide, a variant thereof or a combination thereof effective to suppress an immune response to the exogenously introduced protein or polypeptide, wherein the indication or disease is associated with aberrant or pathogenic antibody production to the endogenous protein, and wherein the epitope peptide is a subunit of the endogenous protein and comprises an immunodominant and/or universal epitope sequence of the endogenous protein.

Also provided is a method to treat an antibody-mediated disease in a mammal wherein the disease is characterized by antibodies specific for an antigen. The method comprises administering to the mammal a dosage form comprising an amount of at least one epitope peptide, a variant thereof or a combination thereof, effective to prevent or inhibit at least one symptom of said disease, suppress or tolerize, or down regulate the priming and/or activity of, T cells specific for the antigen, and/or inhibit or decrease the amount or activity of the antibody which is specific for the antigen. The peptide is a fragment of the antigen and comprises an immunodominant and/or universal epitope sequence of the antigen comprises the immunodominant and/or universal epitope sequence.

The mammal is also subjected to plasmapheresis either before, during or after, or any combination thereof, peptide administration so as to decrease the amount of circulating antibodies which include the antibodies specific for the antigen. Optionally, an immunosuppressive agent may also be administered so as to decrease B cell activation.

BRIEF DESCRIPTION OF THE FIGURES

FIG. 9. Codons for specified amino acids.

FIG. 10. Exemplary and preferred amino acid substitutions for variant peptides or polypeptides of the invention.

FIGS. 16A–D. Human IgG at the neuromuscular junctions of SCID mice transplanted with BL from MG patients containing AChR-specific CD4$^+$ cells. Muscle sections were from SCID mice engrafted with BL from a MG patient or a healthy subject, as indicated (A), or with CD4$^+$ depleted BL from patient #16, supplemented with a CD4$^+$ T cell line specific for tetanus toxoid (TTD), or a CD4$^+$ T cell line specific for the universal epitope sequence α304-322, as indicated (B). The sections were tested for the presence of human IgG at the neuromuscular synapses. Double immunofluorescent staining with α-bungarotoxin (α-BTX) (red fluorescence) to localize the synapses, and with Ab against human IgG (green fluorescence), was used. The panels' "merge" depict the overlay of the images obtained for the same section using α-BTX and the Ab against human IgG. The overlay of the red and green signal resulting from binding of the two probes to the same synapses results in the yellow color of the merged image. SCID mice engrafted with BL from a healthy subject, or with CD4+ depleted BL from Patient 16 plus a TTD-specific CD4+ line, did not have human Ab bound to the neuromuscular junction. Thus, when the overlay is done for sections from these mice, only the red color of α-BTX is present in the merged image.

FIGS. 28A–C. Serum concentrations of anti-TAChR antibodies and their subclasses from IL-4 KO mice engrafted with CD4+ cells of sham and α epitope pool treated B6 mice.

FIGS. 32A–C. CD8+ depleted spleen cells from TAChR immunized IFNγ KO mice. p

FIGS. 41A1–A4, B1–B4, C1–C3. Maximum response to Factor VIII or Factor VIII domain peptides over time of CD4+, CD8+-depleted blood lymphocytes.

FIGS. 48A–H. Responses of hemophilia A mice to individual peptides.

DETAILED DESCRIPTION OF THE INVENTION

Definitions

Figure 1A:
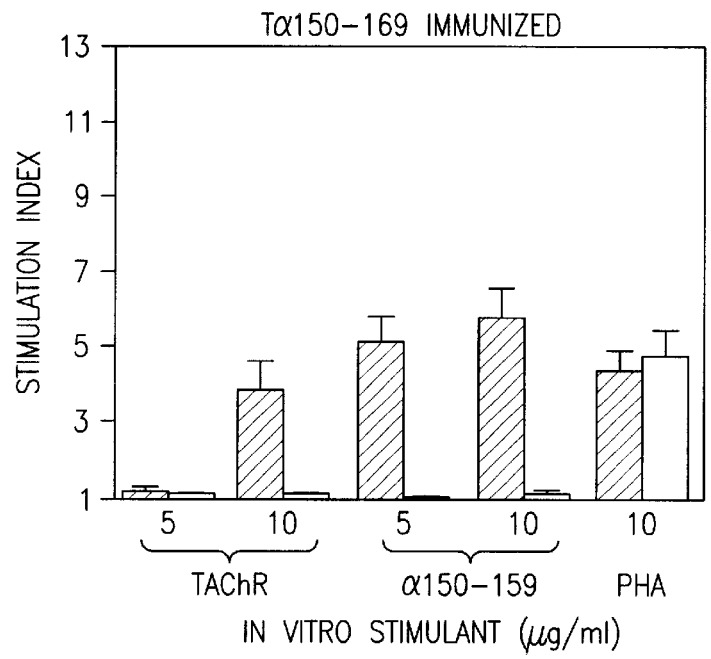
FIGS. 1A–B. Nasal administration of synthetic TAChR epitopes Tα50-169, Tα181-200 and Tα360-378 causes T cell unresponsiveness to those epitopes. Mice were given two nasal administrations of peptide Tα150-169 (panel A, dotted columns), or α pool (panel B, white columns), or peptide-free PBS (black columns) prior to immunization with the peptide(s) used for the nasal treatment. Seven-ten days after the last immunization, the proliferative response of spleen T cells to the immunizing peptide(s) and to TAChR was tested. The data depicted are the results obtained for one mouse from each group, which is representative of the results obtained for all mice of that group. The response induced by 10 μg of PHA is also shown. The columns represent the average S.I. of triplicate cultures. The average c.p.m. obtained in the absence of any stimulation were 297±59 in experiment A and 2,884±106 in experiment B.

"Immunodominant" CD4+ cell epitopes (also referred to as immunodominant T cell epitopes or imrnmunodominant epitope sequences) refer to a sequence of a protein antigen, or the proteinaceous portion of an antigen, that is strongly recognized by the CD4+ cells of a mammal sensitized to that antigen, as detected by methods well known to the art, including methods described herein. "Strongly" recognized means that the peptide elicits a statistically significant response as compared to the background response to a non-related peptide from an antigen to which the mammal is not sensitized, and that such response is at least two times higher than the average response obtained for at least about ⅓ of the peptides which elicit the lowest response from the peptides employed to identify the immunodominant epitopes.

T cell epitopes can vary in size, and as few as 7 consecutive amino acid residues of a particular antigen may be recognized by CD4+ cells. Thus, an immunodominant epitope sequence is an amino acid sequence containing the smallest number of contiguous amino acid residues which are strongly recognized by T cells from an individual mammal. An epitope peptide of the invention may comprise more than one immunodominant epitope sequence, and may comprise sequences which do not contain an immunodominant epitope sequence. Sequences which do not contribute to an immunodominant epitope sequence can be present at either or both the amino- or carboxyl-terminal end of the peptide. The non-immunodominant epitope sequences preferably are no more than about 10–20 peptidyl residues in toto, and either do not affect the biological activity of the peptide or do not reduce the activity of the peptide by more than 10–20%. Preferably, epitope peptides having immunodominant epitope sequences are useful to tolerize, or down regulate the priming and/or activity of T cells of, a mammal to an antigen having said sequences so as to result in a reduction in the amount or activity of antibodies to said antigen in said mammal.

As used herein, a "universal" epitope sequence is an epitope that is recognized by CD4+ cells from a majority, preferably at least about 66%, more preferably at least about 75%, of individuals within a population of a particular mammalian species that is genetically divergent at the immune response loci, e.g., at the HLA loci in humans. T cell epitopes can vary in size, and as few as 7 consecutive amino acid residues of a particular antigen may be recognized by CD4+ cells. Thus, within the scope of the invention, a universal epitope comprises an amino acid sequence containing the smallest number of contiguous amino acid residues which are recognized by CD4+ cells from a majority of mammals from the same species which are genetically different at their immune response loci. A peptide of the invention may comprise more than one universal epitope sequence, and may comprise sequences which do not contain a universal epitope sequence.

Preferably, at least a majority, i.e., 51%, of the amino acid sequence of the peptide comprises a universal epitope sequence. Sequences which do not contribute to a universal epitope sequence can be present at either or both the amino- or carboxyl-terminal end of the peptide. The non-universal epitope sequences preferably are no more than about 10–20 peptidyl residues in toto, and either do not affect the biological activity of the peptide or do not reduce the activity of the peptide by more than 10–20%.

The term "tolerance" is here defined as a reduction in the T cell and/or antibody response which is specific for a given antigen. The reduction in the antibody response may be concomitant with increased sensitization and/or response of special subsets of T cells specific for the antigen, for example CD4+ Th2 cells which have immunoregulatory functions.

As used herein, the terms "isolated and/or purified" refer to in vitro preparation, isolation and/or purification of a peptide or nucleic acid molecule of the invention, so that it is not associated with in vivo substances, or is substantially purified from in vitro substances.

As used herein, the term "immunogenic" with respect to a peptide of the invention means that the peptide can induce non-tolerized peripheral blood mononuclear cells (PBMC) or other lymphoid cells from a sensitized mammal to proliferate or secrete cytokines when those cells are exposed to the peptide relative to cells not exposed to the peptide, and/or that the administration of the peptide to a mammal causes an immune response to the peptide.

A "sensitized" mammal is a mammal that has been exposed to a particular antigen, as evidenced by the presence of antibodies or T cells specific to the antigen. Preferably, the mammal has high affinity, e.g., IgG, antibodies to the antigen. A sensitized mammal within the scope of the invention includes mammals having or at risk of an antibody-mediated indication or disease as defined herein.

As used herein, an "exogenous" antigen preferably does not include antigens, e.g., native antigens, of an infectious agent, i.e., a virus, bacteria or fungus, with the exception of antigens of viruses employed to transfer genes for gene therapy, and fungal components that cause allergic responses.

As used herein, an "endogenous" antigen includes proteins that are normally encoded by the genome of and expressed in a mammal.

As used herein, the term "aerosol" includes finely divided solid or liquid particles that may be created using a pressurized system such as a nebulizer or instilled into a host. The liquid or solid source material contains a peptide or a nucleic acid molecule of the invention, or a combination thereof.

An "epitope" peptide of the invention is a peptide subunit that comprises at least about 7 and no more than 40 amino acid residues which have 100% contiguous amino acid sequence homology or identity to the amino acid sequence of a particular antigen, e.g., human ACHR or factor VIII. An epitope peptide of the invention comprises a universal and/or immunodominant epitope sequence. The administration of an epitope peptide of the invention to a sensitized mammal results in a mammal that is tolerized to the antigen from which the epitope peptide is derived. Preferably, the administration of an epitope peptide of the invention to a mammal does not result in the stimulation of B cells specific for the peptide.

As employed herein, a "variant" of an epitope peptide of the invention refers to a peptide which comprises at least about 7 and no more than about 40, peptidyl residues which have at least about 70%, preferably about 80%, and more preferably about 90%, but less than 100%, contiguous homology or identity to the amino acid sequence of a particular antigen. A variant peptide of the invention comprises a universal and/or immunodominant epitope sequence. The administration of a variant peptide of the invention to a sensitized mammal results in a mammal that is tolerized to the peptide, and to the antigen from which the peptide is derived. Preferred variant peptides of the invention do not reduce the biological activity of the peptide by more than 10–20% relative to the corresponding non-variant peptide.

As used herein, the term "biological activity" with respect to a peptide of the invention is defined to mean that the administration of the peptide, preferably via a mucosal surface such as the respiratory tract, to a mammal results in the mammal developing tolerance to an antigen having at least a portion of the peptide administered.

"Replacement gene therapy" as used herein means therapy intended to supplement reduced amounts or the complete absence of an endogenous protein. The therapy may include the administration of isolated native protein or recombinant polypeptide to the mammal in need thereof, or the administration of a recombinant viral vector encoding said polypeptide.

An "indication or disease" within the scope of the invention includes antibody-mediated diseases as well as cell-mediated diseases. Antibody-mediated diseases include, but are not limited to, autoimmune diseases such as myasthenia gravis, and allergic diseases such as those described below. Antibody-mediated indications within the scope of the invention include, but are not limited to, indications characterized by undesirable antibody responses to substances administered for therapeutic purposes such as antibody responses to endogenous proteins that are exogenously administered, and to viral proteins or the protein encoded by a viral vector that is employed for gene therapy.

I. The Immune Response

The capacity to respond to immunologic stimuli resides primarily in the cells of the lymphoid system. During embryonic life, a stem cell develops, which differentiates along several different lines. For example, the stem cell may turn into a lymphoid stem cell which may differentiate to form at least two distinct lymphoid populations. One population, called T lymphocytes, is the effector agent in cell-mediated immunity, while the other, called B lymphocytes, is the primary effector of antibody-mediated, or humoral, immunity. The stimulus for B cell antibody production is the attachment of an antigen to B cell surface immunoglobulin. Thus, B cell populations are largely responsible for specific antibody production in the host. For most antigens, B cells require the cooperation of antigen-specific T helper (CD4+) cells for effective production of high affinity antibodies.

Of the classes of T lymphocytes, T helper (Th) or CD4+ cells, are antigen-specific cells that are involved in primary immune recognition and host defense reactions against bacterial, viral, fungi and other antigens. CD4+ cells are necessary to trigger high affinity IgG production from B cells for the vast majority of antigens. The T cytotoxic (Tc) cells are antigen-specific effector cells which can kill target cells following their infection by pathologic agents.

While CD4+ cells are antigen-specific, they cannot recognize free antigen. For recognition and subsequent CD4+ activation and proliferation to occur, the antigen must be processed by suitable cells (antigen presenting cells, APC). APC fragment the antigen molecule and associate the fragments with major histocompatibility complex (MHC) class II products (in humans) present on the APC cell surface. These antigen fragments, or T cell epitopes, are thus presented to receptors or a receptor complex on the CD4+ cell in association with MHC class II products. Thus, CD4+ cell recognition of a pathogenic antigen is MHC class II restricted in that a given population of CD4+ cells must be either autologous or share one or more MHC class II products with the APC. Likewise, Tc cells recognize antigen in association with MHC class I products.

In the case of CD4+ cells, this antigen presenting function is performed by a limited number of APC. It is now well established that CD4+ cells recognize peptides derived from processed soluble antigen in association with class II MHC product, expressed on the surface of macrophages. Recently, other cell types such as resting and activated B cells, dendritic cells, epidermal Langerhans' cells, and human dermal fibroblasts have also been shown to present antigen to CD4+ T cells.

If a given CD4+ cell possesses receptors or a receptor complex which enable it to recognize a given MHC class II product-antigen complex, it becomes activated, proliferates and generates lymphokines, such as interleukin 2 (IL-2). The lymphokines in turn cause the proliferation of several types of "killer" cells, including Tc cells and macrophages, which can exhibit antimicrobial and tumoricidal activity.

After stimulation subsides, survivors of the expanded CD4+ cells remain as member cells in the body, and can expand rapidly again when the same antigen is presented.

Numerous attempts have been made to isolate and maintain homogenous populations of Tc or CD4+ cells and to characterize them in terms of their antigen specificity and MHC restriction. These attempts usually involve the stimulation of mononuclear cells from a seropositive human or murine host with antigenic bacterial or viral preparations in combination with nonproliferative APC, such as irradiated autologous mononuclear cells (MNC). Proliferating polyclonal populations of CD4+ cells or Tc cells can be cloned by limiting dilution to obtain homogenous populations and then further proliferated and characterized by a variety of techniques.

Methods of determining whether PBMCs or lymphoid cells have proliferated, or produced or secreted interleukins, are well known in the art. For example, see Paul, *Fundamental Immunology*, 3rd ed., Raven Press (1993), and Benjamini et al. (eds.), *Immunology:A Short Course*, John Wiley & Sons, Inc., 3rd ed. (1996).

II. Indications Amenable to Treatment by the Peptides of the Invention or Nucleic Acid Molecules Fncoding the Peptides The peptides or nucleic acid molecules of the invention are useful to treat a mammal afflicted with, or to inhibit in a mammal at risk of, an indication or a disease characterized by aberrant or pathological, or undesirable, antibody production which is specific for a particular antigen, e.g., an antibody-mediated autoimmune disease. Preferably, these efficacious peptides are recognized by CD4+ cells from a majority of mammals having or at risk of the indication or disease, and, more preferably, these epitopes are recognized by CD4+ cells that induce the synthesis of pathogenic antibody and/or excessive amounts of the antibody. Indications or diseases associated with aberrant, pathological or undesirable antibody production include, but are not limited to, autommune disease (endogenous antigen), replacement gene therapy (endogenous and/or exogenous antigen), proteins administered for therapeutic purposes (endogenous and/or exogenous antigen) or allergies (exogenous antigen). Thus, a peptide may be selected so as to inhibit or treat an indication or disease characterized by aberrant, pathological or undesirable antibody production which is antigen specific, thereby minimizing side effects resulting from disrupting unrelated physiological processes or side effects associated with administration of full-length antigen.

A. Autoimmune Diseases

Autoimmune diseases are characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimrnune diseases include multiple sclerosis, rheumatoid arthritis, Hashimoto thyroiditis, type I diabetes mellitus (Juvenile onset diabetes) and autoimmune uvoretinitis (see Table 1). Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia (see Table 1). The antigen(s) associated with systemic lupus erythematosus is small nuclear ribonucleic acid proteins (Snurps), Graves' disease is the thyrotropin receptor, thyroglobulin and other components of thyroid epithelial cells (Akamizu et al., 1996; Kellerman et al., 1995; Raju et al., 1997; and Texier et al., 1992), pemphigus is cadherin-like pemphigus antigens such as desmoglein 3 and other adhesion molecules (Memar et al., 1996: Stanley, 1995; Plott et al., 1994; and Hashimoto, 1993), and thrombic thrombocytopenic purpura is antigens of platelets.

Other autoimmune diseases and their specific autoantigens and/or target tissues are disclosed in Schwartz, R. S. et al. in *Fundamental Immunology*, Third Edition, Paul, W. E., Ed., Raven Press, N.Y., 1993, which is incorporated by reference herein.

The current treatments for both categories of autoimmune diseases involve administration of drugs which non-specifically suppress the immune response. Examples of such drugs are methotrexate, cyclophosphamide, Imuran (azathioprine) and cyclosporin A. Steroid compounds such as prednisone and methylprednisolone are also employed in many instances. These drugs have limited efficacy against both cell- and antibody-mediated autoimmune diseases. Use of such drugs is limited by virtue of their toxic side effects and also because they induce "global" immunosuppression in a patient receiving prolonged treatment with the drug, e.g., the normal protective immune response to pathogenic microorganisms is downregulated thereby increasing the risk of infections caused by these pathogens. A further drawback is that there is an increased risk that malignancies developing in patients receiving prolonged global immunosuppression.

TABLE 1

| Disease Model | Specific Autoantigen |
|---|---|
| Multiple Sclerosis | MBP |
| Rheumatoid Arthritis | Collagen |

TABLE 1-continued

| Disease Model | Specific Autoantigen |
|---|---|
| Autoimmune Thyroiditis | Thyroglobulin |
| Myasthenia Gravis | Acetylcholine receptor |
| Autoimmune uvoretinitis | S-antigen |
| Systemic Lupus Erythematosus | DNA |
| Diabetes | islet cell extract |
| Chronic Active Hepatitis | Liver extract |
| Adrenalitis | Adrenal gland extract |
| Polymyositis | Muscle extract |
| Autoimmune hemolytic anemia | Hematopoietic cells |
| Rheumatic carditis | Heart extract |
| Scleroderma | Skin cell extract |

An autoimmune disease is a malfunction of the immune system of mammals, including humans. In a mammal afflicted with such a disease, the immune system treats autologous tissues (self or endogenous antigens) and substances as if they were foreign and dangerous, and evokes the immune defense that is usually reserved for use against exogenous and dangerous substances (e.g., foreign tissues or invading organisms), including sensitization of T cells and synthesis of high affinity antibodies.

B. Replacement Therapies Which Employ Protein Therapeutics or Gene Therapy

The identification of underlying genetic defects has made gene therapy an attractive treatment option for a wide variety of diseases. Gene therapy is particularly useful in indications or diseases that result from a defect in a single gene. A deficiency in an endogenous protein in a mammal may occur neonatally or later in the mammal's life. The deficiency may be a complete lack of the endogenous protein, e.g., due to a genetic defect in the gene encoding the protein, or a reduced amount of an endogenous protein relative to a majority of other mammals of the same species. In either case, the deficiency may be enough to result in a particular disorder or disease. For example, a deficiency in factor VIII causes hemophilia A and a deficiency in factor IX causes hemophilia B. To supplement these deficiencies, certain proteins can be administered to the mammal so as to treat or prevent the disease. A different approach to treat or prevent genetic defects which result in disease is to introduce a "normal" gene that encodes the endogenous protein to the mammal having the deficiency. Viral vectors are one method which has been employed to introduce particular genes into mammals. However, the introduction of endogenous proteins, their recombinantly produced counterpart polypeptides, or recombinant viruses having genomes that encode the endogenous protein can result in an immune response to the foreign proteins, the endogenous protein, the recombinant polypeptide, or the viral capsid or glycoproteins.

Thus, therapies in which an endogenous protein is administered to treat a particular disease can result in an antibody mediated response which is specific for that protein. One example of such a disease is hemophilia. For example, certain hemophiliacs lack or have reduced amounts of factor VIII. These patients are treated with isolated native factor VIII or recombinant factor VIII. However, some of these patients develop antibodies to factor VIII that block of inhibit factor VIII activity that reduces the efficacy and increases the cost of the therapy. Likewise, an immune reaction to a native or recombinant protein that is introduced into a mammal to supplement a deficiency in that protein may be prevented or treated by the compounds, compositions and methods of the invention. Such proteins include, but are not limited to factor IX, growth hormone, adenine deamidase (ADA), β-globin, HPRT, purine nucleoside phosphorylase, α1-anti-trypsin, glucocerebrosidase, argininosuccinate synthase, phenylalanine hydroxylase, low density lipoprotein receptor, interleukins, cytokines, dystrophin, ciliary neurotrophic factor (for ALS), fibrosis transmembrane conductance regulator (for cystic fibrosis), p47, alpha-L-hyaluronidase (Hurler syndrome), prolidase, N-acetylgalactosamine (mucopolysaceharidosis type VI), β-glucuronidase (mucopolysaccharidosis type VII), omithine transcarbamylase, liver arginine ureahydrolase, or insulin, may result in the mammal developing antibodies to the administered protein. The methods of the invention are particularly useful to prevent or treat such indications or diseases by tolerizing, or down regulating the priming and/or activity of the T cells of, mammals having such indications or diseases with a peptide having a universal and/or immunodominant epitope sequence from the protein antigen employed for therapeutic purposes.

Successful gene therapy requires the identification of an appropriate therapeutic gene for treatment of the disease, but may also require a delivery system by which that gene can be introduced to the recipient or to a desired cell type both efficiently and accurately. One such delivery system currently employed in clinical trials employs a viral vector to deliver the desired gene to the host organism. The expression of the gene results in the synthesis of the encoded protein in an amount which supplements the amount present in the mammal prior to therapy, preferably so as to inhibit or reduce at least one symptom of the disease.

Viral vectors that have been approved for gene therapy clinical trials include retroviral vectors, adenovirus vectors and adeno-associated virus vectors (see Marshall, *Science*, 262, 1050–1059 (1995)). The introduction of viral vectors and the expression of an endogenous gene product that is not expressed or poorly expressed is that the immune response to the vector-encoded viral proteins (exogenous) results in sensitization of the recipient to those antigens. Thus, the beneficial effects of gene therapy are reduced as a result of the patient's immune system recognizing the viral proteins, as well as the expressed endogenous gene product, as "foreign".

C. Exogenous Antigens

Allergic diseases within the scope of the invention include allergic rhinitis, allergic asthma, atopic dermatitis, allergic gastroenteropathy, anaphylaxis, urticaria and angioedema. Allergens within the scope of the invention include, but are not limited to, protein antigens of *Alternaria altemata* (Alt a I), *Artemisia vulgaris* (Art v II), *Aspergillus fumigatus* (Asp f II), *Dermatophagoides far.* (Der f I), *Dermatophagoides pteron.* (Der p I, Der p III, Der p IV, Der p VI and Der p VIII), mites and domestic animals such as *Felis domesticus*(Fel d I), cows, pigs, poultry, mice, hamsters, rabbits, rats, guinea pigs, dogs and horses. Common fungal antigens include those of Basidiomycetes such as Ustilago, Ganoderna, Alternaria, Cladosporium, Aspergillus, Sporobolomyces, Penicillium, Epicoccum, Fusarium, Phoma, Borrytis, Helminthosporium, Stemphylium and-Cephalosporium; Phycomycetes such as Mucor and Rhizopus; and Ascomycetes such as Eurotium and Chaetomium.

Pollinating plants which may have protein antigens associated with allergies include club mosses, fems, conifers, flowering plants, grasses, sedges, palms, cattails, nettles, beeches, chenopods, sorrels, willows, poplars, maples, ashes, ragweeds (antigen E, antigen K and Ra3) and sages, or proteinaceous plant products such as those found in latex products.

Hymenoptera insects that may have protein antigens associated with allergies include the honeybee, yellow jacket, homet, wasp and fire ant, although protein antigens of other insects are also within the scope of the invention.

Allergies associated with foods may be the result of protein antigens in crustaceans (e.g., shrimp, lobster and crab), mollusks (e.g., clams), fish, legumes (e.g., peanut, pea, beans, and licorice), seeds (e.g., sesame, cottonseed, caraway, mustard, flaxseed, and sunflower), nuts, berrries, egg white, buckwheat and milk.

III. Identification of an Fpitope Peptide Falling Within the Scope of the Invention The identification of a universal and/or immunodominant epitope sequence in an antigen permits the development and use of a peptide-based tolerogen to the antigen. The administration of epitope peptides which contain a universal and/or immunodominant epitope sequence can induce a tolerizing effect in many, if not all, mammals, preferably those of differing immune response haplotypes. Moreover, the use of peptide tolerogens is less likely to produce the undesirable side effects associated with the use of the full-length antigen. These epitope peptides can be identified by in vitro and in vivo assays, such as the assays described hereinbelow (see, for example, Conti-Fine et al., 1997; and Wang et al., 1997). It is recognized that not all agents falling within the scope of the invention can result in tolerization, or result in the same degree of tolerization.

To identify epitope peptides useful to tolerize a mammal having or at risk 30 of an indication or disease within the scope of the invention, the antigen which is associated with the indication or disease is identified. The antigen may be an endogenous antigen, e.g., the AChR, or an exogenous antigen, e.g., a viral glycoprotein or an endogenous antigen, such as factor VIII, administered exogenously to correct a deficiency in that protein. The amino acid sequence of that antigen is then obtained or determined. Generally, 20 residue peptides are obtained or prepared which span the entire amino acid sequence of the antigen and which overlap the adjacent peptide by 5–10 residues, see U.S. application Ser. No.08/564,972. In this manner, a peptide may include sequences which correspond to a portion of a universal and/or immunodominant epitope sequence. These peptides are then individually screened in vitro and in vivo.

In vitro methods useful to determine whether a particular peptide comprises a universal and/or immunodominant epitope sequence include determining the biological activity (e.g., inducing the proliferation of or cytokine secretion by T cells) of the peptide in CD4+ cell lines that are specific for an antigen having the peptide, isolated CD4+ cells, CD8+ depleted spleen or lymph node cells, or CD8+ depleted peripheral blood mononuclear cells (PBMC).

These cells may be obtained from a mammal at risk or of having an indication or disease within the scope of the invention or from a mammal that is "normal" . In either case, the mammal is preferably known to be sensitized to the antigen. Epitope peptides useful in the practice of the invention include a peptide that is strongly recognized by the T cells of the mammal tested, i.e., they have an immunodominant epitope sequence. Preferred epitope peptides are those which are recognized by the T cells of at least a majority of mammals having divergent immune response haplotypes, e.g., MHC class II molecules in humans. This recognition can be measured by the ability of the peptide to induce proliferation or cytokine secretion in T cells obtained from mammals with known or suspected divergent haplotypes and/or by direct HLA class II binding assays (Manfredi et al., 1994; Yuen et al., 1996).

Thus, CD8+ depleted PBMC, CD8+ depleted spleen or lymph node cells or CD4+ lines specific for an antigen or epitope can be contacted with an epitope peptide and the proliferation of the cells measured or the amount and type of cytokine secreted detected. Thl cytokines include IFN-γ, IL-12 and IL-2. Th2 cytokines include IL-4 and IL-10. An immunospot ELISA or other biological assay is employed to determine the cytokine which is secreted after the peptide is added to the culture.

Epitope peptides falling within the scope of the invention may also be identified by in vivo assays, such as animal models for a particular indication or disease. Generally, the animal is contacted with a particular peptide, or a plurality of peptides, preferably ones which were identified as having immunodominant epitope sequences. The animal is then immunized with an antigen having sequences corresponding to at least a portion, i.e., the immunodominant epitope sequence, of the peptide. The tolerogenic efficacy of the peptide is then determined. For example, T cells may be isolated from these animals and their response to antigen or peptide in vitro measured, or the amount of antibody specific for the antigen obtained at time periods before immunization and after immunization compared. Also, the reduction or inhibition of specific phenotypic indicators of disease, e.g., muscle response in animals having EMG, may be used to determine the tolerogenic effect of the peptide.

One animal model is described in Example I (EMG). Another model is described in Example II. Example II describes how Factor VIII sequences having immunodominant epitope sequences are identified using CD4+ spleen and lymph node cells of hemophilia A mice. Then the identified epitope peptides can be administered to naive hemophilia A mice, preferably by nasal administration, followed by immunization with factor VIII. The efficacy of the tolerizing treatment is then determined by methods similar to those described in Example 1.

One example of an antibody-mediated disease for which the cognate antigen is known is MG. Although MG symptoms are due to antibody binding to muscle AChR, circumstantial and direct evidence suggests that $CD4^+$ T helper cells have an important role in the pathogenesis of human MG. The presence of high-affinity anti-AChR IgG antibodies implies that T helper factors lead to a switch to synthesis of antibodies of the IgG isotype by the anti-AChR B cells and to "maturation" of their affinity. Second, anti-AChR reactive $CD4^+$ T cells present in the blood and thymus of MG patients can be propagated in vitro from these tissues, and have T helper finction. Third, the only obvious and early effect on the anti-AChR immune response of thymectomy—a staple in the treatment of MG—is an immediate and pronounced decrease in the anti-AChR reactivity of circulating T cells. Fourth, treatment of MG patients with anti-$CD4^+$ antibodies abolishes the T cell response in vitro to the ACHR and causes clinical and electrophysiological improvement. Fifth, experiments carried out in a chimeric human-SCID mouse model of passively transferred MG demonstrated that CD4+ cells are indispensable for transfer of the symptoms, and that CD4+ cell lines, derived from MG patients and specific for individual universal epitopes of the α subunit of human ACHR can drive the synthesis of pathogenic anti-AChR antibodies that cause MG symptoms.

Several studies have identified sequences of the human AChR α subunit recognized by T cells in MG patients. To determine whether the $CD4^+$ cells recognizing those immunodominant and/or universal epitope sequences can drive the synthesis of pathogenic anti-AChR antibodies, and how the ability of the different sequence regions of the AChR to interact with different HLA DR molecules correlates with the presence of universal CD4+ epitopes, synthetic peptides based on the amino acid sequence of the human α subunit of AChR (Noda et al., *Nature*, 305, 818 (1983); Schoepfer et al., *FEBS Lett.*, 226, 235 (1981)) were prepared. The peptides were approximately 20 residues long, a length that compares with that of naturally processed class II-restricted epitopes, which are 9–14 residues. Extra residues at either end of the epitope sequence do not affect the attachment of the peptide to the binding cleft of the presenting HLA class II molecule, which is open at both its ends. The peptides overlapped by 5–10 residues to reduce the risk of missing epitopes "broken" between peptides.

The response to individual overlapping synthetic AChR peptides spanning the sequence of each AChR subunit, of unselected blood CD4− T cells, and of CD4+ T cell lines enriched with AChR-specific cells by culture in vitro with ACHR antigens, was tested. The use of those two cell populations has different advantages and limitations. AChR-specific CD4+ lines have strong, consistent responses to individual peptides that allow a clear-cut assessment of their epitope repertoire. However, they may have an epitope repertoire different from that of the original CD4+ population due to biased clonal propagation in vitro. Also, denatured forms of the antigen such as synthetic and biosynthetic peptides, which are commonly used for propagation of CD4+ cells specific for rare antigens, may be processed into peptide epitopes different from those obtained from processing of the native antigen in vivo and may expand CD4− clones irrelevant for the immune process in vivo. The use of unselected T cells or CD4+ T cells from the blood of MG patients avoids the risk of detecting a biased repertoire due to the selective clonal loss or enrichment, but, because of the low frequency of antigen-specific CD4+ cells, reliable testing of nonselected blood CD4+ T cells is not always successful, especially when assessing the response to individual epitopes.

Due to the "orthogonal" advantages and shortcomings of unselected blood CD4+ cells and of AChR-specific CD4+ lines, it was from the combined results of those two approaches that many AChR sequence regions forming CD4+ epitopes could be confidently identified. The response to the individual AChR peptides of the anti-AChR cell lines was tested by a proliferation assay, and that of unselected blood CD4+ cells by proliferation and enzyme-linked immunospot (ELISPOT) assays. The latter assay type detects the antigen-induced secretion of cytokines (e.g., IFN-γ) by individual CD4+ Th1 cells, demonstrating their role in the anti-AChR CD4+ response. These different approaches have given consistent and complementary results.

The results from these studies, and those of others, which identify sequence regions on each ACHR sequence regions on each AChR subunit form CD4+ epitopes are summarized in Table 2. Each patient had an individual repertoire, yet a few sequences on each ACHR subunit are recognized by all or most patients, irrespective of the MHC haplotype. The results of studies on the response of blood CD4+ cells indicated that those "universal" epitope sequences are recognized by high numbers of T cells. Thus, they should be considered both universal and immunodominant epitope peptide sequences (indicated by bold characters in Table 2). Their immunodominance may be related to easy cleavage and processing, and to the ability of human DR molecules to interact with many unrelated peptides.

TABLE 2

Sequence Segments of the α, β, γ, δ, and ε Subunits of Human Muscle AChR Forming Epitopes Frequently Recognized by CD4+ Cells in MG Patients α Subunit[a]

| Region α1–80 | Region α101–168 | Region α191–207 | Region α293–337 | Region α387–437 |
| --- | --- | --- | --- | --- |
| α1–14 | α101–120 | α191–207 | α293–308 | α387–405 |
| α19–34 | α118–137 | | α304–322 | α403–421 |
| α32–51 | α135–154 | | α320–337 | α419–437 |
| α48–67 | α151–168 | | | |
| α63–80 | | | | |

β Subunit[b]

| Region β16–50 | Region β181–200 | Region β271–290 | Region β316–350 | Region β361–425 |
| --- | --- | --- | --- | --- |
| β16–35 | β181–200 | β271–290 | β316–335 | β361–380 |
| β31–50 | | | β331–350 | β376–395 |
| | | | | β391–410 |
| | | | | β406–425 |

γ Subunit[c]

| Region γ30–49 | Region γ60–124 | Region γ135–154 | Region γ248–288 | Region γ297–355 | Region γ366–400 | Region γ411–430 | Region γ470–495 |
| --- | --- | --- | --- | --- | --- | --- | --- |
| γ30–49 | γ60–79 | γ135–154 | γ248–267 | γ297–312 | γ366–385 | γ411–430 | γ470–489 |
| | γ75–94 | | γ263–273 | γ306–325 | γ381–400 | | γ476–495 |
| | γ90–109 | | γ269–288 | γ321–340 | | | |
| | γ105–124 | | | γ336–355 | | | |

TABLE 2-continued

Sequence Segments of the α, β, γ, δ, and ε Subunits of Human Muscle
AChR Forming Epitopes Frequently Recognized by CD4+ Cells in MG Patients

δ Subunit[d]

| Region | Region | Region | Region | Region | Region |
|---|---|---|---|---|---|
| δ1–20 | δ61–80 | δ91–185 | δ196–290 | δ346–392 | δ461–496 |
| δ1–20 | δ61–80 | δ91–110 | δ196–215 | δ346–362 | δ461–480 |
| | | δ106–125 | δ213–230 | δ363–386 | δ476–496 |
| | | δ121–140 | δ226–245 | δ373–392 | |
| | | δ136–155 | δ241–260 | | |
| | | δ151–170 | δ256–275 | | |
| | | δ166–185 | δ271–290 | | |

ε Subunit

| Region | Region | Region | Region | Region | Region |
|---|---|---|---|---|---|
| ε51–70 | ε91–110 | ε121–170 | ε231–320 | ε351–370 | ε431–473 |
| ε51–70 | ε91–110 | ε121–140 | ε231–250 | ε351–370 | ε431–450 |
| | | ε141–160 | ε241–260 | | ε451–470 |
| | | ε151–170 | ε261–280 | | ε461–473 |
| | | | ε281–300 | | |
| | | | ε291–310 | | |
| | | | ε301–320 | | |

[a]From Manfredi et al., Neurology, 42, 1092 (1992); Protti et al., Proc. Natl. Acad. Sci. USA, 87, 7792 (1990); and Wang et al., 1997.
[b]From Moiola et al., J. Immunol., 152, 4686 (1994).
[c]From Manfredi et al., J. Clin. Investig., 92, 1055 (1993); and Protti et al., J. Clin. Investig., 90, 1558 (1992).
[d]From Manfredi et al., J. Clin Investig., 92, 1055 (1993); and Protti et al., J. Immunol., 146, 2253 (1991).

Four AChR α subunit sequences—α48-67, α101-137, α304-322, and the carboxyl-terminal sequence α403-437—are recognized by the majority of the patients, irrespective of their HLA class II type, and by a high number of cells. The peptide sequences recognized by 50% or more of the MG patients are clustered in five sequence regions. One corresponds to residues 1–14; the second corresponds to residues α48-80 and comprises peptides α48-67 and α63-80; the third corresponds to residues α101-154 and includes peptides α101-120, α118-137, and α135-154; the fourth corresponds to residues α304-337 and includes peptides α304-322 and α320-337; and the fifth corresponds to residues α403-437 and includes peptides α403-421 and α419-437. Most of the α subunit sequences recognized by the CD4+ cells correlate with the sequence regions that form non-transmembrane domains, which are believed to be at least partially exposed on the ACHR surface. The α48-80 sequence neighbors with, and includes, residues α67-76, which are involved in formation of the MIR. The MIR is a relatively small surface area of the AChR that dominates the antibody response in human MG and rodent EMG. The sequence region α101-154 includes a putative extracellular sequence region between two cysteine residues at positions 128 and 142, which must be at least partially exposed on the AChR surface because it is glycosylated.

The amino-terminus of all AChR subunits is extracellular, although it is not clear whether it is exposed on the AChR surface because it is accessible to the binding of antibody only after mild denaturation of the AChR. The fifth region, α403-407, includes both the carboxyl-terminal end of the α subunit (residues α428-437), which is hydrophilic and likely exposed on the extracellular surface, and the hydrophobic segment α409-427, which is believed to form a transmembrane α helix, called M4. Three other transmembrane segments are believed to exist in α and in the other AChR subunits, called M1 (residues α211-236), M2 (residues α242-261), and M3 (residues α277-298). These putative transmembrane regions largely correspond to three peptides that were recognized by the CD4⁻ cells of MG patients; α214-234, α246-264, and α280-297. Hydrophobic sequences in the core of a protein may form epitopes and possibly universal immunodominant epitope sequences for human CD4+ T cells, provided that they are flanked by sequence loops exposed on the surface of the molecule and accessible to the processing enzymes.

Short-term polyclonal lines specific for the universal AChR sequence regions can be easily propagated in vitro by cycles of stimulation with synthetic ACHR peptides. Given the short time of propagation and the limited potential for biased clonal selection, they should be representative of the clonal repertoire of the CD4+ cells recognizing epitopes within each immunodominant sequence region. Those lines were challenged with single residue-substituted analogues of the relevant immunodominant sequence regions to define the residues involved in formation of "universal" epitopes, to obtain clues about the clonality of the lines, and (if they are polyclonal) to understand whether they recognize one epitope or different overlapping epitopes: the response to the peptide analogues of polyclonal lines recognizing overlapping epitopes would be abolished by substitutions of "core" residues, common to all epitopes, and only partially affected by substitutions of residues included in some, but not all, epitopes.

Four peptides forming universal epitopes, α48-67, α304-322, γ75-94, and γ321-340, were examined. In the same patient, the CD4+ T cells recognizing a given universal epitope were polyclonal and recognized overlapping epitopes: their response was abolished by some substitutions, identifying residues common to all epitopes within a given region, while other substitutions residues (but did not obliterate) the response, indicating residues included in some, but not all, epitopes recognized by the line.

Comparison of the residues involved in epitope formation for different lines supported the conclusion that, within the 20-residue peptides that were investigated, the same sequence segment is involved in formation of universal epitope(s) in DR-discordant patients. Within region α48-67, the segment 55-63 contained most or all of the residues involved in T cell activation for all lines from two different patients (DR4/w53 and DR7/w53 restricted). Within the region α304-322, residues 311-318 were involved in formation of all or most of the epitopes recognized by four lines from two different patients, both DR4/w53 restricted. Epitope recognition by one line from each patient was susceptible to substitutions outside the segment α311-318. Within region γ75-94, the segment 76-88 contained all residues involved in epitope(s) formation for three different patients, restricted by DR2/w51 and DR1. Within region γ321-340, the segment 324-332 contained residues involved in epitope formation for three lines from two different patients, all restricted by DR2/w51.

Some AChR epitopes dominate also the sensitization of $CD4^+$ cells in mice, and tolerization of the $CD4^+$ cells recognizing even just one of those dominant epitopes can protect from development of EMG. On the other hand, other ACHR sequences sensitize mouse $CD4^+$ cells of lesser or no pathogenic potential, whose tolerization does not affect EMG development. To understand whether similar epitope-specific tolerization of pathogenic $CD4^+$ cells could be suitable for the treatment of MG, it was determined whether the immunodominant universal sequences described above are recognized by $CD4^+$ cells able to drive the synthesis of pathogenic antibodies.

The chimeric human-SCID mouse model of MG was used. The effects on appearance of human IgG, anti-AChR antibodies, and MG symptoms of engraftment into SCID mice of PBMC, $CD4^+$-depleted PBMC from the same patient, or CD4+-depleted PBMC supplemented with a $CD4^+$ line from the same patient that was specific for a given immunodominant universal epitope of the α subunit was determined. The lines were propagated by cycles of stimulations in vitro with the individual 20-residue synthetic peptides, corresponding to a given α subunit universal $CD4^+$ epitope. As controls, DTD- or TTD-specific $CD4^+$ lines from the same patients were used.

SCID mice engrafted with PBMC developed anti-AChR antibodies and myasthenic symptoms, while the mice engrafted with $CD4^+$-depleted PBMC or with PBMC supplemented with $CD4^+$ cell lines specific for DTD or TTD did not present myasthenic weakness. Addition to the $CD4^+$-depleted PBMC of any (but one) of the $CD4^-$ cell lines specific for α subunit universal epitopes induced myasthenic weakness in 25–50% of the engrafted mice and appearance of human anti-AChR antibody in the serum and at the neuromuscular junction of most mice.

Those findings clearly demonstrate that most of the anti-AChR CD4+ T cells specific for the universal epitope of the α subunit can drive the synthesis of pathogenic anti-AChR antibodies that cause myasthenic weakness and strongly support an important role of those universal sequence regions in the pathogenesis of MG. Those results underline the usefulness of synthetic epitope sequences for the propagation and study of autoimmune $CD4^+$ cells of pathogenic relevance.

IV. Preparation of the Peptides of the Invention
A. Nucleic Acid Molecules of the Invention
 1. Sources of the Nucleic Acid Molecules of the Invention
   Sources of nucleotide sequences from which a nucleic acid molecule encoding a peptide or variant thereof of the invention, or a variant thereof, include total or polyA$^+$ RNA from any eukaryotic, preferably mammalian, cellular source from which cDNAs can be derived by methods known in the art. Other sources of DNA molecules of the invention include genomic libraries derived from any eukaryotic cellular source.

Sources of nucleotide sequences of viral vectors useful in gene therapy include RNA or DNA from virally-infected cells, plasmids having DNA encoding viral proteins, nucleic acid in viral particles and the like.

Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular peptide.

2. Isolation of a Gene Encoding a Peptide of the Invention
   A nucleic acid molecule encoding a peptide of the invention can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone a preselected cDNA. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp Quant, Biol*, 51, 263 (1987); Erlich, ed., *PCR Technology*, (Stockton Press, N.Y., 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of a particular eukaryotic gene. One primer is prepared which is predicted to anneal to the antisense strand, and another primer prepared which is predicted to anneal to the sense strand, of a nucleic acid molecule which encodes the preselected peptide.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, isolated gel-purified fragments may be directly sequenced.

As used herein, the terms "isolated and/or purified" refer to in vitro isolation of a DNA, peptide or polypeptide molecule from its natural cellular environment, and from association with other components of the cell, such as nucleic acid or polypeptide, so that it can be sequenced, replicated, and/or expressed. For example, an "isolated, preselected nucleic acid" is RNA or DNA containing greater than 9, preferably 36, and more preferably 45 or more, sequential nucleotide bases that encode at least a portion of a peptide of the invention, or a variant thereof, or a RNA or DNA complementary thereto, that is complementary or hybridizes, respectively, to RNA or DNA encoding the peptide, or polypeptide having said peptide, and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of an isolated nucleic acid molecule of the invention is RNA or DNA (e.g., SEQ ID NO:1) that encodes human AChR (SEQ ID NO:2), or a fragment or subunit thereof, and shares at least about 80%, preferably at least about 90%, and more preferably at least about 95%, contiguous sequence identity with the human ACHR polypeptide.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of a peptide of the invention are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the preselected peptide.

Oligonucleotide-mediated mutagenesis is a preferred method for preparing amino acid substitution variants of a peptide. This technique is well known in the art as described by Adelman et al., *DNA*, 2, 183 (1983). Briefly, DNA is altered by hybridizing an oligonucleotide encoding the desired mutation to a DNA template, where the template is the single-stranded form of a plasmid or bacteriophage containing the unaltered or native DNA sequence. After hybridization, a DNA polymerase is used to synthesize an entire second complementary strand of the template that will thus incorporate the oligonucleotide primer, and will code for the selected alteration in the preselected DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the peptide, and the other strand (the original template) encodes the native, unaltered sequence of the peptide. This heteroduplex molecule is then transformed into a suitable host cell, usually a prokaryote such as *E. coli* JM 101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a preselected DNA segment, e.g., having SEQ ID NO:1, encoding a peptide of human AChR, wherein the DNA segment has nucleotide substitutions which are "silent" (see FIG. 9). That is, when silent nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:1 at the sixth codon in AChR (CT<u>C</u> in SEQ ID NO:1) includes the substitution of CT<u>T</u>, CT<u>A</u> or CT<u>G</u> for CT<u>C</u>. Other "silent" nucleotide substitutions in SEQ ID NO:1 which can encode a peptide having a sequence corresponding to a contiguous portion of SEQ ID NO:2 can be ascertained by reference to FIG. 9 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other mammalian, preferably human, or viral, peptides may be modified in a similar manner, so as to yield nucleic acid molecules of the invention having silent nucleotide substitutions, or to yield nucleic acid molecules having nucleotide substitutions that result in amino acid substitutions (see peptide variants hereinbelow).

4. Chimeric Expression Cassettes

To prepare expression cassettes for transformation herein, the recombinant or preselected DNA sequence or segment may be circular or linear, double-stranded or single-stranded. Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a peptide, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the MRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

5. Transformation into Host Cells

The recombinant DNA can be readily introduced into the host cells, e.g., mammalian, bacterial, yeast or insect cells by transfection with an expression vector comprising DNA encoding a preselected peptide by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, ftngal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the peptide, which host cell may or may not express significant levels of autologous or "native" polypeptide.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described hereinabove to identify agents falling within the scope of the invention.

To detect and quantitate RNA produced from introduced preselected 5 DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides, Peptide Variants, and Derivatives Thereof

The present isolated, purified peptides or variants thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem, Soc.*, 85 2149 (1963); Meienhofer in "Hormonal Proteins and Peptides," ed.; C.H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given peptide can be readily prepared. For example, amides of the peptide or peptide variants of the present invention may also be prepared by techniques well known in the art for converting a carboxylic acid group or precursor to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., Science, 276, 276 (1997)).

In addition, the amino acid sequence of a peptide can be modified so as to result in a peptide variant (see above). The modification includes the substitution of at least one amino acid residue in the peptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, and tert-butylglycine.

One or more of the residues of the peptide can be altered, so long as the peptide variant is biologically active. For example, it is preferred that the variant has at least about 10% of the biological activity of the corresponding non-variant peptide. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 10 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic; trp, tyr, phe.

The invention also envisions peptide variants with non-conservative substitutions. Non-conservative substitutions entail exchanging a member of one of the classes described above for another.

Acid addition salts of the peptide or variant peptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

V. Dosages, Formulations and Routes of Administration of the Peptides of the Invention The peptides or nucleic acid molecules of the invention, including their salts, are preferably administered so as to achieve a reduction in at least one symptom associated with a particular indication or disease, a decrease in the amount of antibody associated with the indication or disease, and/or a decreased responsiveness of CD4+ cells to the administered peptide or corresponding antigen. To achieve this effect(s), the peptide, a variant thereof or a combination thereof, agent may be administered at dosages of at least about 0.001 to about 100 mg/kg, more preferably about 0.01 to about 10 mg/kg, and even more preferably about 0.1 to about 5 mg/kg, of body weight, although other dosages may provide beneficial results. The amount administered will vary depending on various factors including, but not limited to, the agent chosen, the disease, the weight, the physical condition, and the age of the mammal, whether prevention or treatment is to be achieved, and if the agent is chemically modified. Such factors can be readily determined by the clinician employing animal models or other test systems which are well known to the art.

Administration of sense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., Immunity, 3, 165 (1995); Stevenson et al., Immunol. Rev., 145, 211 (1995); Molling, J. Mol. Med., 242 (1997); Donnelly et al., Ann. N.Y. Acad. Sci., 772, 40 (1995); Yang et al., Mol. Med. Today, 2, 476 (1996); Abdallah et al., Biol. Cell, 85, 1 (1995)). Pharmaceutical formulations, dosages and routes of administration for nucleic acids are generally disclosed, for example, in Felgner et al., supra.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

To prepare the composition, peptides are synthesized or otherwise obtained, purified and then lyophilized and stabilized. The peptide can then be adjusted to the appropriate concentration, and optionally combined with other agents. The absolute weight of a given peptide included in a unit dose of a tolerogen can vary widely. For example, about 0.01 to about 10 mg, preferably about 0.5 to about 5 mg, of at least one peptide of the invention, and preferably a plurality of peptides specific for a particular antigen, each containing a universal and/or immunodominant epitope sequence, can be administered. A unit dose of the tolerogen is preferably administered either via a mucous membrane, e.g., by respiratory, e.g., nasal (e.g., instill or inhale aerosol) or genitourinary tract administration, or orally, although other routes, such as subcutaneous and intraperitoneal are envisioned to be useful to induce tolerance.

Thus, one or more suitable unit dosage forms comprising the therapeutic agents of the invention, which, as discussed below, may optionally be formulated for sustained release (for example using microencapsulation, see WO 94/ 07529, and U.S. Pat. No. 4,962,091 the disclosures of which are incorporated by reference herein), can be administered by a variety of routes including oral, or parenteral, including by rectal, transdermal, subcutaneous, intravenous, intramuscular, intraperitoneal, intrathoracic, intrapulmonary and intranasal (respiratory) routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. Preferably, orally administered therapeutic agents of the invention are formulated for sustained release, e.g., the agents are microencapsulated. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in anpules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and a-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable mate-rial which is impermeable to the therapeutic agent. The backing layer serves as a protective cover for the matrix layer and provides also a support fimction. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

Preferably, the peptide or nucleic acid of the invention is administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific indication or disease. Any statistically significant attenuation of one or more symptoms of an indication or disease that has been treated pursuant to the method of the present invention is considered to be a treatment of such indication or disease within the scope of the invention.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Examples of such substances include normal saline solutions such as physiologically buffered saline solutions and water.

A preferred route of administration of the therapeutic agents of the present invention is in an aerosol or inhaled form. The agents of the present invention can be administered as a dry powder or in an aqueous solution. Preferred aerosol pharmaceutical formulations may comprise, for example, a physiologically acceptable buffered saline solution containing between about 0.1 mg/ml and about 100 mg/ml of one or more of the agents of the present invention specific for the indication or disease to be treated.

Dry aerosol in the form of finely divided solid peptide or nucleic acid particles that are not dissolved or suspended in a liquid are also useful in the practice of the present invention. Peptide or nucleic acid may be in the form of dusting powders and comprise finely divided particles having an average particle size of between about 1 and 5 μm, preferably between 2 and 3 μm. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the pharmaceutical formulations of the present invention include water and physiologically acceptable buffered saline solutions such as phosphate buffered saline solutions pH 7.0–8.0.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197–224, Butterworths, London, England, 1984).

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The formulations and compositions described herein may also contain other ingredients such as antimicrobial agents, or preservatives. Furthermore, the active ingredients may also be used in combination with other therapeutic agents, for example, bronchodilators.

VI. Management of Antibody-Mediated Disease

To treat an undesirable antibody-mediated immune response, such as the one in MG patients, universal and/or immunodominant epitopes are identified. MG is a disease that is diagnosed after a full sensitization of CD4+ cell to the AChR has occurred, and the synthesis of anti-AChR antibodies is actively occurring. To enhance the efficacy of peptide-based therapies, plasmapheresis is used in combination with the peptide treatment. Plasmapheresis "clears" the antibodies from the patient's blood, and it is in most cases associated with the administration of an immunosuppressant such as azathioprine, to help decrease the activity of the pathogenic immune cells. Thus, the administration of a peptide of the invention in combination with pheresis and optionally an immunosuppressant may be useful to manage MG as such a method would result in a long lasting down regulation of the anti-AChR response, in both the CD4+ and the B cell compartments.

In hemophilia A patients, a treatment similar to that described above for MG could be used for patients that have already developed antibody inhibitors to factor VIII. Moreover, the existence of universal CD4+ epitopes on the factor VIII molecule would allow the use of these approaches for the prevention of inhibitor development. Furthermore, the identification of universal CD4+ epitope sequences for factor VIII would allow their use for nasal tolerization procedures that would be suitable both in the treatment of established factor VIII inhibitors and in the prevention of inhibitor development, by tolerizing or down regulating the priming and/or activity of the T helper clones potentially reactive to factor VIII sequences, prior to the first therapeutic exposure to factor VIII in infancy.

Even if no universal CD4+ epitope sequences were identified on a given antigen, i.e. if every patient had a unique CD4+ repertoire, the peptides of the invention can provide the basis for tolerization to a given antigen towards the therapy of an undesirable antibody response. In the case of established immune resistance to factor VIII, the CD4+ repertoire of each patient is determined prior to "customizing" the tolerizing treatment to the epitopes recognized by that particular patient. This can be accomplished in about 6–8 weeks, at an estimated cost of $20,000/patient. In contrast, the cost of immune tolerance induction using daily intravenous infusions of factor VIII over many months is about $250,000/year per patient.

The invention will be further described by, but is not limited to, the following examples.

EXAMPLE I

Prevention of Experimental Myasthenia Gravis by Nasal Administration of ACHR T Epitope Sequences Materials and Methods Peptide Synthesis and Characterization. Three peptides, 19–20 residues in length, corresponding to residues 150–169, 181–200 and 360–378 of the TAChR α subunit, were synthesized by methods described in Houghton (1985). An additional three 20 residue peptides were synthesized, corresponding to residues 271–290, 321–340, and 431–450 of diphtheria toxin (DTX). These peptides were shown to be highly and universally immunogenic for human CD4+ T cells (Yeh et al., 1990).

Purification and Preparation of *Torpedo californica* AChR. TAChR was purified from *Torpedo californica* electric organ as alkali-stripped TAChR-rich membrane fragments, and characterized as described previously (Bellone et al., 1991). The TAChR concentration was determined as α-bungarotoxin (αBTX) binding sites (Schmidt et al., 1973). The protein concentration was determined by the Lowry assay (Lowry et al., 1981). The TAChR preparations contained 3.8–5.8 nmols of αBTX binding sites/mg protein. The protein composition was assessed by sodium dodecyl-sulphate polyacrylamide gel electrophoresis (Laemmli, 1970). The preparations employed herein consistently showed only the four TAChR subunits as the main protein bands.

For use in cell cultures, the TAChR-rich membrane fragments were diluted in RPMI-1640, and sterilized by UV irradiation.

For immunization, TAChR-rich membrane fragments were solubilized in 1% Triton X-100 (Bellone et al., 1991), diluted to 0.5 mg/ml in PBS and stored at −80° C.

Mice and Induction of Tolerance. B6 mice were purchased from Jackson Laboratory (Bar Harbor, Me.) and housed at the animal facility of the University of Minnesota. After light anesthesia by i.m. injection of Ketaset (100 mg/kg; Alveco Co., Inc., Fort Dodge, Iowa), the mice received into both nostrils a total of 25 µl of PBS containing 50 µg of peptide Tα150-169, either alone or pooled with equimolar amounts of peptides Tα180-200 and Tα360-378 (referred to as "peptide pool" or "αpool"). The dose was based on the results of an experiment in which increasing amounts of peptide α150-169 were used (50 µg, 100 µg, 200 µg, 400 µg and 800 µg). The lowest dose (50 µg) afforded a satisfactory level of protection. The tolerogen was administered as a solution instilled into the nostrils, a method of delivery which allowed accurate administration of a defined amount of solution. Nasal delivery of either aerosol or liquid antigen solutions has been shown to have similar efficacy in suppressing the effects of subsequent immunizations (Al-Sabbagh et al., 1996; Kuper et al., 1992; Liu et al., 1993; Husby et al., 1994; Neutra et al., 1996; Abbas et al., 1996; Conti-Fine et al., 1996; Karpus et al., 1996; Dick et al., 1993).

In protocol A, peptides or peptide-free PBS were administered two weeks before the first TAChR immunization, and then three more times, on the same day as the three immunizations with TAChR (at one month intervals, see below). In protocol B, peptides or peptide-free PBS were administered weekly, starting two weeks before beginning of the immunization with TAChR, for a total of 14 treatments (two before and 12 during TAChR immunization).

Control mice received 25 µl of peptide-free PBS, or a pool of the three synthetic DTX peptides in PBS.

Immunization. Eight-ten week old mice were immunized by subcutaneous injections, along the back and at the base of the tail, with solubilized TAChR (50 µg), peptide Tα150–169 (100 µg), or the peptide pool (100 µg of each peptide). The mice were boosted twice at 4 week intervals with the same amount of antigen. The antigen solutions (in 100 µl PBS) were emulsified with an equal volume of complete Freund's adjuvant (FA) for the first injection, and with incomplete FA for the boosts. Control mice were injected with PBS emulsified in the appropriate adjuvant.

Evaluation of the Clinical Symptoms of EMG. EMG symptoms were quantified by a forced exercise using the inverted hang technique, sensitized by administration of a minute amount of pancuronium bromide (0–03 mg/kg i.p.) just prior to the beginning of the test (Karachunski et al., 1995). The mice hang from a grid, and the time it takes for the mouse to release its hold and fall three times ("holding time") was measured. The test was performed on the day of the first nasal administration, on the day before each immunization, and 7–14 days after the third immunization, just before sacrificing the animal. This test is parametric, and gives a quantitative assessment of the severity of the weakness.

To verify the myasthenic nature of the weakness observed, mice with significant weakness were injected i.p. with the cholinesterase inhibitor edrophonium chloride (Reversol, Organon Inc., West Orange, N.J.). Reversol immediately improved the strength of the animals, and alleviated the paralysis of the most severely affected mice. The test was performed blindly, i.e., without knowledge of the treatment that the mouse had received.

The holding time of normal mice was 10.4±2.1 minutes (n=99). Mice with holding times of eight minutes or longer were considered normal, those with a holding time of more than four minutes but less than eight minutes were considered to have moderate symptoms, and those with a holding time of less than four minutes were considered severely affected. Mice that were paralyzed or had died of respiratory paralysis are represented in the figures as having a holding time of zero.

Lymphocyte Proliferation Assay. Seven-ten days after the last immunization, spleen T cells were purified from individual mice (Bellone et al., 1991). Irradiated (3000 rad) spleen cells from non-immunized mice were diluted in RPMI-1640 (Gibco, Grand Island, N.Y.) supplemented with 10% heat inactivated fetal calf serum (Gibco), 50 µM 2-mercaptoethanol, 1 mM L-glutamine, 10 mM Hepes, 1 mM sodium pyruvate, 100 U/ml penicillin and 100 µg/ml streptomycin (culture medium) and used as antigen presenting cells. The spleen T cells ($1\times10^6$ cells/ml in culture medium, 100 µl/well) were seeded in triplicate in 96 flat-bottom well plates containing 100 µl of $5\times10^6$/ml antigen presenting cells. One of the following Ag was added: 10 µg/ml PHA (Sigma, St Louis, Mo.; 5 or 10 µg/ml TAChR;

5 or 10 µg/ml of the individual peptides; increasing concentrations of pooled DTX peptides (2.5–20 µg/ml of each peptide); or increasing concentrations of pooled DTX peptides (2.5–20 µg/ml of each peptide) plus 10 µg/ml TAChR. Controls were triplicate wells containing T and antigen presenting cells, without any antigen. After 4 days the cells were labeled for 16 hours with $^3$H-thymidine (1 µi per well, specific activity 6.7 Ci/mmol, Dupont, Boston, Mass.) and harvested (Titertek, Skatron, Sterling, Va.). $^3$H-thymidine incorporation was measured by liquid scintillation. The data are represented as stimulation indexes (S.I.), namely the ratio between the c.p.m. obtained for a culture in the presence of a given stimulus, and the average c.p.m. obtained for the unstimulated cultures (blanks).

Determination of Cytokine Secretion in Response to TAChR by Mouse Spleen Cells in vitro. Seven-ten days after the last immunization, spleen cells were cultured as described above for the proliferation assay, using sextuplicate cultures, with and without 10 µg/ml TAChR. Controls were triplicate cultures for each mouse group that did not receive any stimulus. After 12, 24 and 48 hours the supernatants were harvested, and the IL-2 and IL-10 concentration was determined by capture ELISA using duplicate samples (Pharrnigen, San Diego, Calif.). Anti-IL-2 and anti-IL-10 Ab, and recombinant IL-2 and IL-10 (Pharmigen), were employed as standards.

Effect of Pre-Incubation with IL-2 on the Response to TAChR by Mouse Spleen Cells in vitro. Spleen cells from mice tolerized to the α pool following protocol B, or sham-tolerized with PBS, and immunized with TAChR as described above, were incubated in vitro with or without 1 ng/ml of mouse recombinant IL-2 (Pharmigen) in TCM for 5 days in 25 ml flasks (Corning Costar, Cambridge, Mass.). The cells were then tested in the proliferation assay described above, using 5 and 10 µg/ml of TAChR.

Anti-AChR Antibody Assay. Sera was obtained from the mice after each clinical testing. The serum concentration of anti-TAChR antibody was measured by RIPA using TAChR solubilized in Triton X-100 and labeled by the binding of $^{125}$I-αBTX (Bellone et al., 1991). The antibody concentration is expressed as µM precipitated $^{125}$I-αBTX.

Statistical Analysis. The level of significance of the differences of the average responses between two groups was determined by two tailed students't test, using the program Excel.

Results

Distribution in the Respiratory Tract of Solutions Administered Nasally. To determine which parts of the mouse respiratory system came in contact with solutions given nasally, a solution of ethidium bromide was employed. Ethidium bromide is absorbed through the mucosal lining of the respiratory tract and fluoresces brightly under U.V. light. Two mice were anesthetized and 25 µl of a 4% ethidium bromide solution in PBS was instilled into the nostrils. Ten-fifteen minutes later the animals were sacrificed by cervical dislocation. Their nasal cavities, larynx, trachea, bronchi and lungs were dissected, washed in PBS and examined under U.V. light for ethidium bromide staining. The mouse nostrils, larynx and trachea were brightly stained by ethidium bromide administered by the same procedure employed to administer the peptide solutions. The staining was increasingly weaker in the bronchi, and only weak focal signals were present in the lung parenchyma.

T Cells from Mice Treated Nasally and Immunized with TAChR Peptidles Do Not Respond in vitro to the Peptides or to TAChR. To assess the effect of nasal treatment with synthetic TAChR peptides on the ability of CD4+ cells to become sensitized to the same peptides, three groups of mice were nasally administered peptide Tα150-169, the a pool (5.0 µg/peptide), or peptide-free PBS, following protocol A. The mice were immunized three times with the peptide(s) used for the tolerization procedure, administered as subcutaneous immunizing injections in adjuvant. Seven-ten days after the last immunization, the spleen T cells of two mice tolerized with peptide Tα150–169, four mice tolerized with the peptide pool, and two sham-tolerized mice, were tested for their proliferative response in vitro to the immunizing peptides and to the TAChR.

Figure 1B:
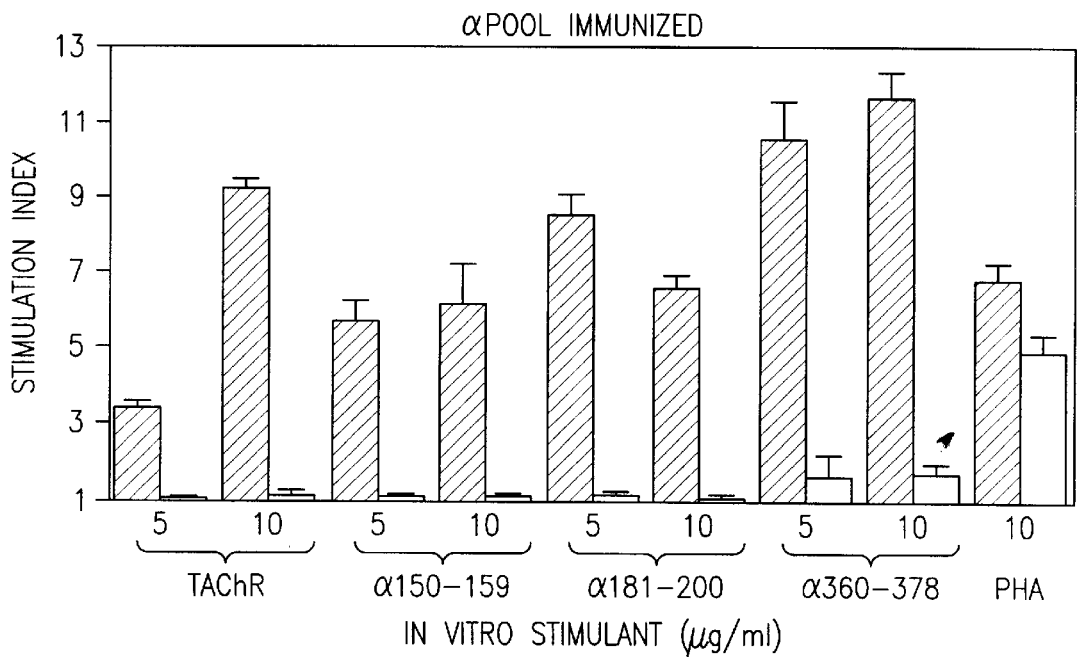

The results obtained within each group were highly consistent. FIG. 1 shows the results obtained with one mouse from each group. The T cells of shamtolerized mice had a good proliferative response in vitro to the immunizing peptide(s) and to TAChR, indicating that they recognize epitopes similar to those originating from TAChR processing (Karachunski et al., 1995), while the T cells of peptide-tolerized mice did not respond to the immunizing peptides(s) or to TAChR.

Nasal Administration of Synthetic ACHR Epitopes Prevents Appearance of EMG Symptoms. FIG. 2 summarizes the results obtained from testing the strength of mice treated nasally with the peptide epitopes and immunized with TAChR. Two groups of mice were studied. One group was treated with the TAChR peptide(s) using protocol A (panel A) while another group was treated with the peptides using protocol B (panel B). Sham-tolerized (panel "PBS") were employed as controls. For each group, the results obtained for the same mice prior to TAChR immunization (panel "naive") is also shown. The results depicted in FIG. 2 were obtained eight or ten weeks after beginning the immunization, when the maximum frequency of EMG symptoms was detected. The results from the two time points were consistent.

In agreement with previous studies which found variable EMG frequency (20–70%) in TAChR immunized B6 mice (Conti-Fine et al., 1997), the frequency of EMG in the sham-tolerized groups varied. In one experiment, 17 of 19 (89%) mice developed EMG. In the experiments shown in FIG. 2, all five sham-tolerized mice, and five of the ten sham-tolerized mice, had EMG symptoms, respectively.

Figure 2A:
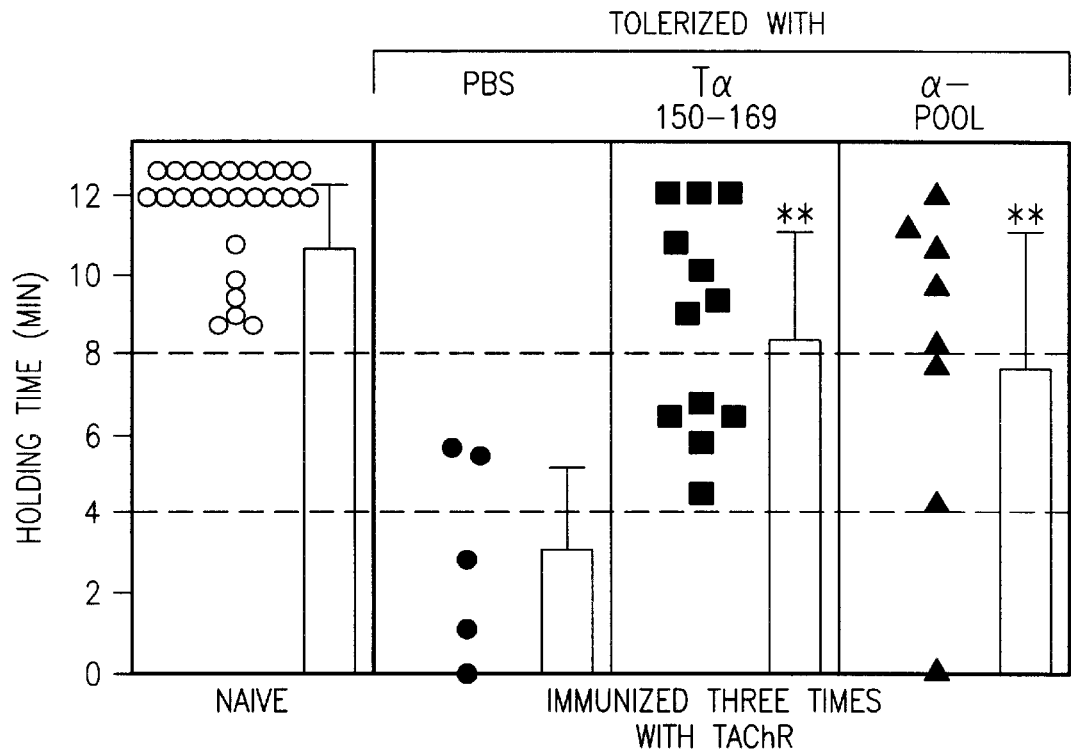
FIGS. 2A–B. Nasal administration of synthetic TAChR CD4+ epitope peptides inhibits EMG. Peptide Tα150-169, α pool or peptide-free PBS was administered nasally twice prior to immunization with TAChR, and at different time intervals during the course of the immunization (monthly, panel A; weekly, panel B). Three immunizations with 50 μg of TAChR, one month apart, were also administered. The data depict the muscle strength of the mice after the third TAChR injection. Muscle strength is measured as holding time using the curare sensitized hanging test described hereinbelow (see Example I). "normal" mice were mice having a holding time of eight minutes or more; moderately sick mice were those with holding times between four and eight minutes; and severely sick mice were those with holding times of less then four minutes. The four and eight minute levels are indicated by dashed horizontal lines. The panel marked "naive" depicts the values obtained for the mice prior to immunization with TAChR. The other plots depict the results obtained for mice sham-tolerized with PBS or mice tolerized with peptide Tα150-169 or with a pool, as indicated above the plots. The average holding time ±S.D. of the different groups is indicated, as is the level of significance of the difference compared to the sham-tolerized group (** P<0.002;*P<0.02).
Figure 2B:
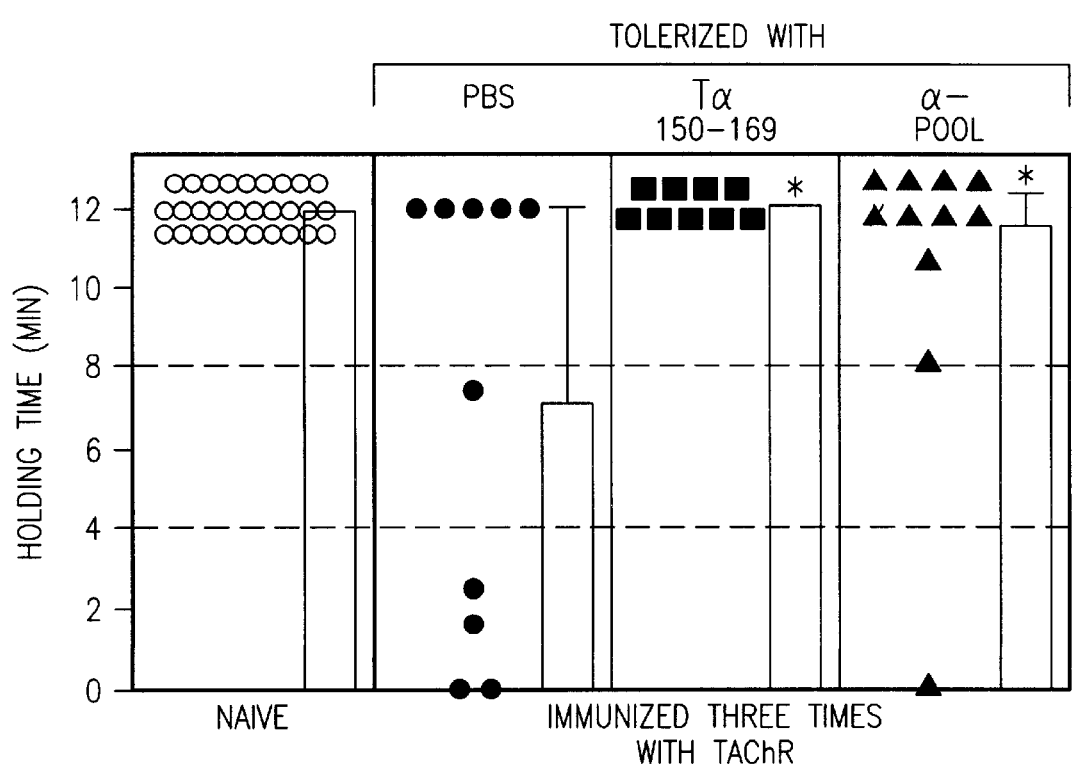
Figure 3A:
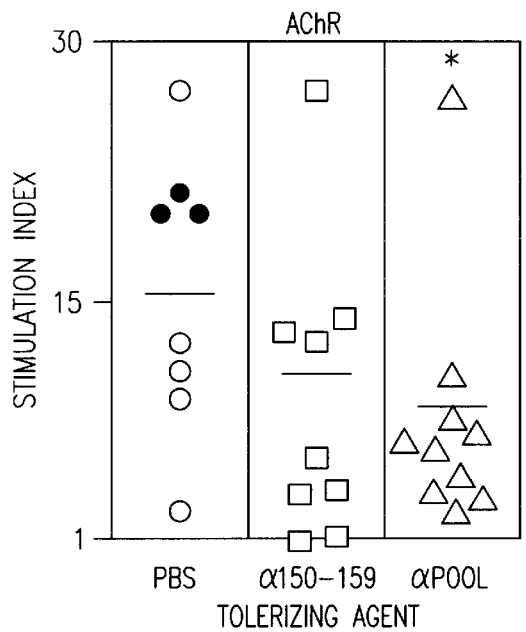
FIGS. 3A–D. Spleen T cells from mice treated nasally with synthetic TAChR T epitope sequences and immunized with TAChR respond minimally to peptide α150-169 and respond to the TAChR to a lesser extent than the T cells from sham-tolerized controls. Mice received weekly nasal administrations of peptide-free PBS (circles), Tα150-169 (squares) or a pool (triangles) as indicated below of each plots, and were immunized three times with TAChR. The spleen T cells of individual mice were tested in proliferation assays with TAChR or individual peptides, i.e., Tα150-169, Tα181-200 or Tα360-378. The data are the average S.I.±S.D. of triplicate cultures. The c.p.m. in the absence of any stimulation were 190±88. The proliferative responses of mice that had EMG are indicated with black symbols. The average responses of the different groups, and the level of significance of the difference between peptide-tolerized and sham-tolerized mice, are shown (**P<0.01; *P<0.03).
Figure 3B:
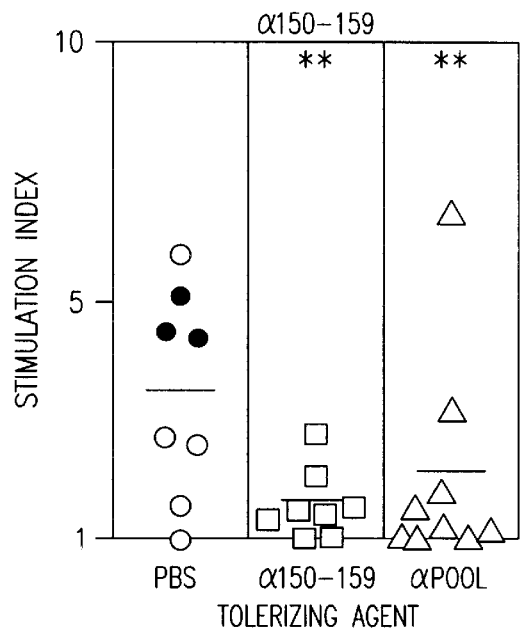
Figure 3C:
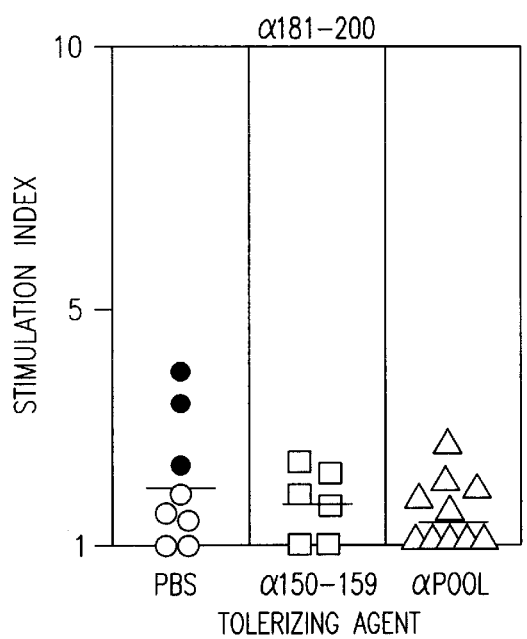
Figure 3D:
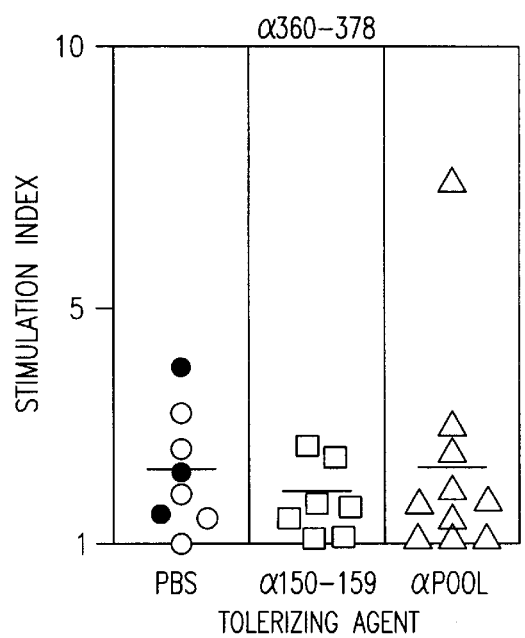

When the tolerizing peptides were administered following protocol A, five of the 12 mice (42%) tolerized with peptide Tα150–169, and three of the eight mice (37%) treated with the a pool, developed EMG, as compared to 100% of the mice sham-tolerized in parallel (FIG. 2A). When the tolerizing peptides were administered following protocol B, none of the mice that received nasal administration of peptide Tα150-169 had detectable weaknesses, and one mouse in the group treated with the peptide pool had a holding time barely below eight minutes at ten weeks. 50% of the sham-tolerized mice had EMG weakness (FIG. 2B).

In both experiments shown in FIG. 2, mice tolerized to peptide Tα150-169 and to the α pool had significantly longer holding times than the sham-tolerized mice.

Reduced T Cell Response to the Sequence Tα150-169 and to TAChR After Immunization With TAChR in Mice Treated Nasally With Peptide Tα150-169 or the α Pool. Mice used for the experiment shown in FIG. 2B were sacrificed ten weeks after beginning the TAChR immunizations. The spleen T cells of each mouse were tested in a proliferation assay with TAChR and the individual peptides Tα150–169, Tα181–200 and Tα360–378. FIG. 3 is organized in four panels, according to the challenging antigen used in the proliferation assay. Each panel summarizes the responses to the challenging antigen for sham-tolerized (PBS) mice, mice tolerized to α150–169 or mice tolerized to the a pool.

All but one of the sham-tolerized mice responded well to TAChR (S.I.=10–29). Two mice died of EMG before the experiment could be carried out. Most peptide-treated mice responded to TAChR: their average responses (horizontal bars in FIG. 3) were slightly lower then those of the sham-tolerized group. However, the difference was significant only for the mice tolerized to the α pool. All groups of mice treated nasally with TAChR peptides had lower proliferative responses to the TAChR than the control mice sham-tolerized in parallel, but the extent of the reduction varied in the different groups. The particular groups of peptide-tolerized mice shown in FIG. 3 are representative of those that had the least reduction in proliferative response to TAChR. In most other groups, the reduction was much more substantial, and some of the αpool-tolerized mice had barely detectable or no proliferative responses to TAChR (e.g., see FIGS. 5B and 6).

The T cells of most sham-tolerized mice responded to peptide Tα150-169 but to a much lesser extent than to TAChR, because the anti-TAChR CD4+ T cells of B6 mice recognize several epitopes on sequence regions other than Tα150-169 (Bellone et al., 1991). The T cells of both peptide-treated groups responded to Tα150-169 significantly less than the sham-treated mice. Several mice did not respond to Tα150-169 (S.I.<1.5).

Peptides Tα181-200 and Tα360-378, which are much less immunogenic for CD4+ cell sensitization than Tα150-169 (Karachunski et al., 1995), were recognized poorly even by the spleen T cells of sham-tolerized mice. Previous reports demonstrated that the T cell response of B6 mice to those epitope sequences can be detected only when using purified CD4+ cells instead of total spleen T cells (Bellone et al., 1991). The response to peptides Tα181-200 and Tα360-378 of the α pool-tolerized mice was the same as that of the control mice. Thus, the reduced T cell recognition of the TAChR molecule of the mice tolerized with the peptide pool is at least partially due to a reduced response to epitopes formed by the sequence Tα150–169.

The extent of the proliferative response to TAChR, Tα150-160 and Tα180-200 of the sham-tolerized mice correlated loosely with the presence of EMG symptoms. The three mice with EMG symptoms were among those with the highest S.I.

Figure 4A:
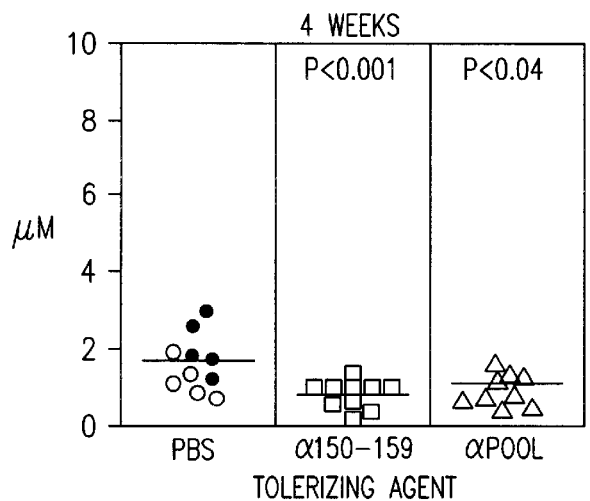
FIGS. 4A–C. Mice treated nasally with TAChR peptides have less serum anti-TAChR antibodies than sham-tolerized mice. The concentration of anti-TAChR antibodies in the sera of individual mice was determined at 4, 8 and 10 weeks after the first TAChR immunization. Mice were tolerized by weekly inhalations (protocol B) of peptide Tα150-169 (squares), α peptide pool (triangles) or sham-tolerized with peptide-free PBS (circles), and immunized three times with TAChR, as indicated above the plots. The antibody concentration is expressed as $\mu$M precipitated $^{125}$I-α-bungarotoxin (BTX) binding sites. Mice that presented EMG symptoms are indicated by black symbols. The average antibody concentrations of the different groups and the level of significance of the difference between peptide-tolerized and sham-tolerized mice are indicated.
Figure 4B:
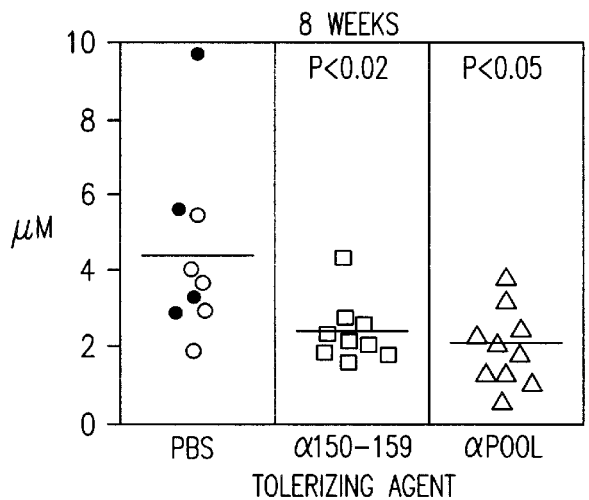
Figure 4C:
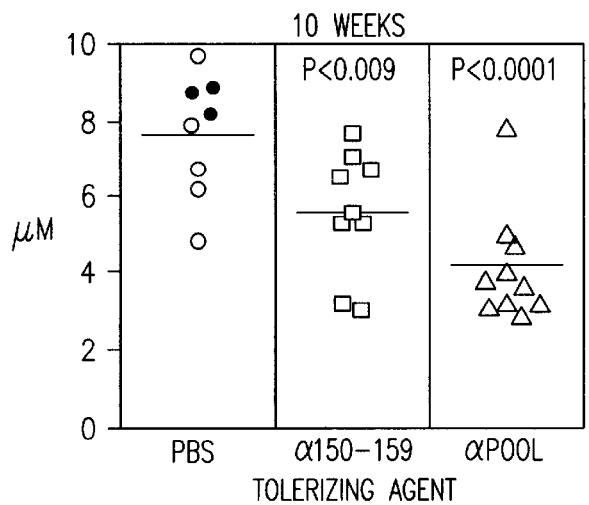

Nasal Treatment with AChR Peptides Causes Reduced Synthesis of TAChR Antibody. The serum anti-TAChR antibody concentration of individual mice tolerized with peptide Tα150-169, tolerized with the α pool or sham-tolerized, four, eight and ten weeks after the beginning of the immunization with TAChR was determined (FIG. 4). Mice treated with Tα150-169 or the a pool had significantly lower concentrations of anti-TAChR antibody than the sham-treated (PBS) group as early as 4 weeks after the first TAChR immunization, although they eventually developed substantial concentrations of anti-TAChR antibody (at ten weeks 5.5±1.5 μM and 4.3±1.6 μM vs. 7.2±1.8 μM in the sham-tolerized group). The anti-TAChR antibody concentration of individual sham-tolerized mice correlated loosely with the presence of EMG symptoms, that is, mice with EMG symptoms were among those with the highest antibody concentrations (black symbols in FIG. 4).

Figure 5A:
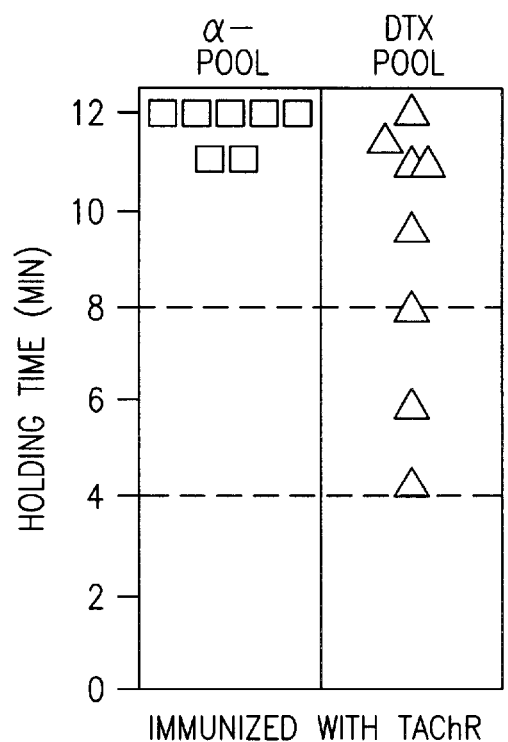
FIGS. 5A–B. Nasal administration of synthetic DTX peptides does not affect the development of EMG or the anti-AChR T cell response. A) Muscle strength of individual mice. Mice were treated nasally with a pool or DTX peptides and their muscle strength measured after the third TAChR injection as described in the legend to FIG. 2. The 4- and 8-minute levels are indicated by dashed horizontal lines. B) Proliferative response to TAChR (5 and 10 $\mu$g, as indicated) of triplicate cultures of pooled spleen T cells of four mice from each group, after the third TAChR immunization (white columns, α-pool treated mice; black columns, DTX peptide treated mice). The columns represent average S.I.±S.D. of triplicate cultures. The c.p.m. in the absence of any stimulation were 228±29 for the DTX peptide-tolerized mice, and 190±17 for the α-pool tolerized mice.
Figure 5B:
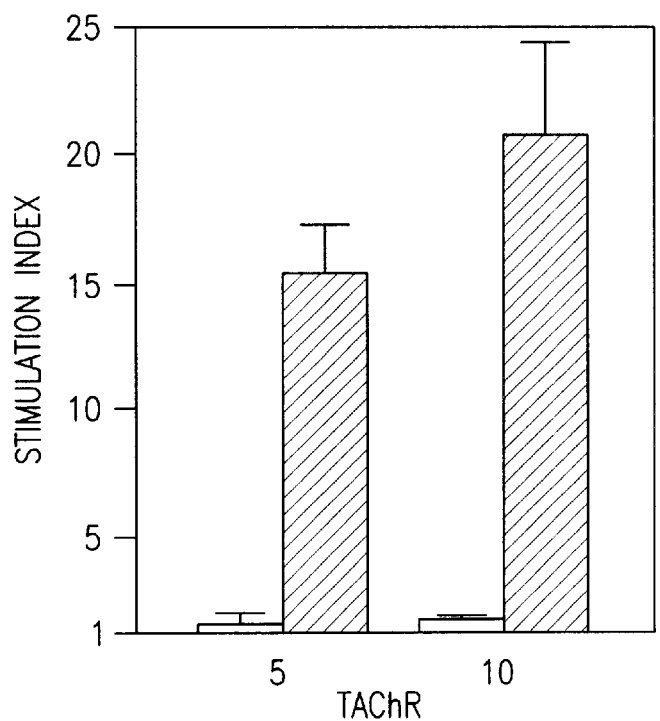

Nasal Administration of Synthetic DTX Peptides Does Not Affect the Anti-AChR T and Antibody Responses, or Development of EMG. To test the specificity of the effects observed after nasal administration of TAChR epitope peptides, the effects on the anti-TAChR response and appearance of EMG after nasal administration of three DTX peptides were tested. The DTX peptides are highly immunogenic for human CD4+ cells (Raju et al., 1995), and were of the same length and synthesized by the same procedure as the TAChR epitope sequences. The peptides were administered following protocol B. At the same time, two other groups of mice were sham-tolerized with PBS or tolerized with the α pool. None of the α-pool treated mice developed EMG, while the DTX peptide- and PBS-treated mice developed EMG with similar frequency (approximately 40%) (FIG. 5A). Mice treated nasally with DTX peptide or PBS developed similar serum anti-AChR antibody concentrations, which were higher than those of the AChR peptide-tolerized mice. After the third TAChR immunization, the spleen T cells of 4 mice from each group were pooled and tested for the proliferative response in vitro to TAChR. The spleen T cells from DTX peptide treated mice responded well to TAChR, while the responses of spleen T cells of the α pool treated mice were consistently very low (FIG. 5B).

Figure 6A:
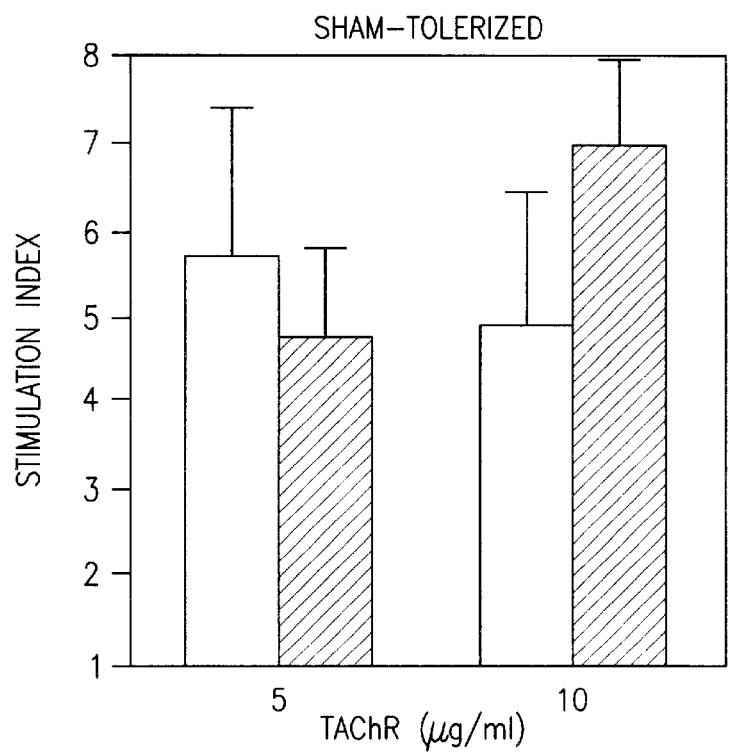
FIGS. 6A–B. The reduction of the in vitro response to TAChR of spleen T cells from ACHR peptide-tolerized mice is reversed by IL-2 treatment. After the third TAChR injection, spleen T cells of mice sham-tolerized or tolerized with the α pool were pooled, incubated with (black columns) or without (white columns) IL-2, and tested in a proliferation assay for their response to TAChR. The columns represent average S.I±S.D. of sextuplicate cultures. The c.p.m. in the absence of any stimulation were 410±124 for the sham-tolerized mice, and 366±78 for the (a pool-tolerized mice). The star indicates a significant difference of the proliferative response of cells treated with IL-2, as compared with the non treated cells (P<0.0001).
Figure 6B:
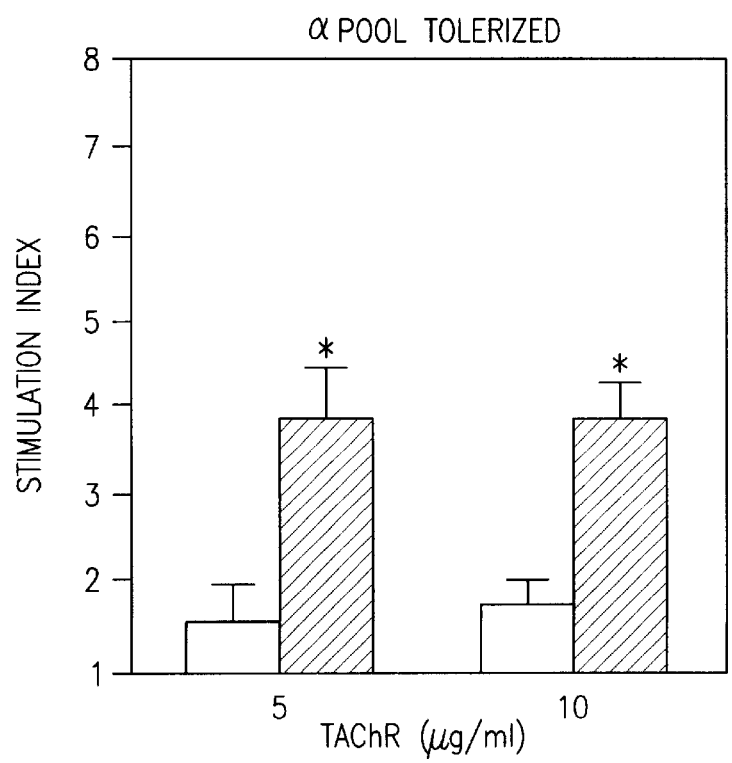

The Reduction of the in vitro Response to TAChR of Spleen T Cells from AChR Peptide-Tolerized Mice Is Reversed by II-2. Anergy of antigen specific CD4+T cells is a possible mechanism of T cell tolerization. A test for T cell anergy is a reversal of the nonresponsiveness in vitro to the antigen, by treatment of the T cells in vitro with IL-2 prior to antigen testing (DeSilva et al., 1991). Two groups of 4 mice each were treated nasally with PBS or with the α pool following protocol B. After the third TAChR injection, the spleen T cells of the mice of each group were pooled, cultured with or without IL-2 as described above, and tested in a proliferation assay for their response to TAChR. FIG. 6 depicts the average of the responses of sextuplets of identical cultures, obtained with the different T cells populations.

In the absence of IL-2 treatment, the spleen cells from α pool-tolerized mice responded to TAChR minimally, while those from sham-tolerized mice had a clear response. The IL-2 treatment did not affect the T cell response to TAChR of the sham-tolerized mice, while it increased substantially that of the αpool-tolerized mice.

Figure 7A:
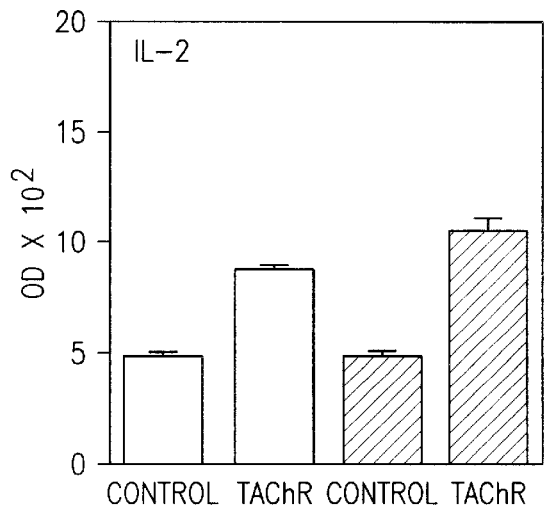
FIGS. 7A–B. Nasal treatment with AChR peptides stimulates AChR specific Th2 cells. Secretion of IL-2 and IL-10 in response to challenge with TAChR (10 $\mu$g) by pooled spleen T cells of 4 mice treated nasally (protocol B) with PBS (white columns) or a pool (black columns), after three TAChR injections. Controls were cultures that did not receive any stimulus. The columns represent the average (n=6) of the data obtained 24 hours after TAChR addition to the culture for IL-2, 48 hours for IL-10. The data are expressed as O.D. units detected in ELISA.
Figure 7B:
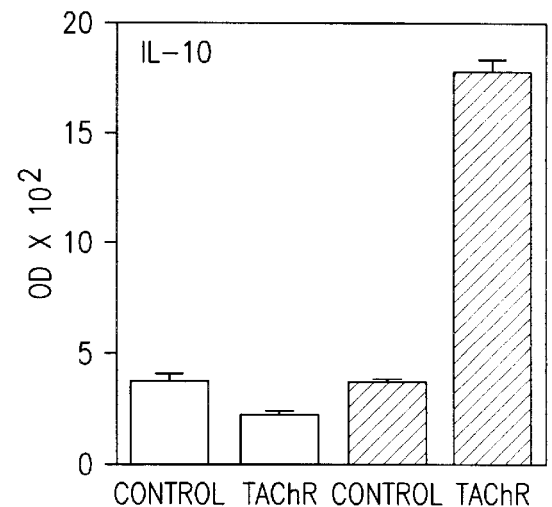
Figure 8:
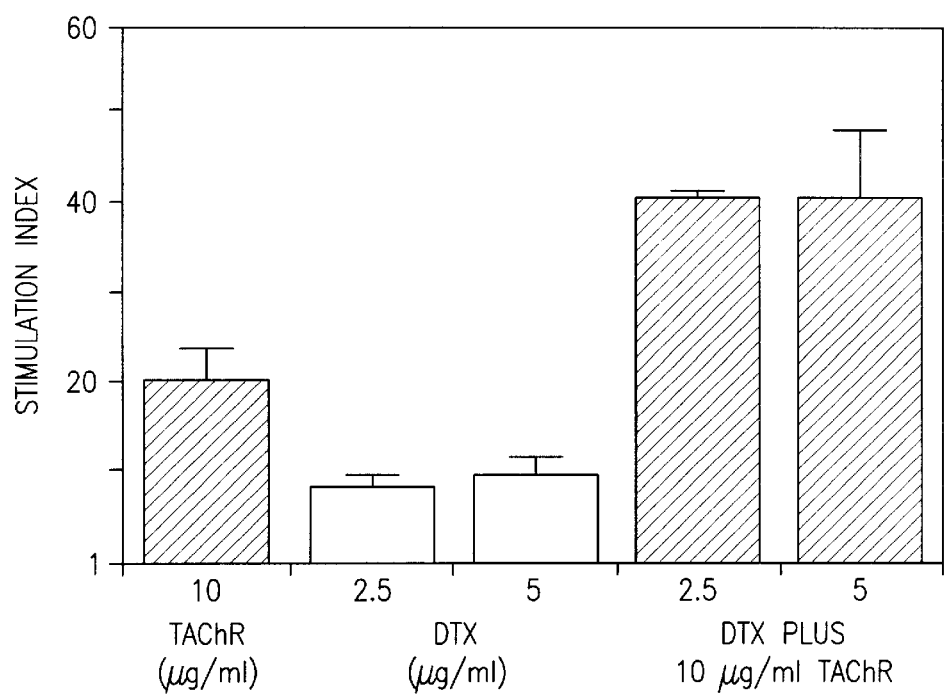
FIG. 8. The proliferative response to the TAChR of spleen T cells from TAChR immunized mice is not affected by the presence in the culture of peptide specific immunoregulatory Th2 cells. Spleen T cells from mice treated nasally with DTX peptides and immunized three times with TAChR were tested in a proliferative assay with TAChR, with the DTX peptide pool (2.5 and 5 $\mu$g of each peptide), and with both TAChR and DTX peptides. The bar is the average S.I. of triplicate cultures. The c.p.m. in the absence of any stimulation were 149±97.

Nasal Treatment with AChR Peptides Stimulates AChR Specific Th2 Cells. Stimulation of modulatory Th2 cells is another possible mechanism of peripheral tolerance. To test this possibility, the secretion of IL-2 and IL-10 by spleen T cells in response to challenge with TAChR was determined. IL-2 and IL-10 are representative cytokines for Th1 and Th2 subsets, respectively. The same mice treated nasally with PBS or with a pool following protocol B were used for the IL-2 treatment experiments. After the third TAChR injection, the spleen T cells of 4 mice of each group were pooled and tested at different time intervals after addition of the TAChR for IL-2 and IL-10 secretion in the culture supernatant. The amount of IL-2 in the media was maximal 24 hours after AChR addition. IL-10 was maximal at 48 hours after ACHR exposure. The average (n=6) of the data obtained at 24 hours for IL-2 and 48 hours for IL-10 are shown in FIG. 7. The presence of TAChR induced the same modest but significant increase of IL-2 secretion in the a pool and sham-tolerized groups. The presence of TAChR did not increase the IL-10 secretion by the T cells from the sham-tolerized mice, while it caused a large increase in the α pool-tolerized group.

Reduced in vitro Response to the TAChR in α pool-tolerized Mice Is Not Due to the Presence in the Culture of Peptide Specific Immunoregulatory Th2 Cells. The reduced anti-AChR responses in vitro of the spleen T cells from TAChR peptide-tolerized mice could be due to immunoregulatory cytokines secreted in the culture medium by Th2 cells sensitized to the peptide(s) administered nasally. The addition to T cell cultures of the tolerizing peptide together with the TAChR may cause a lesser proliferative response than that to the TAChR alone, because of peptide stimulated cytokine secretion by Th2 cells. As spleen T cells from α pool-tolerized mice had small and erratic proliferative responses to TAChR (see FIGS. 1, 3, and 5B), these cells could not be used. Thus, spleen T cells from mice treated with DTX peptides and immunized three times with TAChR were used. These T cells had a good proliferative response in vitro to TAChR, and a significant proliferative response to the DTX peptides, consistent with T cell sensitization resulting from nasal exposure to the DTX sequences (FIG. 8). When DTX peptide was used simultaneously with TAChR, the response obtained was significantly larger than that observed for each of two individual stimulants (FIG. 8), and corresponded reasonably well to the sum of the individual responses against TAChR and DTX peptides.

Discussion. Nasal administration of a 20 residue TAChR synthetic peptide, Tα150-169, that forms an immunodominant epitope recognized by pathogenic CD4+ cells, effectively protected B6 mice from induction of EMG caused by immunization with TAChR. The treatment was effective when administered prior to and during immunization with TAChR. Moreover, monthly or weekly administrations had comparable effects. This suggests that nasal administration did not cause further priming of pathogenic anti-AChR CD4+ T cells. Protection from EMG was associated with reduced T cell reactivity in vitro to the TAChR, reduced levels of anti-TAChR antibody in the blood, and minimal or absent proliferative response of spleen T cells to the immunodominant peptide Tα150-169. These effects were antigen-specific, since they could not be reproduced by nasal administration of a control peptide (a DTX peptide).

Although nasal administration of peptides Tα181-200 and Tα360-360–378 affected subsequent sensitization of T cells to all those sequences (FIG. 1), the protective effects on EMG induction are likely due to tolerization of CD4+ cells that recognize epitopes within the sequence Tα150-169, because nasal administration of peptide Tα150-169 alone was as effective as administration of the α pool in protecting from EMG and reducing the T and B cell responses to TAChR.

Since the AChR destruction and dysfunction that results in EMG symptoms is caused by antibody binding, it is likely that the altered anti-TAChR CD4+ reactivity after nasal tolerization results in protection from EMG because of a change in the anti-AChR antibody repertoire, due to preferential cooperation of different pairs of CD4+ helper T cells and B cells (Palmer et al., 1989; Myers, 1991; Bellone et al., 1994). To support this possibility, mice tolerized with TAChR peptides, while protected from EMG, developed substantial amounts of anti-AChR antibodies, but significantly lower than those observed for the mice sham-tolerized with peptide-free PBS (FIG. 4), or treated with DTX peptides. The pathogenic antibodies missing in the TAChR peptide-tolerized mice are likely synthesized with the help of CD4+ cells recognizing epitopes within the sequence Tα150-169. An important pathogenic role in mouse EMG of CD4+ cells recognizing epitopes within the sequence is supported by several findings: neonatal tolerization to this sequence region reduces susceptibility to EMG (Shenoy et al., 1993); B6 mice primed with AChR and boosted with a synthetic sequence α46-162 developed EMG while mice boosted with a control peptide did not (Shenoy et al., 1994); and in congenic B6 strains carrying the bm12 mutation of the I-A molecule, the ability by CD4+ cells to recognize this sequence correlates with propensity to EMG (Karachunski et al., 1995; Bellone et al., 1991; Infante et al., 1991). That CD4+ cells sensitized to a single dominant AChR epitope may drive the synthesis of pathogenic anti-AChR antibodies has been shown by transfer experiments for both rat (Yeh et al., 1990) and human (Conti-Fine et al., 1997) CD4+ lines against defined AChR epitopes.

Several mechanisms are involved in oral tolerance, including: anergy or deletion by apoptosis of antigen specific T cells, and induction of antigen specific regulatory CD4+ Th2 cells (Weiner et al., 1994; Chen et al., 1995). In EAE, it has been shown that the same CD4+ precursors can develop into regulatory Th2 cell if the antigen is administered orally, or into encephalitogenic Th1 cells if the antigen is administered subcutaneously in adjuvants (Chen et al., 1996). Antigen-specific regulatory CD4+ cells may exert a non-specific down regulating activity through secretion of cytokine, such as IL-4, IL-10, and TGF-β, that act on Th1 cells in topographic proximity, irrespective of their antigen specificity (antigen driven bystander suppression; Weiner et al., 1994).

Oral administration of an antigen can induce tolerance by different mechanisms, depending upon the dose of antigen that was fed (Friedman et al., 1994; Gregerson et al., 1993). Low doses of antigen generate Th2 regulatory cells, whereas high doses induce anergy (Friedman et al., 1994; Gregerson et al., 1993) and/or apoptosis of antigen-reactive Th1 and Th2 cells (Chen et al., 1995). Given the functional similarity of the lymphoid tissues associated with the respiratory and the gastrointestinal systems, similar mechanisms are likely involved in nasal tolerance (Kuper et al., 1992; Neutra et al., 1994).

Both clonal anergy and sensitization of regulatory Th2 cells seem to have 20 occurred (FIGS. 6 and 7). High dose clonal deletion by apoptosis is less likely, since the highest doses used were as effective as the lowest (50 μg, i.e., 20 μmoles). This dose compares in weight to those used for low dose oral tolerance (Friedman et al., 1994). However, the molar concentrations employed in Friedman et al. were lower, as the antigen used in those studies had a higher molecular weight than the peptides employed herein. Epitope-specific anergy induction by nasal treatment with the TAChR peptides is directly supported by the finding that the reduced responsiveness in vitro of T cells to TAChR could be reversed by treatment with IL-2 (FIG. 6). Further circumstantial evidence for anergy of anti-Tα150-169 T cells is the finding that the proliferative response to the TAChR of the spleen T cells of mice tolerized to DTX epitopes and immunized to TAChR was not reduced by simultaneous stimulation of the T cells sensitized to the DTX peptides: the reduced proliferative response in vitro to Tα150-169 and to TAChR is unlikely due to the effects of cytokines released in the culture by Th2 cells.

Anergy or deletion of the T cells recognizing epitopes within the sequence Tα150-169 might suffice to protect from EMG, because, as discussed above, in B6 mice, the CD4+ cells that recognize epitopes within this sequence region are uniquely pathogenic. Also, the CD4+ response of B6 mice, which were hyperimmunized with TAChR and had a high frequency of EMG, focuses almost exclusively on the sequence Tα150-169, rather than spreading to other TAChR epitopes (Bellone et al., 1993). Thus, sensitization of CD4+ cells to epitopes within this sequence suffices to, and is prominent for, driving a pathogenic anti-TAChR atnibodies response. This is different from EAE, where gprogression of the disease correlates with spreading of the CD4+ response to new epitopes within MBP and other myelin components (McRae et al., 1995).

Nasal administration of TAChR peptides sensitized AChR-specific Th2 cells, which were not detectable after TAChR immunization in mice sham-tolerized or tolerized to DTX peptides (FIG. 7). On the other hand, TAChR immunization per se appeared to sensitize Th1 cells only (FIG. 7). In MG, Th1 cells are likely involved in the pathogenic anti-AChR response. In EAE, Th1 cells are the direct effectors of demyelination, and their anergy or down regulation by Th2 subset directly affects their pathogenic action, and has therapeutic effects (Chen et al., 1994). On the other hand, in EMG, the protective effects of nasal administration of TAChR are indirect, and the procedures described herein will not have a therapeutic effect when the tolerogenic peptides are administered only after establishment of the pathogenic anti-TAChR antibody response. This is due to the long antibody life and the long life span of activated B cells (Gray, 1993) relative to the time frame of the experiments described herein.

The use of T cell epitope peptides instead of the whole antigen avoids the risk that the nasally administered antigen will prime synthesis of pathogenic antibodies. Even if nasal administration of peptides causes production of anti-peptide antibodies, they are extremely unlikely to cross-react with the cognate native antigen (Conti-Fine et al., 1996). Several studies have shown that (Conti-Fine et al., 1997) immunization with short TAChR peptides does not result in appearance of EMG. Moreover, short synthetic peptides are easily made.

Nasal tolerization using the approach described herein requires knowledge of the autoantigen sequences forming CD4+ epitopes. The CD4+ cells of most MG patients recognize a limited number of epitope sequences of the human AChR (Conti-Fine et al., 1997). Those sequence regions are recognized with high precursor frequency, and should therefore be considered both immunodominant and universal CD4+ epitopes. These epitopes are ideal candidates for application to human MG. The presence on a protein antigen of a few immunodominant, universal epitope sequences for sensitization of human CD4+ cells occurs also for the normal responses to exogenous antigen, like tetanus and diphtheria toxoid (Raju et al., 1995; Panina-Bordignon et al., 1989; Ho et al., 1990; Diethelem-Okita et al., 1997).

Although the procedure described here affects the anti-AChR antibody secreting B cells indirectly, and it does not have immediate therapeutic effects on established EMG, it also may be a viable candidate for MG management, if associated to plasmapheresis and azathioprine, which eliminate the existing anti-AChR antibodies and affect the activated B cells. The combined effects of such "two pronged" approach might result in a long lasting down regulation of the anti-AChR response, in both the CD4+ and the B cell compartments.

EXAMPLE II

Myasthenia in SCITD Mice Grafted with Lymphocytes from Myasthenia Patients

Methods.

Patients and controls. 19 patients with generalized MG (Table 3) and 5 healthy subjects (3 men and 2 women, 25 to 45 years of age) were studied. Some patients were tested two or more times, as indicated in Table 3, at the time of the different experiments, some of these patients had symptoms of similar severity; in others the severity of the symptoms had changed. Most patients were tested for serum anti-AChR Ab. All but one were Ab positive (Table 3). Patient 13 30 was negative for anti-AChR Ab, as determined by clinical diagnostic tests that included precipitation assay, determination of the Ab ability to block α-bungarotoxin (α-BTX) binding, and ability of the patient's serum to cause accelerated degradation of the AChR in muscle cell cultures.

Cell population used. For engraftment of SCID mice, BL from MG patients and controls were used. For four patients (Patients 16 to 19), BL depleted in $CD4^+$ cells were used, and for Patient 4 BL depleted in $CD8^+$ cells were used. Also, $CD4^+$ lines specific for previously identified "universal" and immunodominant sequences of the AChR α subunit or specific for tetanus toxoid (TTD) or diphtheria toxoid (DTD) from Patient 16 were propagated. SCID mice were engrafted with mixtures of $CD4^+$ depleted BL from Patient 16, supplemented with individual $CD4^+$ lines.

Isolation of BL and depletion in $CD4^+$ and $CD8^+$ T cell. BL were isolated from heparinized venous blood by centrifugation on Ficoll density gradients (Pharmacia, Uppsala, Sweden). Cell viability was assessed by trypan blue exclusion. The BL concentration was adjusted to 7 to $8 \times 10^8$ cells/niL in phosphate buffered saline solution (PBS), and $CD4^+$ or $CD8^+$ T cells depleted using mouse anti-human $CD4^+$ or $CD8^+$ Ab (OKT4 and OKT8; Ortho, Raritan, N.J.) and paramagnetic beads coated with goat anti-mouse IgG Ab (Advanced Magnetic Inc., Cambridge, Mass.). These two populations are referred to as $CD4^+$ depleted and $CD8^+$ depleted BL, respectively. The phenotype of the $CD4^+$ depleted BL and of the $CD8^+$ depleted BL was determined in a FACSt® cell sorter (Becton Dickinson and Co., Mountain View, Calif.), using phycoerythrin (PE) conjugated Leu 4 (anti-CD3) and fluorescein isothiocyanate (FITC) conjugated Leu 2 (anti-CD8) and Leu 3 (anti-CD4) Ab (Becton Dickinson and Co.). The dilutions, washings, and incubations were done in PBS at 4° C.

Yield of the $CD8^+$ depleted BL, which includes a negligible amount of $CD8^+$ cells (<2.5%), is 45 to 55% of the starting BL. Yield of the CD4+ depleted BL, which includes a small number of $CD4^+$ cells (<7%), is 44 to 62% of the starting BL.

Also, by FACS analysis, using PE-labeled anti-CD19 antibody (Ancell, Bayport, Minn.), the mean number of B cells present in $CD4^+$ and $CD8^+$-depleted cell preparations was determined. BL, $CD4^+$ depleted BL, and $CD8^+$-depleted BL preparations from six MG patients were used and an average of 8.6±1.5, 7.2 ±3.5, and 4.5±1.2 B cells for the BL, the $CD4^+$-depleted BL, and the CD8-depleted$^+$ BL, respectively, were found. For the healthy controls, an average of 9.4±1.4, 4.5±1.9, and 7.9±0.8 B cells for the BL, the $CD4^+$-depleted BL, and the CD8-depleted$^+$ BL respectively, was found. Propagation of $CD4^+$ lines and test of their specificity. $CD4^+$ cell lines specific for three synthetic sequence regions of the human AChR a subunit known to form universal, immunodominant epitopes were propagated from Patient 16. The epitopes correspond to residues α48-67, α304-322, and α419-437. Two $CD4^+$ lines specific for TTD and DTD, respectively, were also propagated from this patient. To propagate the lines, cycles of stimulation of the BL with an individual AChR synthetic sequence or TTD or DTD (10 μg/mL) for 2 days in the presence of autologous or DR-matched irradiated (4,000 rad) BL as antigen (Ag) presenting cells were used. This was followed by stimulation with IL-2 (Lymphocult, Biotest Diagnostic Inc., Dreieich, Germany; final IL-2 concentration, 10 U/mL for 5 days).

The phenotype of the lines was determined by FACS analysis in a FACStar® cell sorter (Becton Dickinson), using PE conjugated Leu 4 (anti-CD4) Ab (Becton Dickinson). The cell lines were predominantly or exclusively $CD3^+$, $CD4^+$, $CD8^-$.

TABLE 3

Clinical characteristics of the MB patients used in this study

| Patient No. | Experiment No. | Age, y | Sex | Disease class* | Serum anti-AChR Ab (nM)† | Thymus pathology | Treatment‡ |
|---|---|---|---|---|---|---|---|
| 1 | NA | 24 | F | IV↓ | 13.9 | Hyperplasia | Pred, Mest |
| 2 | NA | 82 | M | IV↓ | Not done | Not done | Aza, Mest |
| 3 | NA | 90 | M | II↔ | Not done | Not done | Aza, Mest |
| 4 | 1 | 36 | F | II↔ | 1,795 (43 mos) | normal | Pred, Mest |
|   | 2 | 38 |   | IV↔ | 1,042 (7 mos) |   | Cycl, Pred, Mest |
| 5 | 1 | 63 | M | IV↓ | 0.04 | Not done | Aza |
|   | 2 | 63 |   | IV↓ | 0 |   | Pred, Mest, Plex |
| 6 | NA | 22 | F | II↔ | 10.6 (22 mos) | hyperplasia | Mest |
| 7 | NA | 27 | F | IV↔ | 0.21 | hyperplasia | Mest, Aza, Pred |
| 8 | 1 | 44 | F | II↓ | 52.8 | hyperplasia | Pred, Mest |
|   | 2 | 45 |   | II↔ | Not done |   | Pred, Mest, Aza |
| 9 | NA | 28 | F | II↔ | 1.68 (22 mos) | thymoma | Pred, Mest, Aza |
| 10 | NA | 40 | F | IV↓ | 15.6 | Not done | Mest |
| 11 | NA | 76 | M | II↔ | 0.37 (17 mos) | Not done | Aza, Pred |
| 12 | NA | 22 | M | IV↓ | 0.63 | hyperplasia | Pred |
| 13 | 1 | 36 | F | II↔ | 0 | normal | Pred |
|   | 2 | 37 |   | II↔ | Not done |   | Pred |
| 14 | 1 | 30 | M | IV↓ | 0.13 | normal | Pred, Mest |
|   | 2 | 31 |   | II↑ | Not done |   | Pred, Mest, Plex |
| 15 | 1 | 60 | M | IV↑ | 2.10 | thymoma | Mest, Plex, Aza, Pred |
|   | 2 | 60 |   | II↔ | Not done |   | Aza, Pred |
| 16 | 1 | 51 | F | II↔ | 2.56 (5 mos) | hyperplasia | Cycl, Mest, Pred |
|   | 2 | 51 |   | II↔ | Not done |   | Cycl, Mest, Pred |
|   | 3 | 52 |   | II↔ | Not done |   | Cycl, Mest, Pred |
| 17 | 1 | 57 | F | IV↓ | 21.2 (2mos) | thymoma | Cycl, Mest |
|   | 2 | 57 |   | II↔ | 5.43 (2 mos) |   | Cycl, Mest, Pred, Aza |
| 18 | NA | 55 | M | II↓ | 16.9 (2 mos) | hyperplasia | Cycl |
| 19 | NA | 64 | F | IV↔ | 148 (12 mos) | thymoma | Mest, Aza |

*At the time of the experiment.
The arrows refer to the evolution of the symptoms at the time of the test.
↑ = improving symptoms;
↓ = worsening symptoms;
↔ = static symptoms.
†The serum anti-AChR Ab concentration reported was assayed at the time of the experiments, or several months before or after the experiments, as indicated in parentheses.
‡During the 6 months before the experiment.
AChR Ab = acetylcholine receptor;
Mest = pyzidostigminin;
Pred = prednisone;
Aza = azathioprine;
Cycl = cyclosporine;
Plex = plasmapheresis.

The antigen (Ag) specificity of the CD4+ cell lines was tested in roliferation assays using $2 \times 10^4$ cells/well and irradiated (4,000 rad) autologous BL ($2 \times 10^5$ cells/well) as Ag presenting cells. The cells were seeded in triplicate in 96 round bottom well plates and cultivated with the following Ag or stimulants: Phytohemoagglutinin (PHA, 10 µg/mL; Wellcome, London, UK); IL-2 (final concentration of IL-2, 10 U/mL, Lymphocult; Biotest Diagnostic Inc., Dreieich, Germany); TTD or DTD (10 µg/mL; Connaught Laboratories, Inc., Swiftwater, Pa.); the individual synthetic ACHR peptide epitopes (10 µg/mL); a control synthetic peptide (E73), 20 residues long, unrelated to the AChR sequence and synthesized with the procedures used for the AChR peptides. The basal growth rate was determined from triplicate wells containing CD4+ cell lines and Ag presenting cells cultivated without any stimulus or with peptide E73. After 1 day the cells were pulsed for 16 hours with $^3$H-thymidine (1 µCi per well, specific activity 6.7 Ci/mmol; Amersham, Arlington Heights, Ill.), collected with a Titertey cell harvester (Skatron Inc., Sterling Va.), and the $^3$H-thymidine incorporation measured by liquid scintillation.

The lines were used for engraftment in SCID mice when they were highly enriched in CD4+ cells specific for the Ag used for their propagation. This occurred after 4 to 6 cycles of stimulation, when the response of the line to the relevant Ag (the AChR peptide used for the propagation of the line, TTD, or DTD) was comparable with that elicited by PHA. The proliferative responses to the relevant Ag were specific because proliferation could not be detected when the control peptide E73, whose sequence was not related to those of the AChR, TTD, or DTD, was used. The lines were used at the end of the Ag stimulation period.

SCID mice. CB17 SCID mice from the Jackson Laboratory (Bar Harbor, Me.) were maintained and bred in a pathogen-free environment using microinsulator barrier cages. All manipulations were performed aseptically. The mice were screened for residual function of the immune system by determining the presence of IgG in their serum by ELISA. Mice were not used if they had IgG in their serum.

Engraftment of human cells in SCID mice. Each mouse received in the peritoneal cavity 0.3 mL of PBS containing one of the following cell types: 20 to $25 \times 10^6$ BL; 15 to $20 \times 10^6$ CD4+ depleted BL; 18 to $26 \times 10^6$ CD8+ depleted BL; 15 to $20 \times 10^6$ CD4+ depleted BL plus 1.1 to $1.5 \times 10^6$ CD4+ cells from a line specific for a universal AChR epitope sequence, or TTD, or DTD.

Mouse blood was obtained from the tail vein just before the engraftment of human cells, and at different times afterwards. The mice were killed by general anesthesia followed by cervical dislocation. Most mice were killed 9 to 12 weeks after the engraftment, five mice 7 weeks after the engraftment, and nine mice 14 to 18 weeks after the engraftment.

Assay of myasthenic symptoms. The myasthenic symptoms were quantified using a forced exercise test sensitized by administration of a minute amount of pancuronium bromide (0.03 mg/kg intraperitoneum) just before the test. The small amount of pancuronium inactivates a fraction of the mouse muscle AChR. This does not affect the muscle strength of normal mice, but it reveals subclinical myasthenic weakness and allows its measurement. The mice hang from a grid suspended above a soft padding, and the time it took the mouse to fall three times ("holding time") was measured. The test is parametric and gives a quantitative assessment of the mouse weakness. The mice were tested without knowledge of the type of cells engrafted.

The holding times of SCID mice injected with BL of healthy subjects did not differ significantly from those of normal mice of different strains (12.4±2.1 minutes, N=99), at any time after the BL engraftment. The average holding times of the SCID mice engrafted with normal BL served as controls for the holding time of individual SCID mice engrafted with immune cells of MG patients, observed at the same time after the engraftnent. This ensured that weakness caused from the nonspecific stress of the mouse manipulation would not result in false-positive results. Mice with holding times 2 SD shorter than the average holding time of all the SCID mice injected with BL of normal subjects when tested the same time after the engraftment of BL were considered significantly affected.

The myasthenic nature of the weakness was verified by injecting intraperitoneum edrophonium chloride (Reversol; Organon Inc., West Orange, N.J.). Reversol is a cholinesterase inhibitor, and it immediately improved the strength of the affected mice (FIG. 12, inset.) Detection of human TgG and IgM in mouse sera. The concentrations of human IgG and IgM in the mouse sera was measured by ELISA. Microtiter plates (Nunc, Roskilde, Denmark) were coated with goat anti-human IgG or IgM Ab (pierce, Rockford, Ill.) in 20 mM sodium carbonate buffer, pH 9.5 (coating buffer), and blocked any uncoated sites with 3% bovine serum albumin (BSA) in coating buffer. Mouse sera diluted serially in PBS was added, and incubated at 4° C. overnight. After four washings with PBS containing 1% Triton X-100, peroxidase conjugated anti-human IgG and IgM Ab (Sigma, St. Louis, Mo.) was added. The color was developed by peroxidase staining and stopped the reaction by adding 2 M $H_2SO_4$, following the manufacturer's instructions. The optical density of the plates was read at 490 nm in an ELISA reader. For each assay, a standard curve was generated using known amounts of purified human IgG and IgM (Sigma). Assay of anti-human AChR Ab in mouse Sera. The concentration of human anti-AChR Ab in the mouse sera was determined by radioimmunoprecipitation assay (RIPA). As Ag, human AChR expressed by the TE671 cell line (American Type Culture Collection, ATCC; Rockville, Md.) was used. The cells were grown in Dulbecco's Modified Eagle Medium (DMEM) containing 8% fetal calf serum. For each preparation of human AChR, 0.7 to $1 \times 10^9$ TE671 cells in 10 mL of homogenization buffer (10 mM sodium phosphate, 5 mM ethylenediaminetetraacetic acid, 3 mM iodoacetate, 20 mM phenylmethylsulfonyl fluoride, pH 7.5) containing 2% Triton X-100 were used, and extracted on a shaker for 2 hours at 4° C. The insoluble debris was pelleted by centrifugation in a 35 rotor (Beckman, Irvine, Calif.) at 14,000 revolutions per minute (rpm) for 30 minutes, recovered the supernatant containing human AChR, and determined the AChR concentration by $^{125}$I-α-BTX binding assay. Typical yields were 26 to 66 fMol/106 TE671 cells.

For the Ab assay, the AChR was labeled with a threefold excess of $^{125}$I-α-BTX at 4° C. overnight. The AChR-containing extract was diluted in PBS to a final concentration of 0.5 pmol of AChR/mL. The mouse sera was diluted 1:10 in PBS and 100 μL or 50 μL aliquots added to 1 mL of $^{125}$I-α-BTX-labeled AChR and 3 μL of normal human serum as a carrier. As a positive control, serial dilutions of serum of Patient 4, who had a high anti-AChR Ab concentration (Table 3), were used. As a negative control normal human serum was used. The human Ab was precipitated by adding 40 μL/sample of affinity purified rabbit anti-human IgG Ab (Sigma) and incubating the samples at 4° C. overnight. The precipitate was pelleted and washed, and the bound radioactivity was measured in a gamma 5500 counter (Beckman). The anti-AChR Ab concentrates are expressed as precipitable AChR/$^{125}$I-α-BTX complexes.

Determination of human IgG bound to muscle AChR The human Ab bound to mouse muscle AChR was measured by RIPA. All procedures were performed at 4° C. Individual mice were skinned, eviscerated, decapitated, and tissues homogenized in two volumes of homogenization buffer. The homogenates were centrifuged at 30,000 rpm for 1 hour in a Beckman 35 rotor, the pellets resuspended in homogenization buffer containing 2% Triton X-100, and extracted at 4° C. for 2 hours with shaking. The extract was centrifuged at 30,000 rpm for 1 hour in a Beckman 35 rotor and the supernatant containing the solubilized AChR collected. 2 pmol of $^{125}$I-α-BXT was added to a four 1.5-mL aliquots of the Triton X-100 extract of each mouse carcass and incubated at 4° C. overnight. Affinity purified rabbit anti-human IgG Ab (Sigma) at 50 μL/sample was added and incubated at 4° C. overnight. The precipitated $^{125}$I-α-BTX/AChR/ human IgG complexes were pelleted by centrifugation in a SH-MT rotor (Sorvall, Newton, Conn.) at 12,000 rpm for 12 minutes. The pellets were washed three times with 10 mM sodium phosphate buffer, pH 7.4, containing 0.1% Triton X-100, and the bound radioactivity counted in a gamma 5500 counter (Beckman).

Detection of anti-AChR IgG bound to muscle ACHR by immunofluorescence microscopy. The hind limb muscles of SCID mice transplanted with human cells was dissected, frozen in liquid nitrogen, and stored at −70° C. The frozen tissue was embedded in O.C.T. Compound Tissue-TEK (Miles Laboratories Inc., Elkhart, Ind.) and sectioned in the transverse direction into 10 μm sections using a Jung Frigout 2800E Kryostat (Leica, Nublach, Germany). The sections were preincubated in PBS for 10 minutes and stained for 1 hour at 20° C. with both rodamine labeled α-BTX (Molecular Probes, Eugene, Oreg.) and FITC labeled anti-human IgG (Sigma), diluted 1:1000 in PBS containing 2% BSA. The sections were washed and viewed in a fluorescence microscopy (Nikon, Diaphot, Japan).

Test of Significance. The significance of differences observed between test and control samples was determined with a two-tailed Student's t-test.

Result.

Figure 13A:
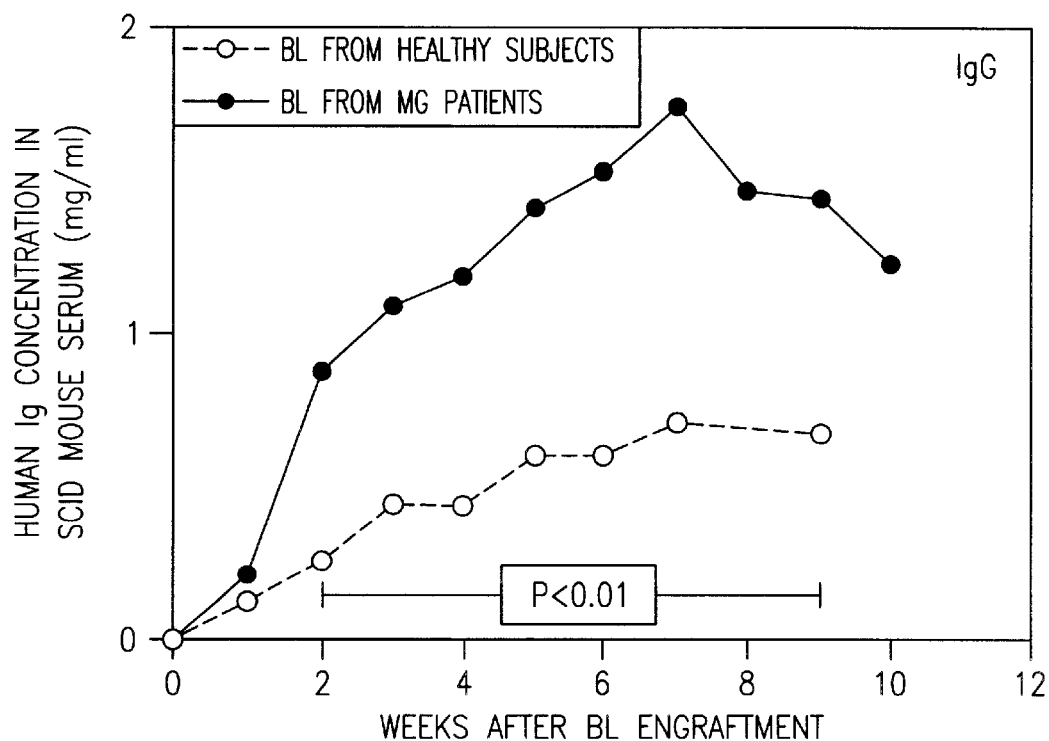
FIGS. 13A–B. Average concentration of human IgG and IgM, as indicated inside each plot, in the sera of 50 SCID mice engrafted with BL from 14 MG patients and 20 SCID mice engrafted with BL from four healthy subjects. Starting from week 2 the average concentrations of IgG and IgM in mice engrafted with BL from MG patients were significantly higher (p<0.01 and p<0.05, as indicated) than those observed in the mice engrafted with BL from healthy subjects.
Figure 13B:
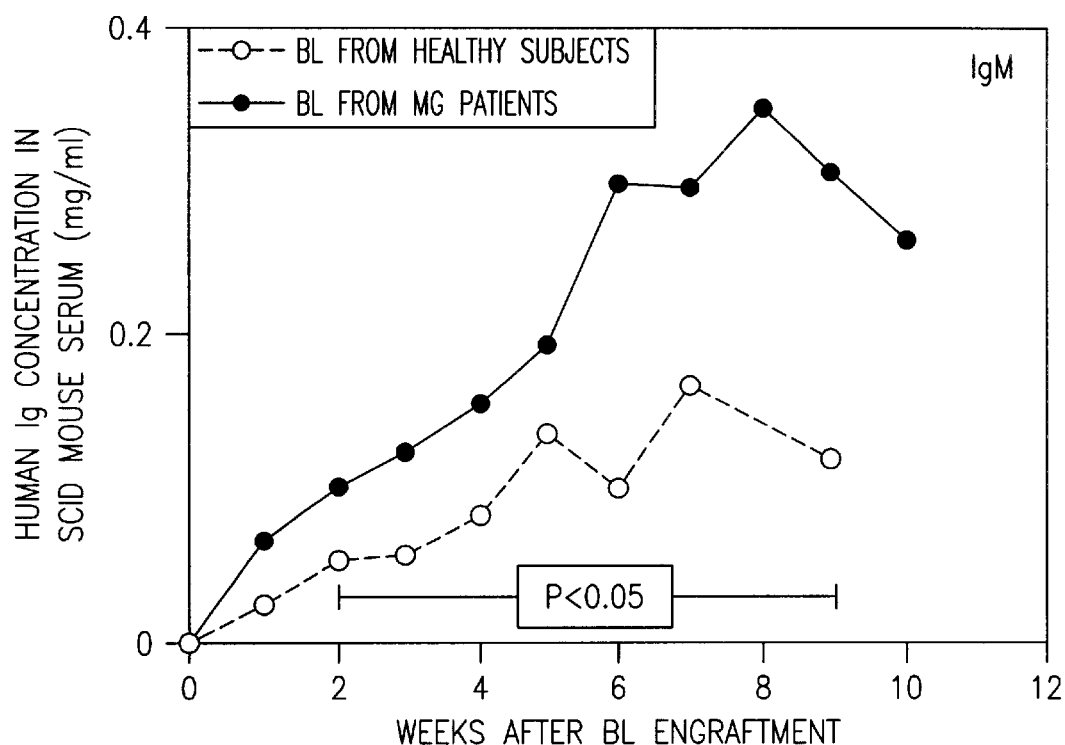

Human IgG and IgM in the sera of SCID mice engrafted with human BL. Weekly, starting on the day of engraftment, the concentration of human IgG and IgM in the sera of mice engrafted with human BL was measured. FIG. 13 reports the average concentrations in the sera of 50 mice engrafted with BL from 14 MB patients (Patients 1 to 14, see Table 4) and 20 mice engrafted with BL from 4 healthy subjects. Some mice were killed 7 to 8 weeks after the engraftment, and a few died of respiratory failure resulting from their myasthenic symptoms. Consequently, some data points do not include the sera from all the mice used in this experiment. Measurable concentrations of human IgG and IgM were detected starting 1 week after engraftment of human BL. The levels of IgG and IgM increased with time and reached a plateau 5 to 6 weeks after the engraftment. Starting from week 2, the average concentrations of IgG and IgM in mice engrafted with BL from MG patients were significantly higher than those observed in the mice engrafted with BL from healthy subjects. The serum IgG 20 reached an average concentration of approximately 0.5 and 1.5 mg/mL in mice engrafted with control and MG BL, respectively (5% and 15% of the IgG concentration in normal human serum). The serum IgM reached an average concentration of approximately 0.1 and 0.3 mg/mL in mice engrafted with BL from healthy subjects and MG patients, respectively (8% and 25% of the IgM concentration in normal human serum).

TABLE 4

Summary of the effects of human BL engraftment into SCID mice

| Subject No. | No. of engrafted mice | Mice with significant weakness* | Mice with serum anti-AChR AB† | Mice with muscular Ab/AChR complexes† | Mice with human Ig at the neuromuscular junction‡ |
|---|---|---|---|---|---|
| BL from MG patients | | | | | |
| 1 | 4 | 1/4 | 4/4 | 4/4 | nd |
| 2 | 2 | 0/2 | 0/2 | 2/2 | nd |
| 3 | 2 | 2/2 | 0/2 | 2/2 | 2/2 |
| 4 | 2 | 0/2 | 1/2 | 0/2 | nd |
| 5 | 5 | 5/5 | 0/5 | 0/2 § | 0/2 |
| 6 | 2 | 2/2 | 0/2 | 0/2 | 0/2 |
| 7 | 2 | 0/2 | 2/2 | 2/2 | 1/1 |
| 8 | 8 | 4/8 | 5/8 | 4/5 ¶ | 4/4 |
| 9 | 2 | 2/2 | 0/2 | 0/2 | 0/2 |
| 10 | 4 | 4/4 | 1/4 | 3/4 | 2/2 |
| 11 | 3 | 3/3 | 1/3 | 1/3 | 1/2 |
| 12 | 3 | 2/3 | 1/3 | 2/2 ¶ | 1/1 |
| 13 | 7 | 6/7 | 3/7 | 1/4 ¶ | 1/1 |
| 14 | 4 | 0/4 | 4/4 | 3/4 | nd |
| 15 | 4 | 2/4 | 3/4 | 3/4 | nd |
| 16 | 4 | 3/4 | 4/4 | 4/4 | nd |
| 17 | 4 | 4/4 | 3/4 | 2/3 ¶ | 2/2 |
| Total | 62 | 40/62 (64.5%) | 32/62 (51.6%) | 33/51 (64.7%) | |
| BL from healthy subjects | | | | | |
| 1 | 7 | 0/7 | 0/6 | 0/7 | nd |
| 2 | 3 | 0/3 | 0/2 | 0/2 | nd |
| 3 | 4 | 0/4 | nd | nd | nd |
| 4 | 7 | 0/7 | 0/7 | 0/7 | nd |
| 5 | 4 | 0/4 | 0/3 | 0/4 | nd |
| Total | 25 | 0/25 | 0/18 | 0/20 | |

*Measured by the pancuronium-sensitized inverted grid test.
†Measured by RIPA.
‡Assessed by double immunofluorescent staining with α-BTX, to localize the synapses, and with Ab against human IgG.
§The carcasses of three mice engrafted with the BL from this patient were not available.
¶Some mice died overnight of respiratory failure resulting form the muscle weakness, and the carcasses could not be assayed.

Variations in the concentrations of human IgG and IgM in the mouse sera were donor dependent. Occasionally, small differences were observed among mice engrafted with BL from the same donor.

Appearance of myasthenic weakness in SCID mice engrafted with BL from MG patients. SCID mice engrafted with BL from 17 MG patients (Patients 1 to 17, see Table 4) and the 5 healthy subjects were examined for appearance of obvious clinical symptoms of EAMG (hunched posture, respiratory distress, death) every second day. Obvious EAMG appears in mice when most AChR at the muscle synapses is destroyed. Only 4 of 62 engrafted mice (6%) had overt symptoms.

Figure 12A:
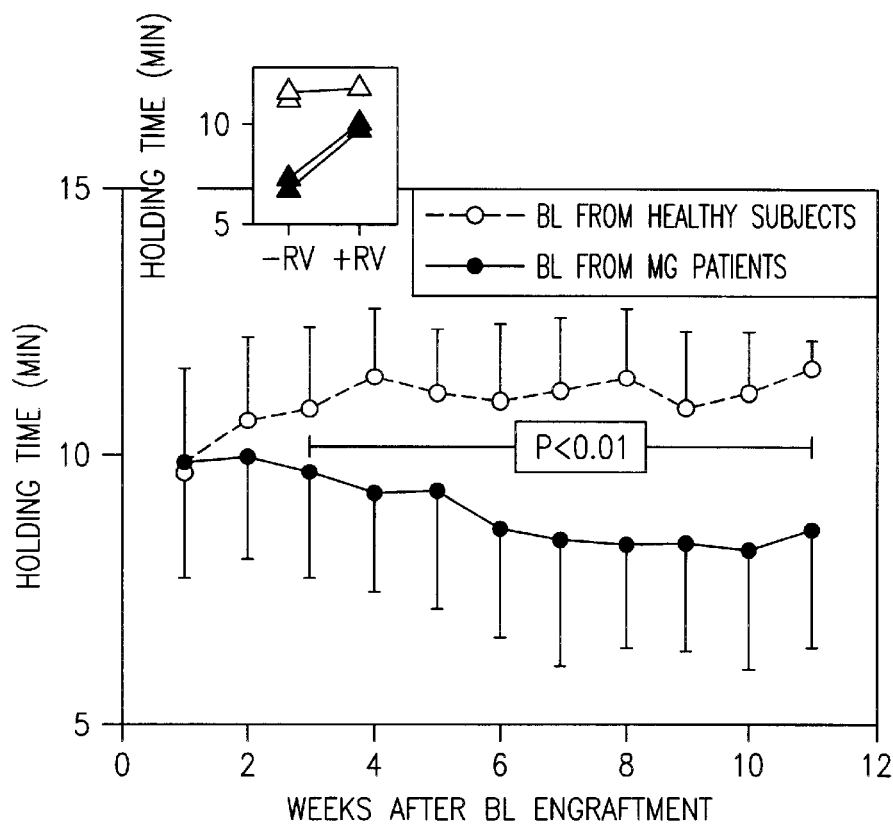
FIGS. 12A–B. (A) Results of weekly tests of subclinical muscle weakness, using the pancuronium sensitized hanging grid test, from 1 to 11 weeks after engraftment of BL from MG patients (black symbols) and healthy subjects (white symbols). The data are the averages ±SD of the holding time of 62 mice engrafted with BL from the 5 healthy subjects. Mice engrafted with blood lymphocytes (BL) from healthy subjects did not develop any strength deficit as compared with normal, untreated mice. The average holding time of mice engrafted with BL from MG patients decreased moderately but steadily during the observation period. Starting from week 3, the average holding times of the mice engrafted with BL from MG patients were significantly lower (p<0.01) than those of mice engrafted with BL from normal subjects. In the inset, improvement of the muscle strength of affected mice after administration of Reversol (black symbols). Reversol did not increase the muscle strength of mice that had normal holding time (white symbols). –Rv, before administration of Reversol; +RV, after administration of Reversol. (B) Frequency of significant muscle weakness in mice engrafted with BL from MG patients, shown by the hanging grid test. The frequency of the significantly affected mice increased with time. It reached a plateau beginning from week 7 after the engraftment, when 40 of the 62 mice (65%) engrafted with BL from MG patients had myasthenic weakness.

The same mice were tested weekly for appearance of subclinical muscle weakness, using the pancuronium sensitized hanging grid test. The observation began at 1 week after engraftment of the BL and continued until week 11. FIG. 12A summarizes the results of hanging grid tests (average±SD) of 62 mice engrafted with BL from the 17 MG patients (Patients 1 to 17) and 25 mice engrafted with BL from the 5 healthy subjects. Some mice were killed 7 to 8 weeks after the engraftment, and a few mice died of myasthenic failure of the respiratory muscles. Consequently, some data points in FIG. 12 do not include all the mice used for these experiments. One week after BL engraftment the average holding times of mice engrafted with BL from healthy subjects and MG patients were identical. They were slightly but not significantly lower than that of normal, untreated mice. This is likely due to the physical stress caused by the intraperitoneal injection. Mice engrafted with BL from healthy subjects did not develop any strength deficit as compared with normal, untreated mice. Their average holding time was constant from week 2 until the end of the observation period. The average holding time was constant from week 2 until the end of the observation period. The average holding time of mice engrafted with BL from MG patients decreased moderately but steadily during the observation period. Starting from week 3, the average holding times of the mice engrafted with BL from MG patients were significantly lower (p<0.01) than those of mice engrafted with BL from normal subjects.

Figure 12B:
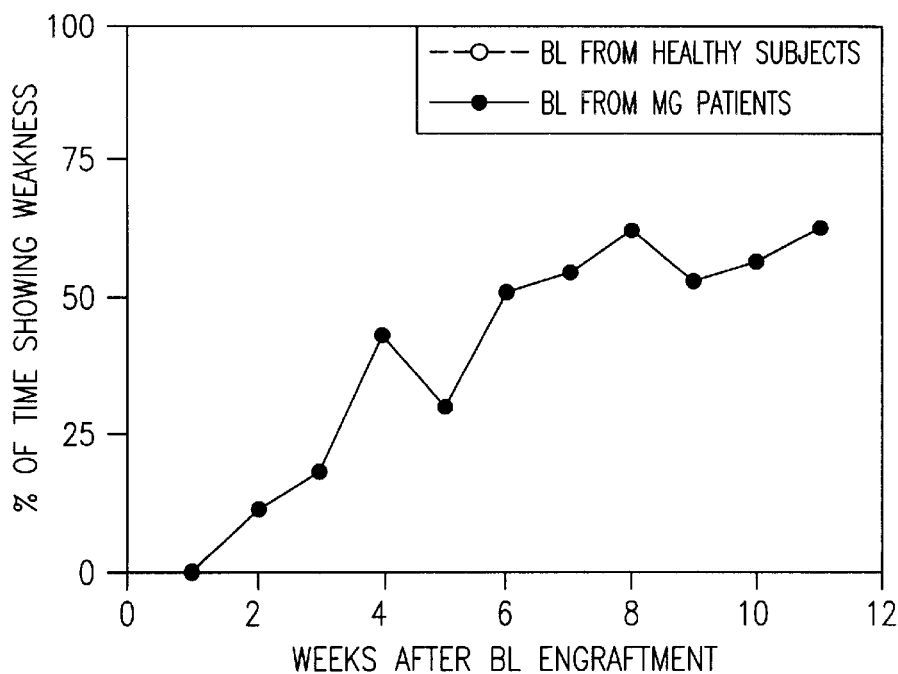

FIG. 12B shows the frequency of significant muscle weakness in mice engrafted with BL from MG patients, depicted by the hanging grid test. Mice with holding times shorter by 2 SD than the average holding time of all the SCID mice infected with BL of normal subjects, tested the same time after the engraftment, were considered to be significantly affected. A few mice engrafted with BL from MG patients had significantly reduced holding times two weeks after the engraftment. The frequency of the mice that were significantly affected increased with time. Starting from week 7 after the engraftment, 40 of the 62 mice (65%) engrafted with BL from MG patients had myasthenic weakness. Table 4 summarizes the frequency of mice showing significant weakness after engraftment of BL from individual MG patients. Table 4 details the results obtained in the mice used for the experiments reported in FIGS. 12 through 15, not in the mice engrafted with BL as a part of the experiments testing the effect on MG transfer of engraftment of CD4+ depleted or CD8+ depleted BL, described below. Engraftment of BL from Patients 2, 4 (experiment 1), 7, and 14 (experiments 1 and 2) did not cause weakness in any mice. Engraftment of BL from Patients 3, 5, 6, 9, 10, 11, and 17 caused weakness in some or most, but not all, of the engrafted mice.

Patient 13 is anti-AChR Ab negative. Yet, three out of seven mice engrafted with her BL had detectable anti-AChR Ab in the serum. Six mice developed EAMG symptoms, and three of them died of respiratory failure (Table 4). All mice engrafted with BL from Patient 13 had substantial levels of human IgG in the blood (six mice had 1.3 to 2.8 mg/mL of human IgG after week 5).

Mice engrafted with BL from healthy subjects never had a significant reduction of the holding time at any time after the engraftment (Table 4).

Correlation between clinical state of the patient and ability of their BL to transfer weakness in engrafted SCTD mice. For several patients (4, 5, 8, and 13 to 17), the effect of engraftment into the SCID mice of BL obtained at different times was determined. Table 5 summarizes the frequency of myasthenic weakness in the mice engrafted with BL in the different experiments. Table 5 also reports the severity of the patient symptoms and the ability of the engrafted BL to transfer myasthenic weakness. For example, BL from Patients 4 and 15 did not cause weakness in any of the engrafted mice when the patients had class II symptoms, whereas they caused myasthenic symptoms in all of the engrafted mice when the patients had class IV symptoms. Similarly, the BL from Patient 17 caused myasthenic weakness in all engrafted mice when the patient has class IV symptoms, and only in 1 of 2 mice when the patient had class II symptoms. When BL were obtained at times when the patient had the same disease class (e.g., experiments with Patients 5, 8, 13, and 16), the engrafted mice developed myasthenic weakness with similar frequency. SCID mice engrafted with BL from Patient 14 did not develop MG weakness, irrespective of the disease class at the time of the blood drawing (Table 5).

TABLE 5

Correlation between the clinical state of the MG patients at the time of the experiment and frequency of SCID mice showing significant muscle weakness* after BL engraftment

| Patient No. | Experiment No. | Months elapsed from experiment 1 | Disease class | Affected mice |
|---|---|---|---|---|
| 4 | 1 | — | II | 0/2 |
|  | 2† | 24.5 | IV | 3/3 |
| 5 | 1 | — | IV | 2/2 |
|  | 2 | 0.3 | IV | 3/3 |
| 8 | 1 | — | II | 3/6 |
|  | 2 | 7 | II | 1/2 |
| 13 | 1 | — | II | 3/3 |
|  | 2 | 3.7 | II | 3/4 |
| 14 | 1 | — | IV | 0/2 |
|  | 2 | 5 | II | 0/2 |
| 15 | 1 | — | IV | 2/2 |
|  | 2 | 4 | II | 0/2 |
| 16 | 1 | — | II | 1/1 |
|  | 2 | 1 | II | 2/3 |
|  | 3† | 15 | II | 1/1 |
| 17 | 1 | — | IV | 4/4 |
|  | 2† | 13.8 | II | 1/2 |

*Measured by the pancuronium-sensitized inverted grid test.
†Experiments not included in Table 4 and FIGS. 12–15.

Figure 14:
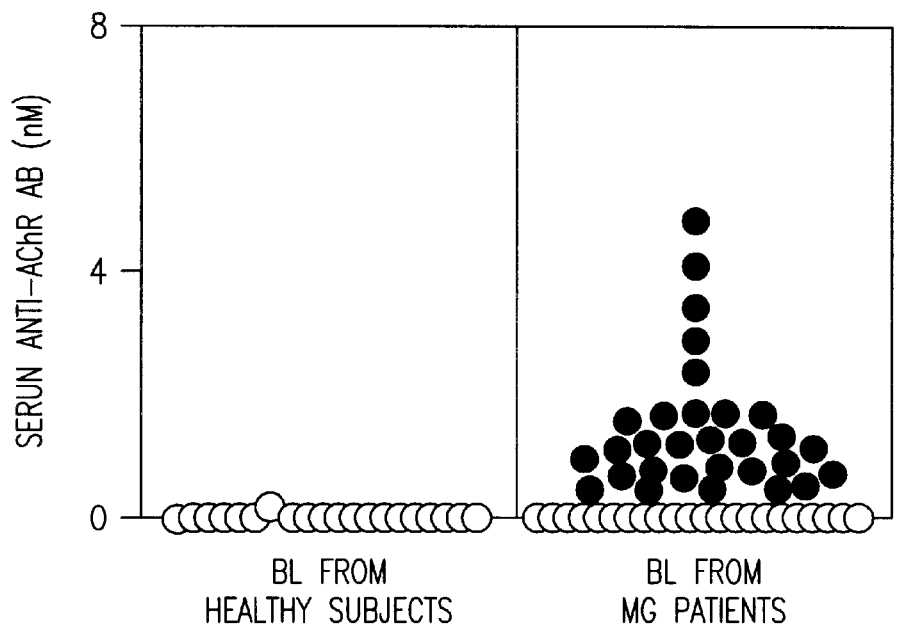
FIG. 14. Serum concentrations of human anti-acetylcholine receptor antibodies (ACHR Ab) in individual SCID mice engrafted with BL from MG patients and healthy subjects, measured by radioimmunoprecipitation assay (RIPA). The sera were obtained seven to ten weeks after the engraftment from 62 mice engrafted with BL from 17 MG patients and 19 mice engrafted with BL from four healthy subjects. The black symbols indicate the presence of a significant Ab concentration; the white symbols indicate that no Ab was detected.

SCID mice engrafted with BL from MG patients have human anti-AChR Ab in their serum and muscle. The presence of human anti-AChR Ab appeared in the serum of 52% of the mice injected with BL from MG patients. The Ab concertration increased during the first 5 weeks after BL engraftment. Anti-AChR Ab in the sera of mice engrafted with BL from healthy controls was never detected. FIG. 14 reports the concentrations observed 7 to 10 weeks after engraftment in the sera of 62 individual mice engrafted with BL from 17 MG patients (Patients 1 to 17, see Table 4) and in 18 mice engrafted with BL from 4 healthy subjects (Controls 1, 2, 4, and 5, see Table 4). The black symbols indicate a significant anti-AChR Ab concentration, and the white symbols indicate that we did not detect any human anti-AChR Ab.

Figure 15:
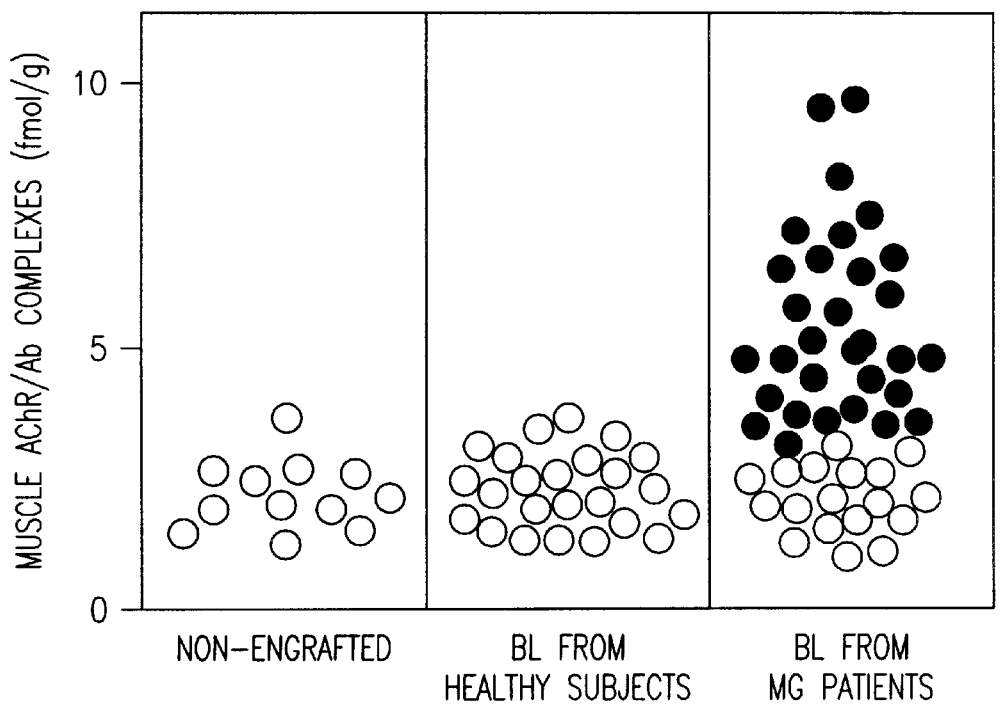
FIG. 15. Concentration of AChR bound by human anti-AChR Ab in the muscle of SCID mice engrafted with BL from MG patients or healthy subjects, measured by RIPA. The muscle tissue was harvested from 51 mice engrafted with BL from 17 MG patients and 20 mice engrafted with BL from 4 healthy subjects, as indicated below the plots. The mice were killed 7 to 18 weeks after the engraftment. As a negative control, muscle tissue from 12 untreated SCID mice was used (plot "nonengrafted"). The black symbols indicate the presence of a significant concentration of AChR/Ab complexes, the white symbols indicate that no AChR/Ab complexes were detected.

The mice were killed at the end of the experiment and the concentration of mouse muscle AChR bound to human Ab measured. This was done for 51 mice engrafted with BL from 17 MG patients (Patients 1 to 17), for 20 mice engrafted with BL from 4 healthy subjects (Controls 1, 2, 4, and 5) and for 12 untreated SCID mice. FIG. 15 reports the results of the assays performed with the carcasses of individual mice. Significant amounts of AChR complexed by human Ab were observed, as compared with the background values determined in the carcasses of untreated SCID mice, in 33 of the 51 mice (65%) engrafted with BL from MG patients. None of the mice engrafted with BL from healthy subjects yielded results significantly different from the background values observed in non-engrafted SCID mice. The background concentration in untreated SCID mice was 2.21±0.7 fmol/g of muscle. The average concentration in mice engrafted with control BL was 2.28±0.68 fmol/g of muscle. The average concentration in mice engrafted with BL from MG patients was 4.12±2.24 fmol/g of muscle. The difference between this value and those found in non-engrafted mice or in mice engrafted with control BL was highly significant ($p<4.8\times10^{-6}$ and $p<1.5\times10^{-6}$, respectively).

Table 4 summarizes the frequency of serum anti-AChR Ab and muscle AChR/Ab complexes after engraftment of BL from individual MG patients and healthy controls. The presence of anti-AChR Ab in the serum and even in muscle did not always correlate with development of muscle weakness. For example, all mice transplanted with BL from Patients 3, 5, 6, 9, 11, and 17 developed muscle weakness. Yet none of the mice engrafted with BL from Patients 3, 5, 6, and 9, only one of three mice engrafted with BL from Patient 11 and three of four mice engrafted with BL from Patient 17 had significant amounts of anti-AChR Ab in their serum. Several of those mice had significant amounts of anti-AChR Ab bound to muscle, others did not. Notice that several mice engrafted with BL from Patients 8, 12, 13, and 17, that had muscle weakness detectable by the inverted grid test, or overt EAMG symptoms, died overnight (see Table 4). These carcasses were not used for the assay.

Three of the seven mice engrafted with BL from Patient 13, which is "Ab negative", had significant concentrations of human anti-AChR Ab in their sera. Four of the seven mice engrafted with BL from this patient were tested for presence of anti-AChR Ab in the muscle. One of them had significant concentrations of muscle AChR/human Ab complexes.

Mice engrafted with BL from healthy subjects never had anti-AChR Ab. SCID mice transplanted with BL from MG patients had human IgG at the neuromuscular junctions. Muscle sections from 21 mice engrafted with BL from 11 MG patients (Table 4) were tested for the presence of human IgG at the neuromuscular synapses. Double immunofluorescent staining with α-BTX to localize the synapses and with Ab against human IgG was used. The mice studied included mice those had measurable AChR/Ab complexes in their muscle extracts, selected among those engrafted with BL from Patients 3, 7, 8, 10, 11, 12, 13, and 17; and mice that did not have detectable AChR/Ab complexes in the muscle extracts, engrafted with BL from Patients 5, 6, and 9. Also one mouse engrafted with BL from Patient 13 that had detectable AChR/Ab complexes in the muscle extract was studied. Muscle sections from mice engrafted with BL from healthy subjects served as negative controls to determine the nonspecific staining for human IgG at the neuromuscular junction.

Figure 17A:
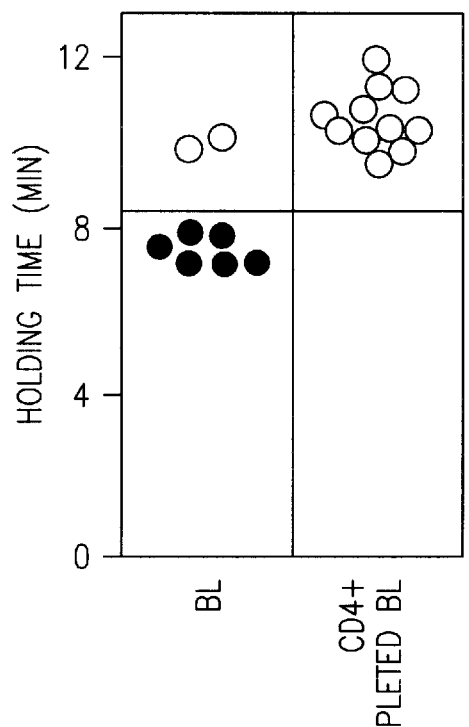
FIGS. 17A–C. CD4+ cells are necessary for transfer of MG symptoms and synthesis of human anti-AChR Ab. Eight SCID mice were engrafted with BL from Patients 16 to 19, and 11 mice with CD4+ depleted BL, obtained at the same time from the same patients. (A) Measurement of the mouse strength by the pancuronium sensitized inverted grid test. A dotted line indicates the time below which the mice were considered to have significant reduction of holding time (average holding time of SCID mice engrafted with BL from normal controls minus 2 SD). Black symbols indicate mice with a significantly shorter holding time as compared with the holding time of control mice engrafted with BL from healthy subjects. None of the mice engrafted with the CD4+ depleted BL developed myasthenic weakness, as measured by the holding time in the pancuronium sensitized inverted grid test. Six of the mice engrafted with BL from these patients had significantly reduced holding times. (B) Serum concentration of human anti-AChR Ab in SCID mice engrafted with BL or CD4+ depleted BL measured by RIPA. The black symbols indicate the presence of a significant Ab concentration; the white symbols indicate that no Ab was detected. All but one of the mice engrafted with BL and none of the mice engrafted with CD4+ depleted BL and significant amounts of human anti-AChR Ab in the serum. (C) Concentration of AChR/human Ab complexes in the muscle of SCID mice engrafted with BL or CD4+ depleted BL. The mice were killed 11 weeks after the engraftrent. the black symbols indicate the presence of a significant concentration of AChR/Ab complexes, the white symbols indicate that no AChR/Ab complexes were detected. Four of the mice engrafted with BL and none of the mice engrafted with CD4+ depleted BL had significant amounts of AChR/Ab complexes in the muscle.

All mice that tested positive in the solubilized AChR/Ab assay of muscle extract had human IgG at the neuromuscular junctions. They included a mouse engrafted with BL from the Ab-negative Patient 13. All but one of the mice that tested negative in the solubilized AChR/Ab assay of muscle extract, and all the mice engrafted with BL from healthy subjects did not have human IgG bound at their neuromuscular junctions. FIG. 17A reports sections obtained from a mouse engrafted with BL from a healthy subject and a mouse engrafted with BL from a healthy subject and a mouse engrafted with BL from Patient 2. These results are representative of those obtained with all negative sections and all positive sections, respectively.

CD4$^+$ cells are necessary for synthesis of anti-AChR Ab and transfer of MG symptoms. To determine whether CD4$^+$ cells are necessary for induction of myasthenic weakness, SCID mice were engrafted with BL, or CD4$^+$ depleted BL from Patients 16 to 19 (Table 3). The experiments described in this section do not include those done with the BL of same patients, using their BL only, whose results are discussed earlier and summarized in Table 4 and FIGS. 12 through 15.

Figure 17B:
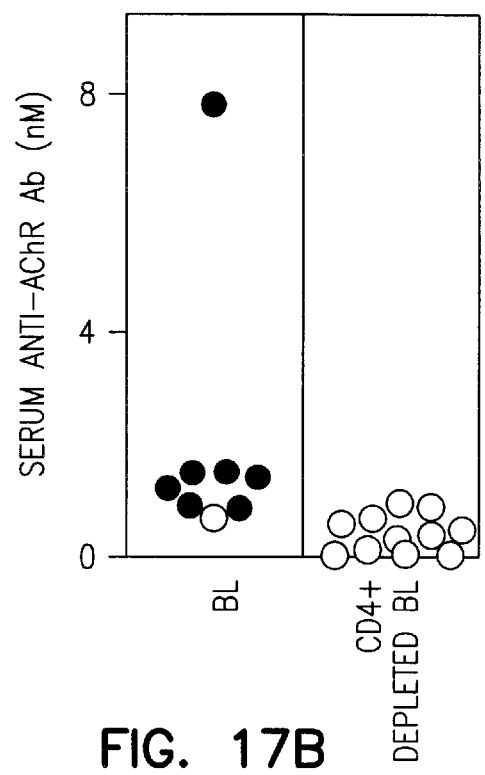
Figure 17C:
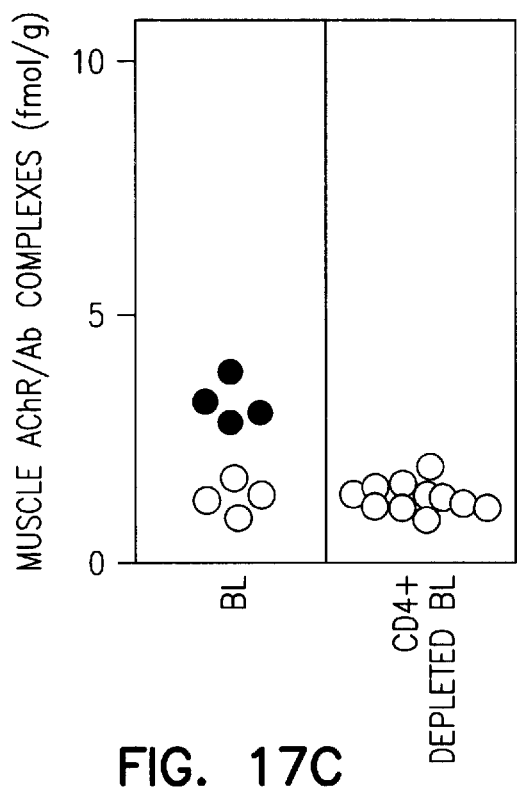

Follow-up of the mice was performed for 11 weeks. Their muscle strength was tested weekly using the pancuronium sensitized inverted grid test. Blood was obtained every second week. The sera obtained on week 5, 7, and 9 (when the human Ab are at a plateau) were pooled for each mouse and used to determine the presence of human IgG and anti-AChR Ab. At the end of the observation period the mice were killed and the concentration of AChR/human Ig complexes in their muscle extract determined. Six of the eight mice engrafted with BL from these patients, and none of the 11 mice engrafted with their CD4$^+$ depleted BL, had significantly shortened holding times (FIG. 17). All but one of the mice engrafted with BL had significant concentrations of anti-AChR Ab in the serum, and four of them had measurable amounts of anti-AChR Ab bound to the muscle AChR (FIG. 17). Engraftment of CD4$^+$ depleted BL resulted in concentrations of human IgG in the sera (0.045±0.041 mg/mL, n=11) that were significantly lower than those observed in mice engrafted with BL from the same patients (1.0±1.54 mg/mL, n=8; p<0.05). Mice engrafted with CD4$^+$ depleted BL never had anti-AChR Ab in the serum or muscle (FIG. 17).

CDS8$^+$ cells are not necessary for synthesis of anti-AChR Ab and transfer of MG symptoms. To determine whether induction of myasthenic weakness in SCID mice requires CD8$^+$ cells, BL and CD8$^+$ depleted BL obtained from Patient 4 were used. The cells were obtained at a time when he had class IV MG symptoms, and engraftment of his BL into SCID mice consistently resulted in myasthenic weakness (Table 5). The experiments described in this section do not include those conducted using the BL only, whose results are described earlier, and in Table 4 and FIGS. 12 through 15.

Three SCID mice were engrafted with BL, and four mice with CD8$^+$ depleted BL. Follow-up of the mice was performed for 12 weeks. Weekly, the mice were tested for muscle strength using the pancuronium sensitized inverted grid test: all mice developed significant weakness. The three mice engrafted with BL had holding times of 7.1±1.5, 7.2±2.1, and 5.6±0.8 minutes, respectively. Blood was obtained every second week. For each mouse, the concentration of human anti-AChR Ab in the pool sera obtained on week 5, 7, and 9 was determined. The mice engrafted with CD8$^+$ depleted BL had concentrations of anti-AChR Ab (9.9, 7.9, 6.2 and 8.2 nM, respectively) that compared with or exceeded those observed in the mice engrafted with the BL from this patient.

CD4$^+$ cells specific for "universal" a subunit epitopes drive the synthesis of pathogenic anti-AChR Ab and permit transfer of MG symptoms. To test whether the CD4$^+$ cells that recognize the universal epitopes of the AChR α subunit can drive the synthesis of pathogenic anti-AChR Ab, SCID mice were engrafted with CD4$^+$ depleted BL from Patient 16, and with CD4$^+$ depleted BL supplemented with individual CD4$^+$ T cell lines propagated from this patient, and specific for the universal AChR epitope sequences, α48-67, α304-322, and α419-437. Mice engrafted with CD4$^+$ depleted BL from Patient 16 supplemented with CD4$^+$ lines specific for TTD or DTD served as controls for unspecific effects resulting from the presence of activated CD4$^+$ cells. Also, five mice engrafted with the BL from this patient served as positive controls for the effectiveness of the transfer of myasthenic weakness and of the synthesis of human anti-AChR Ab. Follow-up of the mice was performed for 12 weeks. Weekly, their strength was measured by the pancuronium sensitized inverted grid test, and every second week their serum anti-AChR Ab concentration was measured by RIPA. At the end of the observation the mice were killed and the concentration of muscle AChR complexed by human Ab measured. In some mice, including all four mice engrafted with CD4$^+$ depleted BL plus a CD4$^+$ line specific for TTD or DTD, the presence of human Ab at the neuromuscular junction was examined by histochemistry.

Figure 18:
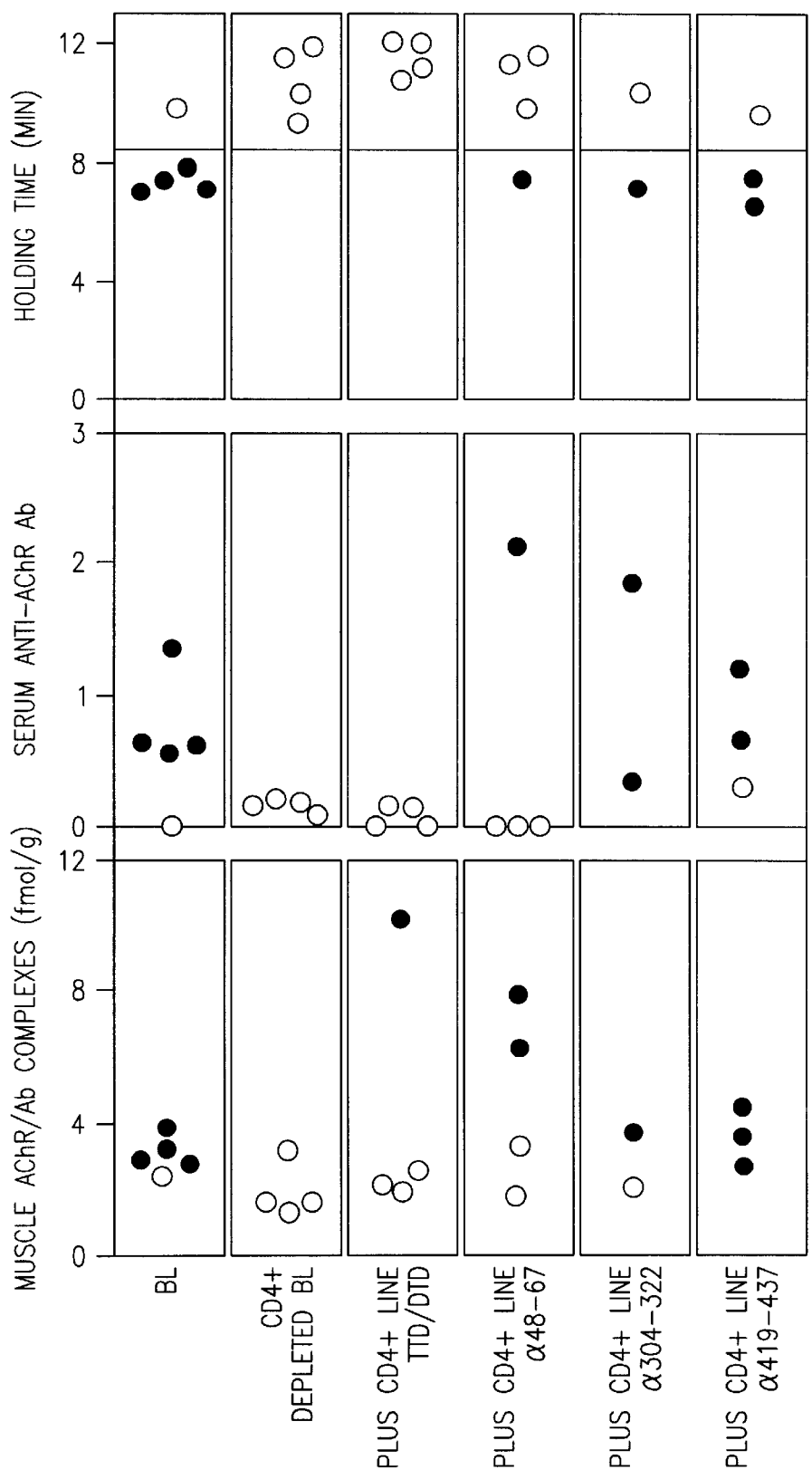
FIG. 18. Results for SCID mice engrafted with CD4+ T cell lines specific for universal epitopes of AChR.
Figure 19A:
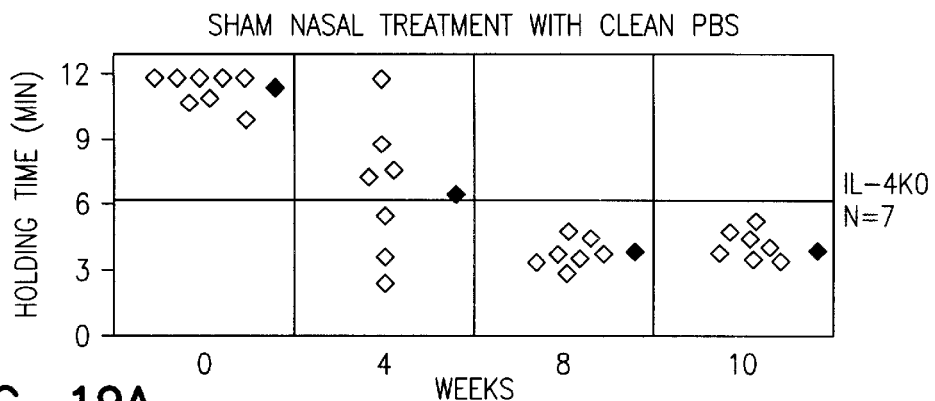
FIGS. 19A–D. IL-4 KO mice are more susceptible to EMG than wild type B6 mice, and are not protected from EMG by nasal administration of synthetic TAChR CD4+ epitopes. Strength of IL-4 KO and B6 mice, as indicated at the right side of the panels, measured by the pancuronium-sensitized hanging test. The mice were sham-treated nasally with clean PBS (top two panels) or treated nasally with the a epitope pool (bottom two panels), and immunized with TAChR. The tests were carried out just before the first TAChR immunizing injection (panels "0 weeks"), and four, eight and ten weeks after beginning of the inmmunization, as indicated below the panels. The horizontal lines indicate a holding time of 6.2 minutes (the holding time of normal mice minus two standard deviations). Mice with holding time of 6.2 minutes or less were considered to have EMG. The average holding time of the different groups of mice is indicated by black diamonds.
Figure 19B:
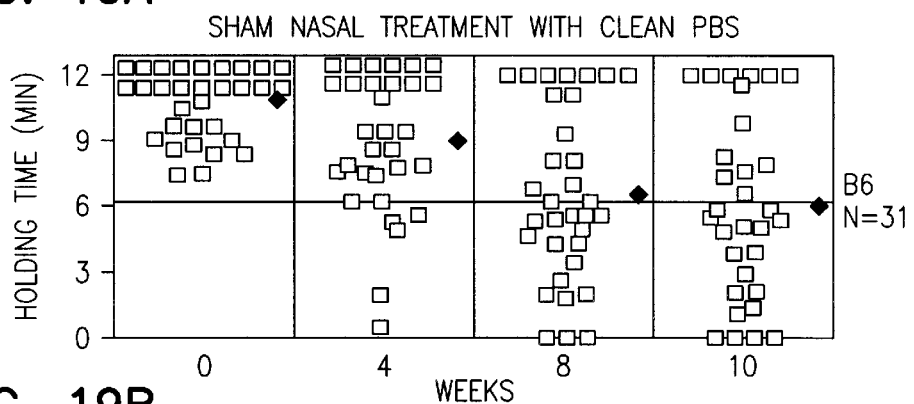
Figure 19C:
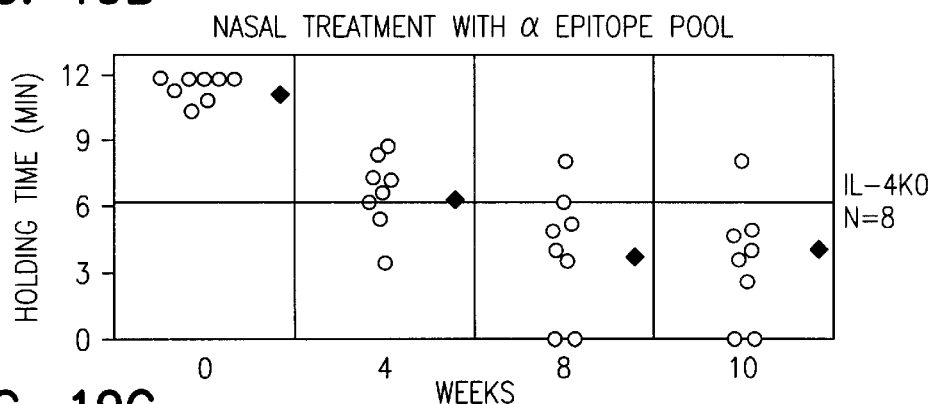
Figure 19D:
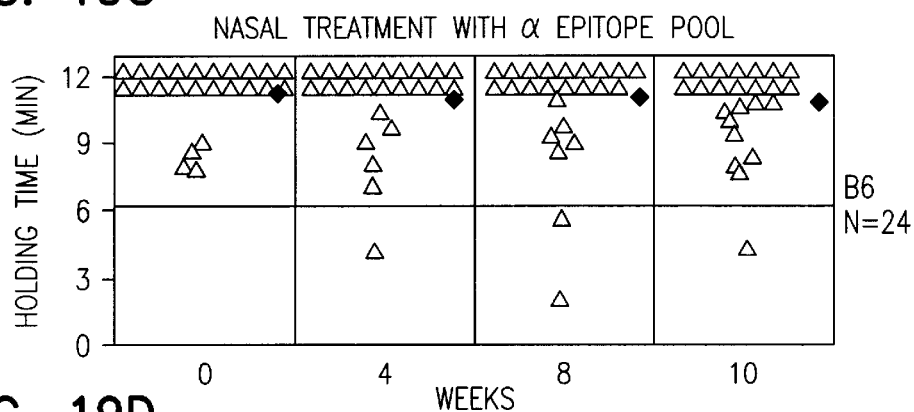

FIG. 18 summarizes the results. Four of the five mice engrafted with BL had significant weakness, serum anti-AChR Ab, and muscle AChR/human Ab complexes. None of the four mice engrafted CD4$^+$ depleted BL or the four mice engrafted with CD4$^+$ depleted BL plus a CD4$^+$ line specific for TTD or DTD developed weakness or serum anti-AChR Ab. However, one of them had AChR/human Ab complexes in the muscle.

One of the four mice engrafted with CD4$^+$ depleted BL plus CD4$^+$ cells specific for peptide α48-67 developed muscle weakness and had human anti-AChR Ab in the serum and bound to its muscle AChR. A second mouse that did not have detectable weakness or serum Ab had significant amounts of AChR Ab complexes in the muscle.

One of the two mice engrafted with CD4$^+$ depleted BL plus CD4$^+$ cells specific for peptide α304-322 developed muscle weakness and had human anti-AChR Ab in the serum and bound to muscle AChR. The second mouse had modest but significant concentrations of serum anti-AChR Ab but normal holding times.

Three mice were engrafted with CD4$^+$ depleted BL plus a CD4$^+$ line specific for peptide α419-437. Two of them developed myasthenic weakness and had human anti-AChR Ab in the serum and bound to muscle AChR. The third mouse had modest but significant concentrations of muscle AChR/human Ab complexes, despite undetectable serum anti-AChR Ab and normal holding times.

The human Ig bound to muscle of SCID mice reconstituted with CD4$^+$ depleted BL supplemented with CD4$^+$ cell lines specific for the universal AChR epitopes was located at the neuromuscular junctions, as detected by double immunoflourescent staining with a α-BTX and anti-human Ig Ab. None of the four mice engrafted with CD4$^+$ depleted BL plus CD4$^+$ cells specific for TTD or DTD had human Ig at the neuromuscular junctions. FIG. 16B reports representative sections obtained from a mouse engrafted with CD4$^+$ depleted BL plus an anti-AChR CD4$^+$ line (specific for rpeptide α304-322) or a control CD4$^+$ line (specific for TTD).

Discussion. This study demonstrates that engraftment intraperitoneum of SCID mice with BL from MG patients reproduces the essential clinical and immunologic characteristics of MG. Most mice engrafted with BL from MG patients, but none of the mice engrafted with BL from healthy controls, developed a reduction of the muscle strength (FIG. 12), which could be reversed transiently by a cholinesterase inhibitor. Also, most of those mice, but none of the mice engrafted with BL from healthy subjects, developed human anti-AChR Ab in the serum and had muscle AChR complexed by human Ab at the neuromuscular junction (FIGS. 14 through 16).

Appearance of muscle weakness did not correlate always with the presence of anti-AChR Ab in the serum and of AChR/Ab complexes in the muscle. The presence of serum anti-AChR Ab and of AChR/Ab complexes in the muscles was not always predictive of reduction in the muscle strength. For example, mice engrafted with BL from Patients 7 and 14 did not develop significant weakness, yet all of them had significant titers of human anti-AChR in the blood, and all but one had human Ab bound to muscle AChR (Table 4). These results suggest that Patients 7 and 14 may synthesize primarily nonpathogenic anti-AChR Ab. This finding agrees with the lack of correlation between anti-AChR Ab titer in the serum of MG patients and the severity of their symptoms. Also, the presence of Ab in the mouse serum was not always predictive of the presence of AChR/Ab complexes in the muscle. For example, mice engrafted with BL from Patients 2 and 3 did not have any detectable serum anti-AChR Ab, yet three of them had detectable AChR/Ab complexes in muscle. All mice engrafted with BL from Patients 3 and 10, and none of those engrafted with BL from Patient 2, developed MG symptoms.

These data are reconciled in a model in which the BL from Patients 2, 3 and 10 secreted small amounts of high affinity anti-AChR Ab that all bound to the muscle AChR, leaving no anti-AChR Ab in the sera. Binding of muscle AChR by the Ab from Patients 3 and 10 impaired the neuromuscular transmission were the Ab from Patient 2 did not. SCID mice engrafted with BL from all these patients had comparable concentrations for muscle AChR/Ab complexes (4.8±0.56 and 4.4±6.6 fmol/g for Patient 2; 4.1±0.8 and 4.8±1.9 fmol/g for Patient 3; 3.6±1.5, 4.8±1.5, 3.9±0.5, and 5.2±0.9 fmol/g for Patient 10). Thus, the Ab secreted by the BL of Patient 2 were less pathogenic than those secreted by the BL of Patients 3 and 10.

A different pattern in the mice engrafted with BL from Patients 5, 6, and 9 (Table 4) was observed. All mice engrafted with BL from these patients developed significant myasthenic weakness, yet they did not have measurable concentrations of human anti-AChR Ab in their sera, or complexed to their muscle AChR. This discrepancy is reconciled considering that the main pathogenic mechanisms of anti-AChR Ab are accelerated destruction of AChR molecules cross-linked by the Ab and complement-mediated destruction of the postsynaptic membrane containing the AChR/Ab complexes. In either case, the binding of pathogenic Ab results in disappearance of the AChR/Ab complexes. Thus, the BL from Patients 5, 6, and 9 appear to have synthesized small amounts of highly pathogenic, high affinity Ab that bound to the muscle AChR and were removed from the serum. Further, the binding of those Ab to the muscle AChR effectively caused destruction and disappearance of the AChR/Ab complexes, resulting in the paradoxical absence of measurable muscle AChR/Ab complexes in mice with significant myasthenic weakness. The findings that Patient 5 had class IV disease, yet he had extremely low serum concentrations of anti-AChR Ab, support this model. Patient 6 had a serum anti-AChR Ab concentration of 10.6 nM 22 months after this experiment (Table 5).

In summary, although the aggregate data observed in the SCID mice engrafted with BL from MG patients clearly indicate the feasibility of transferring MG symptoms and ability to synthesize human anti-AChR Ab, detailed examination of the effects resulting from engraftment of BL from individual patients shows different patterns. All of them are consistent with the observed lack of correlation between anti-AChR Ab titer and symptom severity in MG patients, with the complex repertoire of anti-AChR Ab, and with the mechanisms of their pathogenic effects. The appearance of a significant deficit of muscle strength, rather than the appearance of anti-AChR Ab or their concentration, seems to provide the most reliable assessment of the pathogenic potential of the engrafted BL.

The ability of the BL to induce significant muscle weakness and synthesis of human anti-AChR Ab in the engrafted mice was donor dependent. For most patients, either most or all of the mice engrafted during a given experiment developed weakness, or none of them did (Table 4). However, for some patients (1, 8, and 15, only 25 to 50% of the engrafted mice developed significant weakness (Table 4). The variable rate of survival of engrafted BL and the resulting variations in the amount of human Ab produced may explain the occasional inconsistency in the appearance of muscle weakness in mice engrafted with BL from the same patient.

The relationships that existed between appearance of muscle weakness and presence of anti-AChR Ab in the sera and muscle of the engrafted mice were complex and varied. Yet, a close correlation between the severity of the patient's symptoms and the ability of the engrafted BL to cause muscle weakness was observed (Table 5). The frequency of the affected mice was the same when the BL were obtained at times when the disease class was unchanged. Conversely, that frequency was higher when the BL were obtained at times when the symptoms were more severe. This is well exemplified by the results obtained in Patients 4, 15, and 17. All the engrafted mice developed a reduction of the muscle strength when the patients had class IV disease, but they were never affected when the patients had class II disease. BL from Patient 14 never caused muscle weakness, irrespective of the disease stage.

The good correlation between severity of the patient's symptoms and ability of the engrafted BL to transfer the disease suggests that activated anti-AChR T and B cells are especially abundant in the blood during acute phases of the disease. This agrees with the results of previous longitudinal studies on the response of T cells from MG patients to AChR Ag and on the fluctuations of the anti-AChR Ab titer in the same patients. Those studies found that the extent of the T cell response correlated with the severity of the disease (Manfredi et al., 1992; Wang et al., 1997) Also, studies on the changes over several years in the serum anti-AChR Ab concentration of the same group of MG patients found a correlation with the changes in the disease severity, despite the lack of correlation between Ab concentration and disease severity among different patients (Besinger et al., 1983). These findings support the possibility that fluctuations in the level of anti-AChR T and B cell activation correlate with the severity of the symptoms. The finding that SCID mice engrafted with BL from MG patients developed higher serum concentrations of human IgG and IgM than mice engrafted with BL from healthy subjects (FIG. 13) indicates the presence in the blood of MG patients of more abundant activated immune cells than in normal humans. This might be related to the presence of activated autoimmune T and B cells, either directly or indirectly, through the action on non-autoimmune cells of secreted cytokines.

One of the patients studied (Patient 13) was "Ab negative," namely anti-AChR Ab could not be detected in her sera. Yet, six of the seven mice engrafted with her BL had significant weakness, and three had serum anti-AChR Ab (Table 4). Also, a previous study found that BL from a patient without detectable serum Ab to human AChR, engrafted into SCID mice, produced anti-AChR Ab capable of causing damage of the mouse endplate (Martino et al., 1993). Those authors suggested that fluctuations of the function of and idiotypic-antiidiotypic network and suppressor mechanisms that were poorly transferred into the SCID mice might explain this unexpected finding. Another possible explanation is that, as it occurs in SCID mice that have myasthenic weakness without measurable serum anti-AChR Ab, Patient 13 might synthesize small amounts of high affinity Ab that would bind the AChR even at very low concentrations, and thus disappear from the serum. The small structural differences between the AChR expressed in human and mouse muscle, and the resulting different characteristics of the binding of the same Ab to those different AChR, might explain why three of the six affected mice engrafted with BL from Patient 13 had anti-AChR Ab left in the serum. The ability of engrafted BL to induce myasthenic weakness in SCID mice might be a useful diagnostic test for those patients who do not have detectable anti-AChR Ab in the serum and have electromyographic and clinical symptoms of MG.

Previous studies demonstrated the pivotal role of AChR-specific $CD4^+$ cells in rat EMG, using an in vivo cell transfer model: adoptive transfer into sublethally irradiated, thymectomized rats of a mixture of B cells and $CD4^+$ T cells from rats immunized with AChR caused synthesis of anti-AChR Ab and EAMG symptoms, whereas transfer of B cells alone did not (Hohlfield et al., 1982) The present study proves also in human MG that $CD4^+$ cells, and specifically anti-AChR $CD4^+$ cells, are necessary for production of pathogenic anti-AChR Ab. SCID mice engrafted with $CD4^+$ depleted BL, or $CD4^+$ depleted BL supplemented with $CD4^+$ cells specific for TTD or DTD never developed anti-AChR Ab or reduction of the muscle strength (FIGS. 17 and 18). The finding that SCID mice engrafted with $CD4^+$ depleted BL supplemented with $CD4^+$ cells specific for universal AChR epitopes verifies that synthesis of pathogenic anti-AChR Ab involves primarily AChR-specific $CD4^+$ cells (FIGS. 16B and 18).

The existence of universal, immunodominant epitopes on the AChR α subunit has been deduced from the response of $CD4^+$ cells in vitro to synthetic peptides (Protti et al., 1990; Manfredi et al., 1992; Wang et al., 1997). In principle, a proliferative response in vitro of $CD4^+$ cells to AChR sequences might not indicate a pathogenic role in vivo of the cells recognizing those epitopes. Also, synthetic AChR peptides might be processed differently than the native AChR molecule and yield epitopes that are not representative of those recognized in vivo by the autoimmune anti-AChR $CD4^+$ cells involved in anti-AChR Ab synthesis. The experiments reported in FIGS. 16B and 18 dispel the above concerns. They demonstrate that $CD4^+$ cells recognizing the synthetic universal epitope sequences α48-67, α304-322, and α419-437 can drive the synthesis of pathogenic Ab and can restore the ability of $CD4^+$ depleted BL to transfer MG symptoms. The frequency of muscle weakness and anti-AChR Ab in mice engrafted with $CD4^+$ depleted BL plus the AChR-specific $CD4^+$ lines was lower than that in mice engrafted with the BL from the same patient (FIG. 18). This finding might be because the BL include a variety of anti-AChR $CD4^+$ cells, specific for a broad repertoire of B cells. Conversely, the $CD4^+$ depleted BL reconstituted with an anti-AChR cell line included $CD4^+$ cells specific for a single epitope sequence.

The present results support the prevailing notion that $CD8^+$ cells are not crucial for pathogenesis of MG. However, because the experiments conducted with $CD8^+$ depleted BL were with one patient only, these results do not exclude that in some MG patients $CD8^+$ cells might also have a pathogenic role.

The SCID mice used here, or other mutants with severe immunodeficiency, are suitable for passive transfer of human and experimental autoimmune diseases, including rheumatoid arthritis, autoimmune hair loss, experimental autoimmune encephalomyelitis, and diabetes (in SCID mice). The present study indicates that the SCID system is suitable also to transfer myasthenic symptoms. Thus it will be useful to study the effects of manipulations of the engrafted human cells on the transferred myasthenic syndrome. Also, this study demonstrates that this system can be used to study the ability of autoimmune $CD4^+$ cells of defined epitope specificity to drive the synthesis of auto Ag-specific Ab and therefore quantify their pathogenic potential.

EXAMPLE III

Il-4 Deficiency Facilitates Development of Fxperimental Myasthenia Ciravis $CD4^+$ cells comprise Thl and Th2 cells, that differ in their finction and in the cytokines they secrete (Abbas et al., 1996; Romagnani, 1997; Weigle and Romball, 1997). Thl cells mediate effector functions of the immune response. They secrete pro-inflammatory cytokines, such as IFN-γ, TNF and interleukin (IL)-2, can be cytotoxic and help the synthesis of IgG subclasses that bind complement. Th2 cells help the synthesis of antibodies that do not bind complement, such as IgE, IgG4 in humans and its homologue in mice, IgG1. Also, they modulate immune responses by secreting anti-inflammatory cytokines, like IL-4 and IL-10, that down-regulate the finction of antigen-presenting cells (APC) and Th1 cells.

Th1 cells have been implicated in the pathogenesis of T cell mediated autoimmune diseases, and Th2 cells in their down-regulation (Miller and Karpus, 1994; Racke et al., 1994; Liblau et al., 1995; Cua et al., 1995; Cong-Qui and Londei, 1996; Abbas et al., 1996; Tian et al., 1996; Mueller et al., 1996; Romagnani, 1997; Weigle and Romball, 1997; Prabhu Das et al., 1997; Falcone and Bloom, 1997; Shaw et al., 1997; von Herrath and Oldstone, 1997; O'Garra, 1998). However, Th2 cells may also cause T cell mediated autoimmune diseases (Anderson et al., 1993; Ferber et al., 1996; Hultgren et al., 1996; Willenborg et al., 1996; Lee et al., 1996; Pakala et al., 1997; Lafaille et al., 1997; Manoury-Schwartz et al., 1997; Vermeire et al., 1997), and TGF-β, a cytokine secreted by modulatory T cells that may represent a distinct T cell lineage, may protect from experimental autoimmune responses (O'Garra et al., 1997; Hafler et al., 1997). Thus, in T cell mediated autoimmune diseases both Th2 and Th1 cells, and the cytokines they secrete, may have effector or down regulatory functions, or both.

Both Th1 and Th2 cells may be implicated in antibody-mediated autoimmune disease. Thl cells help synthesis of antibodies able to fix complement (Abbas et al., 1996; Romagnani, 1997; Weigle and Romball, 1997, O'Garra, 1998), that would be especially effective in causing tissue damage. For example, in MR1/Ipr mice deposits of IgG and complement activation cause autoimmune glomerulonephritis, and expression of IFN-γ is necessary for the development of autoimmune glomerulonephritis (Hass et al., 1997). Because of their effective T helper function, also Th2 cells may be involved in antibody-mediated autoimmune diseases (Erb et al., 1997; Fuss et al., 1997;

Nakajima et al., 1997; Peng et al., 1997). However, Th2-induced antibodies do not fix complement or bind the phagocyte Fc receptor (Abbas et al., 1996; Romagnani, 1997; Weigle and Romball, 1997; O'Garra, 1998), and are unlikely to cause severe tissue injury.

Th1 cells may have a roll in the pathogenesis of MG and EMG. MG patients had AChR-specific Th1 cells (Moiola et al., 1994a,b; Wang et al., 1997). Transgenic mice that produced IFN-γ at the neuromuscular junction developed functional disruption of the junction and clinical weakness reminiscent of MG (Gu et al., 1995), and mice deficient in IFN-γ appeared to be resistant to induction of EMG (Balasa et al., 1997). Mice deficient in IL-12 —a cytokine necessary for the development of Th1 responses—were resistant to EMG induction, whereas administration of IL-12 at the time of immunization with AChR facilitated EMG development (Moiola et al., 1998). On the other hand, Th2 cells may have a modulatory role in EMG. Nasal or subcutaneous administration to C57B1/6 (B6) mice of synthetic AChR peptides forming CD4$^+$ epitopes activated Th2 cells specific for the peptides administered, caused reduced synthesis of anti-AChR antibodies, and prevented EMG (Example I; Example IV; Wu et al., 1997).

Induction of EMG in B6 mice requires multiple AChR injections, and the frequency of EMG is 20–70% even after prolonged AChR immunization. IL-4 knock out (KO) mice have an effective Th1 function, but a severely impaired Th2 ftnction. Their CD4$^+$ cells do not express other Th2 cytokines, and they have very low amounts of Th2-driven IgGI in the serum (Lawrence et. al., 1995). The defective Th2 cell activity in IL4 KO mice agrees with the demonstration obtained in studies in vitro, that IL-4 is essential for the generation of Th2 responses (Le Gros et al., 1990; Swain et al., 1990). IL-4 KO mice of B6 background are an excellent model system to investigate the role of IL-4, and indirectly that of Th1 and Th2 cells, in the pathogenesis and prevention of EMG.

Materials and Methods

Mice. B6 and IL-4 KO mice of B6 background (Jackson Laboratory, Bar Harbor, Me.) were housed at the animal facility of the University of Minnesota. Purification of Torpedo AChR. TAChR was purified from *Torpedo californica* electric organ as alkali-stripped TAChR-rich membrane fragments (Bellone et al., 1991). The protein concentration was measured by the Lowry assay (Lowry et al., 1970) and the TAChR concentration as α-bungarotoxin (αBTX) binding sites (Bellone et al., 1991). The TAChR preparations contained 3.8–5.8 nmols of sites/mg protein. The protein composition was assessed by sodium dodecyl sulfate polyacrylamide gel electrophoresis (Laemmli, 1970): the TAChR preparations contained only the four TAChR subunits as the main protein bands. For use in cell cultures, the TAChR-rich membrane fragments were diluted in RPMI-1640 as needed, and sterilized them by ultraviolet irradiation. For immunization and antibody assay, the membranes were solubilized in 1% Triton X-100 (Bellone et al., 1991), diluted them to 0.5 mg/ml in PBS and stored them at $-80°$ C.

Peptide Synthesis and Characterization. Four panels of overlapping peptides were used, about 20 residues long, spanning the sequences of the TAChR α, β, γ and δ subunits, and synthesized as described in Houghten (1985). They overlapped by approximately 5 residues. For proliferation assays, the peptides were used as roughly equimolar pools of all the peptides spanning the sequence of one TAChR subunit. The a subunit peptides were also used individually. For proliferation assays, peptide solutions in PBS, that had been sterilized by ultraviolet irradiation and stored frozen, were used.

Three α subunit sequence regions, corresponding to residues 150–169, 181–200 and 360–378 are dominant for sensitization of the anti-TAChR CD4$^+$ cells in B6 mice (Bellone et al., 1991a; Bellone et al., 1993; Karachunski et al., 1995). These peptides are indicated with codes that include Tα for TAChR α subunit and two numbers, referring to the position on the α subunit sequence of the first and last residues of the peptide. These peptides were used for nasal tolerization procedures. The peptides were routinely characterized them as follows: by reverse-phase high pressure liquid chromatographic analysis of the peptides on a C18 column (Ultrasphere ODS, Beckman, Fullerton, Calif.) and a gradient of acetonitrile in 0.1% trifluoroacetic acid in water. One main peak of optical density was consistently found. The amino acid composition of the peptides was verified by derivatization of the amino acid residues released by acid hydrolysis with phenylisothiocyanate, followed by separation on a reverse-phase high pressure liquid chromatography column. The results of the amino acid composition corresponded closely to the expected theoretical values. The sequence and purity of some randomly selected batches of peptides was verified by mass spectrometry. For all peptides, a major peak of the expected molecular weight was found.

Immunzations. Eight-ten week old mice were immunized by subcutaneous injections, along the back and at the base of the tail, of solubilized TAChR (25 μg in 100 μl PBS) emulsified with an equal volume of complete Freund adjuvant. The mice were boosted twice at four week intervals with the same amount of TAChR emulsified in incomplete Freund adjuvant.

Nasal Administration of Synthetic TAChR CD4$^+$ Epitopes. The mice were anesthetized by intraperitoneum injection of Ketaset (100 mg/kg; Alveco Co., Inc., Fort Dodge, Iowa), and instilled into the mouse nostrils 25 μl of phosphate buffered saline solution PBS: 10 mM Na phosphate buffer, pH 7.4, 2.7 mM KCl, 137 mM NaCl) containing 50 μg of each of peptides Tα150-169, Tα181-200 and Tα360-378 (referred to as "α epitope pool"). Control mice received clean PBS. The α epitope pool or clean PBS was administered weekly, starting two weeks before beginning of the TAChR immunization, for a total of 12 treatments.

Evaluation of Clinical Symptoms of EMG. The symptoms of EMG were quantified using a forced exercise by the inverted hang technique, sensitized by a minute amount of pancuronium bromide (0.03 mg/kg intraperitoneum), given just before the test (Karachunski et al., 1995). The mice hang from a grid, and the time it took for the mouse to release its hold and fall three times is measured ("holding time"). The mice are tested on the day of the first nasal administration, on the day before each immunization, and approximately 14 days after the third immunization, just before sacrificing the mice. The test is performed blindly, i.e., without knowledge of the treatment that the mouse had received. This test is parametric, and gives a quantitative assessment of the severity of the mouse weakness. To verify the myasthenic nature of the weakness edrophonium chloride was injected (Reversol, Organon Inc., West Orange, N.J.) intraperitoneum. Reversol is a cholinesterase inhibitor, and it immediately increased the strength of the mice.

The holding time of normal mice is 10.4±2.1 minutes (n=99) (Karachunski et al., 1995). The mice were considered myasthenic with holding times of 6.2 minutes (the holding time of normal mice minus two SD) or less. Normal mice never have holding times shorter than 6.2 minutes (FIG. 19, Example I and Karachunski et al., 1995). Paralyzed mice or mice that died of respiratory paralysis are represented in the figures as having holding time of zero.

Anti-AChR Antibody Assay. The sera was obtained after each clinical testing. The serum concentration of anti-TAChR antibody was measured by radioimmunoprecipitation assay, using TAChR solubilized in Triton X-100 and labeled by the binding of $^{125}$-α-bungarotoxin (α-BTX) (Bellone et al., 1993). The antibody concentration is expressed as μM precipitated $^{125}$I-α-BTX.

Assay of Anti-TAChR and Anti-peptide IgG Subclasses. The relative concentration of IgG subclasses of anti-TAChR and anti-peptide antibodies in the sera of peptide- and sham-treated mice was measured by ELISA after immunization with TAChR. Pooled sera from three-four mice that had received identical treatments was used. The sera used in this assay was obtained at the end of the observation period (10 weeks after beginning of the anti-TAChR immunization).

Ninety-six well plates (Nunc, Karstrup, Denmark) were washed extensively and incubated as follows: 4 hours with a 10 μg/ml solution of TAChR or of individual peptides Tα150-169, Tα181-200 and Tα360-378 in 0.1 M Na phosphate buffer, pH 9.5 (two wells for each antigen), 1 hr with PBS plus 3% bovine serum albumin (BSA), 2 hours with mouse serum (serial dilutions from 1:100 to 1:40,000 in PBS plus 3% BSA), 1 hr with a dilution 1:1000 in PBS plus 3% BSA of goat antibody specific for the total IgG, or IgG1, or IgG2a, or IgG2b or IgG3 (Mouse Monoclonal Isotyping Kit, Sigma, St. Louis, Mo.), and 30 minutes with a 1:3000 dilution of peroxidase-conjugate rabbit anti-goat IgG (Sigma) in PBS plus 3% BSA. The plates were washed, and developed them for 20–60 minutes with ABTS peroxidase substrate system (Kirkegaard & Perry Laboratories Inc., Gaithersburg, Md.). The reaction was stopped with a 1% solution of SDS in PBS. The OD was read at 405 nanometers.

This assay is qualitative, but it allows comparison of the relative amount of IgG subclasses within the same sample, and in different samples run simultaneously. To accomplish this, the OD values obtained within the linear range of the dose dependence curve were compared.

Detection of Anti-AChR IgG and Mouse Complement Bound to Muscle AChR by Immunofluorescence Microscopy. The hind limb muscle of naive, peptide- and sham-treated IL-4 KO mice were frozen in liquid nitrogen and stored at −70° C. The frozen tissue was embedded in O.C.T. Compound Tissue-TEK (Miles Laboratories Inc., Elkhart, Ind.) and sectioned it in the transverse direction into 10 μm sections using a Jung Frigout 2800E Kryostat (Leica, Nublach, Germany). The sections were incubated at room temperature in PBS for 10 minutes, and for 1 hour with a 1:200 dilution of goat anti-mouse IgG conjugated with biotin (Sigma) in PBS containing 3% BSA. The sections were washed with PBS for 15 minutes three times, and stained them for 1 hour at room temperature with Texas Red labeled a-BTX (Molecular Probes, Eugene, Oreg.), FITC labeled goat anti-mouse complement C3 antibody (Nordic Immunological Laboratories, Capistrano Beach, Calif.), and AMCA-S labeled streptavidine (Molecular Probes) diluted in PBS containing 3% BSA at 1:4000, 1:100 and 1:200 dilutions, respectively. The sections were washed three times for 15 minutes with PBS and viewed them in fluorescence microscopy (Nikon eclipse E 800, Japan). Digital images were collected using Image Pro Plus (Media Cybernetics, L. P., Silver Spring, Md.)

Lymphocyte Proliferation Assay. Two weeks after the last immunization, spleen cells (Bellone et al., 1991) were obtained from three identically treated IL-4 KO mice. The cells were pooled and depleted them in CD8$^+$ cells using paramagnetic beads and rat anti-mouse CD8$^+$ antibody (Pharmingen, San Diego, Calif.). The cells were suspended in RPMI-1640 (Gibco, Grand Island, N.Y.) supplemented with 10% heat inactivated fetal calf serum (Gibco), 50 μM 2-mercaptoethanol, 1 mM L-glutamine, 10 mM Hepes, 1 mM sodium pyruvate, 100 U/ml penicillin and 100 μg/ml streptomycin (×10$^6$ cells/ml). The cells were seeded in triplicate in 96 flat-bottom well plates (200 μl/well). One of the following antigens or stimulants was added: 10 μg/ml phytohemoagglutinine (PHA) (Sigma); 10 μg/ml TAChR; the pools of overlapping peptides spanning the α, β, γ, or δ subunit sequences (5 μg/ml) of each peptide); and 10 μg/ml of the individual a subunit peptides. Controls were triplicate wells cultivated without any antigen, or with or a 20-residue control peptide synthesized by the same method, unrelated to the TAChR sequence (10 μg). After four days the cells were labeled for 16 hours with $^3$H-thymidine (1 μCi per well, specific activity 6.7 Ci/mmol, Dupont, Boston, Mass.), and harvested (Titertek, Skatron, Sterling, Va.). The $^3$H-thymidine incorporation was measured by liquid scintillation.

Cytokine Secretion by CD8$^+$ Depleted Spleen Cells in Response to Stimiilation with TAChR. Two weeks after the last TAChR immunization CD8$^+$ depleted spleen cells were prepared from three identically treated mice, using the procedure described above. The CD8$^+$ depleted spleen cells were suspended at 5×10$^6$ cells/ml, and cultured with and without 10 μg/ml TAChR or α epitope pool (10 μg/ml of each peptide) in 24 well plates. In some experiment two independent cultures were set up for each antigen. Cells cultivated without any antigen served as controls for spontaneous secretion of cytokines. The culture supematants were harvested after 72 and 96 hours. The concentrations of IFN-γ, IL-2, IL-4 and IL-10 were measured by capture ELISA, using duplicate samples. Anti-IFN-γ, anti-IL-2, anti-IL4 and anti-IL-10 monoclonal and polyclonal antibodies were used, (Pharmingen), and recombinant IFN-γ, IL-2, IL-4 and IL-19 (Pharmingen) were used as standards, following the manufacturer's instructions.

Statistical Analysis. The significance of the differences of the average responses of two groups was determined using a two tailed students' t test.

Results

IL-4 KO Mice Had Increased Susceptihility to EMG. The top panels of FIG. 19 report the results from testing the strength of B6 and IL-4 KO mice sham-treated nasally with clean PBS, and immunized with TAChR. The results were obtained four, eight and ten weeks after beginning of the immunization. For each group the results obtained for the same mice before the TAChR immunization (panels "0 weeks") are also reported. The results obtained at eight and ten weeks were consistent. They reflect the maximum frequency of EMG symptoms that were observed. All IL-4 KO mice, and 58% of the wild type B6 mice developed EMG. FIG. 19 reports also the average holding time of the groups of mice used in these experiments (black symbols). Wild type B6 mice had significantly longer holding time than the IL-4 KO mice at eight weeks ($P > 0.001$) and ten weeks ($P > 0.03$).

Nasal Instillation of the a Epitope Pool Did Not Prevent EMG in IL-4 KO Mice. The bottom panels of FIG. 19 report the results obtained testing the strength of B6 and IL-4 KO mice treated nasally with the TAChR peptide epitopes, and immunized with TAChR. The results were obtained at four, eight and ten weeks after beginning of the immunization. The panels "0 weeks" report the results obtained for the same mice before the TAChR immunization. Among the 24 peptide-treated B6 mice, two mice (8%) had EMG symptoms at eight weeks and one (4%) at ten weeks, as compared to 58% of the sham-treated mice. Seven of the eight peptide-treated IL-4 KO mice (88%) had EMG weakness at eight and ten weeks.

FIG. 19 reports also the average holding time of the groups of mice used in these experiments (black symbols). B6 mice treated nasally with the a epitope pool had significantly (P>0.001) longer holding time than the sham-treated B6 mice. The average holding time of peptide-treated IL-4 KO mice was the same as the group that had inhaled clean PBS.

Nasal Treatment of IL-4 KO Mice with the a Epitope Pool Did Not Affect the Synthesis of Anti-TAChR Antibody. Using radioimmunoprecipitation assays, the anti-TAChR antibody concentration in the sera of B6 and IL-4 KO mice treated nasally with the $\alpha$ epitope pool or sham-treated with clean PBS, and immunized with TAChR, was measured. Sera was obtained at four, eight and ten weeks after the beginning of the TAChR immunization.

Figure 20A:
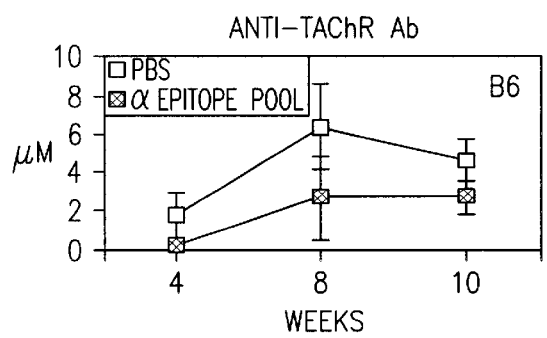
FIGS. 20A–D. Nasal treatment of IL-4 KO mice with the a epitope pool does not cause reduced synthesis of anti-TAChR antibodies or affect the synthesis of Th1-induced anti-TAChR antibodies. (A) Average anti-TAChR antibody concentration (±standard deviation), measured by radioimmunoprecipitation assay, in sera of B6 mice treated nasally with the α epitope pool (n=9) or sham-treated with clean PBS (n=10), and of IL-4 KO mice treated nasally with the α epitope pool (n=8) or sham-treated with clean PBS (n=7). The sera were obtained four, eight and ten weeks after the beginning of the immunization with TAChR, as indicated along the abscissa of the plots. (B) Relative amounts of anti-TAChR IgG of different subclasses, as indicated below the plots, expressed as percent of total anti-TAChR IgG of different subclasses, as indicated below the plots, expressed as percent of total anti-TAChR IgG, in sera from B6 and IL-4 KO mice, as indicated inside the plots. The mice had been treated nasally with the α epitope pool (black columns), or had been sham-treated with clean PBS (white columns). The sera were obtained ten weeks after the beginning of the immunization with TAChR.

In wild type B6 mice the nasal treatment with the synthetic CD4$^+$ epitopes reduced substantially the synthesis of anti-TAChR antibodies (FIG. 20A, top panel). Peptide- and sham-treated IL-4 KO mice had similar serum concentrations of anti-AChR antibodies, which were comparable to those of sham-treated wild type B6 mice (FIG. 20A, bottom panel).

Nasal Treatment of IL-4 KO Mice with the $\alpha$ Epitope Pool Did Not Affect the Synthesis of Th1-induced Anti-TAChR Antibodies. The effect of nasal treatment with the $\alpha$ epitope pool on the synthesis of Th1-dependent antibodies against the TAChR was investigated. The relative concentrations of total anti-TAChR IgG and of different anti-TAChR IgG subclasses, in the sera of peptide-treated and sham-treated IL-4 KO and B6 mice immunized with TAChR, was assessed by ELISA. The relative concentration of IgG subclasses synthesized with the help of Th1 (IgG2a and IgG2b, IgG3) or Th2 (IgG1) cells was determined. Sera was obtained at 10 weeks after beginning of the TAChR immunization.

Figure 20B:
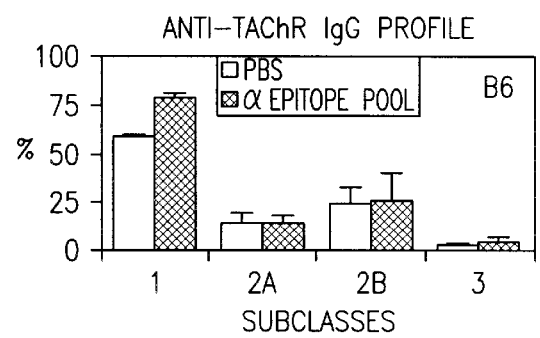
Figure 20C:
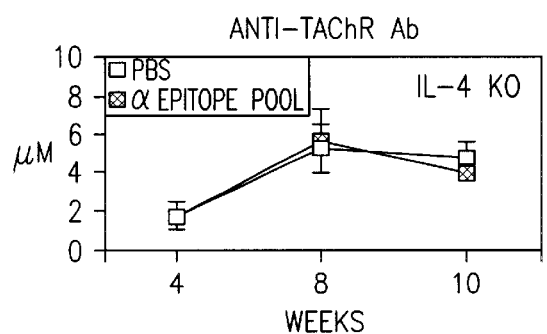
Figure 20D:
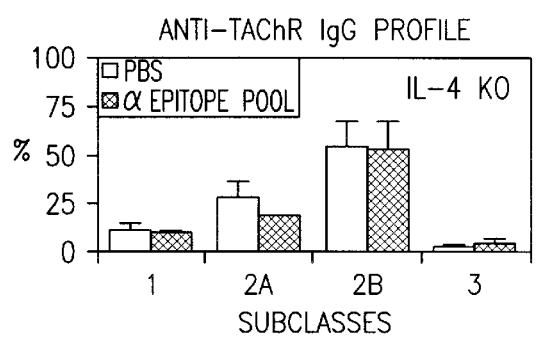

In agreement with the results of the radioimmunoprecipitation assays, the amount of total anti-AChR IgG was identical in sham- and peptide-treated IL-4 KO mice, whereas it was significantly and substantially reduced in the peptide-treated B6 mice as compared to the sham-treated B6 mice. FIG. 20B reports the results of one of three consistent experiments that assessed the relative concentrations of anti-TAChR IgG1, IgG2a, IgG2b and IgG3, using pooled sera from three-four mice that had received identical treatments. In B6 mice the relative concentration of Th1-dependent IgG subclasses were similar in peptide- and sham-treated mice, whereas the relative concentration of the Th2-driven anti-TAChR IgG1 was significantly (P<0.001) increased in the peptide-treated mice. This is likely related to synthesis of antibodies to the peptides administered (see below). Anti-peptide antibodies may cross-react with TAChR in ELISA because of the partial denaturation of the TAChR when absorbed onto the plastic plates (Conti-Fine et al., 1996). In IL-4 KO mice the relative concentrations of all IgG subclasses were the same in the peptide-treated and in the sham-treated mice. The IL-4 KO mice had substantial amounts of anti-TAChR IgG2a and IgG2b, that were lower than but comparable to the amount of total anti-TAChR IgG. This suggests that in IL-4 KO mice the anti-TAChR IgG are mostly IgG2a and IgG2b. The mice had minimal amounts of anti-TAChR IgG3. IL-4 KO mice had significantly less (P<0.0001) anti-TAChR IgGI than B6 mice. Synthesis of IgGI is both IL-4 and IL-2 dependent, and therefore IL-4 KO mice may still synthesize IgGI.

Figure 21A:
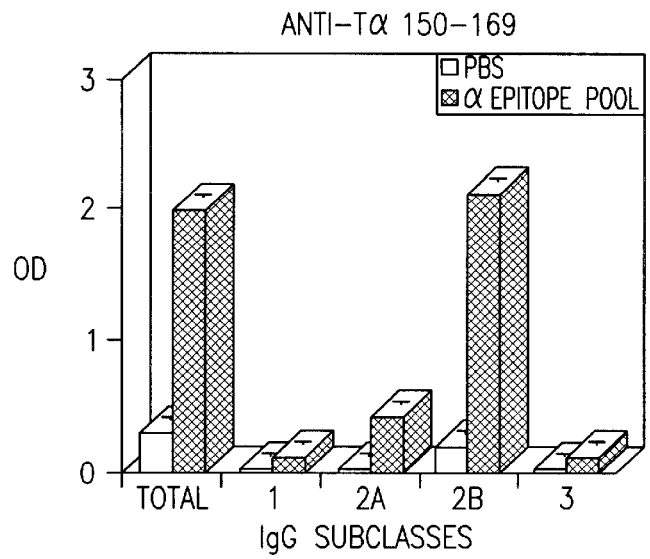
FIGS. 21A–C. Nasal treatment of IL-4 KO mice with the 60 epitope pool causes synthesis of Th1-induced IgG isotypes against the peptides administered. Concentrations of total IgG and of IgG different subclasses, as indicated below the plots, against the sequences Tα150-169, Tα181-200 and Tα360-378, as indicated above each panel, in sera of IL-4 KO mice treated nasally with the α epitope pool (black columns), or sham-treated with clean PBS (white columns). The columns represent the average±standard deviation of triplicate ELISA determinations, using pooled sera from three-four identically treated mice from each group. The sera were obtained ten weeks after beginning of the anti-TAChR immunization.
Figure 21B:
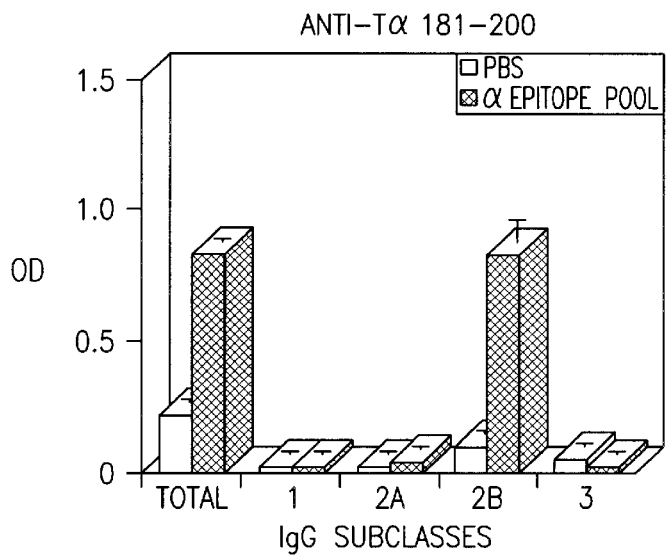
Figure 21C:
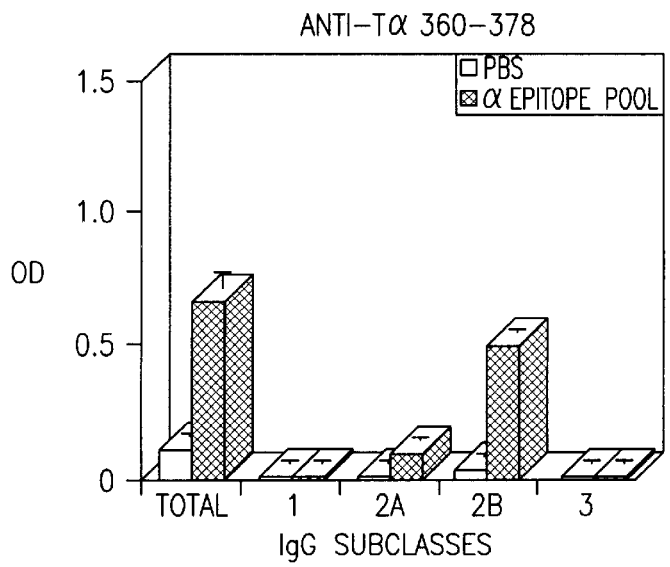

Synthesis of Th1 -induced Anti-Peptide Antibodies in Peptide-Treated IL-4-KO Mice. In B6 mice nasal instillation of the CD4$^+$ epitope peptides used here stimulated the synthesis of Th2-induced anti-peptide antibodies (Example I). To determine whether nasal treatment of IL-4 KO mice with the $\alpha$ epitope pool stimulated the synthesis of anti-peptide antibodies, the relative concentration of total IgG and of IgG subclasses against the three epitope peptides used for the nasal treatment was determined. Pooled sera of three-four mice that had been peptide- or sham-treated, and immunized with TAChR, was used. The sera was obtained 10 weeks after beginning of the TAChR immunization. FIG. 21 reports the results of one of two consistent experiments. Sham-treated mice had very little IgG antibodies reactive with the peptides. Nasal treatment with the a epitope pool caused synthesis of Th1-induced antibodies against each of the peptides administered. The antibodies were primarily or exclusively IgG2b. Peptides T$\alpha$150-169 and T$\alpha$360-378 elicited also a moderate synthesis of IgG2a. Th2-induced anti-peptide IgGI could not be detected in IL-KO mice.

Figure 22:
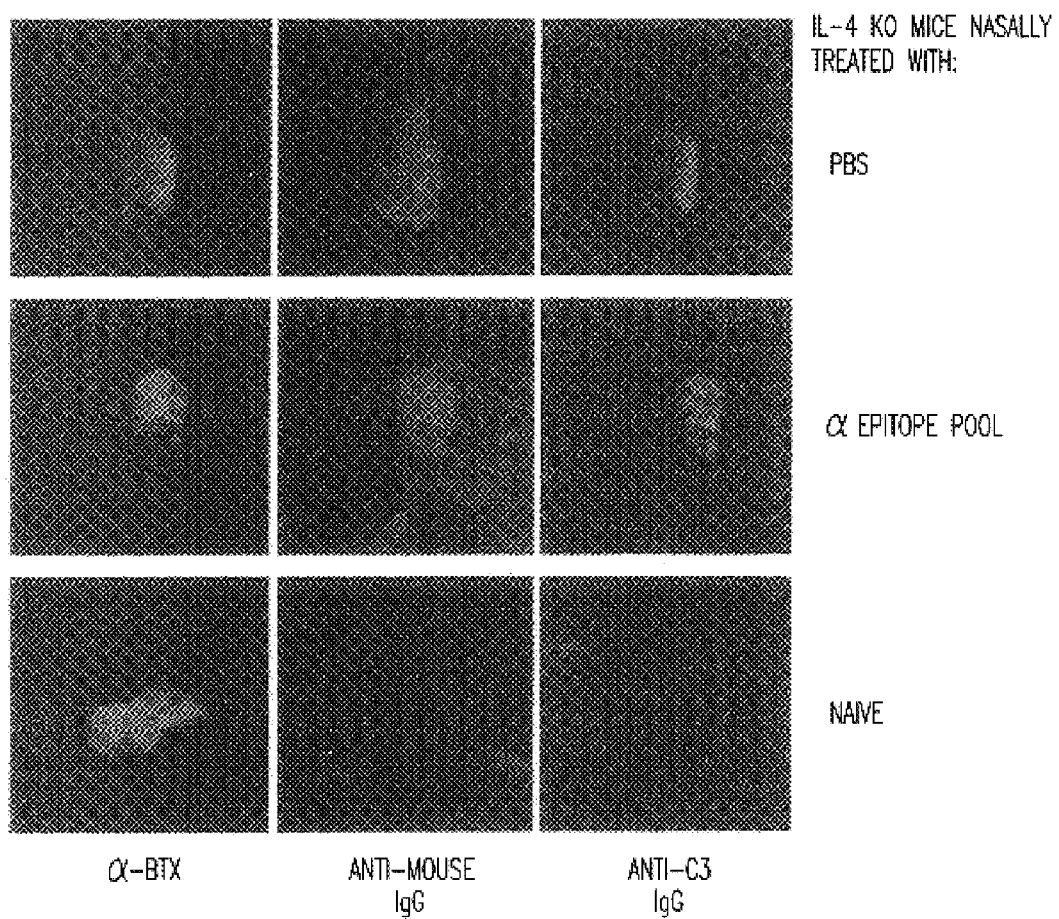
FIG. 22. Presence of mouse IgG and complement at the neuromuscular junction of IL-4 KO mice. Muscle sections frpm IL-4 KO mice treated nasally with the α epitope pool or sham-treated nasally with clean PBS and immunized with TAChR, and from naive IL-4 KO mice, as indicated at the right of the panels. The sections were stained for the presence of mouse IgG (blue fluorescence) and of the C3 component of complement (green fluorescence) as indicated below the panels. Neuromuscular synapses were localized using triple immunofluorescence staining with α-BTX (red fluorescence), as indicated below the panels. Magnification: 1000×.

Presence of Mouse IgG and Complement at the Neuromuscular Junction of IL-4 KO Mice Immunized with TAChR. Rodents immunized with TAChR, as well as MG patients, have complement at the neuromuscular junction, and complement-induced destruction of the neuromuscular junction is believed to be an important pathogenic mechanism in both EMG and MG (reviewed in Conti-Fine et al., 1997). The presence of IgG and of the C3 component of complement at the neuromuscular synapses of sham-treated and peptide-treated IL-4 KO mice, immunized with TAChR, was investigated. FIG. 22 reports the results of one of several consistent experiments. Both peptide-treated and sham-treated mice had IgG and C3 bound to the muscle synapses.

Nasal Treatment of IL-4 KO Mice with the $\alpha$ Epitope Pool Caused Reduced Proliferative Responses of CD4$^+$ Cells to the TAChR and to the Administered Peptides. The effect of nasal treatment of IL-4 KO mice with the epitope peptides, on sensitization of CD4$^+$ cells to the TAChR and to the administered epitopes, was assessed. IL-4 KO mice treated nasally with the $\alpha$ epitope pool or sham-treated with clean PBS and immunized with TAChR, were sacrificed ten weeks after beginning of the TAChR immunization. The proliferative responses of their CD8$^+$ depleted spleen cells to the TAChR, to the different TAChR subunits ($\alpha$, $\beta$, $\gamma$ and $\delta$), and the individual peptides screening the $\alpha$ subunit sequence, was tested. As representative antigens of the TAChR subunits, equimolar pools of overlapping synthetic peptides spanning the sequence of each subunit were used. The proliferative responses to those peptide pools of CD4$^+$ cells from TAChR-immunized mice compared well with the responses to purified TAChR subunits (Bellone et al., 1991).

Figure 23:
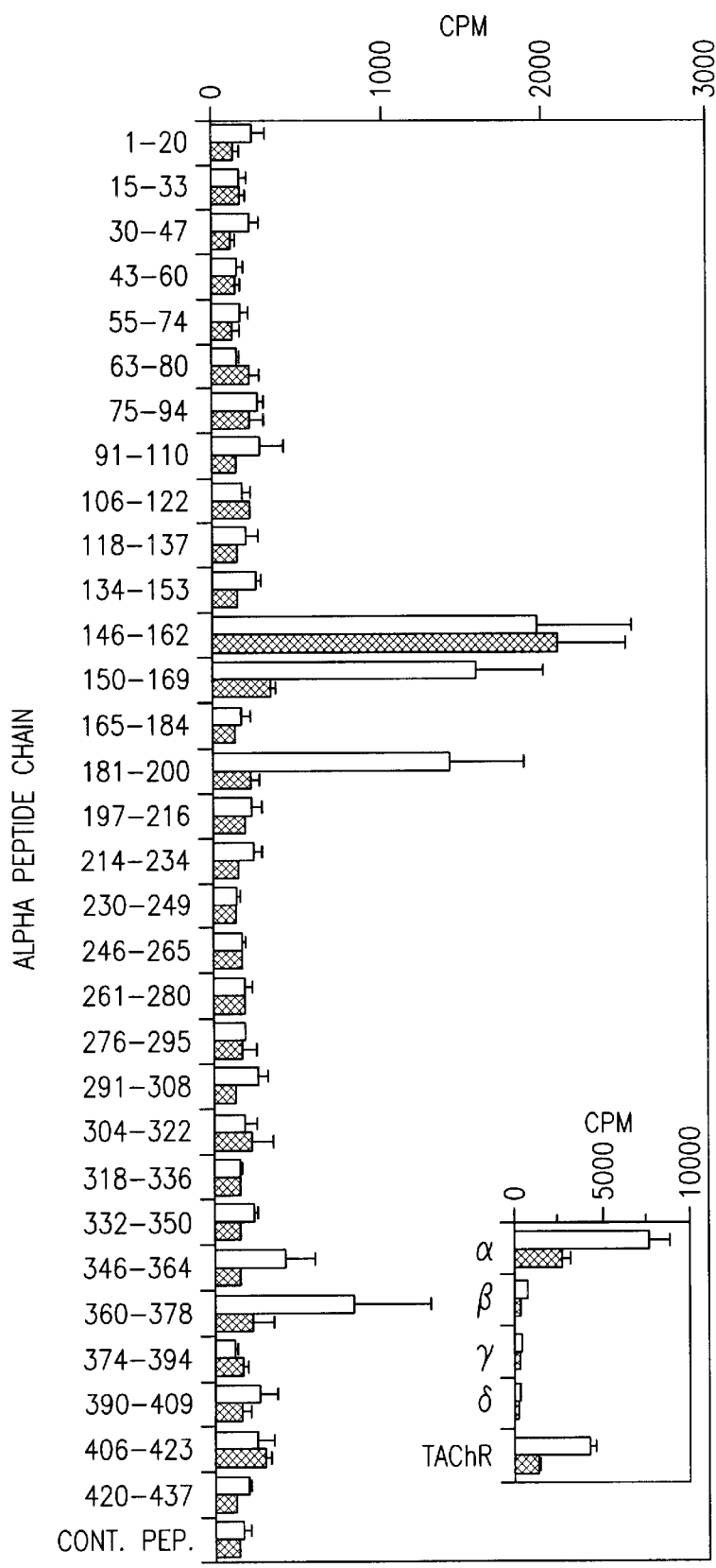
FIG. 23. CD8+ depleted spleen cells from IL-4 KO mice treated nasally with the α epitope pool and immunized with TAChR have a reduced proliferative response to the TAChR, and to the peptides administered nasally. Responses of CD8+ depleted spleen cells from mice treated nasally with the a epitope pool (black columns) or sham-treated with clean PBS (white columns) to the TAChR and to pools of overlapping synthetic peptides spanning the sequence of each TAChR subunits (inset), and to individual overlapping synthetic peptides screening the TAChR α subunit sequence, as indicated at the bottom of the panel. The columns represent average cpm±standard deviation of triplicate cultures. The columns indicated as "Cont. pep." are average cpm±standard deviation of triplicate cultures cultivated in the presence of a 20-residue peptide synthesized by the same method, unrelated to the TAChR sequence.
Figure 24A:
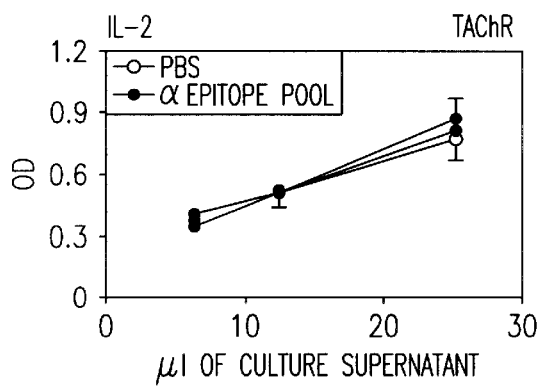
FIGS. 24A–D. Secretion of Th1 cytokines by CD8+ depleted spleen cells from IL-4 KO mice immunized with TAChR, after challenge in vitro with TAChR or α epitopes pool. IL-2 (top panels) and IFN-γ (bottom panels) in the supernatant of cultures of CD8+ depleted spleen cells from IL-4 KO mice treated nasally with the α epitope pool (black symbols) or sham-treated with clean PBS (white symbols), and immunized with TAChR. Two independent cell cultures were cultivated in the presence of TAChR, and one culture in the presence of the α epitope pool, as indicated inside the plots. The symbols represent the average ±standard deviation of duplicate ELISA determinations, using increasing amounts of the supernatant of each culture, as indicated below the plots, after 72 hours of incubation with the antigen. The spontaneous secretion of IL-2 and IFN-γ by cells cultivated in the absence of any stimulus has been subtracted from these data.
Figure 24B:
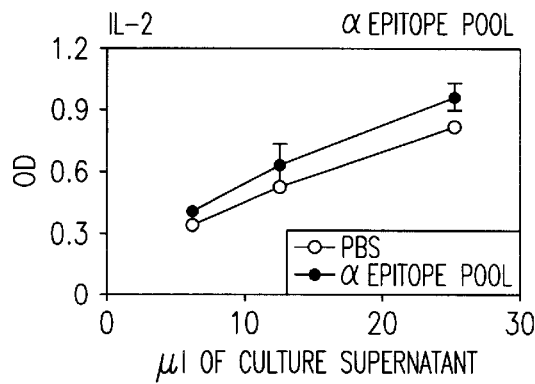
Figure 24C:
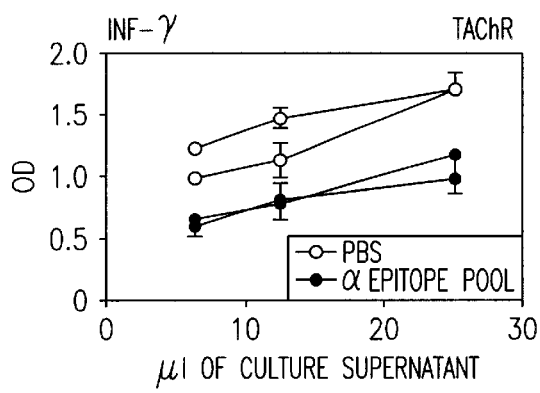
Figure 24D:
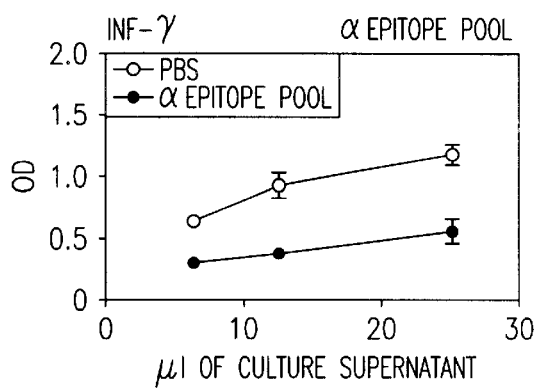

For each mouse group pooled CD8+ depleted spleen cells from three mice that had received identical treatments were used. This was necessary to obtain sufficient CD8$^+$ depleted cells to test all the antigens. FIG. 23 reports the results of one of two experiments that yielded consistent results. The cells from sham-treated mice (white columns) responded vigorously to the TAChR and to the $\alpha$ subunit, whereas they responded minimally or not at all to the other subunits (FIG. 23, inset). This agrees with the results of previous studies (Bellone et al., 1991; Bellone et al., 1993; Karachunski et al., 1995), that demonstrated that the $\alpha$ subunit dominated the sensitization of anti-TAChR CD4$^+$ cells in B6 mice. The cells from peptide-treated mice (black columns) responded well to the TAChR and to the $\alpha$ subunit (FIG. 23, inset). However, their responses were significantly lower than those observed for cells of sham-treated mice (P<10$^6$ for the response to the TAChR, and P<0.002 for the response to the $\alpha$ subunit).

Similar to the wild type B6 mice (Bellone et al., 1991; Bellone et al., 1993; Wall et al., 1994; Karachunski et al., 1995), CD8$^+$ depleted spleen cells from sham-treated IL-4 KO mice recognized strongly peptides Tα150-169, Tα181-200, Tα360-378 and Tα46-162, that overlaps Tα150-169 (FIG. 23, white columns). The CD8$^+$ depleted spleen cells from peptide-treated mice responded minimally or not at all to the peptides administered nasally, but they recognized Tα146-162 strongly (FIG. 23, black columns).

Cytokine Secreted by CD8$^+$ Depleted Spleen Cells from IL-4 KO Mice Immunized with TAChR. After Challenge with TAChR or a Epitope Pool.

The secretion of IL-2, IFN-γ, IL-4 and IL-10 by CD8$^+$ depleted spleen T cells from peptide-treated and sham-treated IL-4 KO mice immunized with TAChR, after challenge in vitro with TAChR or with the α epitope pool, was assessed. Two independent experiments were carried out. For each experiment, pooled CD8$^+$ depleted spleen cells from three identically treated mice, obtained 10 weeks after the beginning of the TAChR immunization, were used. Two independent cultures for the TAChR were set up, and one for the α epitope pool. Cells cultivated without any antigen served as controls for spontaneous cytokine secretion. Consistent results in the two independent experiments, and in the duplicate cultures of each experiment, we e obtained. The concentration of secreted cytokines after 72 and 96 hours of culture was assessed with comparable results.

FIG. 24 reports the results obtained in one experiment, that assessed the secretion of IL-2 and IFN-γ after 72 hours of culture with TAChR or the a epitope pool, as indicated in each panel. The symbols represent the average of duplicate ELISA assays of IL-2 (top panels) and IFN-γ (bottom panels) in the supernatant of cultures of CD8$^+$ depleted spleen cells from sham-treated (white symbols) or α epitope pool treated (black symbols) IL-4 KO mice, immunized with TAChR. The spontaneous secretion of IL-2 and IFN-γ by cells cultivated without any stimulus has been subtracted. The cells from peptide- and sham-treated mice, after challenge with TAChR or the α epitope pool, secreted similar levels of IL-2. The cells from peptide-treated mice secreted significantly less (P<0.005) IFN-γ than the cells from sham-treated mice, both after challenge with TAChR or with the α epitope pool. The secretion of IL-4 and IL-10 by CD8$^+$ depleted spleen cells from IL-4 KO mice could not be detected.

Figure 25A:
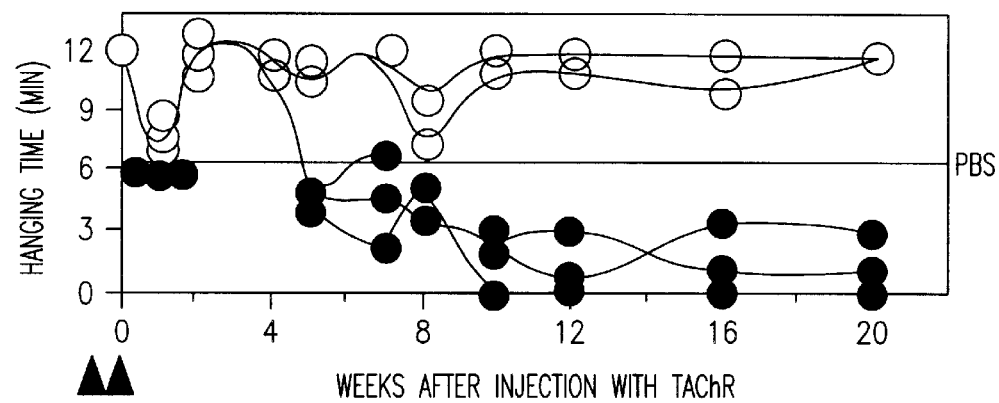
FIGS. 25A–B. Plot of the hanging time of IL-4 KO mice engrafted with CD4+ cells from B6 mice treated with PBS or the α epitope pool over time. The engraftment was just prior to a single immunization with TAChR.
Figure 25B:
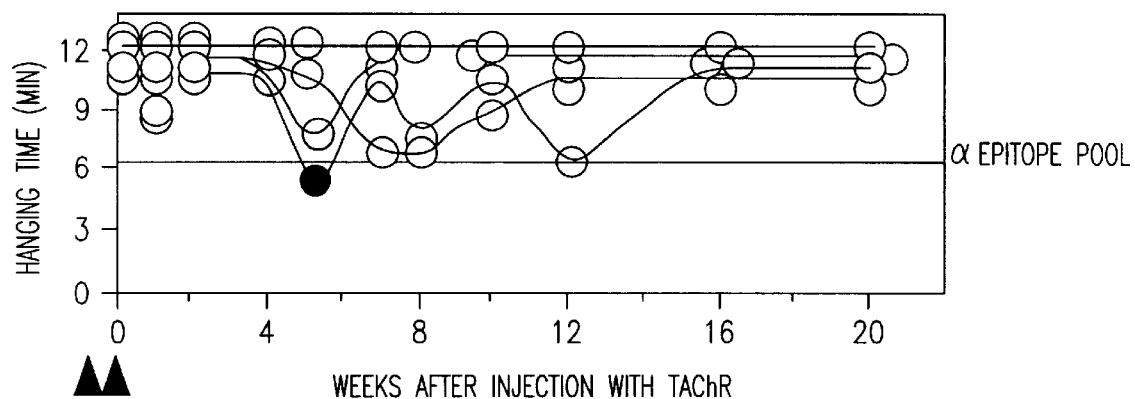

CD4$^+$ cells from wild type B6 mice that sniffed TACBR CD4$^+$ epitopes protect IL-4 KO R6 mice from development of EMG. Spleen CD4$^+$ cells were purified from wild type B6 mice that had sniffed a pool of the AChR a subunit peptide epitopes α50-169, α81-200 and α361-380, or peptide-free PBS (sham-treated). 10×10$^6$ CD4$^+$ cells from peptide-treated or sham-treated B6 mice to IL-4 KO B6 mice were administered i.v. (blue arrowhead in FIG. 25), just prior to a single immunization with TAChR (red arrowhead in FIG. 25). The strength of the mice was measured every 2 weeks, for 20 weeks after the TAChR immunization (FIG. 25). Three of the five IL-4 KO mice treated with CD4$^+$ cells from sham-treated B6 donors had EMG from week five on, that persisted for the whole duration of the observation period. The lesser frequency of EMG as compared to the experiments described above is likely due to the use of a single immunizing injection of TAChR, or to variability in the susceptibility to EMG in different batch of IL-4 KO mice, similar to that described in other mouse strains. None of the mice that received CD4$^+$ cells from a peptide-treated B6 donor developed EMG.

Figure 26A:
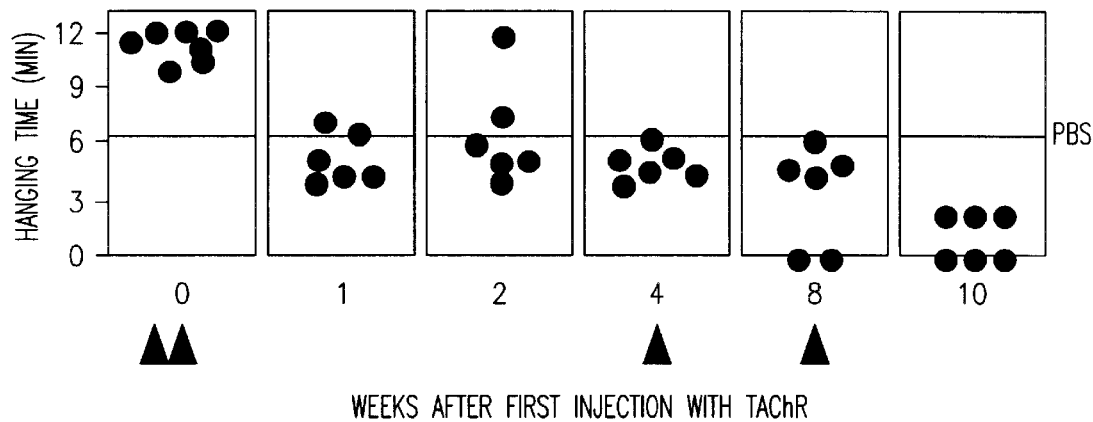
FIGS. 26A–B. Plot of the hanging time of IL-4 KO mice engrafted with CD4+ cells from B6 mice treated with PBS or the α epitope pool over time. The engraftment was just prior to three immunizations with TAChR.
Figure 26B:
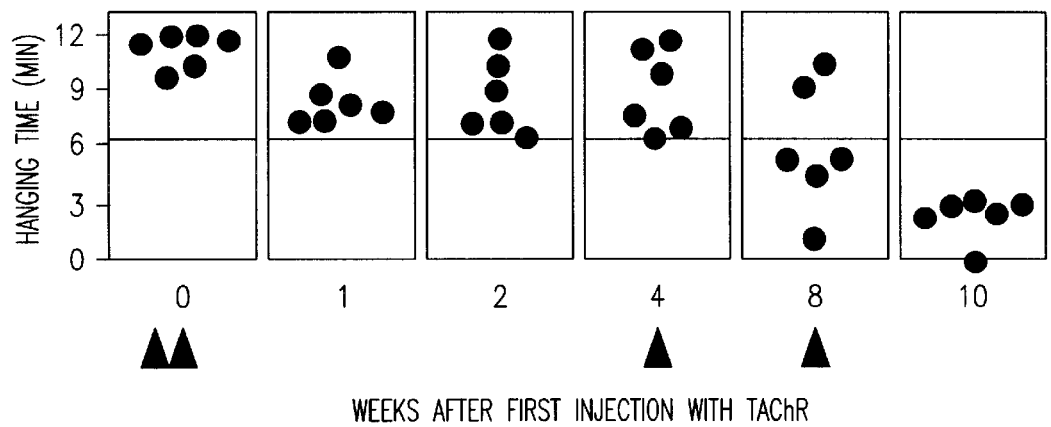

In a second experiment, the CD4$^+$ cells were administered once (blue arrowhead in FIG. 26), just before the first of three immunizations with TAChR (red arrowheads in FIG. 26). All IL-4 KO mice treated with CD4$^+$ cells from sham-treated B6 donors developed EMG from week four onwards (FIG. 26). None of the mice that received CD4$^+$ cells from peptide-treated B6 donors had EMG at week four: they started presenting EMG from week 8 onward (i.e., four weeks after the second TAChR immunization). By week 10 (i.e., two weeks after the second TAChR immunization). By week 10 (i.e., two weeks after the third TAChR immunization), all mice engrafted with CD4$^+$ cells from peptide-treated or sham-treated donors had EMG weakness: this is likely related to the short life span of the activated protective CD4$^+$ cells engrafted prior to the immunization, that could not block the anti-TAChR priming resulting from the second and the third boost.

Figure 27A:
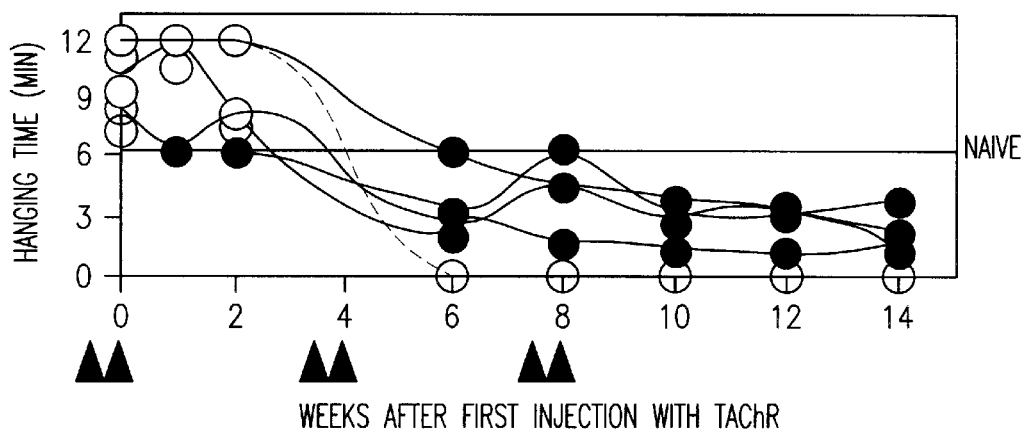
FIGS. 27A–C. Plot of the hanging time of IL-4 KO mice (naive), or IL-4 KO mice engrafted with CD4+ cells from B6 mice treated with PBS or CD4+ cells from B6 mice treated with Tα150-169, over time.
Figure 27B:
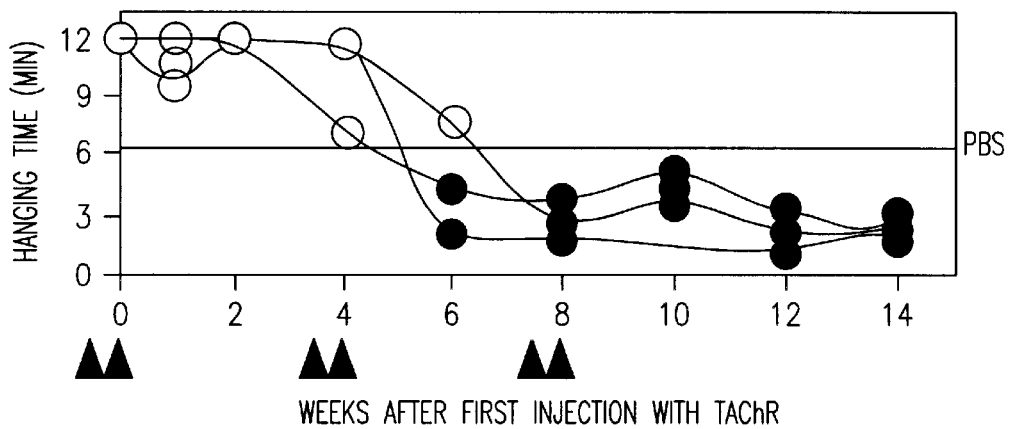
Figure 27C:
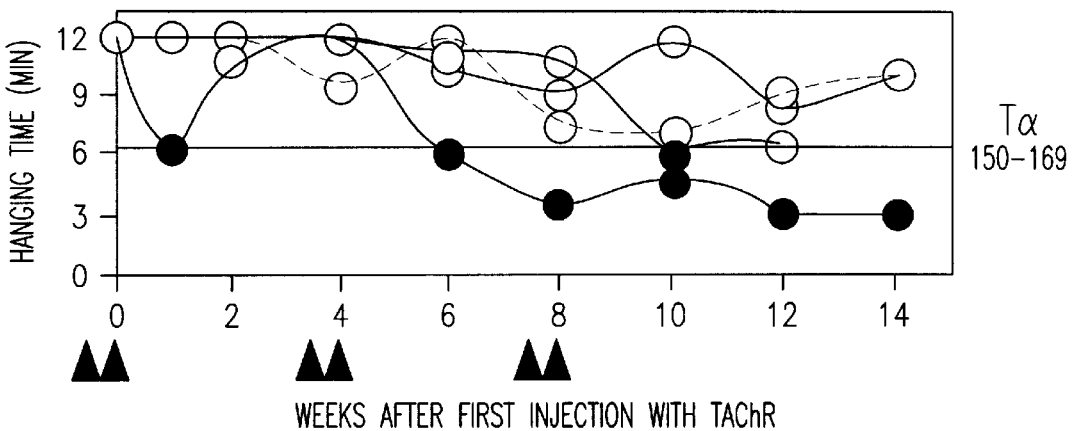

In a third experiment, CD4$^+$ cells from wild type B6 mice that had sniffed either a solution of peptide α150-169, or peptide-free PBS, were used. 10×10$^6$ CD4$^+$ cells were administered i.v. to IL-4 KO mice three times (blue arrowheads in FIG. 27) just before each one of the three immunizing injections with 20 µg of TAChR (red arrowheads in FIG. 27). As a further control group, some mice did not receive any CD4$^+$ cells. The appearance of EMG in the three groups during the 14 weeks after the first TAChR injection (FIG. 27). All IL-4 KO mice that did not receive a CD4$^+$ cell graft from wild type B6 mice had EMG from week five-six onwards. The mice engrafted with CD4$^+$ cells from B6 mice that had inhaled clean PBS also developed EMG, but the onset of the symptoms appeared to be slightly delayed. Only one mouse that received CD4$^+$ cells from peptide-treated B6 developed EMG.

Figure 28A:
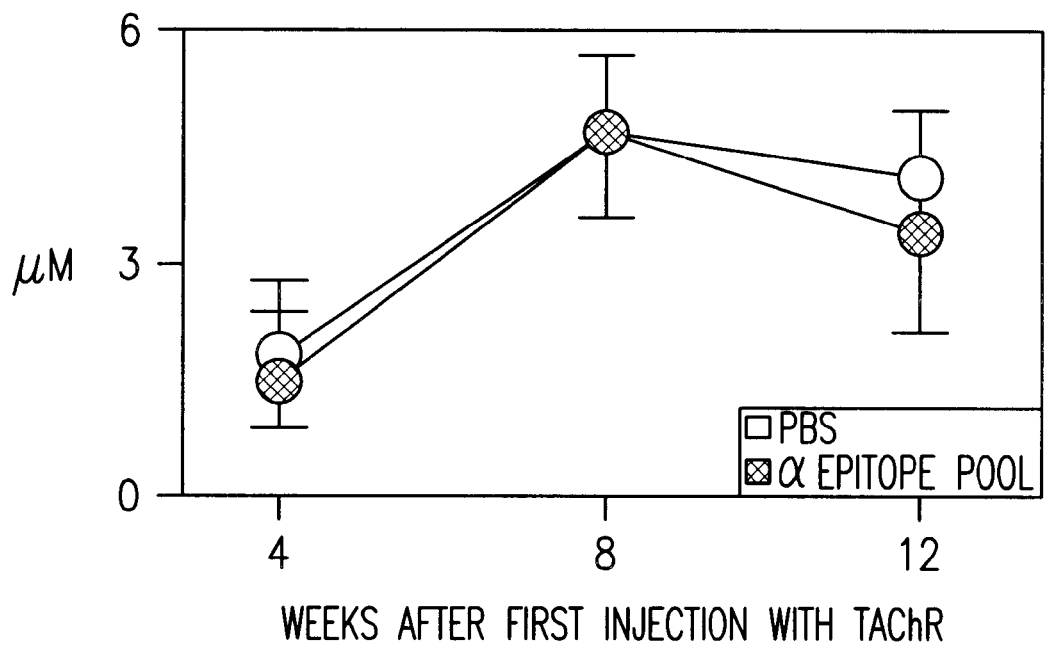
Figure 28B:
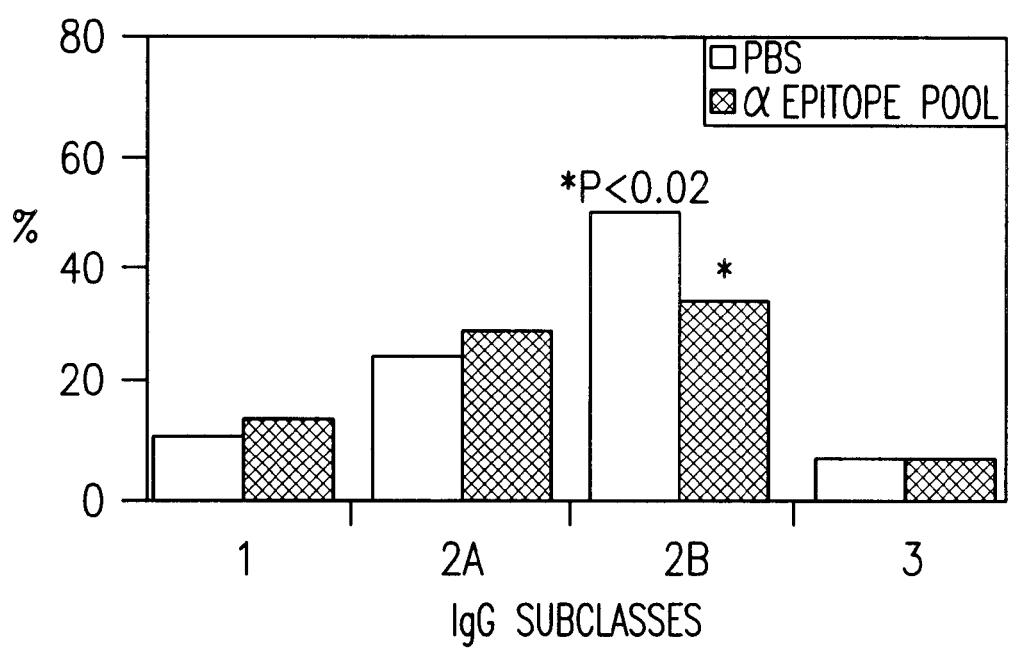
Figure 29A:
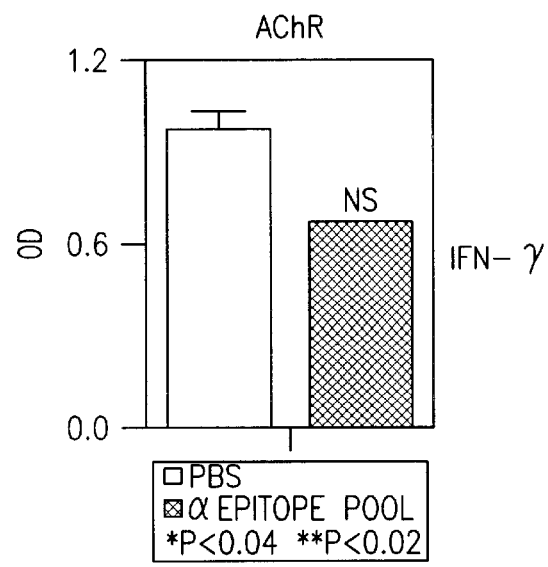
FIGS. 29A–H. IFN-γ and IL-2 secretion of engrafted IL4 KO CD4+ cells challenged with AChR or immunodominant TAChR epitopes.
Figure 29C:
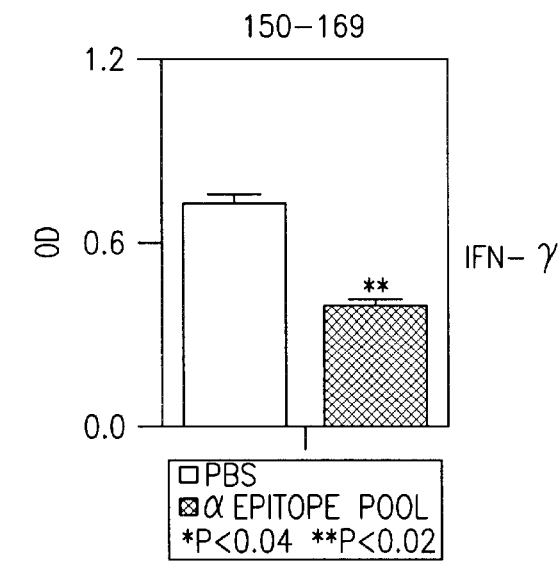
Figure 29B:
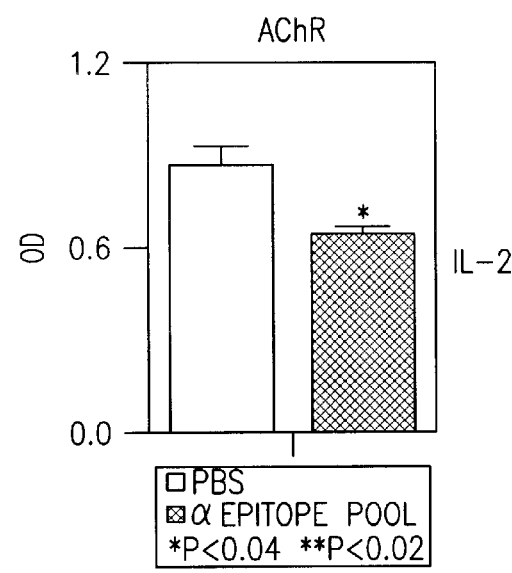
Figure 29D:
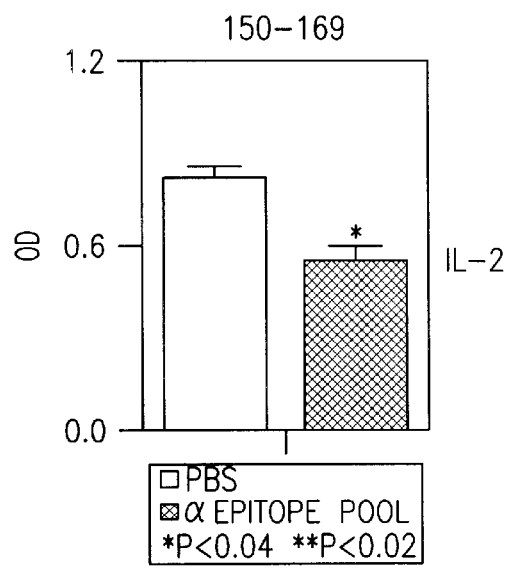
Figure 29E:
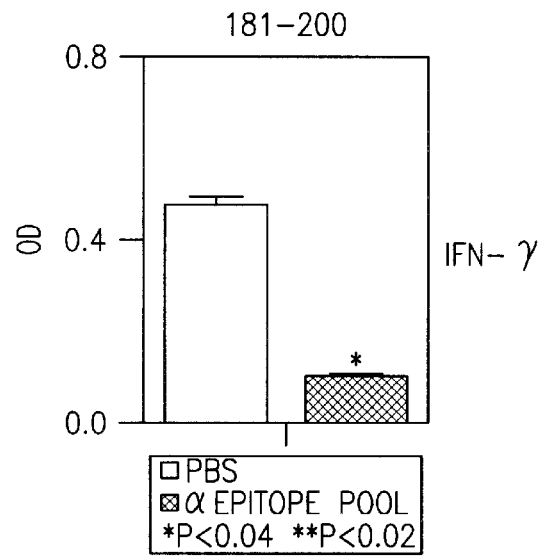
Figure 29G:
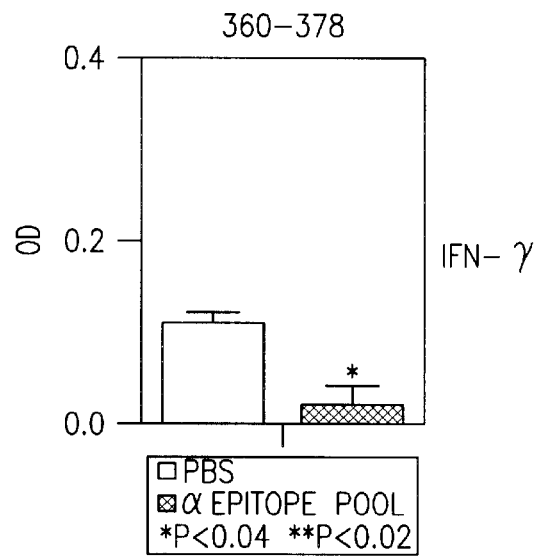
Figure 29F:
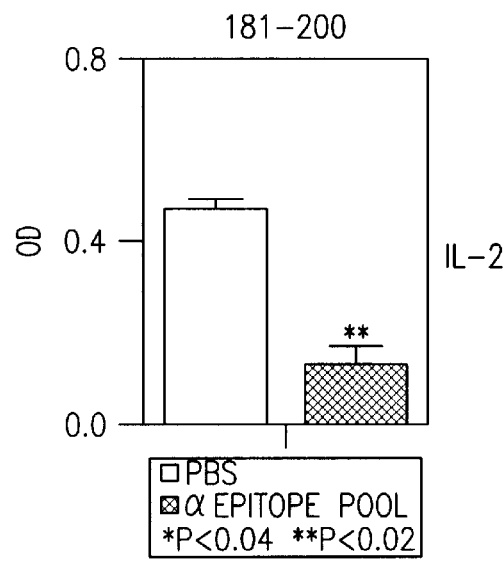
Figure 29H:
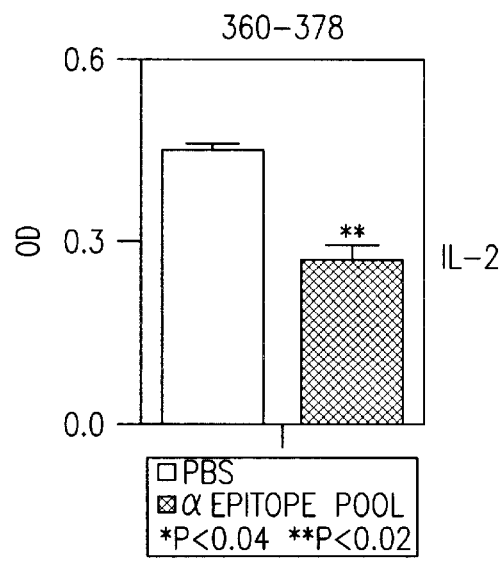

IL-4 KO mice engrafted with CD4$^+$ cells from peptide-treated donor had similar serum concentrations of anti-TAChR Ab as the mice engrafted with CD4$^+$ cells from sham-treated donors, but a significantly reduced concentration of anti-TAChR IgG2b—a subclass that is Thl-induced (FIG. 28). Also, their CD4$^+$ cells, challenged in vitro with AChR or the immnunodominant TAChR epitopes, secreted significantly less IFN-γ and IL-2 as compared to the spleen CD4$^+$ cells from IL-4 KO mice that had received CD4$^+$ cells from sham-treated B6 donors (FIG. 29).

Figure 30A:
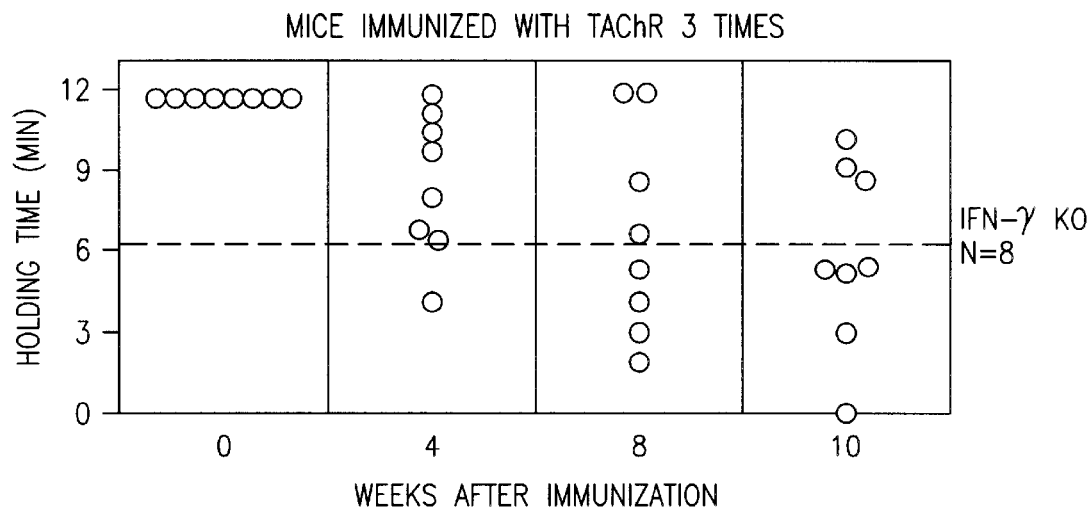
FIGS. 30A–B. Holding time of TAChR immunized IFN-γ KO and B6 mice over time.
Figure 30B:
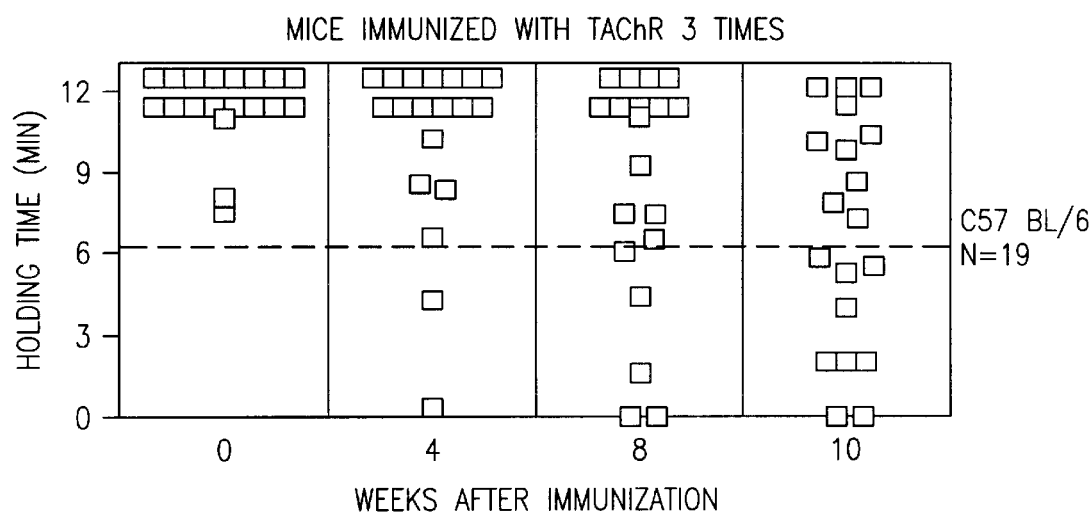
Figure 31A:
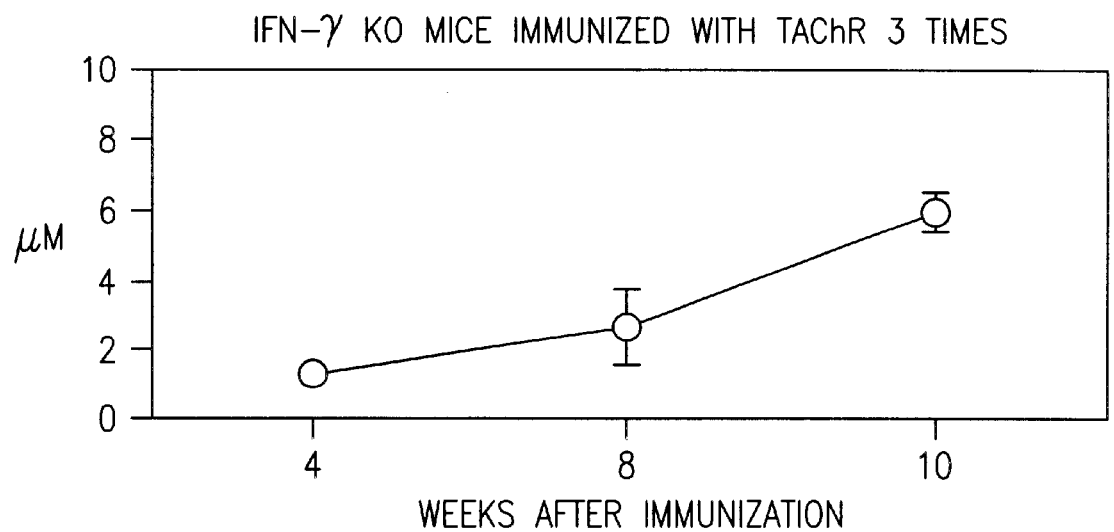
FIGS. 31A–B. Serum concentrations of anti-TAChR antibodies in TAChR immunized IFN-γ KO and B6 mice.
Figure 31B:
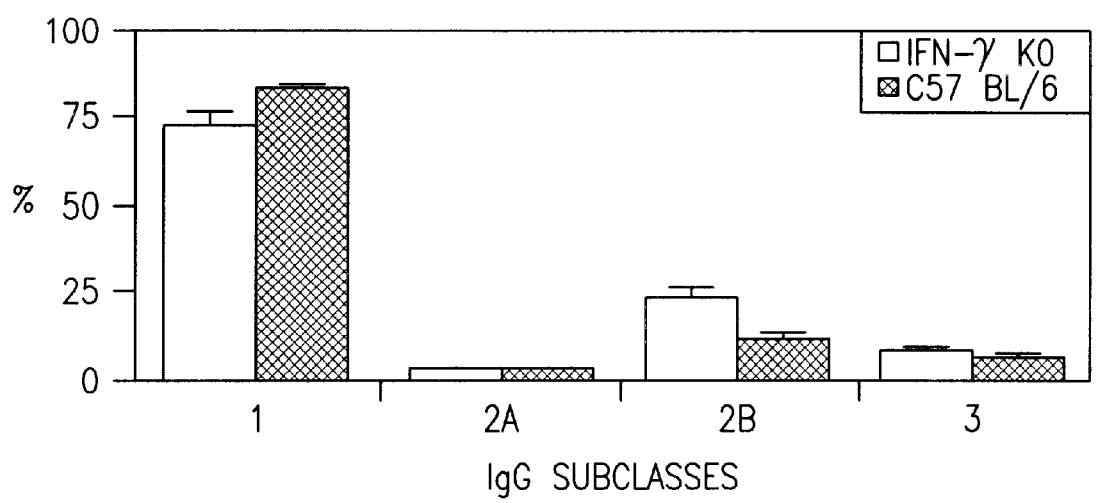

Genetic absence of IFN-γ does not prevent EMG in B6 mice. To investigate the role of Th1 cytokines in the synthesis of pathogenic anti-AChR Abs, the susceptibility to EMG and the anti-TAChR immune response of IFN-γ knock out (KO) B6 mice was determined. IFN-γ KO mice and wild type B6 mice were immunized with TAChR, using the usual dose and schedule that cause EMG in B6 mice (three 20 µg injections, one month apart, in Freund's adjuvant). The IFN-γ KO mice developed EMG weakness with comparable frequency and time course as B6 mice (FIG. 30). They synthesized amounts of anti-TAChR Ab comparable to those observed in B6 mice (FIG. 31). The anti-TAChR Ab were primarily Th2-induced IgG1, but they also included a sizable fraction (about 25%) of IgG2b. The synthesis of IgG2b, a subclass of complement fixing Ab, is stimulated by both IFN-γ and IL-2. The latter cytokine is likely responsible for the synthesis of those Ab in the absence of IFN-γ. That the IFN-γ KO mice immunized with TAChR synthesized anti-AChR Ab able to fix complement was directly proven by the presence of the C3 complement component at their neuromuscular junctions.

Figure 32A:
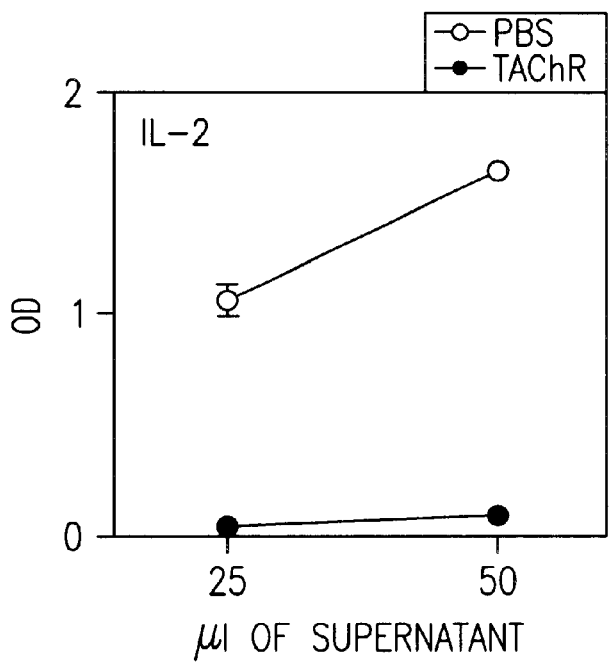
Figure 32B:
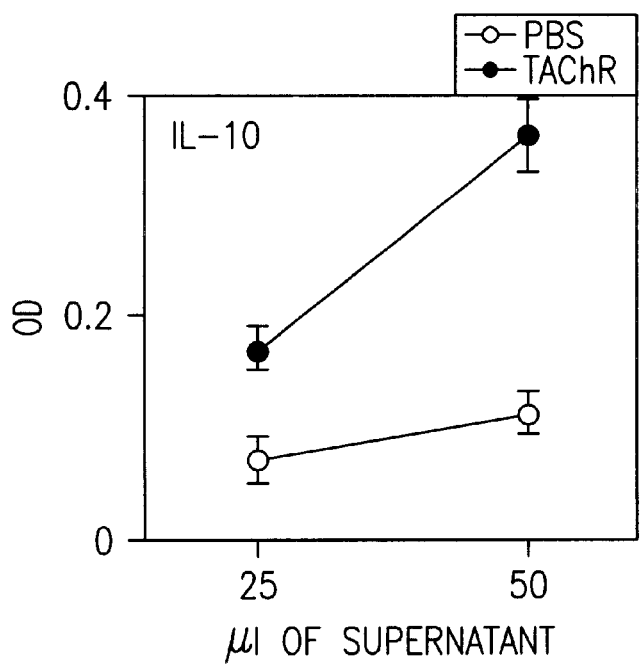
Figure 33A:
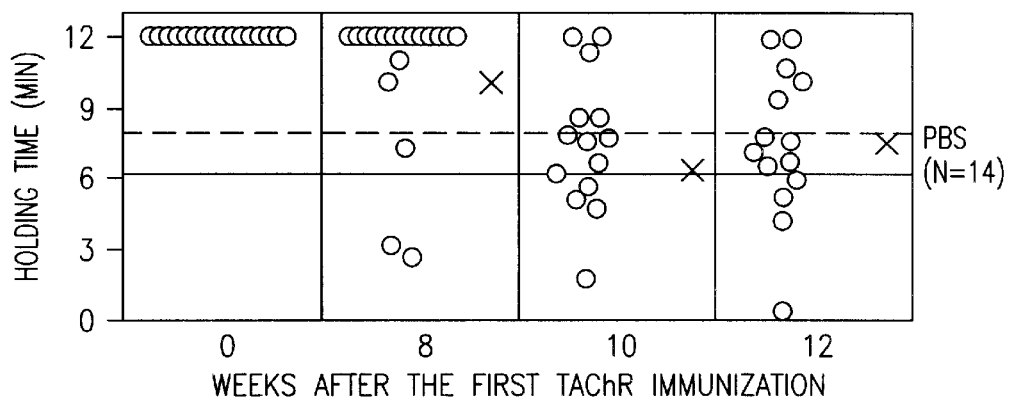
FIGS. 33A–F. The s.c. administration of a pool of synthetic TAChR CD4+ epitopes protects mice from EMG. Increasing amounts of peptide pool or 10 μg of solubilized TAChR in PBS or clean PBS, as indicated to the right of the plots, were administered s.c. prior to and during the immunization with TAChR in adjuvants (prevention protocol). The number of mice in the different groups is indicated at the right of the plots. Three immunizing injections of TAChR were administered, at 4 week intervals (at weeks 0, 4 and 8), as indicated at the bottom of the figure. The open symbols represent the muscle strength of individual mice, measured as holding time using the curare sensitized hanging test. Mice with holding times of 6.2 minutes (solid horizontal line) or less were considered to have fully developed EMG. Holding times between 6.2 and 8 minutes (dashed horizontal line) may indicate the beginning of EMG. The average holding time of the different groups are indicated as crosses. The levels of significance of the difference between the average holding time of the tolerized groups and that of the sham-tolerized group are reported (NS: not significant).
Figure 33B:
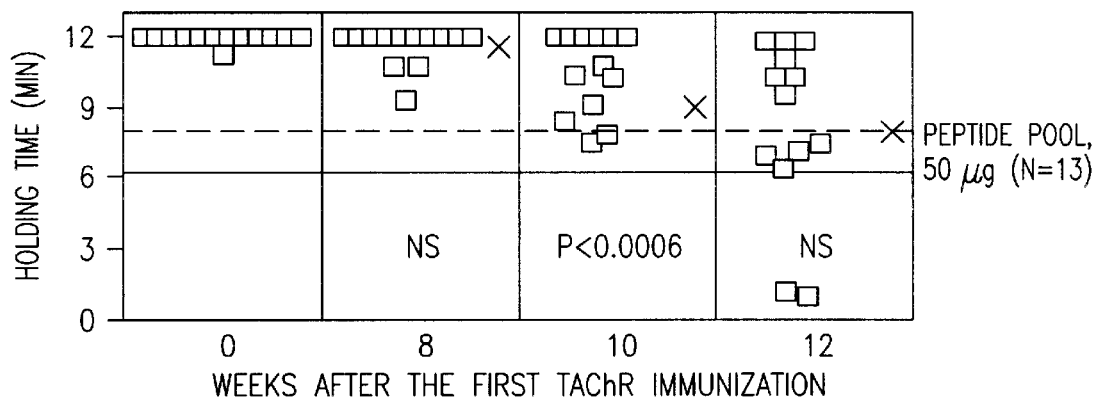
Figure 33C:
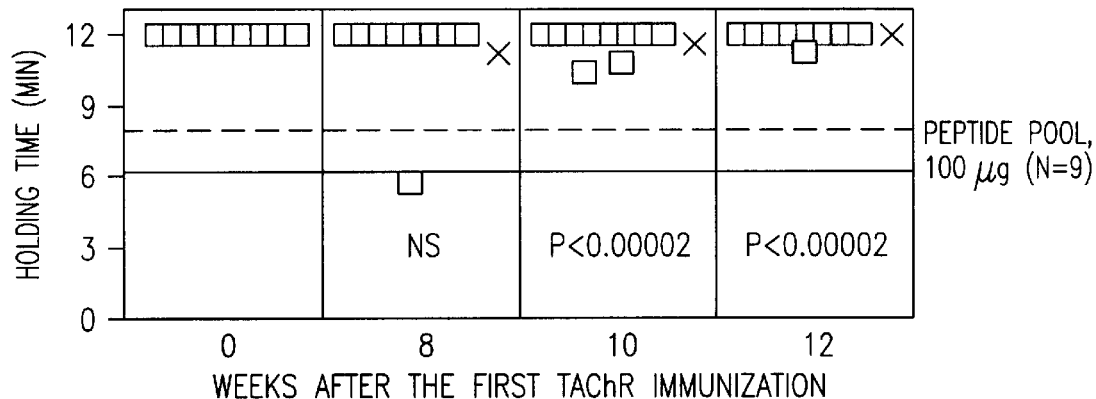
Figure 33D:
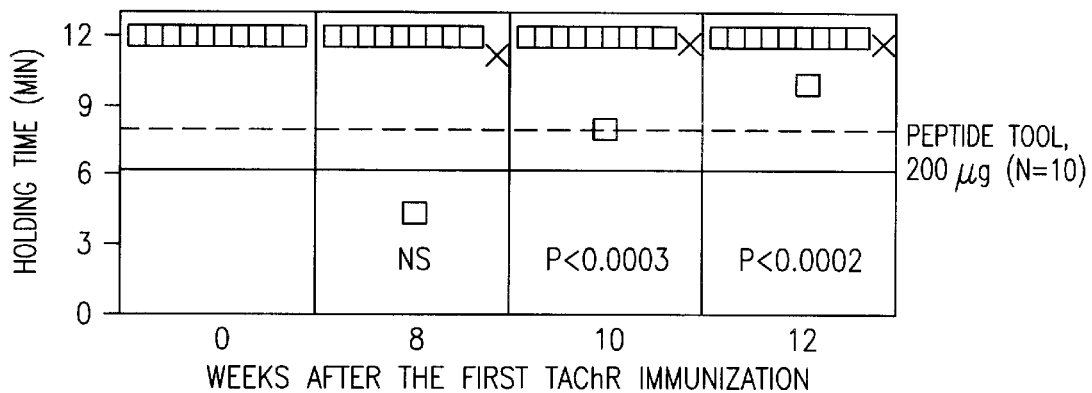
Figure 33E:
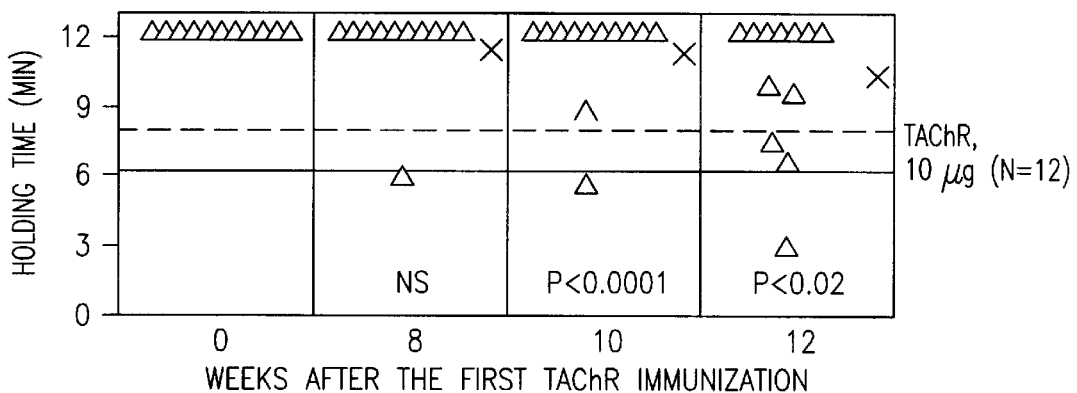
Figure 33F:
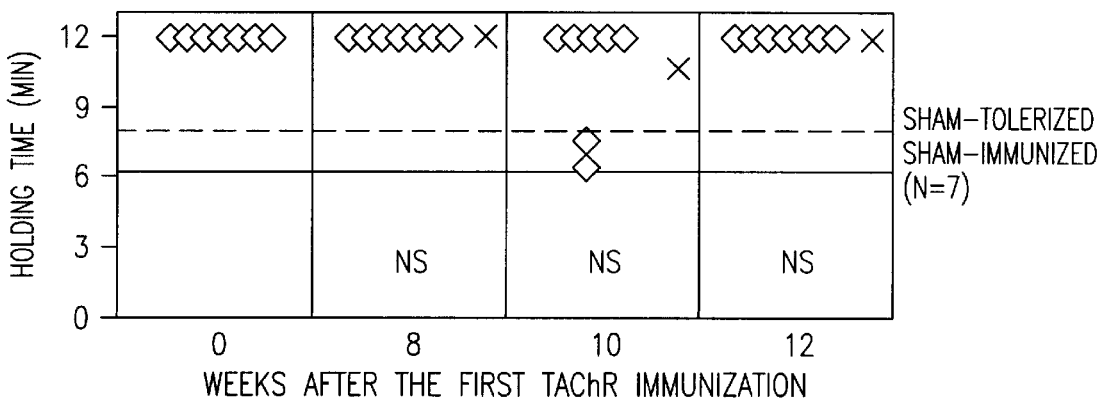

Spleen CD4$^+$ cells from IFN-γ KO mice immunized with TAChR proliferated strongly in response to the TAChR and the a subunit, and the immunodominant α subunit epitopes recognized by the wild type B6 mice. This response likely reflects that of anti-TAChR Th2 cells, in addition to residual Th1 cells that are present in these mice. This is supported by the cytokine secretion in vitro of spleen CD4+ cells from IFN-α KO mice immunized with TAChR. In the absence of any Ag stimulation, the spleen CD4+ cells secreted measurable amounts of IL-2 and IL-10. After stimulation with TAChR, the secretion of IL-10 increased significantly, that of IL-2 decreased drastically (FIG. 32). This likely reflects the inhibitory actions of the cytokines secreted by the anti-TAChR Th2 cells.

DISCUSSION

This study demonstrates that IL-4 is not necessary for development of EMG, and suggests that this cytokine, and therefore Th2 cells, may have a down-regulatory fuction on the development of anti-TAChR antibodies, and of the resulting EMG symptoms. Absence of IL-4 and of an effective Th2 function facilitated EMG development, and anti-TAChR Th2 cells appeared to have an important role in the protection from EMG resulting from nasal "tolerization" procedures.

IL-4 KO mice have functional Th1 cells. Consequently, the present results indicate that sensitization of Th1 cells is sufficient to cause EMG. This agrees with the conclusion of a recent study, that demonstrated that IL-12 is involved in induction of EMG (Moiola et al., 1998). Another study also suggested that Th1 cells are indispensable for EMG induction, because IFN-γ KO mice immunized with TAChR did not develop EMG (Balasa et al., 1997). However, in that study, IFN-γ KO mice immunized with TAChR had very low levels of serum anti-TAChR antibodies of all subclasses, including Th2-dependent subclasses, as compared to wild type mice (Balasa et al., 1997). IFN-γ enhances the expression of MHC proteins and antigen presentation, and therefore facilitates priming of all CD4+ cells. Also, it may facilitate sensitization of Th2 cells by up-regulating IL-4 production and down-regulating IL-2 production, or both (Vermeire et al., 1997). The reported absence of EMG in IFN-γ KO mice (Balasa et al., 1997) might have been caused by ineffective sensitization of anti-TAChR Th1 or Th2 cells or both, and inadequate help for anti-TAChR antibody synthesis.

Tolerance induced by nasal, oral or systemic administration of an antigen or of epitope sequences can result from several mechanisms. They include: anergy or deletion of antigen-specific T cells and induction of antigen-specific regulatory CD4+ Th2 cells (Weiner et al., 1994; Chen et al., 1995, 1996). The present results suggest that modulatory Th2 cells have an important role in the protective effect of nasal administration of synthetic TAChR epitopes, because nasal treatment of IL-4 KO mice with peptide epitopes did not affect the development of EMG. Anergy or deletion of Th1 cells had occurred in the peptide-treated IL-4 KO mice, because their CD8+ depleted spleen cells had reduced proliferative responses to the TAChR, to the TAChR α subunit and to the individual peptides administered nasally (FIG. 22). Also, their CD8+ depleted spleen cells synthesized less IFN-γ after challenge in vitro with TAChR or the α epitope pool (FIG. 23). The reduced anti-TAChR Th1 response did not suffice to protect from EMG (FIG. 19) or to reduce the synthesis of anti-TAChR Th1 antibodies (FIGS. 20 and 21). Consequently, the strong reduction in synthesis of anti-TAChR antibodies observed in B6 mice after nasal or subcutaneous administration of the TAChR peptide epitopes (FIG. 20, Example I, and Example IV; Wu et al., 1997) must be mediated by activation of regulatory Th2 cells. Anergy of anti-TAChR Th1 cells might protect from EMG if one could use a full complement of the TAChR epitope sequences recognized by the pathogenic Th1 clones, in doses adequate to cause anergy or deletion of all the specific Th1 clones.

When proliferative assays were used that detect primarily the response of Th1 cells, the pattern of recognition of the TAChR subunits and the epitope repertoire on the α subunit of CD8+ depleted spleen cells from IL-4 KO mice (FIG. 23) was identical to that of wild type B6 mice (Bellone et al., 1991,1993; Karachunski et al., 1995). Thus, the absence of IL-4 does not appear to affect the sensitization of Th1 cells to the TAChR. Th1 and Th2 cells may recognize different epitopes on the same antigen (Julia et al., 1996; Mikszta and Kim, 1996; Das et al., 1997). B6 mice must have anti-TAChR Th2 cells, because they have a strong anti-TAChR IgGI response (FIG. 20). Anti-TAChR Th2 cells in B6 mice may recognize the same epitope sequences as the Th1 cells, or other epitopes, whose detection might require assays other than the proliferative assay.

Spleen cells from IL-4 KO mice that sniffed the α epitope pool responded to peptide Tα150-169 much less than the sham-treated mice, but they still responded strongly to the overlapping peptide Tα146-162 (FIG. 23). This indicates that the sequence region α146-169 contains overlapping epitopes that sensitize different pathogenic CD4+ clones. The residual population of Th1 cells that recognized epitopes within the amino terminal part of the sequence region α146-169 (i.e., those that responded to Tα146-162, not to Tα150-169) sufficed to cause EMG in the peptide-treated IL-4 KO mice. This verifies the importance of this sequence for sensitization of pathogenic Th1 cells (Bellone et al., 1991; Infante et al., 1991; Asthana et al., 1993; Karachunski et al., 1995).

Nasal administration of α epitope pool to IL-4 KO mice caused synthesis of Th1-induced anti-peptide antibodies (FIG. 23). The anti-peptide antibodies did not cross-react significantly with native TAChR, because the serum concentration of anti-TAChR antibodies measured in radioimmunoprecipitation assays was identical in peptide- or sham-treated mice (FIG. 20). Anti-peptide antibodies seldom cross-react with the cognate native antigen (reviewed in Conti-Fine et al., 1996). The Th2-induced anti-peptide antibodies synthesized by wild type B6 mice after nasal peptide treatment may have recognized partially denatured TAChR in the ELISA, which revealed a significantly higher relative concentration of anti-TAChR IgGI antibodies—an IgG subclass that is primarily Th2-induced—in peptide-treated B6 mice (FIG. 21).

Sensitization of modulatory Th2 cells that protect from EMG explains the previous findings, that nasal or subcutaneous administration of a single TAChR CD4+ epitope peptide, Tα150-169 (Examples I and IV) or Tα146-162 (Wu et al., 1997), protected from EMG. Regulatory Th2 cells against one epitope can down-regulate the Th1 response to the whole cognate antigen through secretion of cytokine, such as IL-4 and IL-10, that act on all Th1 cells in topographic proximity, irrespective of their specificity (antigen-driven bystander suppression) (Weiner et al., 1994). Furthermore, Th2 determinant spreading may occur (Tian et al., 1997), that also explains how sensitization of Th2 cells to an individual epitope protects from an autoimmune disease that involves the whole cognate autoantigen.

A recent study has also investigated EMG in IL-4 KO mice (Balasa et al., 1998). In agreement with the results reported herein, that study also concluded that IL-4 was not required for the induction and progression of EMG. However, at difference with the data reported herein, that study did not find a different susceptibility to EMG of IL-4

KO and wild type B6 mice, and concluded that IL-4 does not influence the susceptibility to EMG. EMG is difficult to assess in mice because the symptoms are frequently subclinical (reviewed in Conti-Fine et al., 1997), and their presence and quantification requires sensitized, parametric tests of muscle strength, like the one used here. The study of Balasa et al. (1998) may have missed the higher susceptibility to EMG of IL-4 KO mice because the test of muscle strength used was not sensitive enough, and it was qualitative.

The main pathogenic mechanisms of anti-AChR antibodies in MG and EMG are activation of complement and accelerated degradation of AChR molecules cross linked by the antibodies (reviewed in Conti-Fine et al., 1997). Complement components are consistently present at the neuromuscular junction in both MG and EMG (Nakano and Engel et al., 1993). The present results underline the importance of complement in the pathogenesis of EMG, since Th1-dependent antibodies are most effective at binding complement. The present results raise the possibility that one of the protective mechanisms of IL-4 and of anti-TAChR Th2 cells is stimulation of synthesis of anti-TAChR IgG that do not activate complement, and may compete for AChR binding with the Th1-induced, complement activating antibodies. The finding that IL-4 KO and B6 mice develop similar levels of anti-AChR antibodies, but in B6 mice the anti-TAChR IgG include a substantial fraction of IgG1 (FIG. 20), is consistent with this possibility.

The present results do not exclude the possibility that Th2 cells may have also a pathogenic role, at least in certain circumstances. Anti-AChR antibodies may cause accelerated degradation of the AChR without the need of complement (reviewed in Drachman et al., 1994). Th2-induced anti-AChR antibodies may be pathogenic in muscle groups that are especially susceptible to myasthenic weakness when the concentration of AChR at the synapses is reduced, even in the absence of complement-mediated damage of the neuromuscularjunction. The functional properties of extrinsic ocular muscles (EOM) make them especially susceptible to weakness when a reduction of the AChR function occurs (Kaminski et al., 1990; Kaminski and Ruff, 1997). Thus, Th2 cells might be pathogenic in ocular MG, given the extreme susceptibility of the EOM to develop myasthenic weakness when the concentratoin of AChR at the synapses is reduced.

EXAMPLE IV

Subcutaneous Administration of T Cell Epitope Sequences of the AChR Prevents Experimental Myasthenia Gravis Materials and Methods Peptide synthesis and characterization. Three synthetic peptides were used, 19–20 residues long, corresponding to residues 150–169, 181–200 and 360–378 of the TAChR α subunit. The peptide nomenclature is for the TAChR α subunit and includes two numbers, that indicate the position on the α subunit sequence of the first and last residues of the peptide. A 20-residue control peptide was also used, synthesized with the same procedure and unrelated to the AChR sequence (residues 1–19 ofthe major intrinsic protein of bovine lens). Purification of TAChR. TAChR was isolated and purified from *Torpedo californica* electric organ as alkali-stripped TAChR-rich membrane fragments (Bellone et al., 1991a). The TAChR preparations contained 3.8–5.8 nmols of αBTX binding sites/mg protein. Their SDS PAGE consistently showed only the four TAChR subunits as the main protein bands. Occasional minor bands of low m.w. are proteolytic products of the TAChR (Bellone et al., 1991a). For use in cell cultures, the membrane fragments were diluted in RPMI-1640 as needed, and sterilized by UV irradiation. For s.c. tolerization and immunization, the membranes were solubilized in 1% Triton X-100 in PBS (Bellone et al., 1991a), diluted them to 0.5 mg of protein/ml in PBS and stored at −80° C.

B6 mice (Jackson Laboratory, Bar Harbor, Me.) were injected s.c. with 100 μl of PBS containing increasing amounts of a pool of the same amount in weight of each of the three epitope peptides Tα150-169, Tα180-200 and Tα360-378 ('peptide pool'), or 200 μg of Tα150-169 alone, or 100 μl of PBS containing 0.1% Triton X-100 and 10 μg of solubilized TAChR. Two different treatment schedules were used, referred to as prevention and post-priming protocols. In the prevention protocol, the peptides or solubilized TAChR were administered twice per week for 14 weeks, starting 2 weeks before the beginning of the immunization with TAChR. In the post-priming protocol, peptides or solubilized TAChR were administered twice per week for 44 weeks, starting 8 weeks after the beginning of the TAChR immunization. Control mice received 100 μl of peptide-free PBS, following the same schedules.

Immunization 8–10 week old mice were immunized by s.c. injections, along the back and at the base of the tail, of TAChR (a total of 50 μg in 100 μl of PBS for each immunization) emulsified in an equal volume of CFA for the first injection, and IFA for the following two boosts. The mice were injected for a total of three times at 3–4 week intervals. At the end of the observation period, the mice received a third boost, and were sacrificed 5–7 days later. Control mice were injected with clean PBS in the appropriate adjuvant.

Evaluation of the symptoms of EMG The EMG symptoms were quantified using a forced exercise test sensitized by i.p. injection of a minute amount of pancuronium bromide (0.03 mg/kg) just before the test (Karachunski et al., 1995). The mouse hangs from a grid suspended above a soft padding, and the time it takes the mouse to fall three times ('holding time') was measured. The test is parametric, and gives a quantitative assessment of the mouse weakness. The myasthenic nature of the weakness was verified by injecting i.p. edrophonium chloride (Reversol, Organon, West Orange, N.J.), which is a cholinesterase inhibitor. Reversol immediately improved the strength of the mice. The mice were tested without knowledge of their treatment.

The holding time of normal mice was 10.4±2.1 minutes (n=99). Mice with holding times of 8 minutes or longer were considered normal. Mice with holding times less than 6.2 minutes (the holding time of normal mice minus two SD) were considered to have fully developed EMG. Holding times of 6.2–8 minutes were considered to potentially indicate initial EMG. Normal or sham-immunized mice had occasionally holding times of 6.2–8 minutes, but never less than 6.2 minutes. Paralyzed mice and mice that died of respiratory paralysis are indicated as having holding time of 0 minutes.

Anti-TAChR Ab assay. Sera was obtained from each mouse after each clinical testing and at the end of the observation period (12 weeks after beginning of the TAChR immunization). The serum concentration of anti-TAChR IgG and IgGI was determined by radioimmunoprecipitation assay, using TAChR solubilized in Triton X-100 and labeled by the binding of $^{125}$I-α-BTX (Bellone et al., 1991a). As a secondary Ab, either rabbit anti-mouse IgG produced, or goat anti-mouse IgG1 (Sigma, St. Louis, Mo.), was used. The anti-TAChR Ab concentration is expressed as μM precipitated $^{125}$I-α-BTX binding sites.

Two types of experiments were carried out. In one of them the total anti-TAChR Ab in the sera of individual mice, obtained 8, 10 and 12 weeks after the first TAChR immunization, was determined. In the other, the anti-TAChR IgG1 concentration was determined, as well as the total anti-TAChR IgG concentration, in sera obtained at the end of the observation period. For this second assay pooled sera from five mice that had received identical treatments was used.

Anti-peptide Ab assay. The anti-peptide Ab in sera of peptide- and sham-tolerized mice, immunized with TAChR, was measured by ELISA. Ninety-six well plates (Nunc, Karstrup, Denmark) were incubated as follows: 4 hours with a 10 μg/ml solution of each peptide in PBS (2 wells/peptide), 1 hour with PBS/Tween plus 3% BSA, 2 hours with mouse serum (serial dilutions from 1:100 to 1:2000 in Tris buffer), 1 hour with a dilution 1:1000 in PBS of goat Ab specific for the total mouse IgG or IgG1 (Mouse Monoclonal Isotyping Kit, Sigma), and 30 minutes with a 1:3000 dilution n PBS of peroxidase conjugate rabbit anti-goat IgG (Sigma). The plates were developed for 20 minutes with ABTS peroxidase substrate (Kirkegaard & Perry Laboratories, Gaithersburg, Md.). The reaction was stopped with 1% SDS, and the OD read at 405 nm.

Each assay was carried out using several dilutions of the sera, and the slope of the OD values relative to the serum concentration calculated. This assay is qualitative, but it allows comparison of the concentration of the anti-peptide Ab in different samples tested simultaneously, and of the amount of IgG1 relative to the total IgG.

Lymphocyte proliferation assay. Five to seven days after the last TAChR immunization, CD4$^+$ T-cells (Bellone et al., 1991a) were purified from the pooled spleens of three to four mice that had received identical treatments. Irradiated (3000 rad) spleen cells from non-immunized mice were diluted as needed in RPMI-1640 (Gibco, Grand Island, N.Y.) supplemented with 10% heat inactivated fetal calf serum (Gibco), 50 μM 2-mercapto-ethanol, 1 mM L-glutamine, 10 mM HEPES, 1 mM sodium pyruvate, 100 U/ml penicillin and 100 μg/ml streptomycin (culture medium) and used as APC. The spleen CD4$^+$ T-cells (1×10$^6$/ml in culture medium, 100×1/well) were seeded in triplicate in 96 flat-bottom well plates containing 100×1 of 5×10$^6$/ml APC. One of the following Ag was added: 10 μg/ml PHA (Sigma); 5 or 10 μg/ml TAChR; 5 or 10 μg/ml of the individual epitope peptides. The concentrations of TAChR and epitope peptides are in the saturating range of the dose dependence curve (Bellone et al., 1991a), and yielded consistent results. Controls were triplicate wells containing CD4$^+$ cells and APC without any Ag, or with the control peptide (10 μg/ml). After 4 days the cells were labeled for 16 hours with $^3$H-thymidine (1 μCi per well, specific activity 6.7 Ci/mmol, Dupont, Boston, Mass.) and harvested (Titertek, Skatron, Sterling, Va.). The $^3$H-thymidine incorporation was measured by liquid scintillation, and represented the results as stimulation indexes (S.I.: the ratio between the cpm obtained in the presence of a given stimulus, and the average cpm obtained for non-stimulated control cultures).

Cytokine secretion in response to TAChR by spleen CD4$^+$ cells in vitro. Five to seven days after the last immunization, spleen cells of three identically treated mice were pooled, and depleted them of CD8$^+$ cells using paramagnetic beads and rat anti-mouse CD8$^+$ Ab (Pharmingen, San Diego, Calif.), following the manufacturer's instructions. The CD8$^+$ depleted, CD4$^+$ enriched cells were cultured with 10 μg/ml TAChR, or without any stimulus. 24 well plates were used, and duplicate cultures prepared. The supernatants were harvested after 72 hours, and the concentrations of IFN-γ, IL-4 and IL-10 determined in duplicate samples by capture ELISA using anti-INF-γ, anti-IL-4, anti-IL-10 Ab, and recombinant INF-γ, IL-4 and IL-10 (Pharmingen) as standards, and following the manufacturer's instructions.

Statistical analysis. A two-tailed Students' t-test was used to determine the significance of the differences of the average responses between two groups.

Result

Figure 34A:
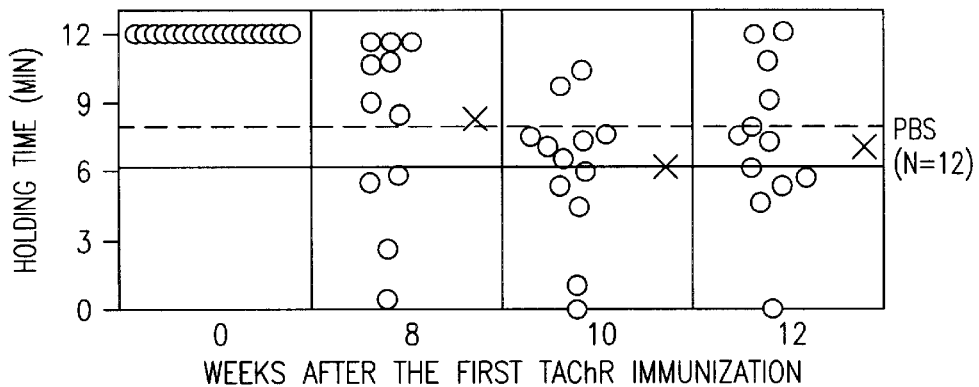
FIGS. 34A–C. The s.c. administration of the immunodominant TAChR CD4+ epitope Tα150-169 protects mice from EMG. The s.c. injections of peptide pool (200 μg of each peptide for each injection) or peptide Tα150-169 (200 μg for each injection) in PBS or of clean PBS, as indicated at the right of the plots, were administered prior to and during the immunization with TAChR in adjuvants (prevention protocol). The number of mice in the different groups is indicated at the right of the plots. Three immunizing injections of TAChR were administered, at 3-week intervals (at weeks 0, 3 and 6), as indicated at the bottom of the figure. The open symbols represent the muscle strength of individual mice, measured as holding time using the curare sensitized hanging test. Mice with holding times of 6.2 minutes (solid horizontal line) or less were considered to have fully developed EMG. Holding times between 6.2 and 8 minutes (dashed horizontal line) may indicate the beginning of EMG. The average holding time of the different groups are indicated as crosses. The levels of significance of the difference between the average holding time of the tolerized groups and that of the sham-tolerized groups are reported (NS: not significant).
Figure 34B:
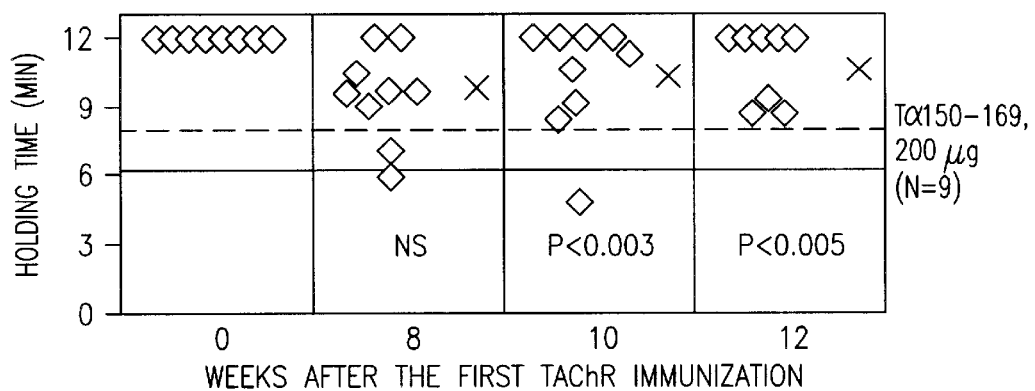
Figure 34C:
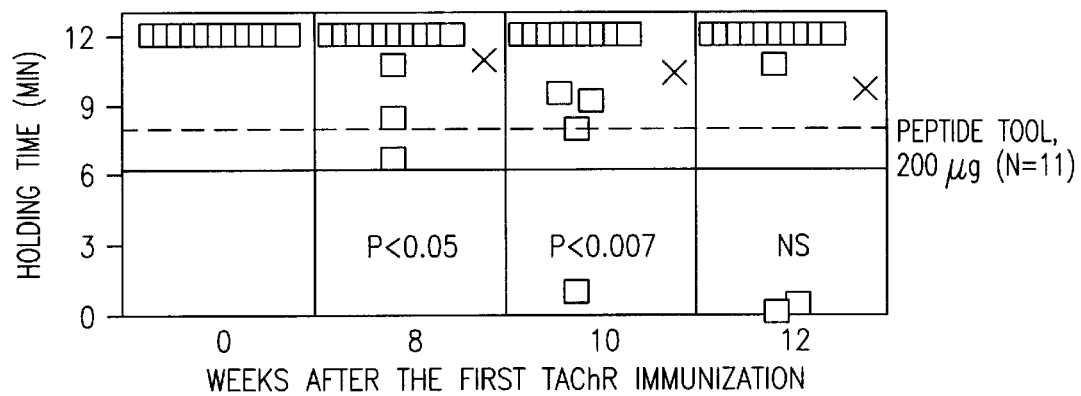
Figure 35A:
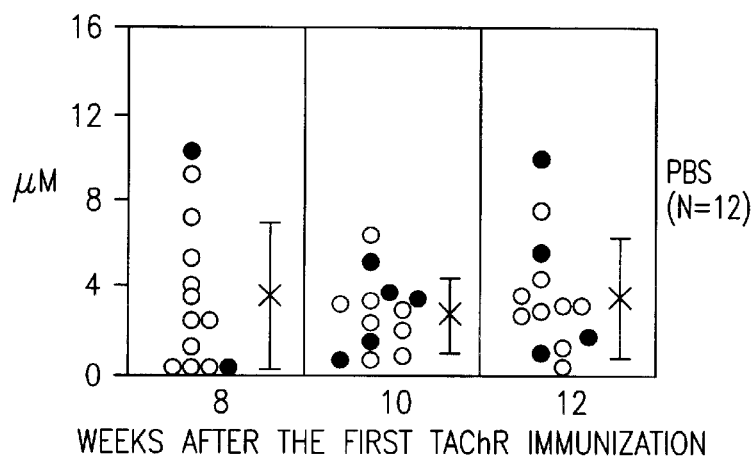
FIGS. 35A–E. Mice treated s.c. with a pool of synthetic TAChR CD4+ epitopes have less serum anti-TAChR Ab than sham-tolerized mice. Concentration of anti-TAChR Ab in the sera of individual mice treated with increasing amounts of peptide pool or solubilized TAChR in PBS or clean PBS, as indicated at the right of the plots, administered s.c. prior to and during the immunization with TAChR (prevention protocol). The number of mice in the different groups is indicated at the right of the plots. Three immunizing injections of TAChR were administered, at 4-week intervals (at weeks 0, 4 and 8), as indicated at the bottom of the figure. Serum anti-TAChR Ab concentrations (expressed as micromolars ($\mu$M) precipitated $^{125}$I-α-BTX binding sites) were measured 8, 10 and 12 weeks after the first TAChR immunization, as indicated below the plots. Mice with EMG (holding time<6.2 minutes) are indicated by black symbols. The average Ab concentrations of the different groups±SD, and the level of significance of the difference between peptide- and sham-tolerized mice are indicated.
Figure 35B:
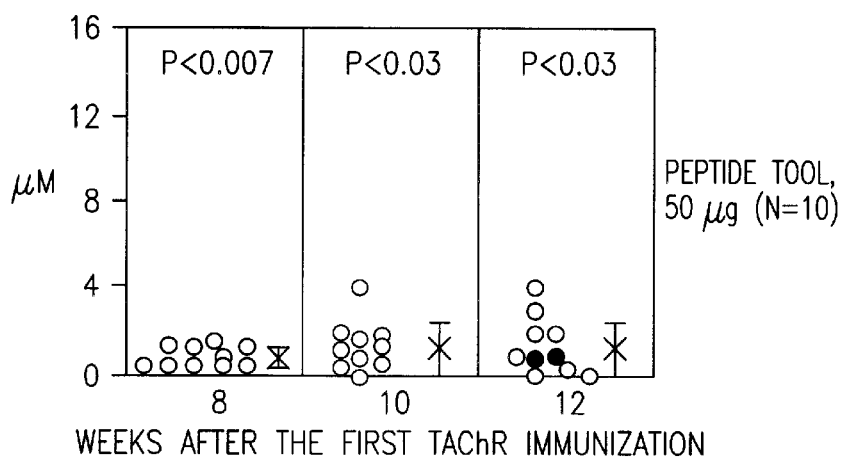
Figure 35C:
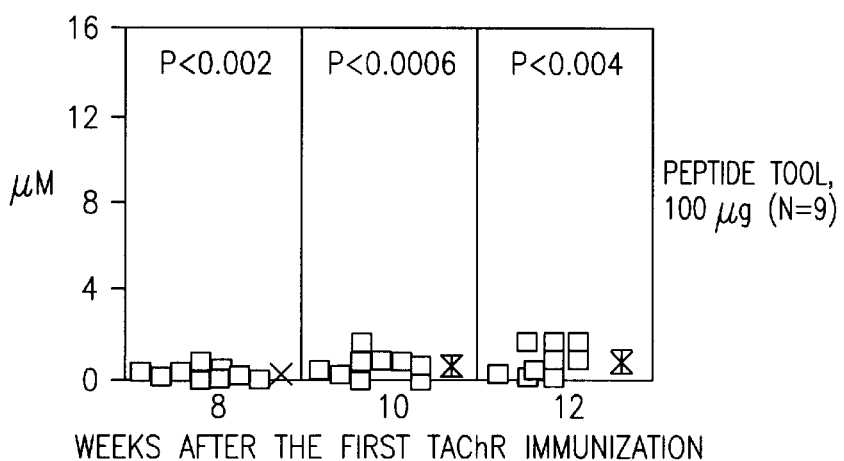
Figure 35D:
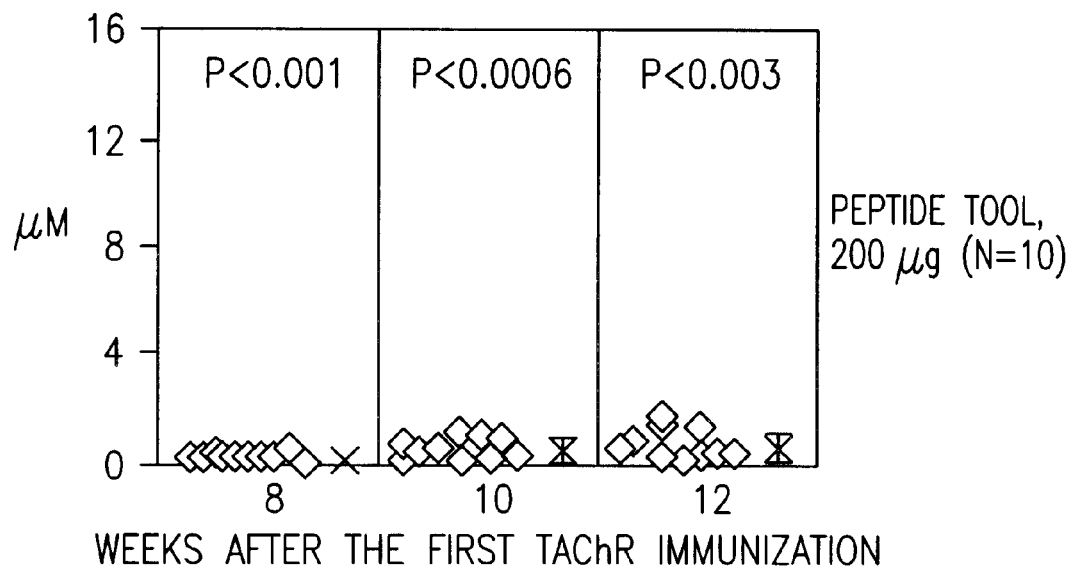
Figure 35E:
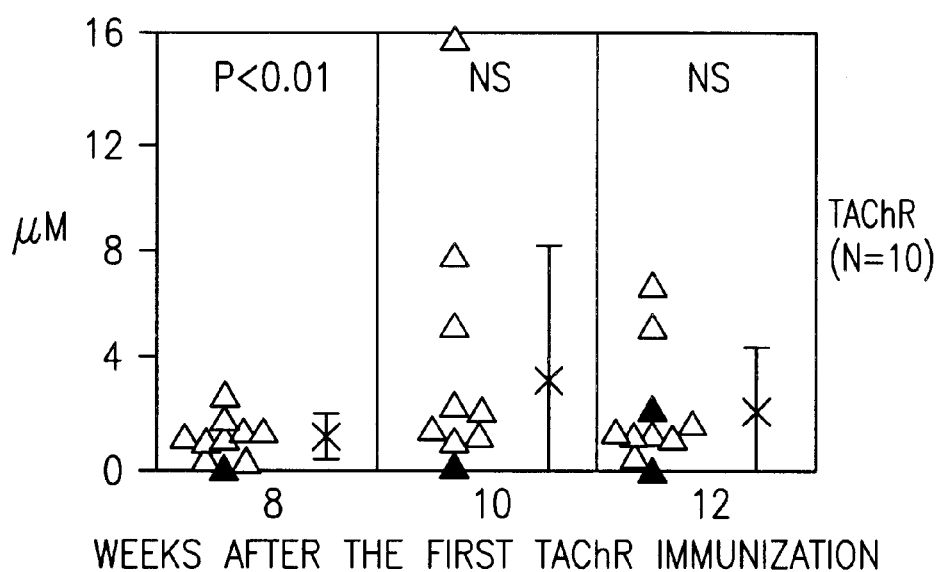

The s.c. administration of synthetic TAChR epitopes prevents EMG. FIGS. 33 and 34 summarize the results of two independent experiments, testing the strength of mice treated s.c. with solution of peptide epitopes or TAChR following the prevention protocol, and immunized with TAChR. B6 mice develop EMG consistently 50–80 days after beginning of the TAChR immunization (Example I). Consequently, the results of holding tests carried out just before the beginning of immunization (day 0) and 8, 10 and 12 weeks after the first TAChR immunization are reported. Several previous studies found small differences between batches of B6 mice in their susceptibility to EMG and the time course of the symptoms. In agreement with the results of those studies, sham-tolerized mice had EMG with maximal frequency 10 weeks after beginning of TAChR immunization in the first experiment, 8 weeks in the second experiment.

In the first experiment the effect of increasing concentrations of peptide pool (50, 100 and 200 μg of each peptide/injection) or solubilized TAChR (10 μg/injection) was tested. Positive controls for EMG induction were sham-tolerized by s.c. injections of clean PBS. Negative controls for non-specific effects of the treatments were sham-tolerized with PBS and sham-immunized with PBS in the proper adjuvant. 7–14 mice were used for each treatment, as indicated in FIG. 33. Eight to twelve weeks after beginning of the immunization, 29% of the sham-tolerized mice had clear EMG and 36% mice had holding times of 6.2–8 minutes.

The s.c. treatment with 100 and 200 μg of the peptide pool protected from EMG effectively (FIG. 33). Only two of 19 mice treated with 100 or 200 μg of peptide pool developed transient EMG. Among the 13 mice treated with 50 μg of peptide pool, a few had holding times of 6.2–8 minutes from 8 weeks onward, and two (15%) had holding times of <6.2 minutes at 12 weeks. The s.c. treatment with soluble TAChR following the prevention protocol protected from EMG to levels comparable to those observed in mice treated with the peptide pool. At 12 weeks one of 12 mice had clear EMG weakness and two mice had holding times of 6.2–8 minutes (FIG. 33).

In the second experiment groups 9–12 mice were treated with 200 μg/injection of peptide pool or peptide Tα150-169 or clean PBS, following the prevention protocol (FIG. 34). Four to five of the 12 sham-tolerized mice developed EMG, and four to five mice had holding times of 6.2–8 minutes. Treatment with the peptide pool or peptide Tα150-169 prevented EMG effectively. One mouse treated with Tα150-169 had transient EMG weakness at 8 weeks. One mouse treated with the peptide pool had EMG at 8 weeks, and two mice had EMG at 12 weeks.

FIGS. 33 and 34 report also the average holding time of the groups of mice used in these experiments (crosses), and the significance of the difference between the average holding times of the tolerized groups, and that of the ham-tolerized groups. Mice tolerized to peptide Tα150-169 or to the peptide pool had significantly longer holding times than the sham-tolerized groups.

Figure 36A:
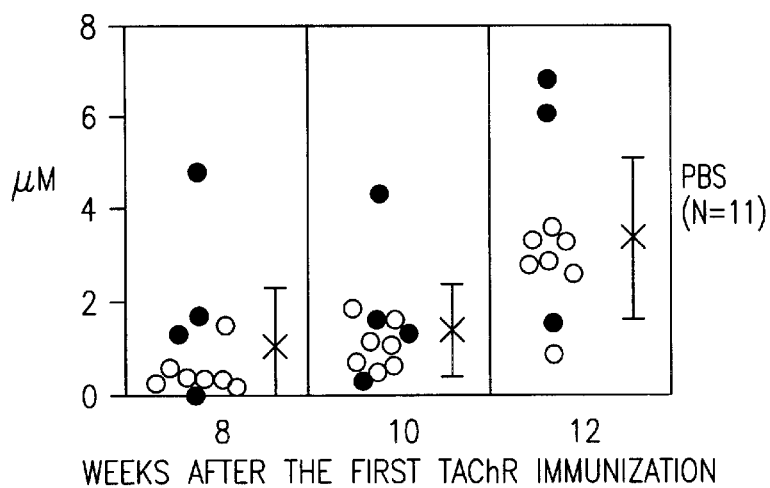
FIGS. 36A–C. Mice treated s.c. with peptide Tα150-169 have less serun anti-TAChR Ab than sham-tolerized mice. Concentration of anti-TAChR Ab in the sera of individual mice treated s.c. prior to and during the immunization with TAChR (prevention protocol) with peptide pool (200 μg of each peptide for each injection) or peptide Tα150-169 (200 μg for each injection) in PBS, or with clean PBS as indicated at the right of the plots. The number of mice in the different groups is indicated at the right of the plots. Three immunizing injections of TAChR were administered, at 3-week intervals (at weeks 0, 3 and 6), as indicated at the bottom of the figure. The serum anti-AChR Ab concentration (expressed as micromolars ($\mu$M) precipitated $^{125}$I-α-BTX binding sites) was measured 8, 10 and 12 weeks after the first TAChR immunization, as indicated below the plots. Mice with EMG (holding time<6.2 minutes) are indicated by black symbols. The average Ab concentrations of the different groups±SD, and the level of significance of the difference between peptide- and sham-tolerized mice are indicated.
Figure 36B:
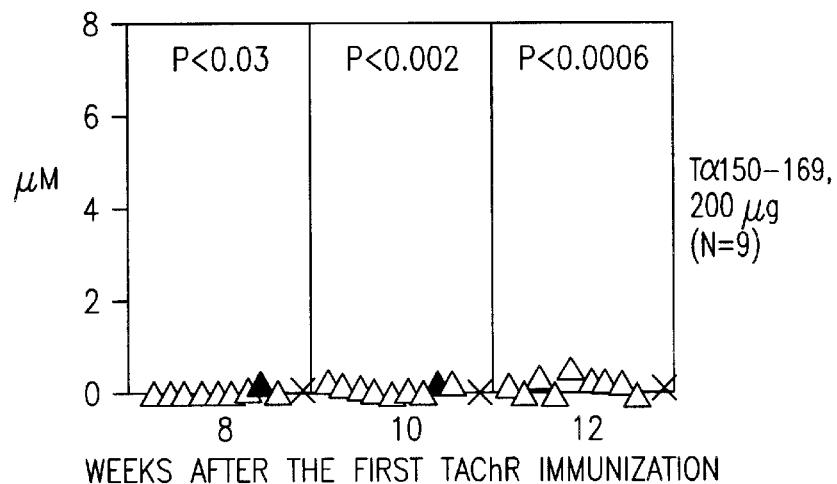
Figure 36C:
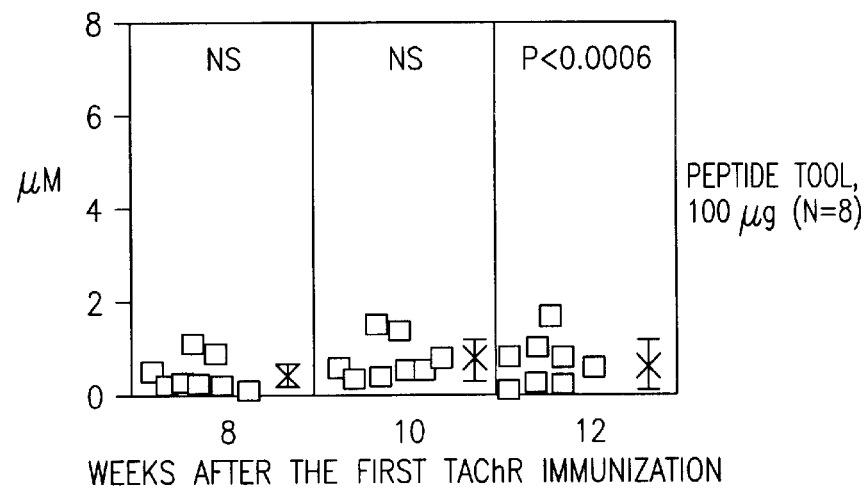
Figure 37A:
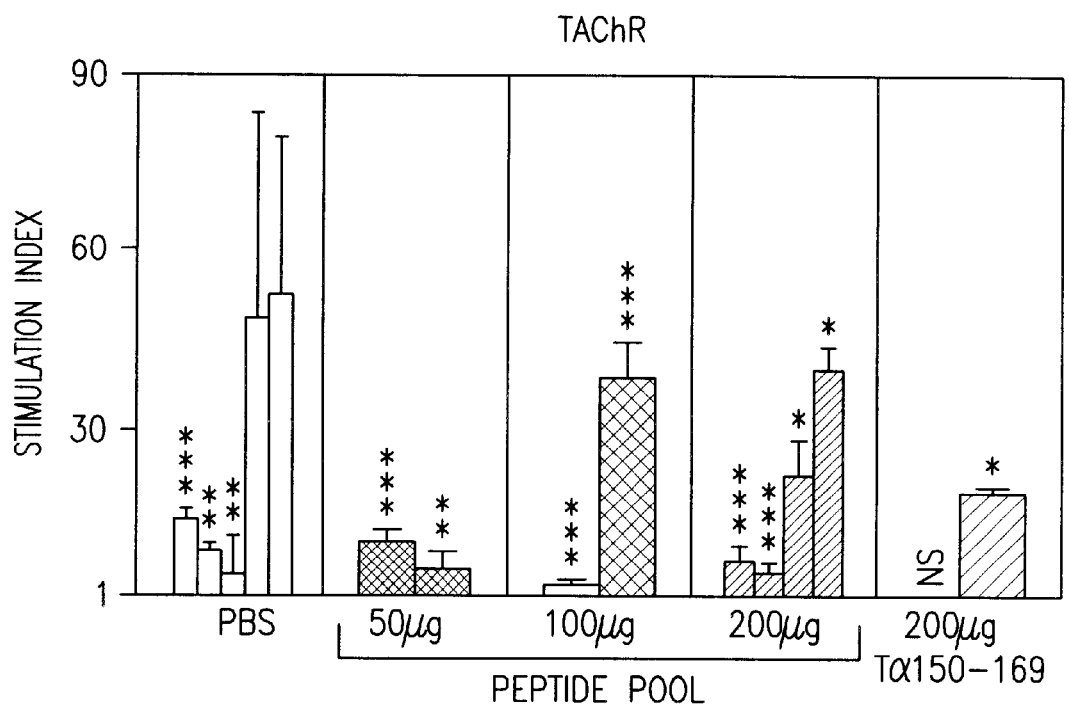
FIGS. 37A–D. Spleen CD4+ cells from mice treated s.c. with synthetic TAChR epitopes and immunized with TAChR respond poorly to the tolerizing epitopes, and respond to the TAChR to an extent similar to sham-tolerized mice. Solutions of increasing amounts of peptide pool or peptide Tα150-169 in PBS, or PBS, as indicated below the panels, were administered s.c. prior to and during the immunization with TAChR (prevention protocol). Each column represents the results obtained with pooled spleen CD4+ cells of three individual mice that had received identical treatments (as indicated below the panels), tested in proliferation assays with TAChR or the individual peptides Tα150-169, Tα181-200 or Tα360-378, as indicated above each panel. In all experiments 5 and 10 μg of each Ag was used with comparable results. The highest responses observed for each Ag are reported. The data are the average S.I.±SD of triplicate cultures. The cpm in the absence of any stimulation in the different experiments were from 64±9 to 2690±2310. The level of significance of the responses, as compared the $^3$H-thymidine incorporation of non-stimulated cultures, are reported (*p<0.05; p<0.01; *p<0.005).
Figure 37B:
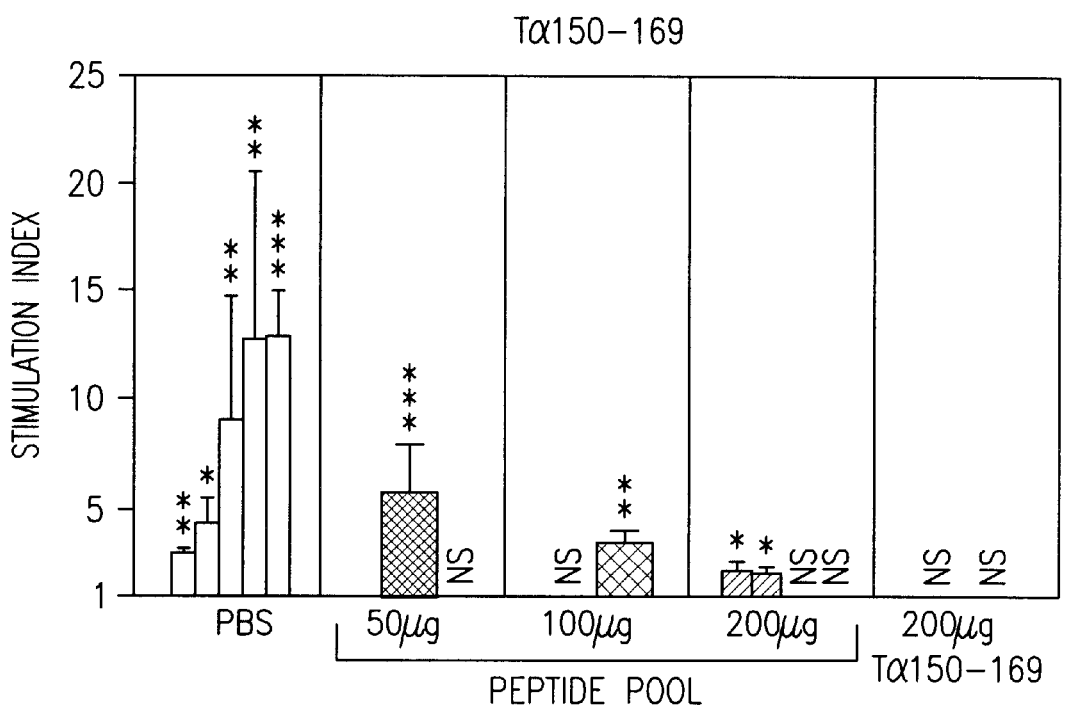
Figure 37C:
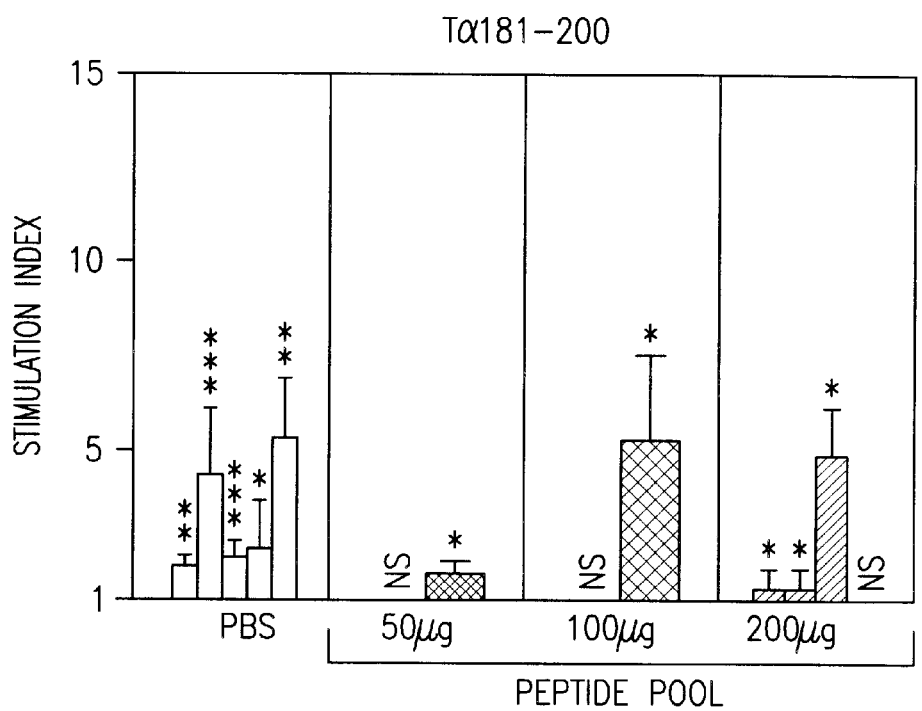
Figure 37D:
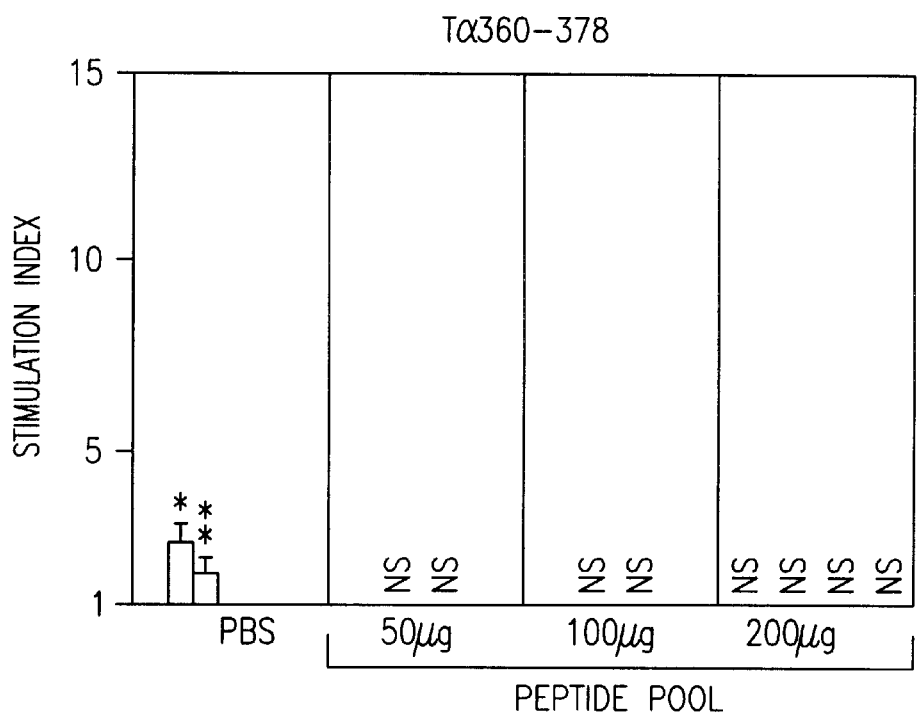
Figure 38A:
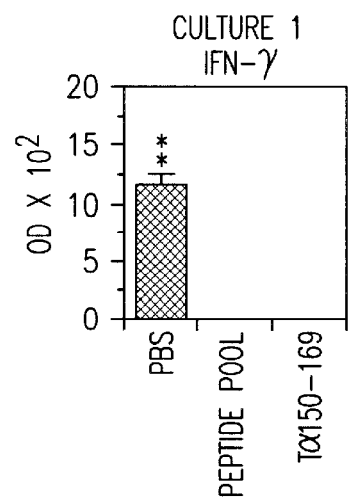
FIGS. 38A–D. The s.c. treatment with TAChR peptides stimulates TAChR-specific Th2 cells. Secretion of IFN-γ, IL4 and IL-10 in response to challenge with TAChR in vitro, by CD8$^+$ depleted spleen cells of mice treated s.c. (prevention protocol) with peptide pool (200 µg of each peptide for each injection) or peptide Tα150-169 (200 µg for each injection), or clean PBS, as indicated below the plots. Pooled CD8$^+$ depleted spleen cells from three mice that had received identical treatment were used to set up duplicate cultures, that were cultivated with 10 µg/ml of TAChR. Identical cultures did not receive any stimulus and served as controls for basal secretions of the cytokines studied. The concentration of the cytokines in the supernatants of those control cultures are subtracted from the data reported here. The columns represent the averages of duplicate, independent assays for each culture and for each condition, using supernatant samples obtained 72 hours after TAChR addition. The data are expressed as OD units detected in ELISA. The asterisks represent a significant (*p<0.05;**p<0.006) difference between the concentration of the cytokine in the TAChR stimulated cultures and that in the supernatant of control non-stimulated cultures.
Figure 38C:
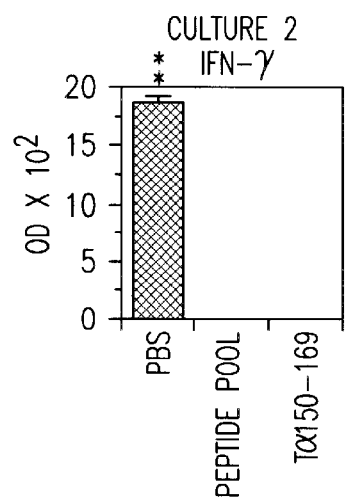
Figure 38B:
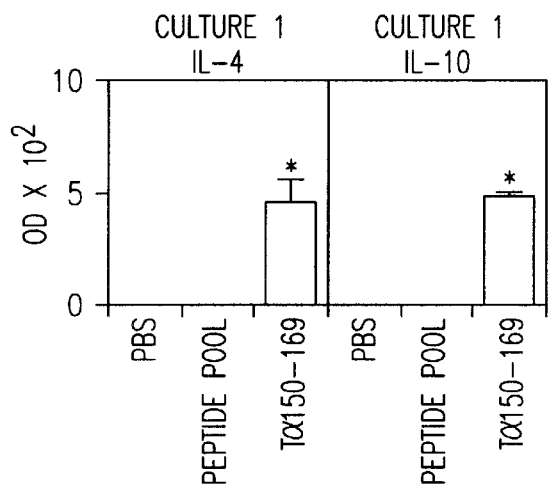
Figure 38D:
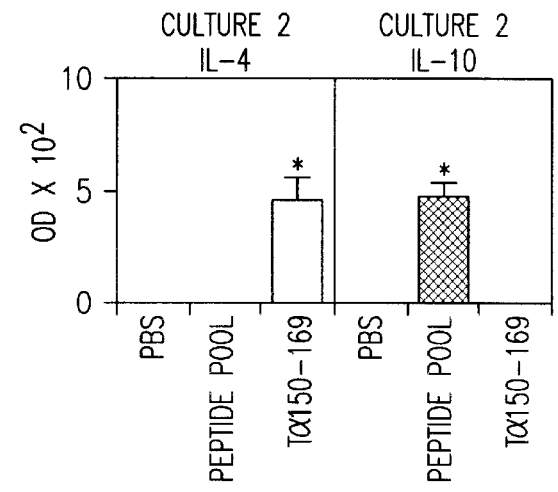
Figure 39A:
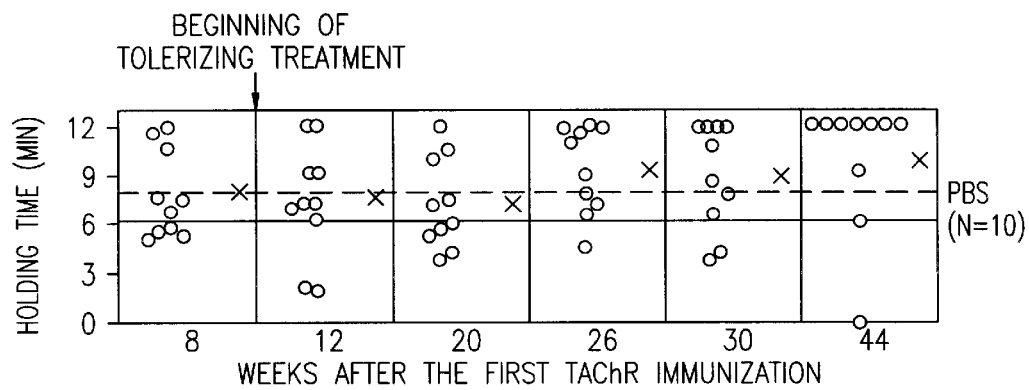
FIGS. 39A–D. Effect on established EMG of s.c. administration of TAChR CD4$^+$ epitope peptides or solubilized TAChR. Peptide pool (200 µg of each peptide) or peptide Tα150-169 (200 µg) or solubilized TAChR (10 µg) in PBS, or clean PBS, as indicated at the right of the plots, were administered s.c. starting 8 weeks after beginning of the immunization with TAChR, after appearance of EMG (post-priming protocol). The number of mice in the different groups is indicated at the right of the plots (notice that three mice of the group treated with Tα150-169 are missing from the panel '44 weeks' because they died from causes unrelated to EMG). Three immunizing injections of TAChR were administered, at 4-week intervals (at weeks 0, 4 and 8) as indicated at the bottom of the figure. The open symbols represent the muscle strength of the individual mice, measured as holding time using the curare sensitized hanging test. Mice with holding times of 6.2 minutes (indicated by a solid horizontal line) or less were considered to have fully developed EMG. Holding times of more than 6.2 and less than 9 minutes (dashed horizontal line) may indicate the beginning of EMG. The average holding time of the different groups (crosses) and the level of significance of the difference as compared to the sham-tolerized group is also reported.
Figure 39B:
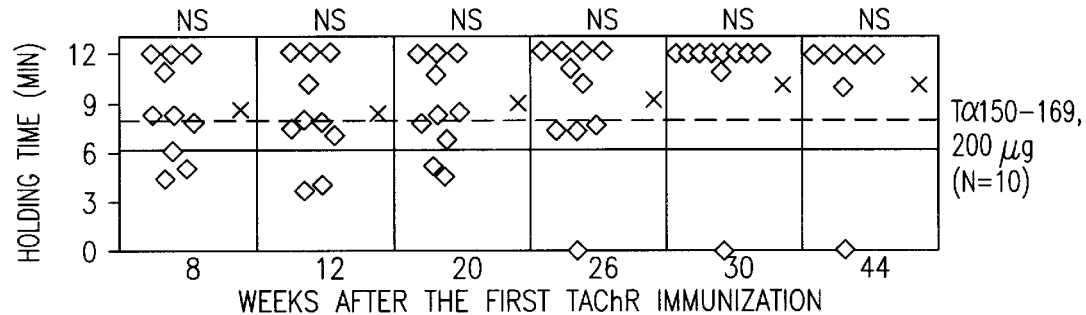
Figure 39C:
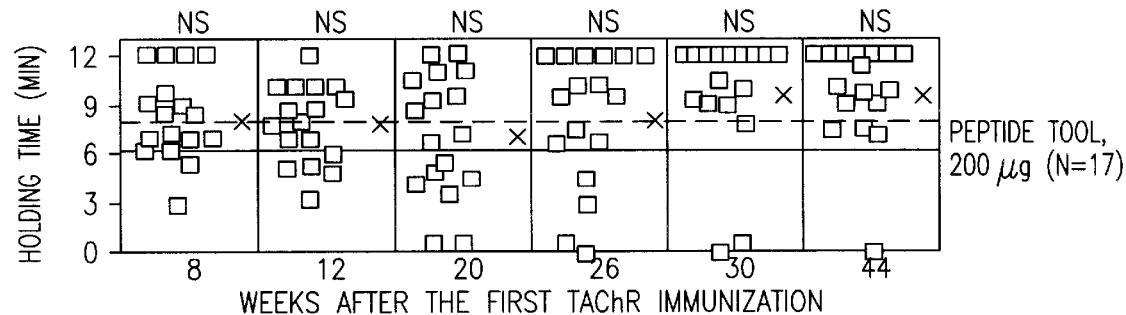
Figure 39D:
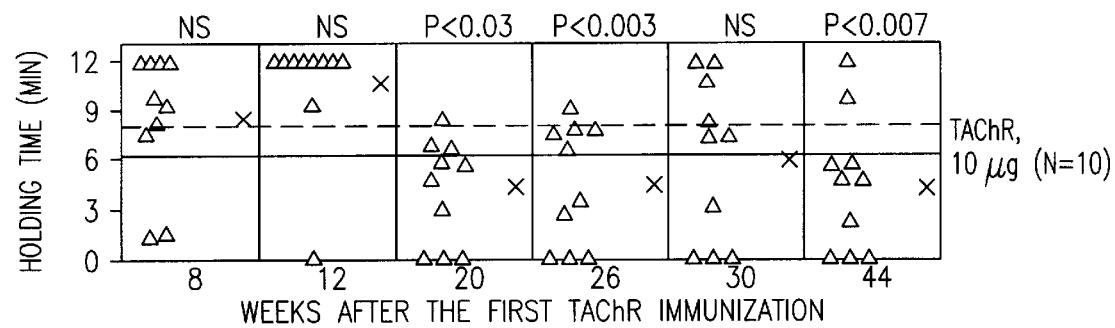
Figure 40A:
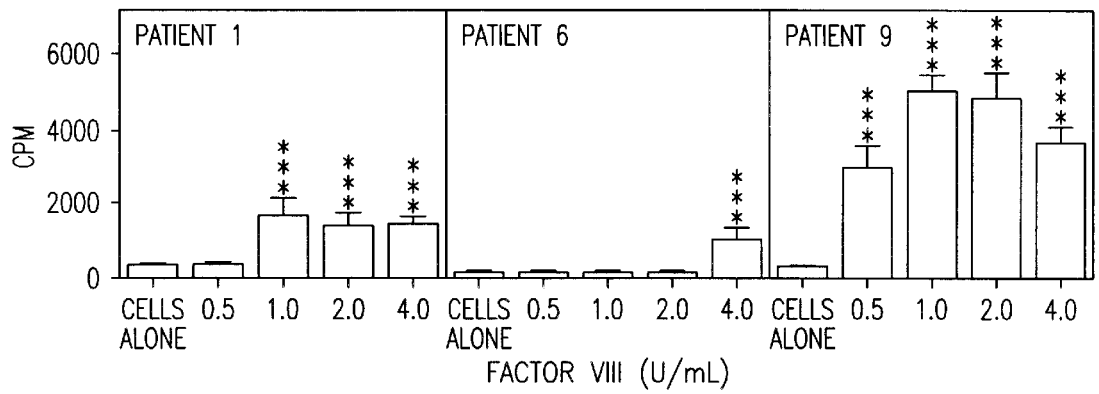
FIGS. 40A–F. Dose dependency of the response to Factor VIII in patients with autoimmune acquired hemophilia, hemophilia A with inhibitors, and hemophilia A without inhibitors.
Figure 40B:
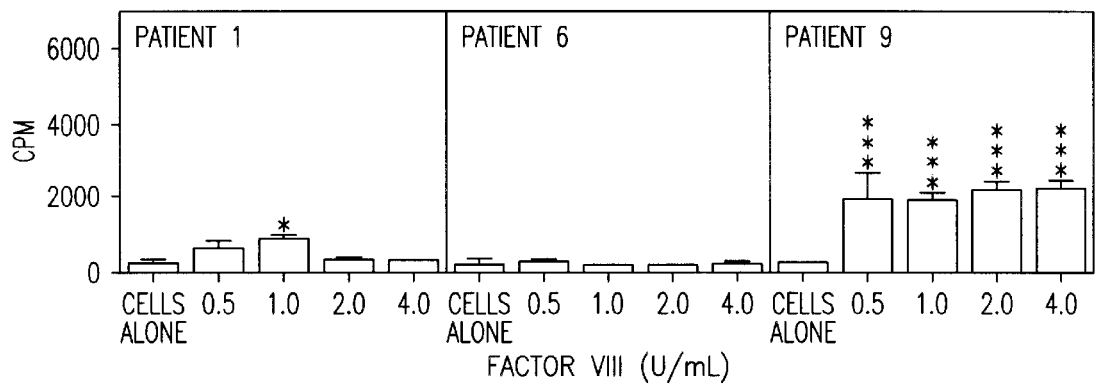
Figure 40C:
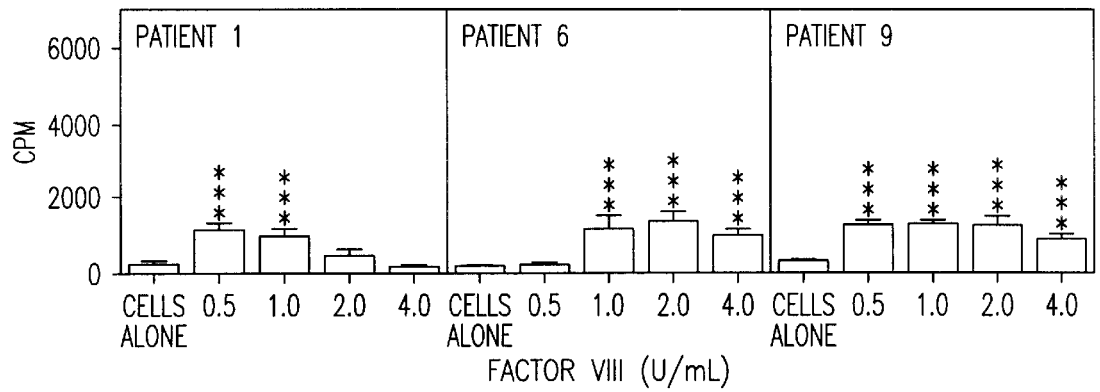
Figure 40D:
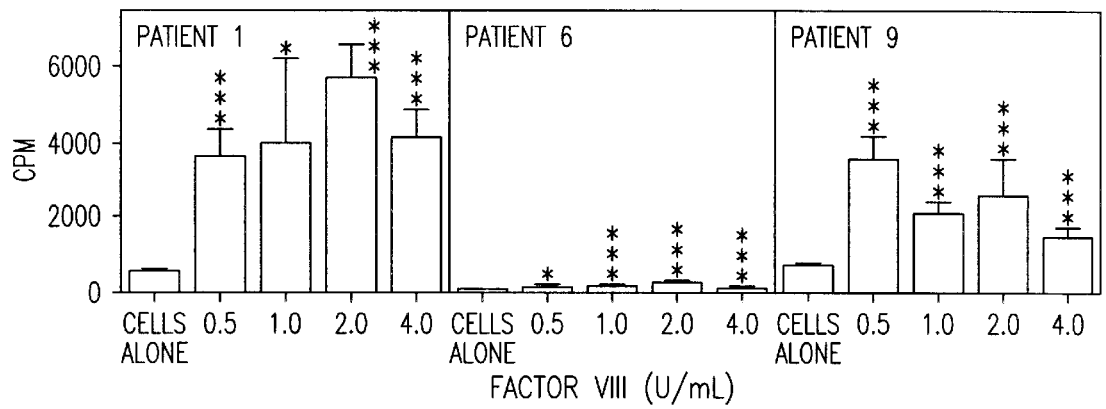
Figure 40E:
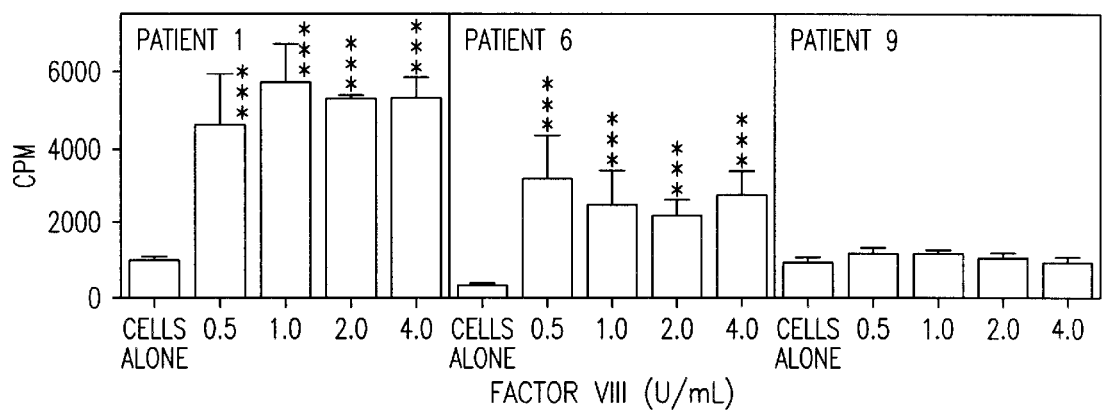
Figure 40F:
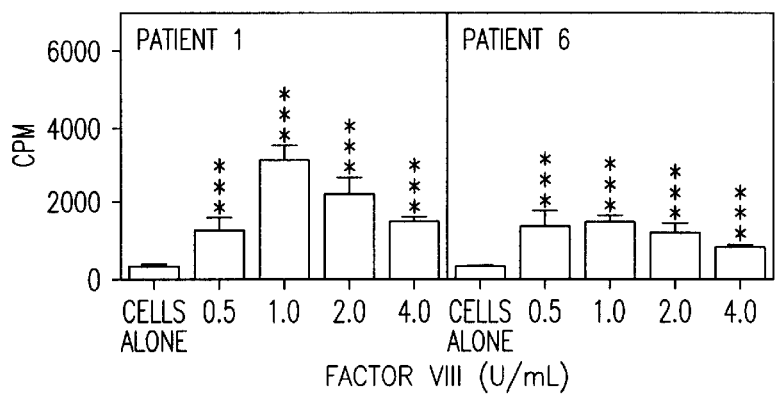
Figure 42A:
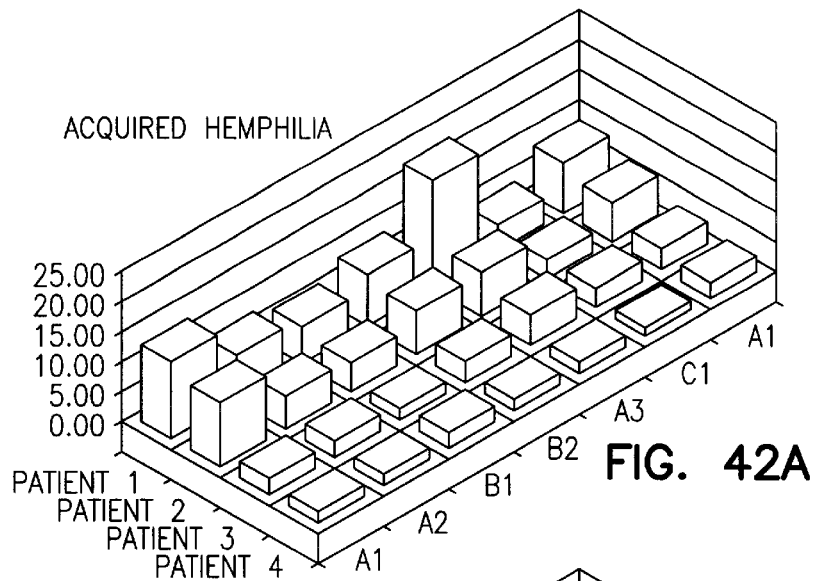
FIGS. 42A–F. Average intensity of the responses to different Factor VIII domain pools. L FIGS. 43A–L. Stimulation indices for 12 healthy patients over time.
Figure 42B:
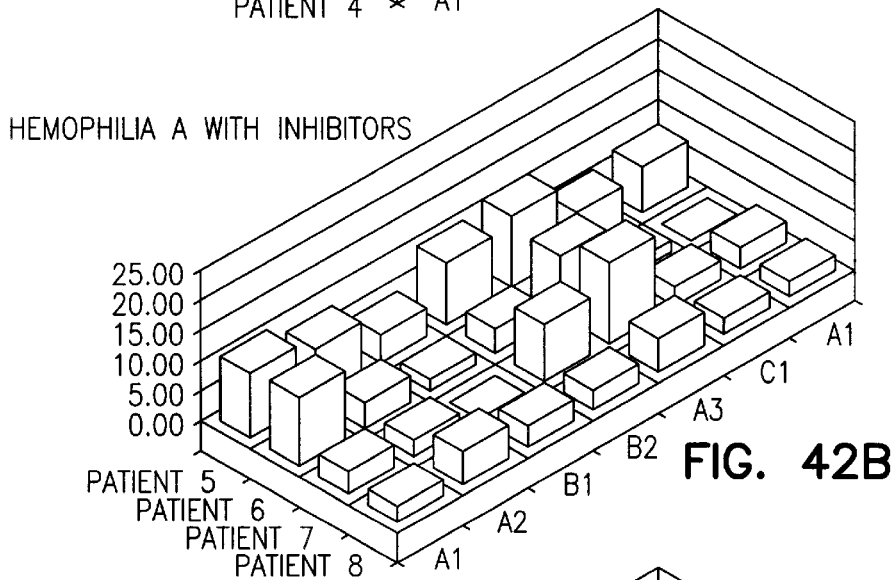
Figure 42C:
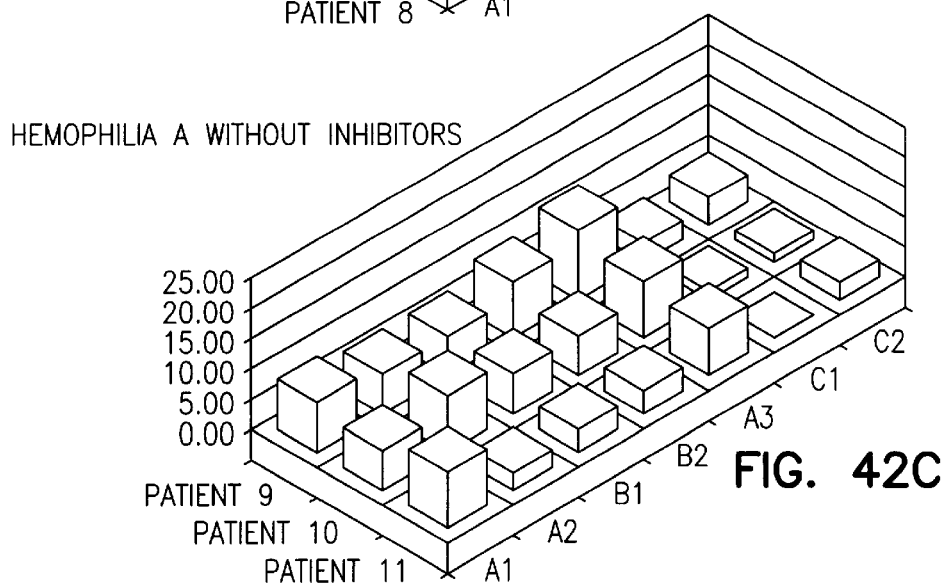
Figure 42D:
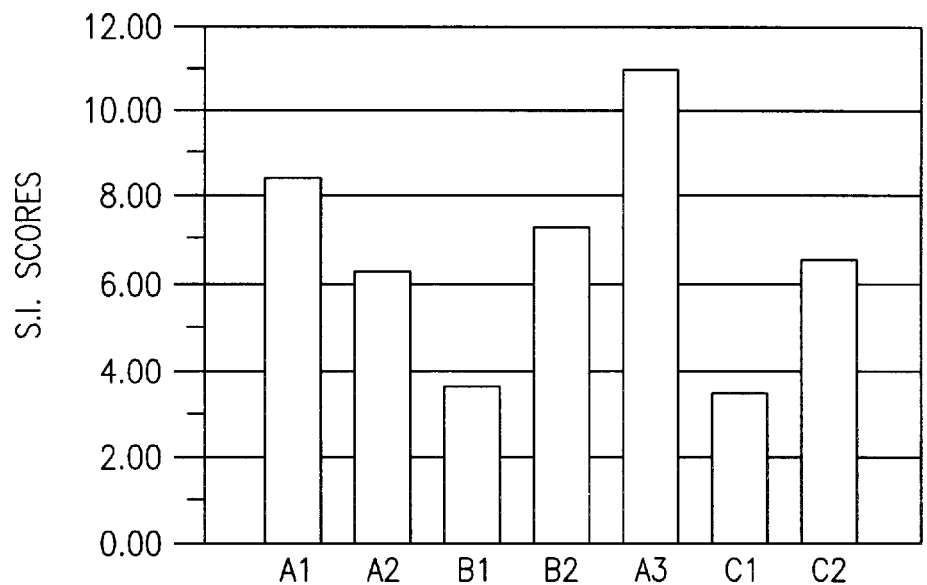
Figure 42E:
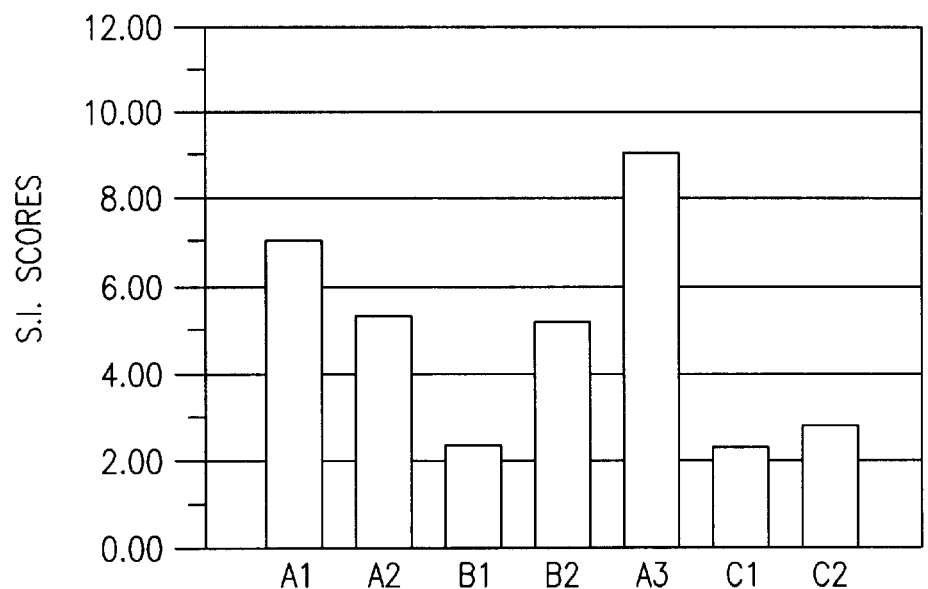
Figure 42F:
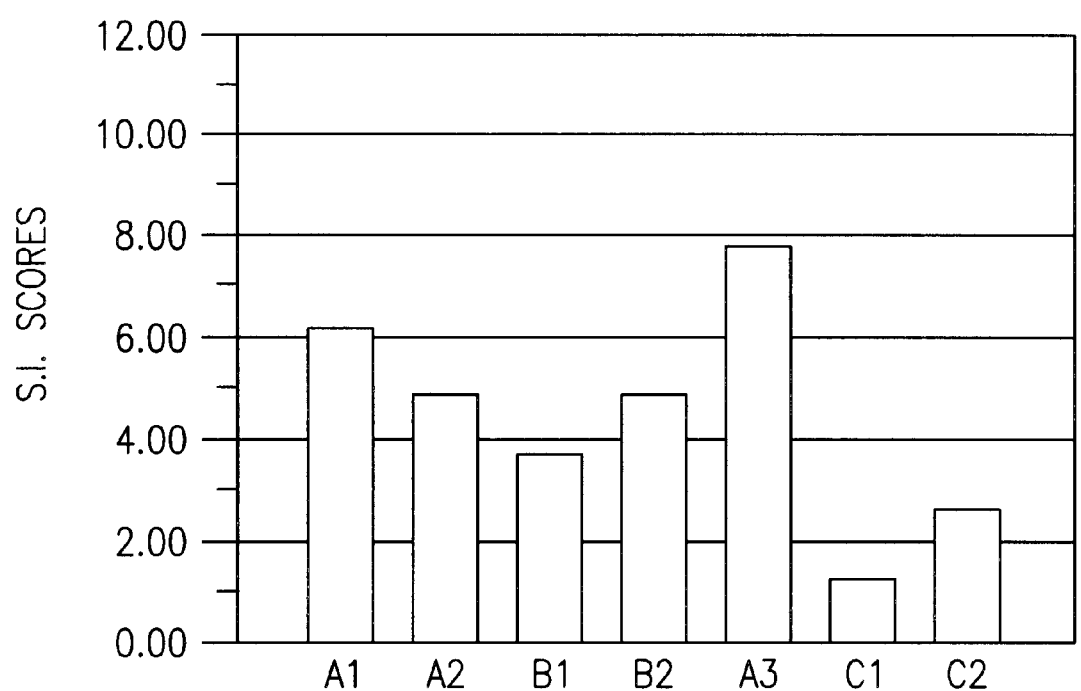
Figure 43A:
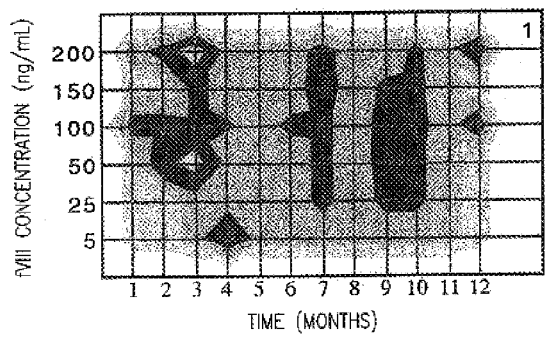
Figure 43B:
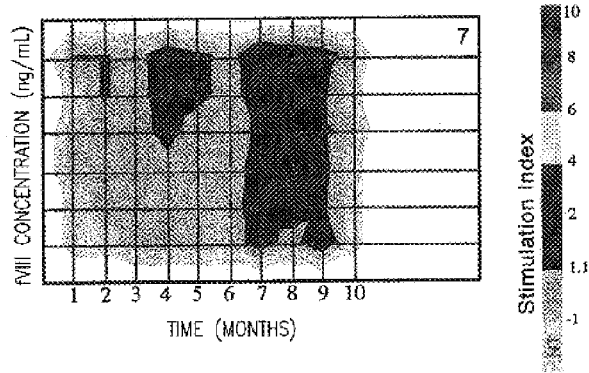
Figures 43C, 43D:
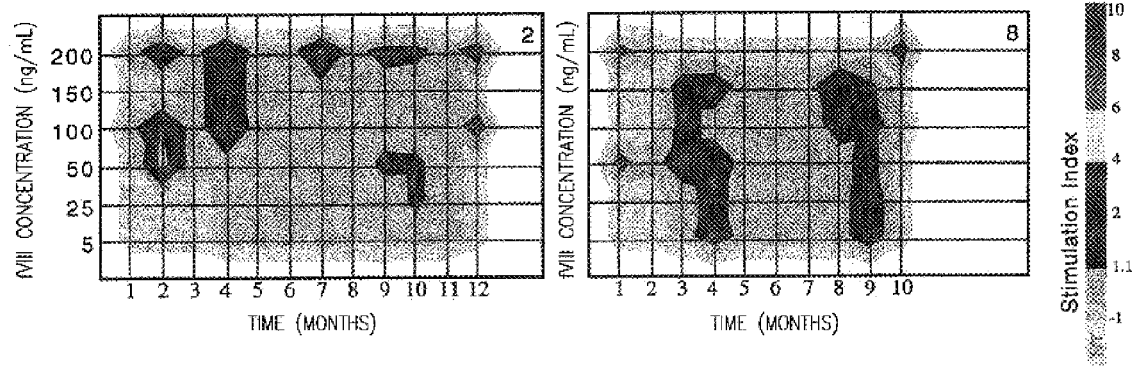
Figure 43E:
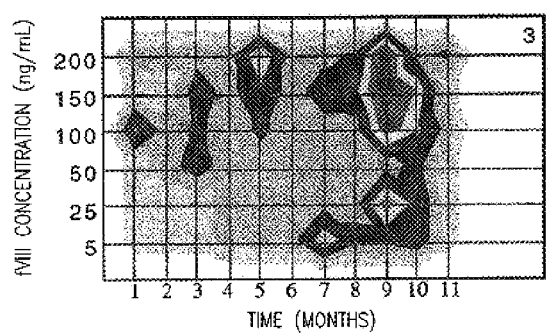
Figure 43F:
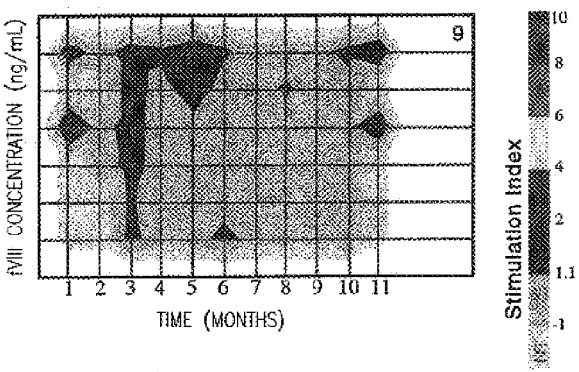
Figure 43G:
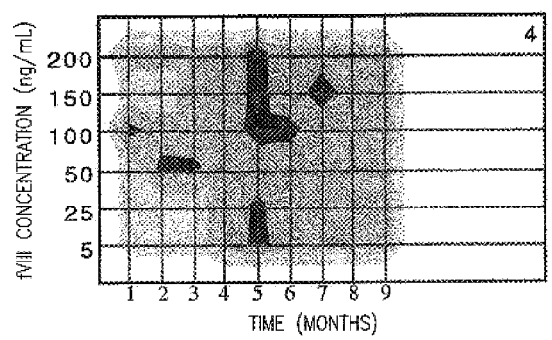
Figure 43H:
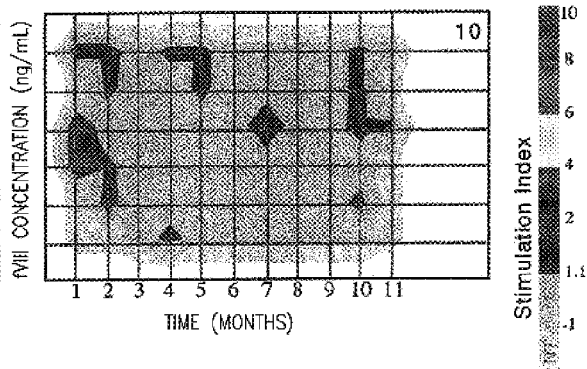
Figure 43I:
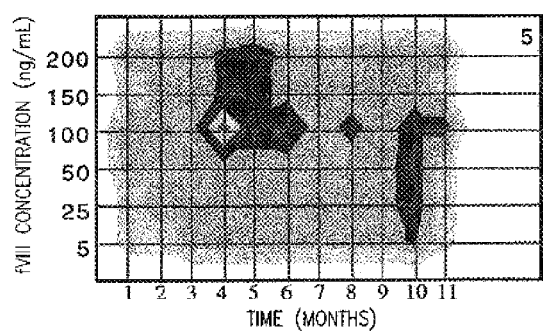
Figure 43J:
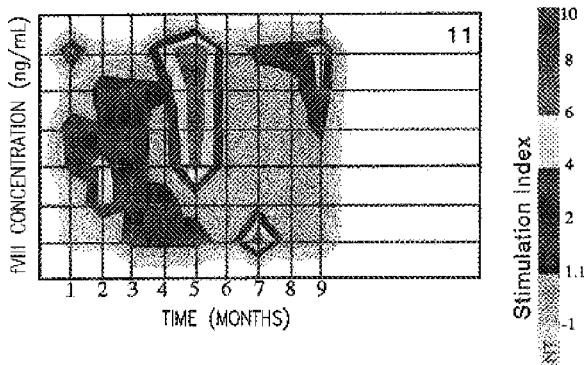
Figure 43K:
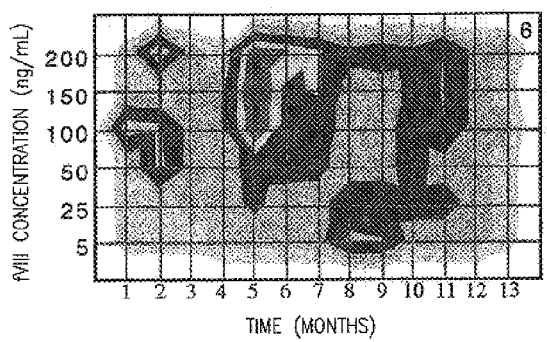
Figure 43L:
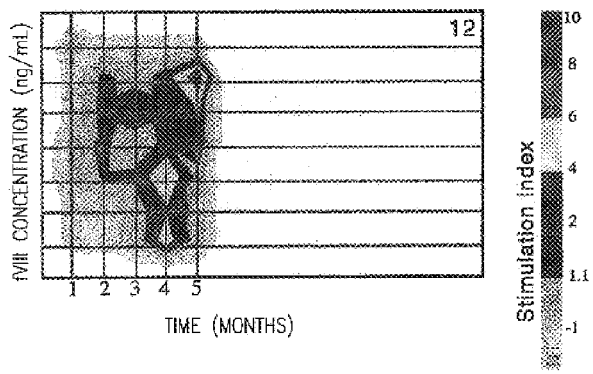

The s c. treatment with TAChR peptides reduces anti-TAChR Ah synthesis. The concentration of anti-TAChR Ab in the sera of individual mice tolerized with the peptide pool or peptide Tα150-169 or sham-tolerized, at different times after beginning of the TAChR immunization, was measured. The mice were the same used in the experiments reported in FIGS. 33 and 34. FIGS. 35 and 36 report the anti-TAChR Ab concentration in the sera of individual mice, the average concentrations±SD of the different groups of mice (crosses), and the significance of the differences between the average concentration of the tolerized groups and that of the corresponding sham-tolerized groups. Mice treated with the peptide pool or with peptide Tα150-169 had anti-TAChR Ab concentrations significantly and substantially lower than the sham-treated groups at 12 weeks, and frequently at all the times tested (FIGS. 35 and 36). The s.c. tolerization with TAChR delayed but did not ultimately affect anti-TAChR Ab synthesis (FIG. 35).

In agreement with previous studies, the anti-TAChR Ab concentrations of the individual mice did not correlate with the EMG symptoms. Some mice with EMG symptoms (black symbols in FIGS. 35 and 36) were among those with highest Ab concentrations, but others had low anti-TAChR Ab titers.

The s.c. treatment with TAChR peptides affects primarily Th1-helper synthesis of anti-TAChR Ab To determine if the reduced anti-TAChR Ab synthesis observed in the peptide-treated mice was due to a reduction of the Th1- or Th2-driven IgG subclasses, the concentration of anti-TAChR IgG1, which are synthesized with the help of Th2 cells (Abbas et al., 1996; O'Garra, 1998), and the total concentration of anti-TAChR IgG in mice tolerized s.c. with the peptide pool or Tα150-169 or TAChR, or sham-tolerized, was measured. The sera was obtained at the end of the observation period. Table 6 reports the concentrations of anti-TAChR IgG1 and total anti-TAChR Ab in pooled sera from five mice randomly selected among those that had received identical treatment. The different samples tested included sera from different mice. Peptide-treated mice had concentrations of anti-TAChR IgGI comparable with or slightly lower than the sham-treated mice, while their total anti-TAChR Ab concentrations were much lower (see also FIGS. 35 and 36). Only mice treated with 200 μg of peptide pool or peptide Tα150-169 had a significant (p<0.008), albeit very modest reduction of anti-TAChR IgG1.

TABLE 6

Anti-TAChR IgG and IgG1 Ab[a] in sera from mice treated s.c. with the epitope peptides

| Tolerizing treatment | Total IgG (μM) | IgG1 (μM) | IgG1 (%) |
|---|---|---|---|
| PBS | 1.25 ± 0.05 | 0.33 ± 0.012 | 26 ± 1 |
| | 0.81 ± 0.05 | 0.31 ± 0.009 | 39 ± 1.4 |
| | 2.45 ± 0.25 | 0.39 ± 0.02 | 15.3 ± 2.4 |
| | 2.45 ± 0.05 | 0.52 ± 0.03 | 21 ± 1.4 |
| peptide pool 50 μg | 0.37 ± 0.02 | 0.34 ± 0.005 | 94 ± 3.8 |
| | 1.1 ± 0.025 | 0.36 ± 0 | 32 ± 1.4 |
| peptide pool 100 μg | 0.83 ± 0.08 | 0.44 ± 0.03 | 54 ± 2.2 |
| | 0.3 ± 0.008 | 0.26 ± 0.03 | 88 ± 8.5 |
| peptide pool 200 μg | 0.29 ± 0.002 | 0.17 ± 0 | 59 ± 0 |
| | 0.19 ± 0.02 | 0.15 ± 0 | 83 ± .45 |
| | 0.43 ± 0.02 | 0.38 ± 0.02 | 89 ± 4.8 |
| Tα150-169 μg | 0.47 ± 0.01 | 0.22 ± 0.005 | 46 ± 1.15 |
| | 0.28 ± 0.015 | 0.27 ± 0.01 | 96 ± 3.5 |

[a]Samples were pooled sera from five identically treated mice. The Ab concentration is expressed as micromolars (μM) precipitated $^{125}$I-α-BTX binding sites (average ± SD of the three determinations).

Th2-dependent anti-peptide Ab synthesis in peptide-treated mice. To determine whether s.c. peptide treatment stimulated synthesis of anti-peptide Ab, and whether that involved the help of Th1 or Th2 CD4[+] cells, or both, the presence of anti-peptide IgG and IgG1 in the sera of mice that had been peptide- or sham-tolerized, and immunized with TAChR, was assessed. The sham-tolerized mice had low levels of Ab reactive with the peptide epitopes after TAChR immunization (Table 7). The presence of anti-peptide Ab did not correlate with the protective effect of the treatment. For example, mice treated with 200 μg of peptide Tα150-169 did not have EMG symptoms at 12 weeks (FIG. 34), yet some of them did not have a good Ab response to this peptide (Table 7). When good titers of anti-peptide Ab were present (slopes of 9 OD/μl of serum or larger), many or most Ab were IgG1 (Table 7).

TABLE 7

Anti-peptide Ab (total IgG and IgG1) in sera from mice treated s.c. with the epitope peptides

| Treatment | Total IgG[a] | IgG1[a] | % IgG1 |
|---|---|---|---|
| A. Antibody to peptide Tα150–169 | | | |
| PBS | 2.4 | nd[b] | — |
| peptide pool, 200 μg | 5.8 | 0.3 | 5 |
| Tα150–169, 200 μg | 2.6 | 0.5 | 19 |
| Tα150–169, 200 μg | 80 | 40 | 50 |
| B. Antibody to peptide Tα181–200 | | | |
| PBS | 3 | nd[b] | — |
| peptide pool, 200 μg | 79 | 44 | 56 |
| C. Antibody to peptide Tα360–378 | | | |
| PBS | 1.5 | 0.2 | 13 |
| peptide pool, 200 μg | 9 | 7 | 78 |

[a]Samples were pooled sera from five identically treated ice. Titers are expressed as OD units × $10^{-3}$/μl of serum, i.e., the slope observed for ELISA assay carried out with increasing dilutions of each sera. Comparison between the total IgG and the IgG1 titers against a given peptide was obtained by employing slopes obtained n the same experiment, and using as 100% the slope observed in that experiment for the total IgG to that peptide.
[b]nd: Not detectable.

The s.c. treatment with peptide epitopes affects the CD4[+] T-cell response to the peptides, not to TAChR. The mice used for the experiments reported in the previous figures were sacrificed about I week after a last TAChR boost. The proliferative response of their spleens CD4[+] T-cells to TAChR and peptides Tα150-169, Tα181-200 and Tα360-378 was tested. Several experiments were carried out and these are summarized in FIG. 37. In all experiments 5 and 10 μg of each Ag was used with comparable results, although 10 μg sometimes elicited stronger responses. In FIG. 37 the highest responses observed for each Ag are reported. The columns represent the average response to the Ag of triplicate cultures of pooled CD4[+] spleen cells from three mice that had received identical treatments. The results are organized in four panels, according to the Ag used in the proliferation assay. Each panel depicts the responses to that Ag of sham- or peptide-tolerized mice, as indicated below the plots. The pattern of responses to the different Ag was comparable in mice that had received identical treatments, but the size of the responses varied in the different experiments. For example, sham-tolerized mice always responded to TAChR significantly, but their S.I. were between 5 and 58. This variability, that we observed previously (Bellone et al., 1991a,b, 1993; Karachunski et al., 1995, 1997) did not correlate with the clinical state of the mice when the spleens were removed.

Spleen CD4[+] cells from sham- and peptide pool-treated mice always responded to TAChR. CD4[+] cells from mice treated with Tα150-169 responded to the TAChR significantly and to an extent comparable to the responses observed in the sham-tolerized group in one experiment. In the other experiment they did not respond (FIG. 37).

CD4$^+$ cells from sham-tolerized mice responded consistently to peptides Tα150-169 and Tα181-200 (FIG. 37). The lesser response to the peptides than to TAChR (notice the different vertical axis of the plots in FIG. 37) is because the anti-TAChR CD4$^+$ T-cells of B6 mice recognize also epitopes on sequence regions other than those used. Only three of the five pools of spleen CD4$^+$ T-cells from sham-tolerized mice responded to Tα360-378. This peptide is much less immunogenic for CD4$^+$ cell sensitization than Tα150-169 (Bellone et al., 1991a, 1993; Karachunski et al., 1995). The responses to Tα150-169 and Tα181-200 of mice tolerized to the peptide pool were erratic and, when present, modest (FIG. 37). The CD4$^+$ cells of these mice never responded to Tα360-378 (FIG. 37). CD4$^+$ spleen cells from mice tolerized with Tα150-169 never responded to this peptide (FIG. 37).

The s.c. treatment with TAChR peptides stimulates TAChR-specific Th2 cells. The secretion of IFN-γ, IL-4 and IL-10 by CD8$^+$ depleted spleen cells from sham- or peptide-tolerized mice immunized with TAChR, in response to challenge in vitro with TAChR, was determined. IFN-γ is a representative cytokine for Th1 cells, IL-4 and IL-10 for Th2 cells (Abbas et al., 1996; O'Garra, 1998). Mice treated s.c. with PBS or with 200 μg/injection of peptide pool or Tα150-169, following the prevention protocol, were tested. One week after the fourth TAChR immunization, the mice were sacrificed, the CD8$^+$ depleted spleen cells of three mice for each group pooled, and duplicate cultures of those pooled cells set up which were cultivated with TAChR (10 μg/ml) or without any stimuli (as controls for basal secretions of the cytokines studied). IFN-γ, IL-4 and IL-10 was measured in the supernatants of TAChR-stimulated and non-stimulated cultures, 72 hours after addition of the TAChR. Two independent assays of IFN-γ and IL-10 were carried out, using duplicate samples for each supernatant. For IL-4, given the relatively large amount of supernatant needed, its concentration was tested in the pooled supernatants of the two cultures. The results of one of two consistent experiments is reported in FIG. 38. The cytokine concentration in the control non-stimulated cultures has been subtracted from the data in FIG. 38.

The presence of TAChR in cultures of CD8$^+$ depleted spleen cells from sham-tolerized mice induced a significant increase in the secretion of INF-γ, but not of IL-4 and IL-10. In cultures of cells from peptide pool-tolerized mice, the presence of TAChR did not cause increased INF-γ or IL-4 secretion, but it caused an increase of IL-19 secretion in one of the two cell cultures tested. In cultures of cells from mice tolerized to Tα150-169, the presence of TAChR did not cause increased INF-γ secretion, but it induced a significant increase in secretion of IL-4, and in one of the two cultures tested also of IL-10.

Effect on established EMG of s.c. administration of TAChR peptide epitopes or soluble TAChR. To determine whether s.c. administration of TAChR epitopes or of solubilized TAChR, given after establishment of the anti-TAChR immune response and appearance of EMG, affected existing EMG symptoms, groups of mice treated s.c. with PBS, TAChR, peptide pool or peptide Tα150-169 following the post-priming protocol were used (FIG. 39).

Sham-treated mice had stable EMG frequency from 8 to 20 weeks after beginning of the TAChR immunization (FIG. 39). Later, the number of affected animals decreased (FIG. 39). This likely reflects the spontaneous improvement of EMG in the absence of further boosts with TAChR. The mice treated with peptide pool or Tα150-169 had similar EMG frequency. Similar to the sham-treated mice, the number of affected mice decreased over time (notice that three mice treated with Tα150-169, that died from causes unrelated to EMG, are missing from the panel '44 weeks').

Mice that received s.c. injection of solubilized TAChR without adjuvant developed a very high EMG frequency after the s.c. treatment had started, that persisted for the duration of the observation period (FIG. 39). At 44 weeks, 80% of these mice had holding times of 6.2 or less, as compared to 20% of the sham-treated mice, 15% of the peptide pool treated mice, and 6% of the mice treated with peptide α150-169.

Discussion. S.c. administration of a pool of three CD4$^+$ epitopes of the TAChR α subunit, or of a single immunodominant epitope recognized by pathogenic CD4$^+$ cells, Tα150-169, effectively reduced the anti-TAChR Ab response and protected B6 mice from EMG. The peptide treatment was effective when administered before and during immunization with TAChR, suggesting that s.c. administration of peptide epitopes did not cause priming of pathogenic CD4$^+$ T-cells. This possibility is supported by the finding that s.c. peptide treatment started after appearance of EMG did not worsen existing EMG symptoms.

The s.c. administration of peptides causes production of anti-peptide Ab (Table 7). However, the anti-peptide Ab were not pathogenic, because prolonged s.c. treatment with the peptide epitopes did not worsen EMG symptoms (FIG. 39). Immunization with short TAChR peptides does not cause EMG (Bellone et al., 1995) because anti-peptide Ab do not cross-react with the cognate native Ag (Conti-Fine et al., 1996). EMG symptoms did not improve in mice treated with peptides after the onset of EMG. This is not surprising, considering the long half-life of anti-AChR Ab and of activated B-cells, and the likely persistence of the immunizing TAChR during the period of observation.

The s.c. treatment with solubilized TAChR effectively reduced the appearance of EMG symptoms when started before the immunization procedure, but it made the symptoms worse and more frequent when administered after the appearance of EMG (FIG. 39). This suggests that administration of soluble TAChR following the prevention protocol reduced the subsequent priming of TAChR-specific immune cells, but administration following the post-priming protocol stimulated the synthesis of pathogenic Ab. These results underline the potential dangers of the use of native autoAg for tolerization procedures that may stimulate the synthesis of pathogenic Ab.

Peripheral tolerance may be due to different mechanisms, including: anergy or deletion of Ag-specific T-cells, and induction of Ag-specific regulatory CD4$^+$ Th2 cells (Burstein et al., 1992; de Wit et al., 1992; Gregerson et al., 1993; Chen et al., 1995; Weiner et al., 1994; Abbas et al., 1996; Chen et al., 1996; O'Garra, 1998). Th2 cells can down-regulate or anergize Th1 cells (Groux et al., 1996; constant and Bottomly, 1997 and references therein), and reduce immune responses by their ability to induce a resting state of APC (Ding and Shevach, 1992; Enk et al., 1993; Macatonia et al., 1993). Ag-specific regulatory CD4$^+$ cells may down-regulate Th1 cells in topographic proximity, irrespective of their Ag specificity, through secretion of cytokine, such as IL-4, IL-10, and TGF-P (Weiner et al., 1994). As for Th1 cells, Ag recognition by Th2 cells may spread to an increasingly larger repertoire of epitopes (Tian et al., 1997). Low Ag doses generate Th2 regulatory cells, whereas high doses induce anergy (Gregerson et al., 1993; Weiner et al., 1994; Chen et al., 1996) and/or apoptosis of Ag-reactive Th1 and Th2 cells (Chen et al., 1995). The s.c. injection of peptides from the major cat allergen in mice induced unresponsiveness of Ag-specific Th1 and Th2 cells (Briner et al., 1993; Normal et al., 1996). Other studies suggested that aqueous solutions of Ag administered parenterally selectively tolerize Th1, rather than Th2 cells (Burstein et al., 1992; de Wit et al., 1992).

Both anergy or deletion of Th1 cells specific for the peptides administered, and sensitization of peptide-specific regulatory Th2 cells, appear to have occurred in this system. The first mechanism is suggested by the findings that peptide-treated mice had a reduced proliferative response to the peptide epitopes (FIG. 37) and a reduced TAChR-induced secretion of Th2 cytokine (FIG. 38). Also, the synthesis of anti-TAChR Ab was much reduced, but not that of Th2-driven IgGI subclass (Table 6). Anergy or deletion of CD4$^+$ cells recognizing epitopes within the sequence Tα150-169 might suffice to protect from EMG, because in B6 mice the CD4$^+$ cells recognize epitopes within this sequence are uniquely pathogenic. B6 mice hyperimmunized with TAChR develop EMG with high frequency, and their CD4$^+$ response focuses on the sequence Tα150-169 (Bellone et al., 1993). Thus, sensitization of CD4$^+$ cells to this sequence suffices to, and is prominent for, driving a pathogenic anti-TAChR Ab response. A further mechanism of protection from EMG resulting from anergy or deletion of Th1 cells in the reduction of Th2-driven, complement-fixing pathogenic anti-TAChR Ab. In the peptide-treated mice, most anti-TAChR Ab were Th2-driven IgG1, which fix complement poorly (Table 6).

Administration s.c. of peptides also sensitized specific Th2 cells. This is demonstrated by the synthesis of anti-peptide Ab of Th2-driven IgG1 subclass (Table 6) and by the secretion of IL-4 and IL-10 in response to TAChR by spleen CD4$^+$ cells from peptide-treated mice (FIG. 38). TAChR-specific Th2 cells in sham-tolerized mice were not detected (FIG. 38). This suggests that immunization with the TAChR sensitizes predominantly Th1 cells. Also, in human MG, Th1 cells appear to be involved in the pathogenic anti-AChR response (Wang et al., 1997, 1998). The peptide treatment that was administered might down-regulate the Th2 cell response at high doses, because mice treated with 200 μg of peptide pool or Tα150-169 had less anti-TAChR Th2-dependent IgG1 than sham-tolerized mice (Table 6). This finding may be due also to an overall inhibition of the priming of CD4$^+$ cells to the TAChR, due to strong stimulation of anti-inflammatory Th2 cells.

Wu et al. (1997) reported that s.c. or i.p. injections of large amounts (300 μg) of a peptide Tα146-162 in IFA, given 7 days before or 7–18 days after the first immunization with TAChR, prevented EMG. The results of that and of the present study agree in the important conclusion that CD4$^+$ tolerance to epitopes within the inimunodominant sequence region Tα146-169 blocks EMG development. However, the mechanisms of the protective effects appear to be different. In the study of Wu et al., the protective effects appeared to result from a reduction of the activity of both anti-TAChR Th1 and Th2 cells. T-cells from the peptide-treated mice did not proliferate or secrete Th1 or Th2 cytokines in response to challenge with TAChR or the administered peptide, or the TAChR peptides Tα182-198. The profound down-regulation of both Th1 and Th2 cells observed in that study (Wu et al., 1997) is likely due to the high peptide dose used and the presence of IFA in the administered peptide.

Wu et al. (1997) obtained protection from EMG when they administered the peptide after priming with TAChR, while in the present study the peptide treatment following the post-priming protocol did not affect existing EMG symptoms. However, the fact that in Wu et al. (1997) the mice received a large amount of peptide shortly after the first TAChR immunization, well before anti-TAChR Ab reached a high concentration and caused EMG symptoms, reconciles this discrepancy. The procedure used by Wu et al. appears to have inhibited further priming of CD4$^+$ cells to the TAChR. Also, it may have anergized or deleted the T-cells primed by encounter with TAChR before administration of the peptide. The profound suppression of the proliferative and cytokine responses of CD4$^+$ cells to the TAChR observed in that study supports both of the above possibilities.

The s.c. tolerization using the approach described here requires knowledge of the autoAg sequences forming dominant CD4$^+$ epitopes. For example, the CD4$^+$ cells of most MG patients recognize a limited number of epitope sequences of the human muscle AChR (Conti-Fine et al., 1997). Those sequence regions are recognized with high precursor frequency (Wang et al., 1997), and should therefore be considered both immunodominant and universal CD4$^+$ epitopes. Thus, they are ideal condidates for human MG.

The procedure described here affects the anti-TAChR Ab secreting B-cells indirectly, and it did not have measurable therapeutic effects on established EMG. Still, it could be a viable candidate for MG management if associated to plasmapheresis and azathioprine. These treatments eliminate the existing anti-AChR Ab and affect the activated B-cells. The combined effects of such a 'two-pronged' approach might result in a long-lasting down-regulation of both the CD4$^+$ and the B-cell responses to the anti-AChR. At least theoretically, immunomodulatory therapies may neutralize each other when combined, or they may lead to unexpected adverse results (Hohlfeld, 1997). Thus, any treatment that entails the use of a combination of different immunosuppressive agents needs to be evaluated with great caution.

EXAMPLE V

Treatment of Factor VIII-Specific Disease

Approximately 25% of patients with severe hemophilia A develop blocking antibodies (inhibitors) to the missing coagulation factor, factor VIII (FVIII). Inhibitors block FVIII activity, and significantly compromise the ability to achieve therapeutic homeostasis during bleeding episodes. FVIII inhibitors also develop also during autoimmune hemophilia A, a rare but frequently fatal disease in which FVIII is the target of autoimmune response. Hemophilia A results from a genetic defect in the FVIII gene while acquired (autoimmune) hemophilia is the result of an autoimmune response to FVIII. FVIII inhibitors are high affinity IgG. Their synthesis requires the action of CD4$^+$ T helper cells specific for FVIII.

A panel of about 240 synthetic peptides, 20 residues long and overlapping by 10 residues, spanning the FVIII sequence, is screened on T cells to determine which peptides have universal and/or immunodominant epitope sequences. The peptide length compares with that of naturally processed class II restricted epitope peptides, that are 9–14 residues long (Rudensky et al., 1991; Hunt et al., 1992; Stem et al., 1994). Extra residues at either end of the epitope sequence do not affect the attachment to the binding cleft of the DR molecules, which is open at both its ends (Hunt et al., 1992; Stem et al., 1994). The ten residue overlap reduces the risk of missing epitopes "broken" between peptides.

The peptides synthesized by this method are 70–85% pure (Houghton, 1985; Protti et al., 1990; Protti et al., 1990;

Manfredi et al., 1992). Contaminants are a mixture of shorter analogs in which one or more residues are missing randomly, due to incomplete coupling. The analogs might bind the restricting class II molecule, but not the specific TCR in a manner conducive to measurable T cell response. This would result in a shift of the dose dependence of the CD4$^+$ cell responses to the peptide, towards higher doses than when using purified peptides. Because the doses used to test human and mouse anti-FVIII CD4$^+$ cells are generous, the risk of missing detection of the response to a peptide because of the presence of contaminating analogs is negligible.

The sequence and purity of several peptides have been checked, selected randomly, by determination of their amino acid composition (Henrickson et al., 1983) and mass-spec determination of the m.w. of the species present in the peptide preparation. Amino acid composition analysis yielded results corresponding to the theoretical values for all peptides. Mass-spec analysis consistently yielded a major peak with the m.w. calculated for the peptide. Further purification, if necessary, can be carried out by reverse phase HPLC.

The T cells are obtained from hemophilia A patients, autoimmune hemophilia patients, and healthy individuals that have a CD4$^+$ response to FVIII. Identification of the CD4$^+$ epitope repertoire on FVIII recognized by the patients or healthy individuals can be accomplished by using at least one of three sets of complimentary experiments, as follows: 1) Identification of the epitope repertoire of unselected CD4$^+$ cells from the patient's blood by proliferation experiments using CD8$^+$ depleted, CD4$^+$ enriched peripheral blood lymphocytes (PBL), challenged with each individual peptide. 2) Identification of the CD4$^+$ subset (Th1 or Th2) recognizing the different FVIII epitopes, by inununospot assays of the cytokines secreted by individual blood CD4$^+$ cells in response to challenge with the difference FVIII peptides. Preferably, IL-2 and γ-interferon are employed to detect Th1 cells, and IL-4 is employed to detect Th2 cells. 3) Propagation of FVIII-specific CD4$^+$ lines, by cycles of stimulation in vitro of the PBL with FVIII followed by IL-2 or IL-4, and determination of their epitope repertoire and the Th1 or Th2 subset involved in the anti-epitope response, by challenging them with individual synthetic sequences in proliferation and immunospot assays.

To identify the CD4$^+$ epitope repertoire on FVIII in the hemophilia A mice (Bi et al., *Nature Genet.*, 10, 119 (1995)), CD8$^+$ depleted, CD4$^+$ enriched spleen cells are employed instead of PBL. The mice have been injected with FVIII i.v. three times prior to spleen cell isolation, or by other routes that result in an immune response to FVIII. Alternatively, CD4$^+$ cells are purified from the spleen and reconstituted with autologous antigen presenting cells. Peptides are screened by assays described herein to identify universal and/or immunodominant epitopes of FVIII. The C1 and the C2 domains of FVIII appeared to dominate the CD4$^+$ response to FVIII of the mice. Once peptides having a universal and/or immunodominant epitope sequences are identified, they are administered nasally to hemophilia A mice prior to and during immunization with FVIII. Control mice are sham tolerized with peptide-free PBS. The effects of the tolerization on the antibody and CD4$^+$ response to FVIII of the nasal administration of peptides is then determined.

Healthy humans have recurrent, transient sensitization of CD4$^+$ cells to FVIII. This is likely due to extravasation of FVIII at sites, such as bruises, where FVIII sequence may be presented by professional antigen presenting cells, able to prime potentially autoreactive CD4$^+$ cells specific for FVIII epitopes. In normal individuals, who have high blood levels of FVIII, the activated anti-FVIII CD4$^+$ cells quickly disappear, possibly as a result of anergy or deletion by peripheral mechanisms of tolerance. Such cells persist in hemophilia A patients because their low FVIII levels, even after therapy, do not suffice for tolerization. Thus, the presence of anti-FVIII CD4$^+$ cells in healthy humans can assist in the identification of universal CD4$^+$ epitopes for FVIII.

Figure 11:
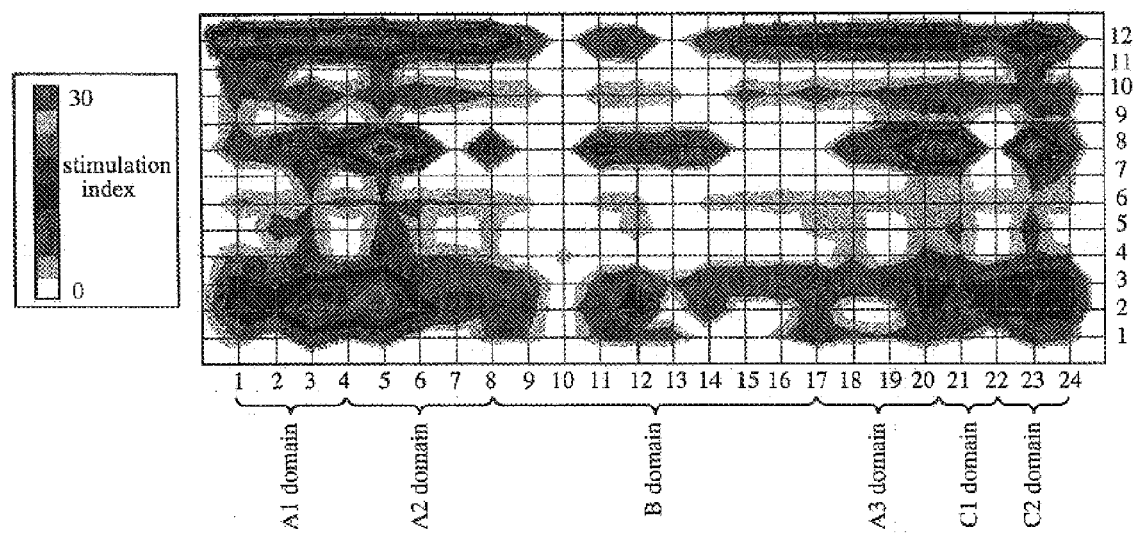
FIG. 11. Response of human T cells to factor VIII peptides.

The CD4$^+$ cells from twelve healthy subjects were screened with a pool of FVIII peptides, e.g, 24 pools of 10 peptides each (FIG. 11). All subjects recognized one or more peptide pools. The pools comprising the sequence of the A2, A3 and C2 domains were recognized most strongly and most frequently. Anti-FVIII antibodies, including the inhibitors in hemophilia patients recognize primarily (but not exclusively) epitopes formed by the A2 and C2 domains. Thus, it appears that those domains may dominate both the pathogenic immune response to FVIII that leads to inhibitor formation in hemophilia A and the ephemeral, nonpathogenic responses of healthy subjects. Some subjects did not have a detectable response to the complete FVIII molecule, in spite of their significant response to one or more peptide pools. This is likely due to the much higher concentration of epitope sequences in the assays carried out with the peptides, than in those testing the response to FVIII.

To further investigate the response of CD4$^+$ cells, two approaches were used. One approach utilizes pools of synthetic peptides spanning the sequence of individual FVIII domains, referred to as "FVIII domain pools". For the B domain, which is much longer than the others, two pools are used, corresponding to the amino terminal and carboxyl terminal halves of the B domain. In the second approach, the synthetic FVIII sequences are grouped in 24 pools of about peptides each, starting with the amino terminal region of the FVIII precursor ("pools 1 to 24"). Both in the studies in human subjects, and in hemophilia mice, the use of FVIII domain pools, immediately followed by screening with the individual peptides, appears to be the most effective strategy. This is likely because a number of epitopes is recognized on each domain: thus, the use of the pools 1 to 24 does not allow to exclude any of them from further investigation of that sequence region for the presence of CD4$^+$ epitopes.

Studies in Hemophilia Patients. The CD4$^+$ response to FVIII in four hemophilia A patients with inhibitors, three hemophilia A patients without inhibitors and four patients with acquired (autoimmune) hemophilia was studied. CD8$^+$ depleted, CD4$^+$ enriched blood lymphocytes (hereafter referred to as CD4$^+$ BL) of these patients was obtained approximately every month, for up to six months. The response of the CD4$^+$ BL to increasing concentrations of FVIII and to the individual FVIII domain pools was tested.

All patients had a detectable CD4$^+$ response to FVIII most of the time. The CD4$^+$ response was not constant: in most patients it was detectable at most, but not all, the time points tested. When present, the intensity of the response generally increased with the concentration of FVIII used in the assay. In most cases it reached a maximum at concentrations around 1 unit of FVIII/mL (i.e., similar to the physiologic concentration of FVIII in the blood in normal subjects). FIG. 40 reports the dose dependency of the response to FVIII over time in three patients, which are representative of the results obtained in autoimmune-acquired hemophilia, in hemophilia A with inhibitors, and hemophilia A without inhibitors, respectively.

FIGS. 41 *a*, *b*, and *c* report the maximum response to FVIII of the CD4$^+$ BL of the patients studied detected in the different experiments, as indicated. As mentioned above, the intensity of the response changed over time. Although all patients had a significant CD4+ response to FVIII in most experiments, several patients had brief periods of time when a CD4+ response to FVIII could not be detected.

FIGS. 41 a, b, and c report also the CD4+ responses to the FVIII domain peptide pools that was observed over time. The CD4+ BL of most patients in all groups recognized most or all the FVIII domain pools. Like the CD4+ response to FVIII, the responses to the domain pools were not stable over time in their intensity: for most patients, the response to one or more of the domain pools decreased for short periods to undetectable levels.

The data reported in FIGS. 41 a, b and c indicated that the CD4+ BL recognized the different FVIII domain pools with different intensity. This is well illustrated by the summary representation of the data of FIG. 41, as reported in FIG. 42. In this figure, the intensity of the responses to the different FVIII domain pools obtained for each patient in the different experiments was averaged (top three panels). In the bottom panels the intensity of the responses to each FVIII domain pool observed in the different patients within each group (acquired hemophilia, hemophilia A with inhibitors, and hemophilia A without inhibitors, as indicated) was averaged. Most patients, and all three groups, had very similar patterns of recognition of the FVIII domains. This supports the hypothesis that universal immunodominant CD4+ epitopes exist also for FVIII, as they do for the other antigens. Domains A3, A1, or both were the most strongly recognized in all groups and in all patients.

In all patients, the concentration of anti-FVIII antibodies at the time of the experiment testing the response to FVIII of the CD4+ BL was detennined. As expected, the correlation between these two parameters was loose. Studies in Healthy subjects. The "danger" theory of tolerance predicts that the immune response does not discriminate on the basis of "self" and "non-self", but rather whether an Ag is perceived as potentially dangerous or not. Self- proteins processed and presented to the CD4+ cells in the context of "danger" situations (i.e., by professional APC at the site of an inflammatory reaction) will become the target of a CD4+ cell response. FVIII might be recognized by CD4+ cells in healthy controls due to is extravasation at hemorrhagic sites such as bruises, where FVIII sequences may be presented by APC able to prime potentially autoreactive CD4+ cells specific for FVIII epitopes. To test this model, monthly, for up to 13 months, the proliferative response to FVIII of blood CD4+ cells from 12 healthy subjects was tested.

FIG. 43 summarizes the results obtained with the 12 subjects tested. Each panel reports the results obtained in one subject in several experiments, carried out approximately one month apart, as indicated below each panel. Most subjects were tested for 11–13 months. The results are reported as stimulation indexes, namely, the ratio between the $^3$H-thymidine incorporation obtained in the presence of a given concentration of FVIII, and the basal incorporation of $^3$H-thymidine, in the absence of any Ag stimulus. The results are reported as contour maps. Each vertical line indicates the results obtained in one experiment. The horizontal lines represent the results obtained with the different doses of FVIII used in the proliferative assays, as indicated at the left of the plot. The extent of the responses is represented using the color code indicated at the right of the plots. In all subjects, transient, yet significant and sometimes vigorous responses to FVIII were observed. The activated anti-FVIII CD4+ cells disappear in one or more months, possibly as a result of anergy or deletion by peripheral mechanisms of tolerance, in the presence of the high normal blood levels of FVIII. Such cells would persist in hemophilia A patients because their low FVIII levels, even after periodic replacement therapy, would not suffice for tolerization of the autoreactive CD4+ cells. Circumstantial evidence in support of this model is the negative correlation that has been described between development of inhibitors and presence of circulating "FVIII Ag" (Reisner et al., 1995, however, see also McMillan et al., 1988). These findings are consistent with the presence of low levels of Ab to FVIII in normal people (Gilles et al., 1994; Algiman at el., 1992; Batlle et al., 1996). That FVIII may be commonly processed and presented by class II molecules in healthy humans is supported by the finding that a FVIII-derived peptide was eluted from purified human DR molecules (Chicz et al., 1993).

Figure 44:
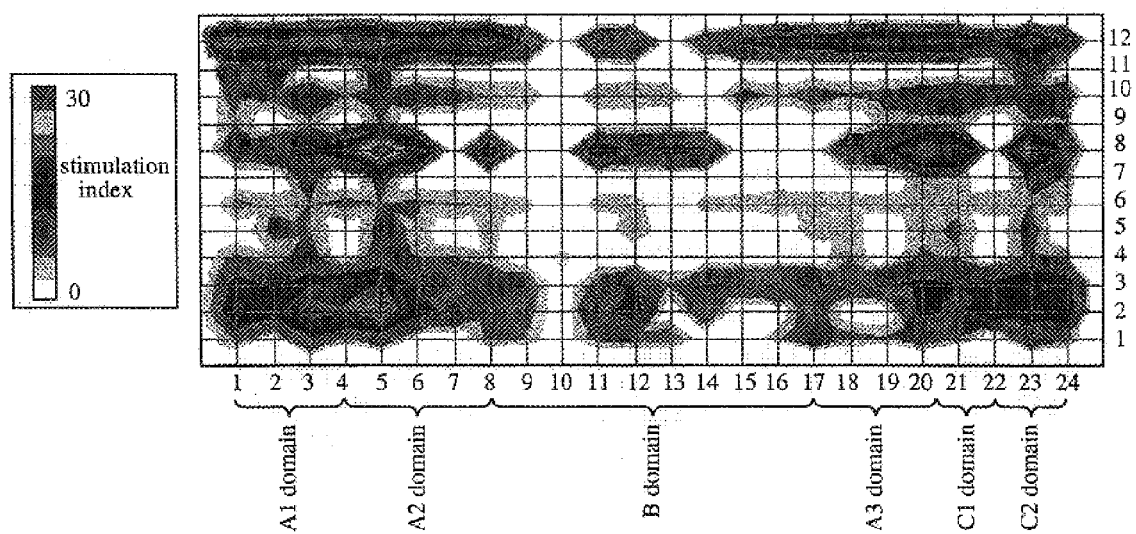
FIG. 44. Response of CD4+, CD8+-depleted blood lymphocytes from healthy subjects to Factor VIII peptide pools.
Figure 45A:
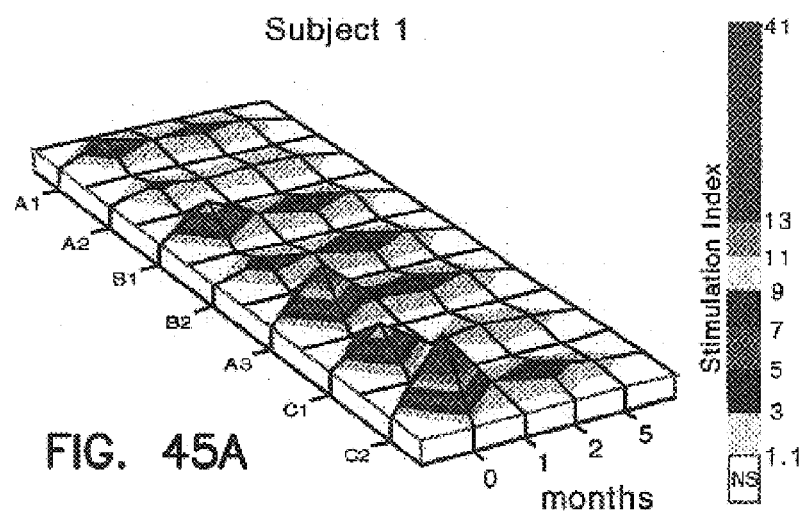
FIGS. 45A–K. Response of CD4+, CD8+-depleted blood lymphocytes from healthy subjects to Factor VIII domain pools.
Figure 45B:
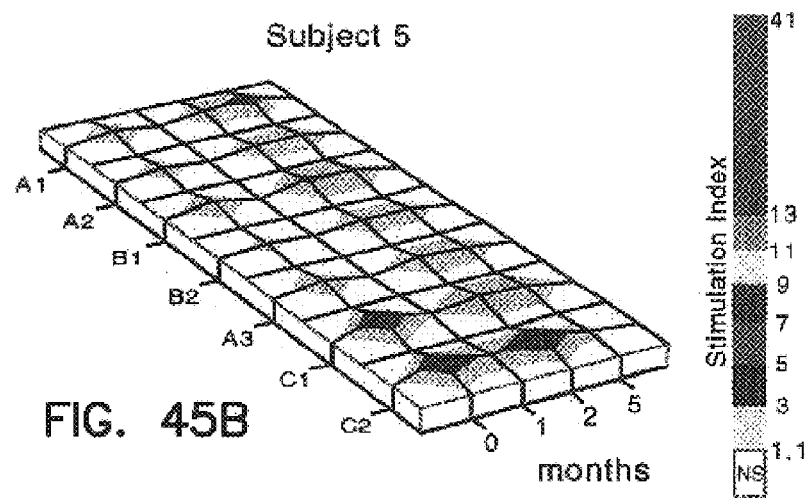
Figure 45C:
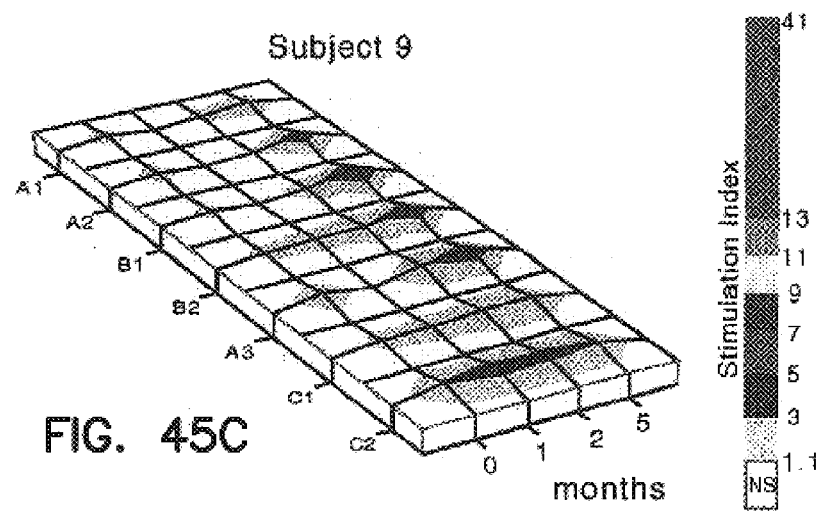
Figure 45D:
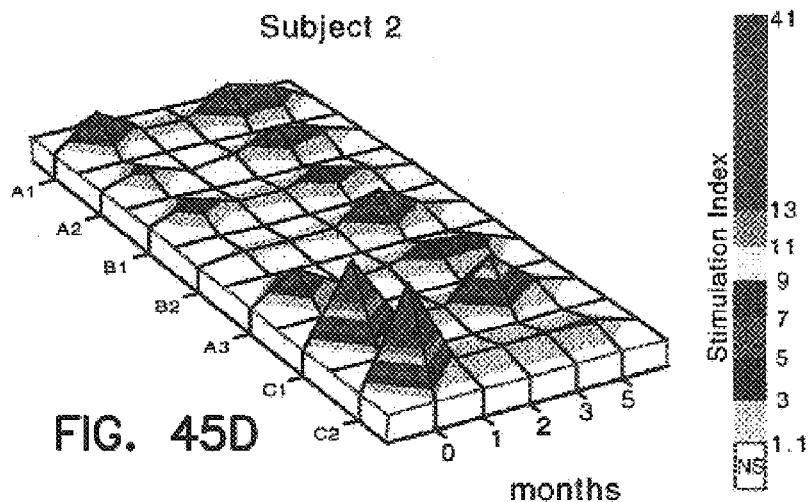
Figure 45E:
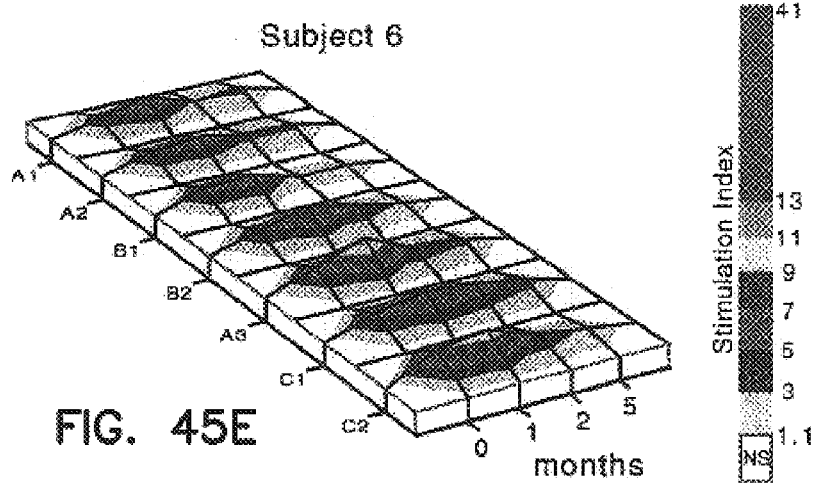
Figure 45F:
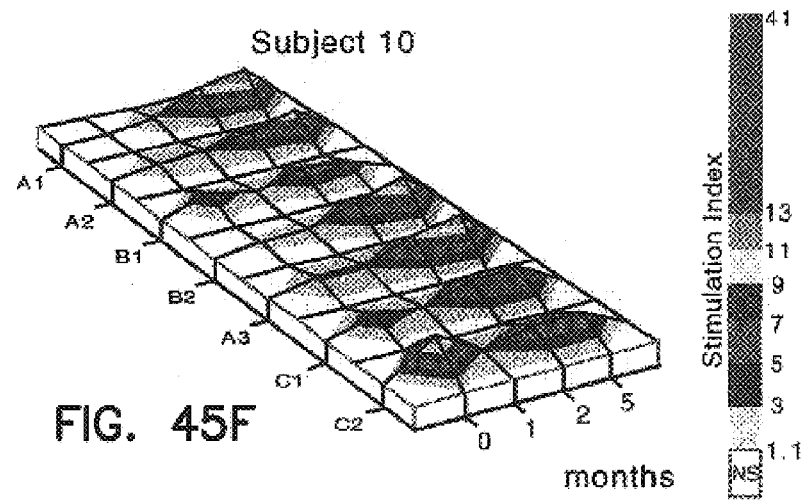
Figure 45G:
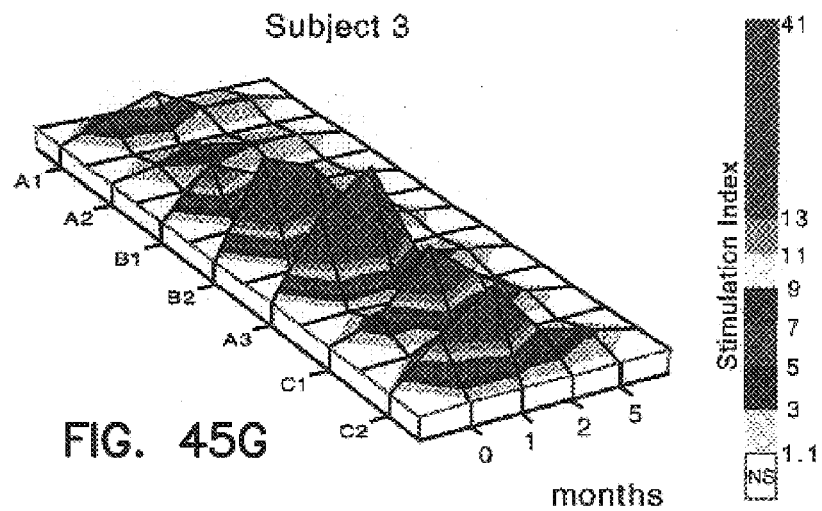
Figure 45H:
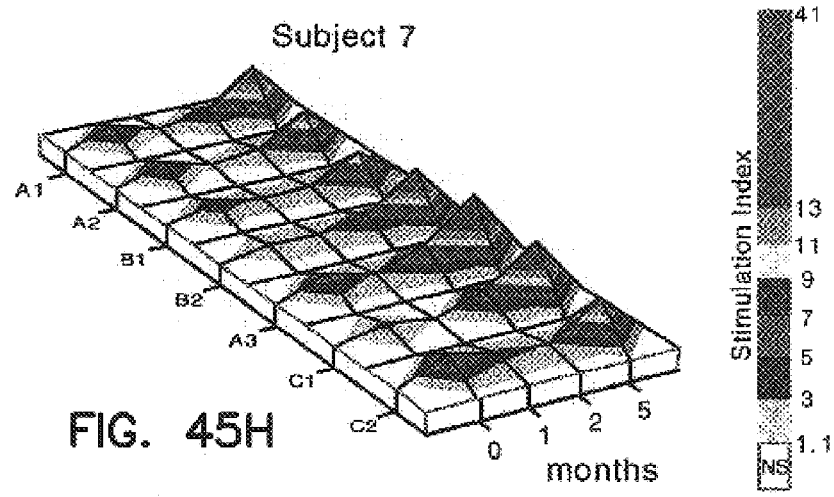
Figure 45I:
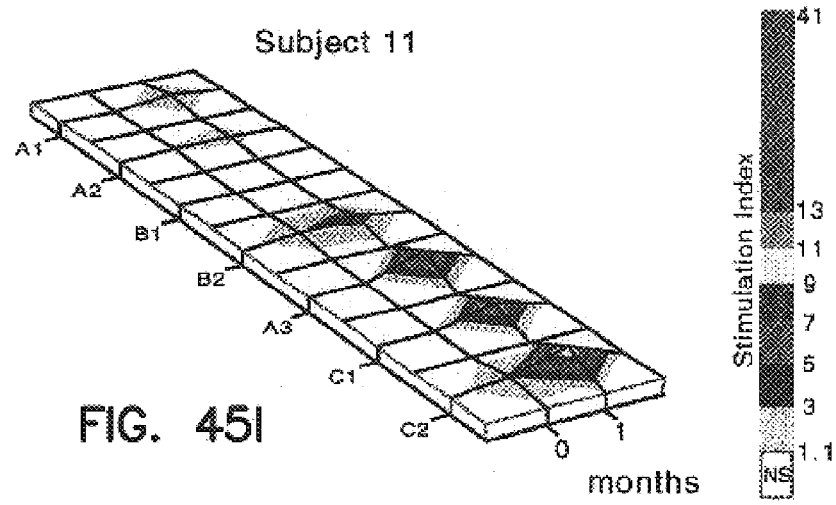
Figure 45J:
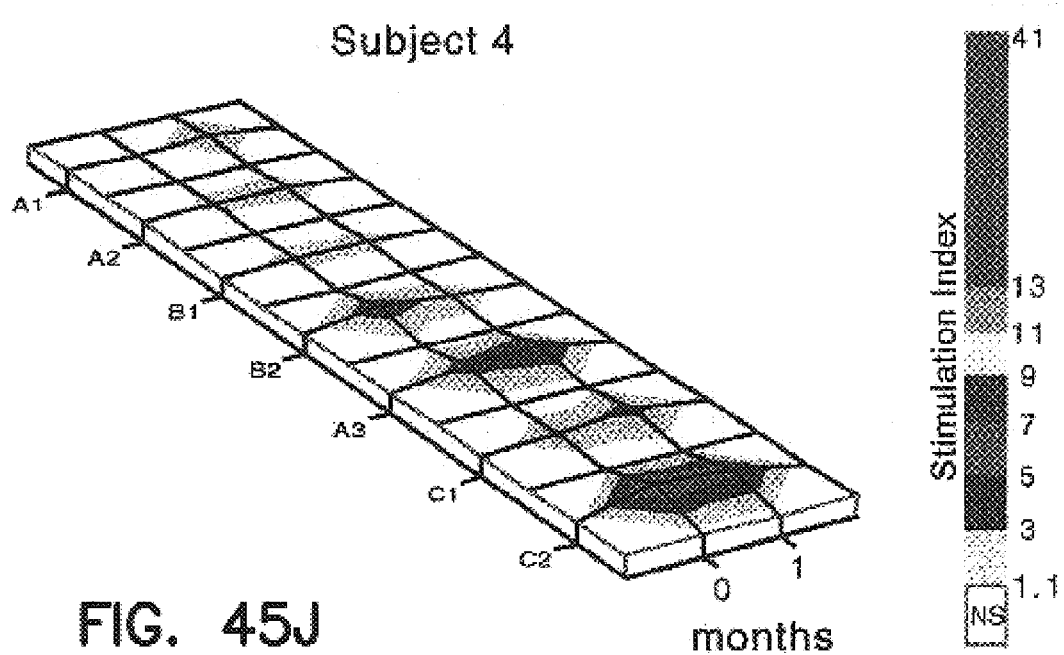
Figure 45K:
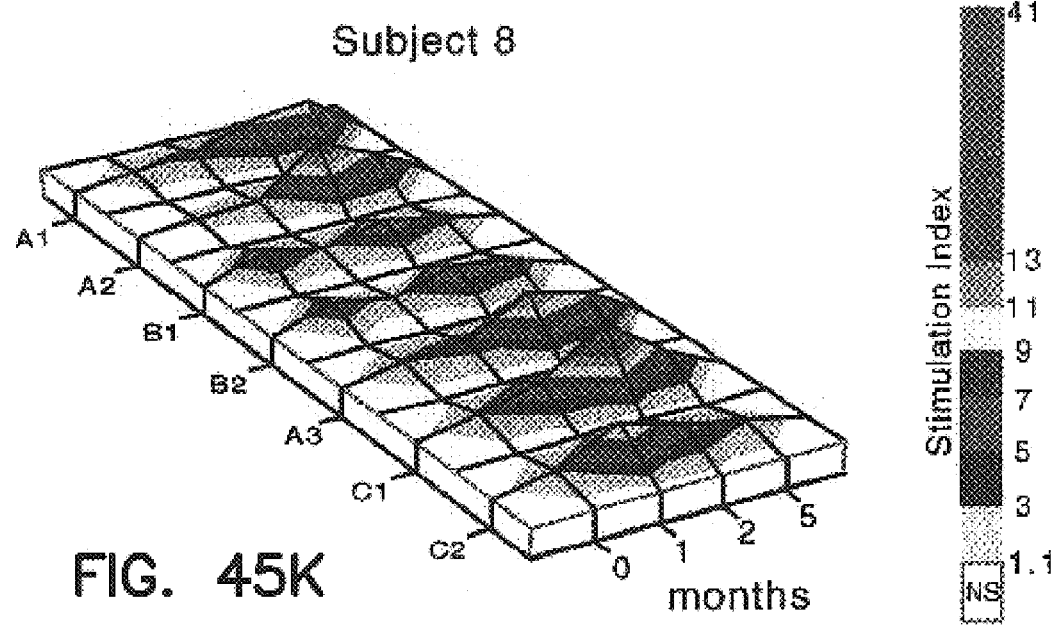

FVIII domains recognized by CD4+ cells of healthy subjects: use of peptide pools 1–24. The response of CD4+ BL from the same 12 subjects to the FVIII peptide pools 1–24 described above was tested. Two sets of experiments were carried out, roughly one year apart, with the same set of subjects and with overall consistent results. The results we obtained in the first set of experiments are summarized in FIG. 44. The figure reports a summary, depicted as a contour map, of the response of the blood CD4+ cells of the different subjects to the individual 24 FVIII peptide pools (1 µtg/mL of each peptide). The abscissa indicates how the peptide pools correspond to the different FVIII domains. Each horizontal strip represents the results obtained with the CD4+ cells of one subject, as indicated at the right of the plot. The response of the cells to the individual 24 peptide pools (one peptide pool for each vertical strip) starts with the amino terminal region of the A1 domain and ends, at the extreme right, with the carboxyl terminal region of the C2 domain. The responses to the peptide pools are represented using the color code indicated in the figure.

The results obtained in both experiments had a similar overall pattern. All subjects recognized several peptide pools. Pools within the sequence of the A1, A2, A3, C1 and C2 domains were recognized more strongly and more frequently than those spanning the B domain. Anti-FVIII abs, including the inhibitors in hemophilia patients recognize primarily (but not exclusively) epitopes formed by the A1, A3 and C2 domains (Scanella, 1996; Scanella et al., 1995; Healy et al., 1995; Shima et al., 1995). Thus, these domains may dominate both the pathogenic immune response to FVIII that leads to inhibitor formation in hemophilia A and the ephemeral, non-pathogenic responses of healthy subjects.

FIII domains recognized by CD4+ cells of healthy subjects use of FVIII domain pools. The CD4+ response of 11 healthy subjects to the FIII domain pools was tested, and how it evolves over time. Towards this goal the CD4 BL of 11 healthy subjects was challenged every one-three months, up to four times. The CD4+ BL were tested in proliferation assays, using each of the FVIII domain pools. FIG. 45 reports the results obtained with the different experiments, carried out at least one month apart, as indicated, in the different subjects. The pattern observed was reminiscent of that observed in the hemophilia A patients, although several subjects had overall low responses to the FVIII domain pools. The responses observed were not stable over time. Positive responses may be followed or preceded by absence of response to the same FVIII domain pools.

Figure 46A:
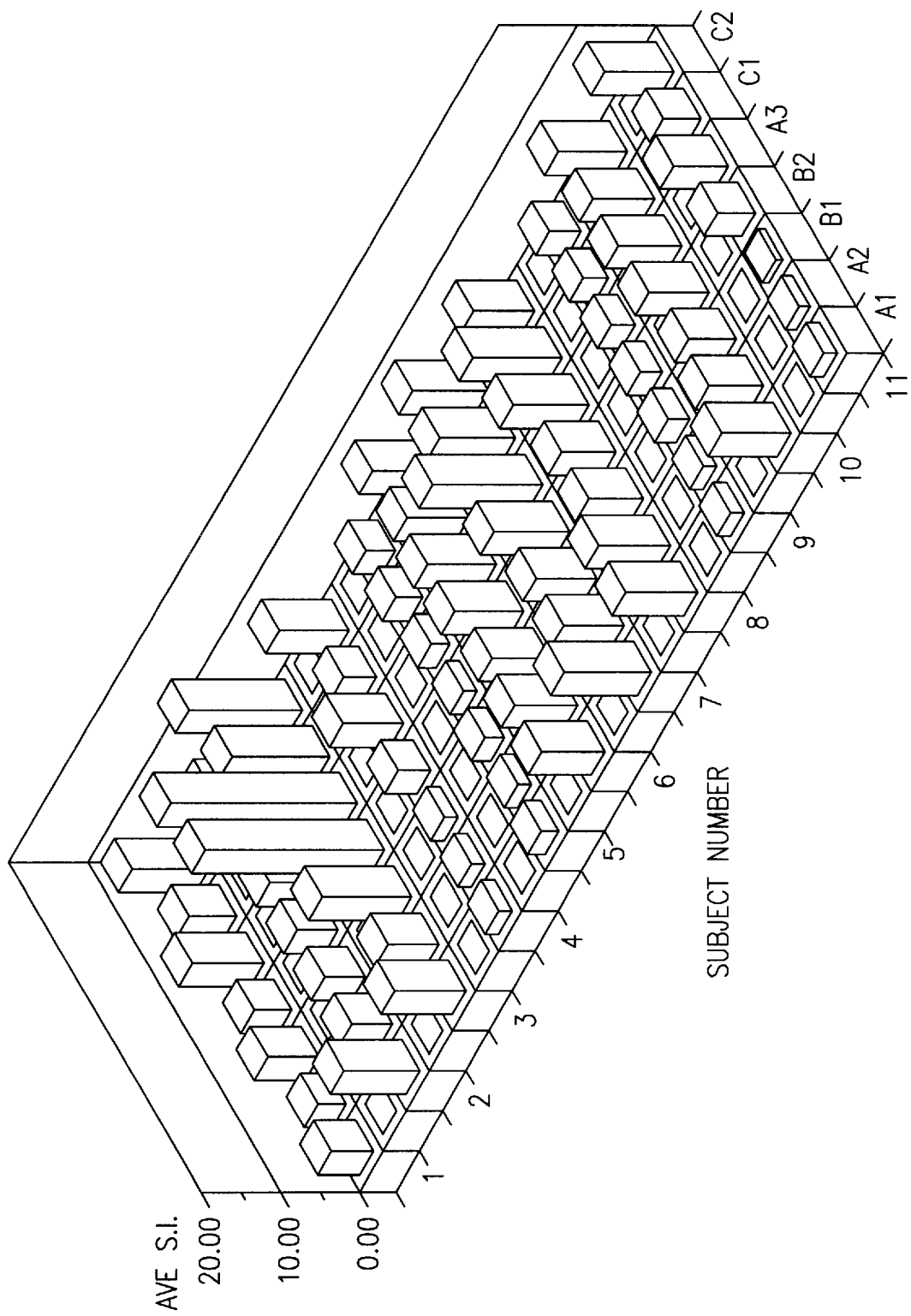
FIGS. 46A–B. Average response for each healthy subject (top panel) and the average results for each pool in the different subjects (bottom panel).
Figure 46B:
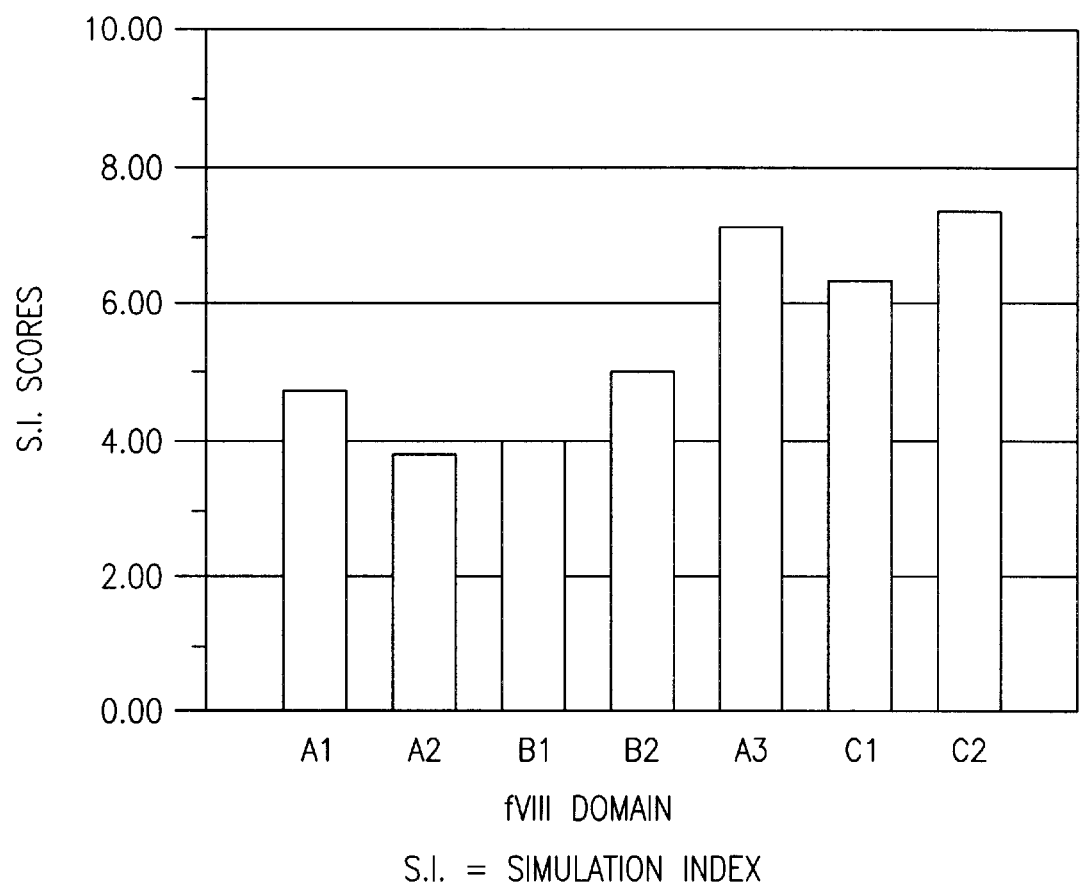

FIG. 46 reports the average for each subject of the responses to the different pools obtained in the different experiments (top panel), as well as an average of the results obtained for each pool in the different subjects (bottom panel). The FVIII domain pools A3, C2 and C1 were the most strongly recognized. The domain pools A1 and B1 were the least strongly recognized overall.

EXAMPLE VI

Studies in Hemophilia a Mice

Mutant mice have been developed with targeted gene disruption of the FVIII gene, that results in severe FVIII deficiency (Bi et al., 1995). These mutant FVIII deficient mice (hereafter referred to as hemophilia A mice) are an excellent model of hemophilia A, including the development of FVIII inhibitor Ab and of a CD4$^+$ response after intravenous (i.v.) exposure to human FVIII (Qian et al., 1997; Qian et al., 1996). Hemophilia A mice develop anti-FVIII Ab after two or three i.v. infusions of 0.2 mg of human FVIII (an exposure comparable, on a weight basis, to that given in hemophilia A patients) (Ding et al., 1993; Macatonia et al., 1993). The concentration of serum anti-FVIII Ab increases with the number of exposures to FVIII, and the dose used. All mice injected five times with human FVIII had inhibitors (Ding et al., 1993; Macatonia et al., 1993) Approximately 50% of the hemophilia A mice treated with human FVIII i.v. had a detectable proliferative response of spleen T cells (Macatonia et al., 1993) (also, see below).

Figure 47A:
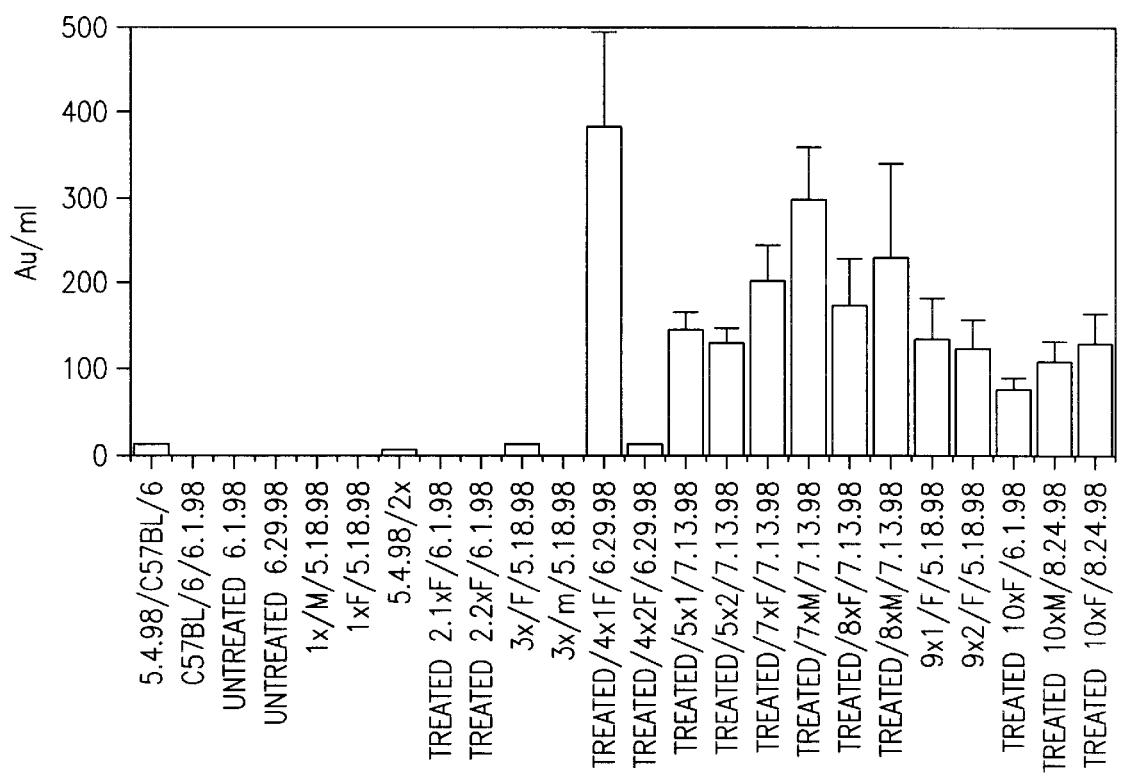
FIGS. 47A–B, Results of antibody response in hemophilia A mice.
Figure 47B:
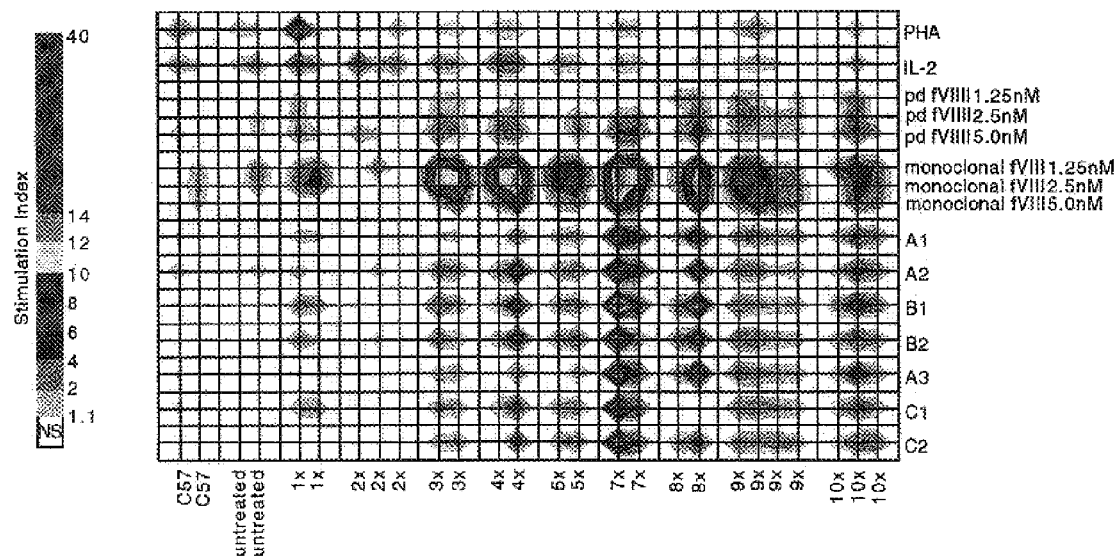
Figure 48A:
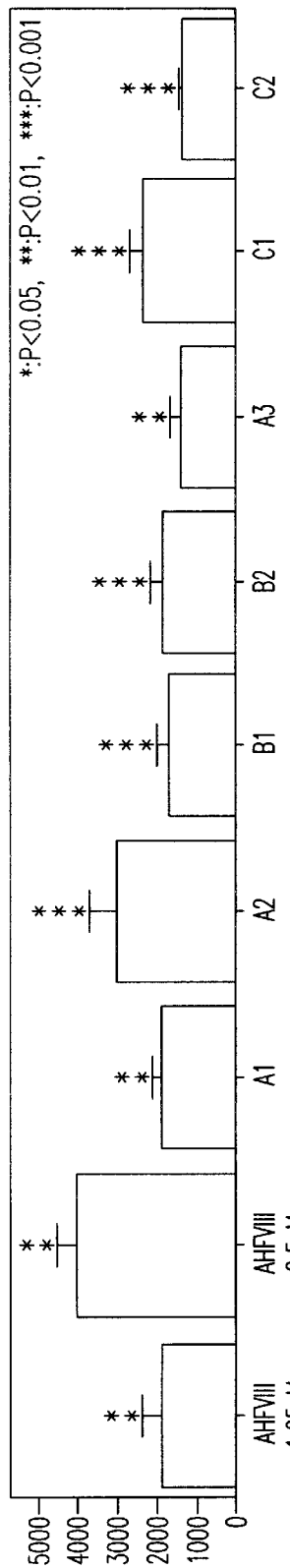
Figure 48B:
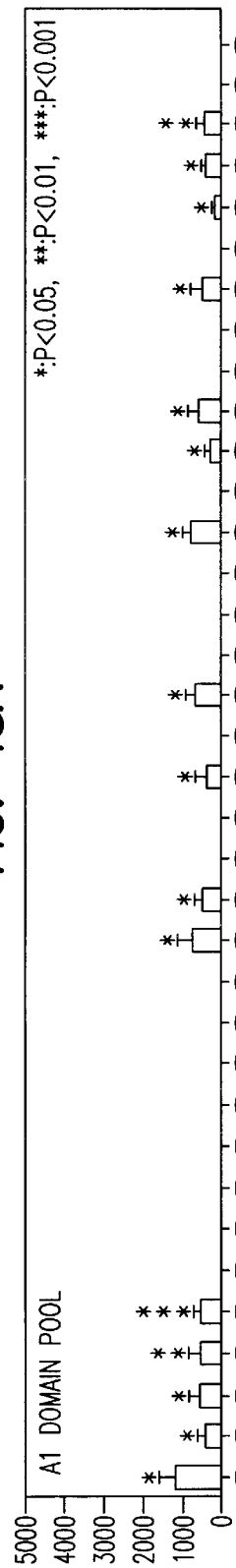
Figure 48C:
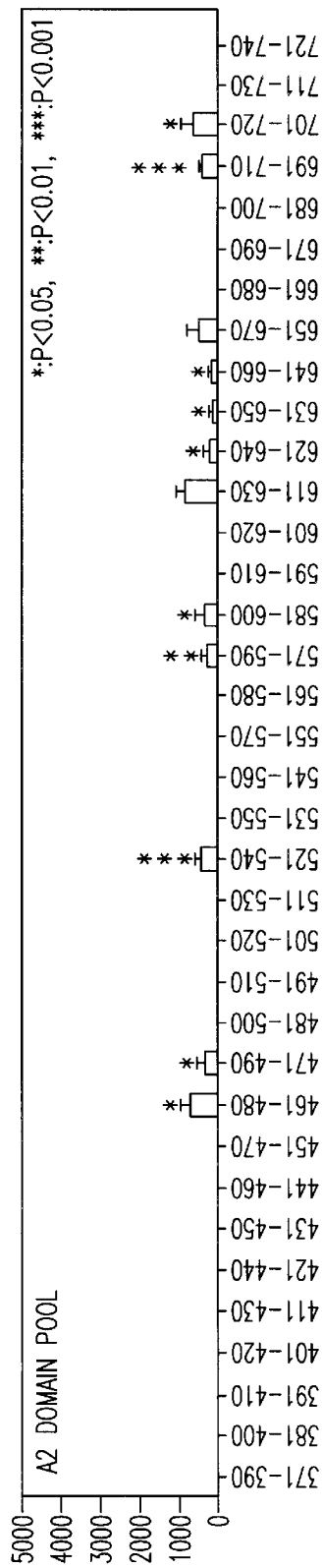
Figure 48F:
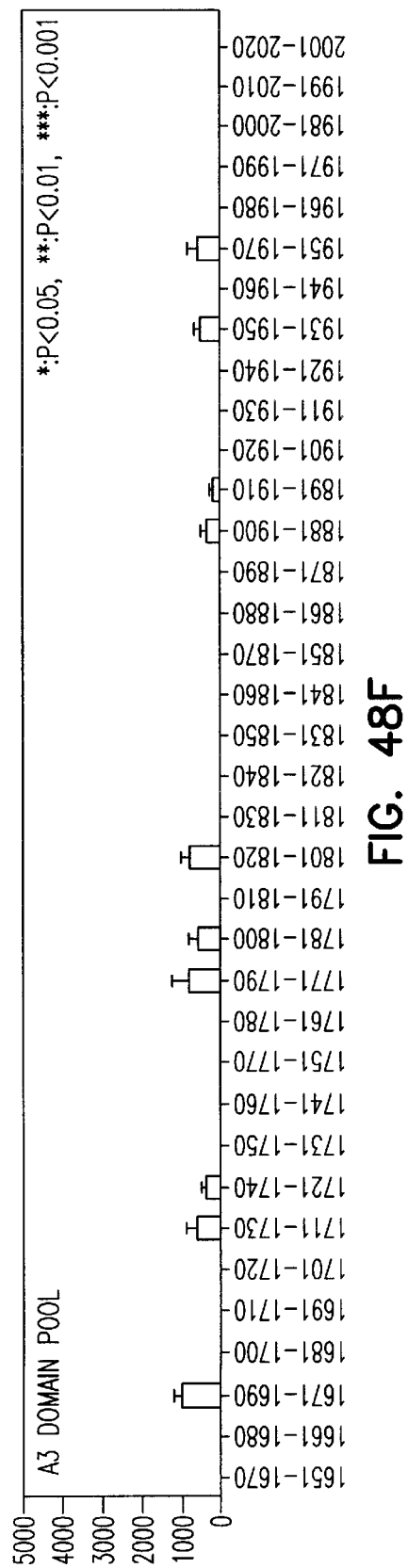
Figure 48H:
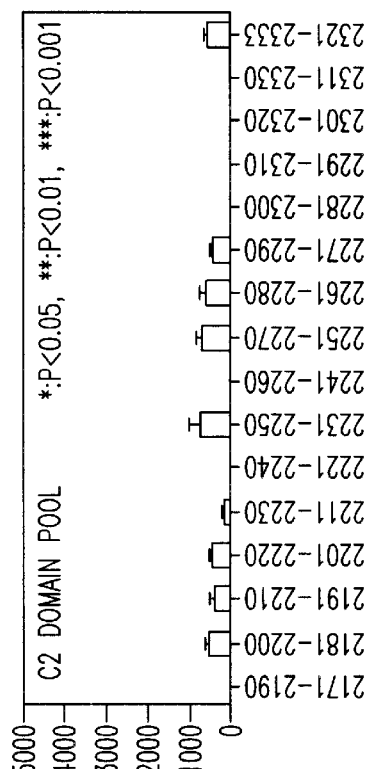
Figure 48G:
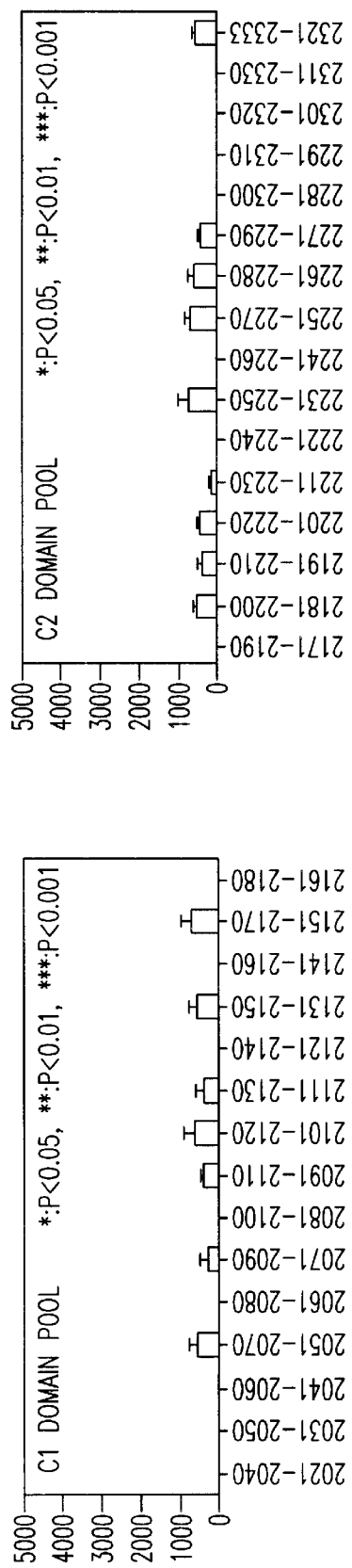

CD4$^+$ T cell and antibody response to FVIII in hemophilia A mice. Hemophilia A mice were treated up to 10 times with injections i.v. of 1 microgram of purified, solubilized recombinant human FVIII. The immunizations occurred every two weeks. In the mice thus treated the antibody and the CD4$^+$ response to FVIII, as well as the CD4$^+$ responses to the FVIII domain pools that the mice developed as the immunization progressed, was tested. The anti-FVIII antibody concentration was measured in the mouse serum. The CD4$^+$ response was measured in proliferation assays using CD8$^+$-depleted, CD4$^+$-enriched spleen cells. For each time point (from time 0, i.e., prior to the beginning to the immunization, to three days after the tenth immunization), at least two mice were sacrificed and their anti-FVIII antibody titer and CD4$^+$ response to FVIII determined in independent experiments. For the CD4$^+$ response to FVIII increasing concentrations of two different preparations of FVIII were used, of increasing purity, purified from human plasma. As negative controls, two naive wild type B6 mice were used FIG. 47 summarizes the data obtained. The mice developed anti-FVIII antibodies after four-five injections of FVIII (the antibody concentration reported in the top panel in FIG. 47 is expressed as arbitrary units, AU/mL). After the first immunization, the antibody concentration in the serum remained relatively constant. Also the CD4$^+$ response to FVIII increased with the number of FVIII injections. However, a significant CD4 response to FVIII could be detected in some mice as early as after the first or second immunization. A CD4 response to FVIII was consistently present following the third FVIII injection onwards. The responses detected were always stronger for the more purified preparation of FVIII (indicated in FIG. 47 as mpFVIII).

Although some FVIII domain pools were recognized by the spleen CD4$^+$ cells of some mice after just one FVIII administration, the response became consistent, and extended to all FVIII domain pools only after the fourth immunization. Some domains were recognized overall more strongly than the others, similar to the observations for the hemophilia patients.

In hemophilia A mice Th2 cells respond to FVIIT. To investigate the CD4$^+$ subset that responded to FVIII, based on the cytokines secreted by the CD4$^+$ spleen cells from hemophilia A mice immunized by three i.v. injections of FVIII, the concentration in the supernatant of FVIII-stimulated CD4$^+$ spleen cell cultures, of IFN-γ (for the Th1 cells) and IL-4 (for the Th2 cells) was determined The presence of FVIII caused a significant and substantial increase of IFN-γ secretion as compared to control cultures cultivated without any stimulus. No increase in the secretion of IL-4 could be detected after exposure to FVIII. These data indicate that Th1 CD4$^+$ cells are involved in anti-FVIII response, but do not exclude the involvement of Th2 cells as well, given the low sensitivity of the assay used. Another study that used a more sensitive ELISPOT assay that detects individual IL-4 producing cells, and obtained results suggesting that Th2 cells responded to FVIII (Qian et al., 1996; Qian et al., 1997). Thus, both Th1 and Th2 cells appear to be sensitized to FVIII. The response of Th2 cells may reflect sensitization of pathogenic T cells that cooperate in the synthesis of inhibitors of Th2driven IgG subclasses, or of protective T cells.

CD4$^+$ epitope repertoire to FVIII in hemophilia A mice. Mice were immunized with 1 microgram of purified recombinant human FVIII emulsified in Freund adjuvant, and injected subcutaneously three times. The first injection utilized complete Freund adjuvant. This procedure, as opposed to i.v. injections of soluble FVIII, was selected to ensure a strong immunization to FVIII and to reveal the broadest epitope repertoire recognized by anti-FVIII CD4$^+$ cells.

FIG. 48 summarizes the results obtained regarding the anti-FVIII CD4$^+$ repertoire in the mice thus immunized. The individual peptides are indicated with codes that include two numbers, corresponding to the position of the first and last peptide residue on the sequence of the FVIII precursor. The responses to the individual peptides are organized in panels corresponding to the different domains, as indicated. Significant responses, as demonstrated by a double tailed student's t test, are indicated with stars. The mice had a clear, significant CD4 response to FVIII, and to each of the FVIII domain pools. The A2 and C1 domain pools were recognized somewhat most strongly in this experiment. Within each domain, several peptides were recognized significantly. Some peptides were recognized especially strongly (e.g., peptides 1–20, 1671–1690).

REFERENCES

Abbas, A. K., K. M. Murphy, and A. Sher. 1996. Functional diversity of helper T lymphocytes. *Nature* 383:787–793.

Akamizu, T., F. Matsuda, J. Okuda, H. Li, B. Kanda, T. Watanabe, T. Honjo and T. Mori. 1996. Molecular analysis of stimulatory anti-thyratropin receptor antibodies (TSAbs) involved in Graves' disease. *J. Imrnunol.* 157:3148–3152.

Algiman, M., Dietrich, G., Nydegger, U. E., Boieldien, D., Sultan, Y. and Kazatchkine, M. D. 1992. Natural antibodies to factor VIII (anti-hemophilic factor) in healthy individuals. *Proc. Natl. Acad. Sci. USA*, 89:3795–3799.

Al-Sabbagh, A., P. Nelson, Y. Akselband, R. Sobel, and H. Weiner. 1996. Antigen driven peripheral immune tolerance—suppression of experimental autoimmune encephalomyelitis and collagen-induced arthritis by aerosol administration of myelin basic protein or type II collagen. *Cell Immunol.* 171:111–119.

Anderson, T. T., Cornelius, J. G., Jarpe, A. J., Winter, W. E. and Peck, A. B. 1993. Insulin-dependent diabetes in the NOD mouse model. II. Beta cell destruction in autoimmune diabetes a Th2 and not a Th1 mediated event. *Autoimmunity.* 15: 113–122.

Asthana, D., Fujii, Y., Huston, G. E. Lindstrom, J. 1993. Regulation of antibody production helper T cell clones in experimental autoimmune myasthenia gravis is mediated by IL-4 and antigen-specific T cell factors. *Clin. Immunol. Immunopath*. 67:240–248.

Balasa, B., Deng, C., Lee, J., Bradleyu, L. M., Dalton, D. K., Christadoss, P. and Sarvetnick, N. 1997. Interferon y (IFN-γ) is necessary for the genesis of acetylcholine receptor-induced clinical experimental autoimmune myasthenia gravis in mice. *J Exp. Med*. 186: 385–391.

Balasa, B., Deng, C., Lee, J., Bradleyu, L. M., Dalton, D. K., Christadoss, P. and Sarvetnick, N. 1998. The Th2 cytokine IL-4 is not required for progression of antibody-dependent autoimmune myasthenia gravis. *J. Immuno*. 161: 2856–2862.

Bathle, J., Gomez, E., Rendal, E., Torea, J., Loures, E., Cousela, M., Vila, P., Sedano, C., Tusell, X., Magallon, M., Quintana, M., Gonzalez-Boullosa, R. and Lopes-Femandez, M. F. 1996. Antibodies to factor VIII in plasma of patients with hemophilia A and normal subjects. *Ann. Hematol*., 72:321–326.

Bellone, M., Ostlie, N., Lei, S., Wu, X-D. and Conti-Tronconi B. M. 1991b. The I-A$^{bm12}$ mutatio which confers resistance to Experimental Myasthenia Gravis, drastically affects their epitope repertoire of murine CD4$^+$ cells sensitized to nicotinic acetycholine receptor. *J. Immunol*. 146: 2253–2261.

Bellone, M., N. Ostlie, S. Lei, X-D. Wu, and B. Conti-Tronconi. 1991. The I-A bm12 mutation, which confers resistance to experimental myasthenia gravis, drastically affects the epitope repertoire of murine CD4+ cells sensitized to nicotinic acetylcholine receptor. *J. Immunol*. 147:1484–1491.

Bellone, M., N. Ostlie, S. Lei, and B. Conti-Tronconi. 1991. Experimental myasthenia gravis in congenic mice. Sequence mapping and H-2 restriction of T helper epitopes on the α subunits of *Torpedo californica* and murine acetylcholine receptors. *Eur. J. Immunol*. 21:2303–2310.

Bellone, M., N. Ostlie, P. Karachunski, A. Manfredi, and B. Conti-Tronconi. 1993. Cryptic epitopes on the nicotinic acetylcholine receptor are recognized by autoreactive CD4$^+$ cells. *J. Immunol*. 151:1025–1038.

Bellone, M., P. Karachunski, N. Ostlie, S. Lei, and B. Conti-Tronconi. 1994. Preferential pairing of T and B cells for production of antibodies without covalent association of T and B epitopes. *Eur. J. Immunol*. 24:799–804.

Bellone, M., Karachunski, P., Ostlie, N., Lei S., Conti-Tronconi, B. M., 1995. Clustering of B-and T-epitopes within short sequence regions of the nicotinic acetylcholine receptor. *Scand. J. Immunol*. 41: 135–140.

Benjamini et al. (eds.), *Immunology:A Short Course*, John Wiley & Sons, Inc., 3rd ed. (1996).

Besingej, U. A., Toyka, K. V., Hamberg, M. Et al. 1983. Myasthenia Gravis: Long Term Correlation at Binding and Burgarotoxin Blocking Antibodies against Acetylcholine Receptors with Changes in Disease Severity. *Neurology*, 33: 1316–1321.

Bi, L., Lawler, A. M., Antonarakia, S., High, K., Gearhart, J. and Kazazian, H. Jr. 1995. Targeted disruption of the mouse factor VIII gene produces a model of hemophilia A. *Nature Genet*., 10:119–123.

Briner, T. J., Kuo, M. C., Keating, K. M., Rogers, B. L., Greenstein J. L., 1993. Peripheral T-cell tolerance induced in naive and primed mice by 10 subcutaneous injection of peptides form the mahor cat allergen Feld I. *Proc. Nat. Acad. Sci. USA* 90: 7608–7612.

Burnstein, H. J., Shea, C. M., Abbas, A. K., 1992. Aqueous antigens induce in vivo tolerance selectively in IL-2 and IFN-gamma-producing (Th1 ) cells. *J. Immunol*. 148: 3687–3691.

Chen, Y., V. K. Kuchroo, J. Inobe, D. A. Hafler, and H. L. Weiner. 1994. Regulatory T cell clones induced by oral tolerance: suppression of autoimmune encephalomyelitis. *Science* 265:1237–1240.

Chen, Y., J. Inobe, R. Marks, P. Gonnella, V. Kuchroo, and H. Weiner. 1995. Peripheral deletion of antigen-reactive T cells in oral tolerance. *Nature* 376:177–180.

Chen, Y., J. Inobe, V. Kuchroo, J. Baron, C. J. Janeway, and H. Weiner. 1996. Oral tolerance in myelin basic protein T-cell receptor transgenic mice: suppression of autoimmune encephalomyelitis and dose-dependent induction of regulatory cells. *Proc. Natl. Acad. Sci. USA* 93:388–391.

Chicz, R. M., Urban, R. G., Gorga, J. C., Vignali, D. A. A., Lane, W. S. and Strominger, J. L. 1993. Specificity and promiscuity among naturally processed peptides bound to HLA-DR alleles. *J. Exp. Med*., 178:27–47.

Cong-Qui, C. and Londei M. 1996, Induction of Th2 cytokines and control of collagen-induced arthritis by nondepleting anti-CD4+ antibodiess. *J. Immunol*. 157: 2685–2689.

Constant, S. L., Bottomly, K., 1997. Induction of Th1 and Th2 CD4 T-cell responses: the alternative approach. *Annu. Rev. Immunol*. 1: 297–322.

Conti-Fine, B. M, K. E. McLane, and S. Lei. 1996. Antibodies as a tool to study the structure of membrane proteins. The case of the nicotinic receptor. *Ann. Rev. Biophys. Biomol. Struct*. 25:197–229.

Conti-Fine, B. M., M. P. Protti, M. Bellone, and J. F. Howard, Jr. 1997. Myasthenia Gravis: The Immunobiology of an Autoiminune Disease. R. G. Landes Company, Austin. 230pp.

Cua, D. J., Hinton, D. R. and Stohlman, S. A. 1995. Self-antigen-induced Th2 responses in experimental allergic encephalomyelitis (EAE)-resistant mice. Th2-mediated suppression of autoimrnmune disease. *J. Immunol*. 155; 4052–4059.

Das, M. P., Nicholson, L. B. and Greer, J. M. 1997. Autopathogenic T helper cell type 1 (Th1 ) and protective Th2 clones differ in their recognition of the autoantigenic peptide of myelin proteolipid protein. *J. Exp. Med*. 186: 867–876.

DeSilva, D. R., Urdahl, K. B., and M. K. Jenkins. 1991. Clonal anergy is induced in vitro by T cell receptor occupancy in the absence of proliferation. J. *Immunol*. 147:3261–3267.

De Wit, D., Van Mechelen, M., Reylandt, M., Figuerido, A. C. Abramovitz, D., Goldman, M., Bazin, H., Urbain, J., Leo, O., 1992. The injection of degraded gamma globulins in adult mice induced-antigen-specific unresponsiveness of T-helper type I but not type2 lymphocytes. *J. Exp. Med*. 175: 9–14.

Dick, A., Y. Cheng, A. McKinnon, J. Liversidge, and J. Forrester. 1993. Nasal administration of retinal antigens suppresses the inflammatory response in experimental allergic uveoretinitis. A preliminary report of intranasal induction of tolerance with retinal antigens. *Brit. J. Ophthalmol*. 77:171–175.

Diethelem-Okita, B., R. Raju, D. Okita, and B. Conti-Fine. 1997. Epitope repertoire of human CD4+ T cells on tetanus toxin: identification of inunnodominant sequence segments. *J. Infect. Dis*. 175:382–391.

Ding, L., Shevach, E. M., 1992. IL-10 inhibits mitogen-induced T-cell proliferation by selectively inhibiting macrophage co-stimulatory function. *J. Immunol*. 148: 3133–3139.

Ding, L., Linsley, P. S., Huang, L. Y., Germain, R. N. and Shevach, E. M. 1993. IL-10 inhibits macrophage costimulatory activity by selectively inhibiting the up-regulation of B7 expression. *J. Immunol.*, 15:1224–1234.

Enk, A. H., Angeloni, V. L., Udey, M. C., Katz, S. I., 1993. Inhibition of Langerhans cell antigen-presenting function by IL-10: a Erb, K. J., Ruger, B., von Brevem, M., Ryffel, B., Schimpl, A. and Rivett, K. 1997 Constitutive expression of Interleukin (IL-4) in vivo causes autoimmune-type disorders in mice. *J. Exp. Med.* 185: 329–339. role for IL-10 in induction of tolerance. *J. Immunol.* 151:2390–2398.

Falcone, M. and Bloom, B. R. 1997. A T helper 2 (Th2) immune response against non-self antigens modifies the cytokine profile of autoimmune T cells and protects against experimental allergic encephalomyelitis. *J. Exp. Med.* 185: 901–907.

Ferber, I. A., Brocke, S., Taylor-Edwards, C., Ridgway, W., Dinisco, C., Steinman, L., Dalton, d. and Fatham, C. G. (1996) Mice with a disrupted IFN-γ gene are susceptibe tothe induction of experimental autoimmune encephalomyelitis (EAE). *J. Immunol.* 156, 5–7.

Friedman, A., and H. L. Weiner. 1994. Induction of anergy or active suppression following oral tolerance is determined by antigen dosage. *Proc. Natl. Acad. Sci. USA* 91:6688–6692.

Fuss, I. J., Strober, W. J., Dale, K., Fritz, S., Pearlstein, G. R., Puck, J. M., Lenardo, M. J. and Strauss, S. E. 1997. Characteristic T helper 2 T cell cytokine abnormalities in autoimmune lymphoproliferative syndrome, a syndrome marked by defective apoptosis and humoral autoimmunity. *J. Immunol.* 158: 1912–1918.

Genain, C. P., K. Abel, N. Belmar, F. Villinger, D. P. Rosenberg, C. Linington, C. S. Raine, and S. L. Hauser. 1996. Late complications of immune deviation therapy in a nonhuman primate. *Science* 274:2054–7.

Gilles, J. G. and Saint-Remy, J-.R. 1994. Healthy subjects produce both anti-factor VIII and specific anti-idiotypic antibodies. *J. Clin. Invest.*, 94:1496–1505.

Gray, D. 1993. Immunological memory. *Ann. Rev. Immunol.* 11:49–77.

Gregerson, D., W. Obritsch, and L. Donoso. 1993. Oral tolerance in experimental autoimmune uveoretinitis. Distinct mechanisms of resistance are induced by low dose vs. high dose feeding protocols. *J. Immunol.* 151:5751–5761.

Groux, H., Bigler, M., de Vries, J. E., Roncarolo, M-G., 1996. Interleukin-10 induces a long-term antigen-specific anergic state in human CD4+ T-cells. *J. Exp. Med* 184: 1–8.

Gu, D., Wogensen, L., Calcutt, N. A., Xia, C., Zhu, S., Merlie, J. P., Fox, H. S., Lindstrom, J., Powell, H. C., Sarvetnick, N. 1995. Myasthenia gravis-like syndrom induced expression of interferon-y in neuromuscular junction. *J. Exp. Med.* 181: 547–557.

Hafler, D. A., Kent, S. C., Pietrusewicz, M. J., Khoury, S. J., Weiner, H.L. and Fukaura, H. 1997. Oral sadministrartion of myelin induces antigen-specific TGF-beta 1 secreting T cells in patients with multiple sclerosis. Ann. N.Y. *Acad. Sci.* 835: 120–131.

Hashimoto, T. 1993. Cadherins and blistering skin diseases. *Curr. Opin. Dermatol.* 2:244–249.

Hass, C., Ryffel, B. and Le Hir, M. 1997, IFN-γ is essential for the development of autoimmune glomerulonephritis in MRL/1pr mice. *J. Immunol.* 158; 5484–5491.

Healey, J. F., Lubin, I. M., Nakai, H., Sarnko, E. L., Hoyer, L. W., Scandella, D. and Lollar, P. 1995. Residues 484–508 contain a major determinant of the inhibitory epitope in the A2 domain of human factor VIII. *J. Biol. Chem.*, 270(24):14505–14509.

Heinrickson, S. and Meredith, B. 1983. Amino acid analysis by reverse-phase high-performance liquid chromatography: precolumn derivatization with phenylisothiocyanate. *Anal. Biochem.*, 136:65–74.

Ho, P., D. Mutch, K. Winkel, A. J. Saul, G. L. Jones, T. J. Doran, and C. M. Rzepczyk.1990. Identification of two promiscuous T cell epitopes from tetanus toxin. *Eur. Immunol.* 20:477–483.

Hohlfeld, R., 1997. Biotechnological agents for the immunotherapy of multiple sclerosis: principles, problems and perspectives. *Brain* 120: 865–916.

Hohlfeld, R., Kalie, I., Ernst, M., et al. 1982. T lymphocytes in experimental myasthenia grains: isolation of T helper cell lines. *J. Neurol. Su.* 57: 265–280.

Houghten, R. 1985. General method for the rapid solid phase synthesis of large numbers of peptides: specificity of antigen-antibody interaction at the level of individual amino acids. *Proc. Natl. Acad. Sci. USA* 82:5131–5135.

Hultgren, B., Huang, X, X., Dybdal, N. and Stewart, T. A. 1996. Genetic absence of gamma interferon delays but does not prevent diabetes in NOD mice. *Diabetes.* 45: 812–817.

Hunt, D. F., Michel, H., Dickison, T. A., et al. 1992. Peptides presented to the immune system by the murine class II major histocompatibility complex molecule I-Ad. *Science* 256:1817–1820.

Husby, S., J. Mestecky, Z. Moldoveanu, S. Holland, and C. Elson. 1994. Oral tolerance in humans. T cell but not B cell tolerance after antigen feeding. *Immunol.* 152:4663–4670.

Infante, A., P. Thompson, K. Krolik, and K. Wall. 1991. Determinant selection in murine experimental autoimmune myasthenia gravis: Effect of the bm12 mutation on T-cell recognition of acetylcholine receptor epitopes. *J. Immunol.* 146:2977–2982.

Julia, V., Rassoulzadegan, M. and Glaichenhaus, N. 1996. Resistance to Leishmania major induced by tolerance to a single antigen. *Science* 274: 421–423.

Kaminski, H. J., Maas, E., Spiegel, P., and R. Ruff. 1991. Why are Eye Muscles Frequently Involved in Myasthenia Gravis? *Neurology.* 40: 1663–1669.

Kaminski, H. J. and R. Ruff. 1997. Ocular muscle involvement in Myasthenia Gravis. *Anal. Neurol.* 41: 419–420.

Karachunski, P., N. Ostlie, M. Bellone, A. Infante, and B. Conti-Fine. 1995. Mechanisms by which the I-A bml2 mutation influences susceptibility to experimental myasthenia gravis: a study in homozygous and heterozygous mice. *Scand. J. Immunol.* 42:215–225.

Karachunski, P., Ostlie, N., Okita, D., Conti-Fine, B. M. 1997. Prevention of Experimental Myasthenia Gravis by nasal administration of synthetic acetylcholine receptor T epitope sequences. *J. Clin. Invest.* 100:3027–3035.

Karpus, W. J., K. J. Kennedy, W. S. Smith, and S. D. Miller. 1996. Inhibition of relapsing experimental autoimmune encephalomyelitis in SJL mice by feeding the immunodominant PLP 139–151 peptide. *Neuroscience Research* 45:410–423.

Kellerman, S. D. McCormick, S. Freeman, John C. Morris and B. M. Conti-Fine. 1995. TSH receptor sequences recognized by CD4+ cells in Graves' disease patients and in healthy controls. *J. Autoimmunity* 8:685–698.

Kreuz, W., Escuriola-Ettinghausen, C., Martinez-Sauguer, I., Gungor, T. and Kornhuber, B. 1996. Epidemiology of inhibitors in haemophilia A. *Vox Sang*, 70(Suppl. 1):2–8.

Kuper, C., P. Koomstra, D. Hameleers, J. Biewenga, B. J. Spit, A. M. Duijvestijn, P. J. van Breda Vriesman, and T. Sminia. 1992. The role of nasopharyngeal lymphoid tissue. *Immunol. Today* 13:219–224.

Laemmli, U. 1970. Cleavage of structural proteins during the assembly of the head of bacteriophage T4. *Nature* 227:680.

LaFaille, J. J., Van de Keere, F., Hsu, A. L., et al. 1997. Myelin basic protein-specific T helper 2 (Th2) cells cause experimental autoimmune encepholomyelitis in immunodeficient hosts rather than protect them from the disease. *J. Exp. Med.* 186:307–312.

Lafaille J., Van de Keere F, Hsu,AL, Baron, J. L., Haas, W., Raine, C. S. and Tonegawa, S. 1997. Myelin basic protein-specific T helper 2 (Th2) cells cause experimental autoimmune encephalomyelitis in immunodeficient hosts rather than protect them from the disease. *J. Exp. Med.* 186: 307–312.

Lawrence, R. A., Allen, J. E., Gregory, W. F., Kopf, M. and Manizes, R. M., 1995. Infection of IL-4-deficient mice with the parasitic nematode Brugia malayi demonstrates that host resistance is not dependent on a T helper 2-dominated immune response. *J. Immunol.* 154: 5995–6001.

Lee, M. S., Mueller, R., Wicker, L. S., Peterson, L. B. and Sarvetnick, N. 1996. IL-10 is necessary and sufficient for autoimmune diabetes in conjunction with NOD MHC homozygosity. *J Exp. Med.* 183: 2663–2668.

Le Gros, G., Ben-Sasson, S. Z., Seder, R., Finkelnan, F. D. and Paul, W. E. 1990. Generation of interleukin 4 (IL-4)-producing cells in vivo and in vitro: IL-4 are required for in vitro generation of IL-4-producing cells. *J. Exp. Med.* 172:921–9.

Liu, L., and G. G. MacPherson. 1993. Antigen acquisition by dendritic cells: intestinal dendritic cells acquire antigen administered orally and can prime naive T cells in vivo. *J. Exp. Med.* 177:1299–1307.

Lowry, O., N. Rosebrough, A. Farr, and R. Randall. 1981. Protein measurement with Folin phenol reagent. *J. Biol. Chem.* 193:256.

Ma, C., G. Zhang, B. Xiao, J. Link, T. Olsson, and H. Link. 1995. Suppression of experimental autoimmune myasthenia gravis by nasal administration of acetylcholine receptor. *J. Neuroimmunol.* 58:51–60.

Ma. C., Zhang, G., Xiao, B., Link H., 1996. Cellular mRNA of inter-feron-gamma (IFN-gamma), IL-4 and transforming growth factor-beta (TGF-beta) in rats nasally tolerized against experimental autoimmune myasthenia gravis (EAMG). *Clin. Exp. Immunol:* 104, 509–516.

Macatonia, S. E., Doherty, T. M., Knight, S. C. and O'Garra, A. 1993. Differential effect of IL-10 on dendritic cell-induced T cell proliferation and IFN-gamma production. *J. Immunol.,* 150:3755–3765.

Mamoury-Schwartz B, Chiocchia G, Bessis N, Abehsira-Amar, O., Batteux, F., Muller, S., Huang, S., Boissier, M.C. and Fournier, C. 1997. High susceptibility to collagen-induced arthritis in mice lacking IFN-γ receptors. *J. Immunol.* 158:5501–5506.

Manfredi, A. M. H. Yuen, L. Moiola, M. P. Protti and B. M. Conti-Tronconi. 1994. Human acetylcholine receptor presentation in Myasthenia Gravis: DR restriction ofautoimmune T epitopes and binding of synthetic receptor sequences to DR molecules. *J. Immunol.* 152: 4165–4174.

Manfredi, A. A., Protti, M. P., Wu, X. D., Howard, J. F. Jr. and Conti-Tronconi, B. M. 1992. CD4+ T epitope repertoire on the human acetylcholine receptor a subunit in severe myasthenia gravis. A study with synthetic peptides. *Neurology* 42:1092–1100.

Manfredi, A. A., Protti, M. P., Dalton, M. W. M., Howard, J. F. Jr, Conti-Tronconi, B. M. 1993. T helper cell recognition of muscle acetylcholine receptor in myasthenia gravis: epitopes on the γ and δ subunits. *J. Clin. Invest.* 92:1055–1067.

Martino G., DuPont B. L., Wollmann R. L., et al. 1993. The human-SCID myasthenic mouse; a new approach for study of myasthenia gravis. *Ann Neurol.* 34:48–56.

Matzinger, P. 1994. Tolerance, danger, and the extended family. *Ann. Rev. Immunol.* 12:991–1045.

McMillan, C. W., Shapiro, S. S., Whitehurst, D., Hoyer, L. W., Rao, A. V. and Lazerson, J. 1988. The natural history of factor VIII:C inhibitors in patients with hemophilia A: A national cooperative study. II. Observations on the initial development of factor VIII:C inhibitors. *Blood* 71:344.

McRae, B., C. Vanderlugt, M. Dal Canto, and S. Miller. 1995. Functional evidence for epitope spreading in the relapsing pathology of experimental autoimmune encephalomyelitis. *J. Exp. Med.* 182:75–85. Memar, B. Christensen, S. Raiararnan, R. Goldblum, K. Tyring, M, M. Brysk, D. J. McCormick, H. El Zaim, J-L. Pan and B. S. Prabhakar. 1996. Induction of blister-causing antibodies by a recombinant full-length, but not the extracellular, domain of the pemphigus vulgetris antigen (Desmoglein 3). *J. Immunol.* 157: 3171–3177.

Metzler, B., and D. C. Wraith. 1993. Inhibition of experimental autoimmune encephalomyelitis by inhalation but not oral administration of the encephalitogenic peptide: influence of MHC binding affinity. *Int. Immunol.* 5:1159–1169.

Mikszta, J. A. and Kim, B. S. 1996. Conversion of low antibody responders into high responders by up-regulating the T cell response to a selective epitope. *J. Immunol.* 157: 2883–2890.

Miller, A., O. Lider, O. Abramsky, and H. L. Weiner. 1994. Orally administered myelin basic protein in neonates primes for immune responses and enhances experimental autoimmune encephalomyelitis in adult animals. *Eur. J. Immunol.* 24:1026–32.

Miller, S. D. and Karpus, W. J. 1994. The immunopathogenesis and regulation of T cell mediated demyelinating diseases. *Immunol. Today* 8: 356–361.

Mima, T., Saeki, Y., Oshima, S., et al. 1995. Transfer of rheumatoid arthritis into severe combined immunodeficient mice. The pathogenetic implications of T cell populations oigocolonally expanding in the rheumatoid joints. *J. Clin. Invest.* 96:1746–1758.

Moiola, L., Karachunski P., Protti, M. P., Howard, J. F. and Conti-Tronconi, B. M. 1994. Epitopes on the P subunit of human muscle acetycholine receptor recognized by CD4+ cells of Myasthenia Gravis patients and healthy subjects. *J. Clin. Invest.* 93: 1020–1028.

Moiola, L., Protti, M. P., Howard, J. F. and Conti-Tronconi, B. M. 1994. Myasthenia Gravis: Residues of the α and δ subunits of muscle acetylcholine receptor involved in formation of immunodominant CD4+ epitopes. *J. Immunol.* 152: 4686–4698.

Moiola, L. Galbiati, F., Martino, G., Amadio, S., Brambilla, E., Comi, G., Vincent, A., Grimaldi, L. M. E. and Adorini, L. 1998. IL-12 is involved in the induction of experimental autoimmune myastenia gravis, an antibody-mediated diseases. *Eur. J. Immunol.* 28: 2487–2497.

Mueller, R., Krahl, T. and Sarvetnick, N. (1996. Pancreatic expression of interleukin-4 abrogates insulitis and autoimmune diabetes in nonobese diabetic (NOD) mice. *J. Exp. Med.* 184:1093–1099.

Myers C. 1991. Role of B cell antigen processing and presentation in the humoral immune response. *FASEB* 5:2547.

Nakajima, A., Hirose, S., Yagita, H. and Okurama, K. 1997. Roles of IL-4 and IL-12 in the development of lupus in NZB/W F$_1$ mice. *J. Immunol.* 158: 1466–1472.

Nakona S. and Engel, A. G. 1993. Myasthenia gravis: quantitative immunocytochemical analysis of inflammatory cells and detection of complement membrane attack complex at the end-plate in 30 patients. *Neurology* 43: 1167–1172.

Neutra, M., E. Pringult, and J. Kraehenbuhl. 1996. Antigen sampling across epithelial barriers and induction of mucosal immune response. *Ann. Rev. Immunol.* 14:275–300.

Norman, P. S., Ohman, J. L. Jr., Long, A. A., Gefter, P. S., Shaked, Z., Wood, R. A., Eggleston, P. A., Hafner, K. B., Rao, P., Lichtenstein, L. M., Jones, N. H., Nicodemus, C. F., 1996. Treatment of cat allergy with T-cell reactive peptides. *Am. J Res. Crit. Med.* 154, 1623–1628.

Nossal, G. 1995. Choices following antigen entry: antibody formation or immunologic tolerance? *Ann. Rev. Immunol.* 13:1–27.

O'Garra, A., Steinman, L. and Gijbes,K. 1997, CD4$^+$ T-cell subsets in autoimmunity. *Curr. Opin. Immunol.* 9: 872–883.

O'Garra A. 1998, Cytokine induce the development of functionally heterogenous T helper cell subsets. *Immunity* 8: 275–283.

Pakala, S. V., Kurrer, M. O. and Katz, J. D. 1997. T helper 2 (Th2) T cells induce acute pancreatitis and diabetes in immune-comprised nonobeses diabetic (NOD) mice. *J. Exp. Med.* 186: 299–306.

Pakala. S. V., Kurrer, M. O., Katz, J. D. 1997. T helper 2 (Th2) T cells induce acute pancreatis and diabetes in immune-compromised nonobese diabetic (NOD) mice. *J. Exp. Med.* 186:299–306.

Palmer, M, and Sercarz, E. 1989. Determinant preferences in the relationship between T and B cell specific for lysozyme. In: The Immune Response to Structurally Defined Proteins: The Lysozyme Model. S. Smith-Gill, E. Sercarz, editors. New York:Academic Press, pp. 285–321.

Panina-Bordignon, P., A. Tan, A. Termijtelen, S. Demotz, G. Corradin, A. Lanzavecchia. 1989. Universally immunogenic T cell epitopes: promiscuous binding to human MHC class II and promiscuous recognition by T cells. *Eur. J. Immunol.* 19:2237–2242.

Paul, *Fundamental Immunology*, 3rd ed., Raven Press (1993).

Peng, S. L., Mosiehi, J. and Craft, J. 1997. Roles of interferon-γ and enterleukin4 in murine lupus. *J. Clin. Invest.* 99: 1936–1946.

Plott, R. T., M. Amagai, M. C. Udey and J. R. Stanley. 1994. Pemphigus vulgaris antigen lacks biochemical properties characteristic of classical cadherins. *J.; Invest. Dermatol.* 17:168–172.

Prabhu Das, M., Nicholson, L. B., Greer, J. M. and Kuchroo, V. K. 1997. Autopathogencic T helper cell type 1 (Th1) and protective Th2 clones differ in their recognintion of the autoantigenic peptide of myelin proteolipid protein. *J. Exp. Med.* 186: 867–876.

Protti, M. P., Manfredi, A. A., Straub, C., Howard, J. F. Jr. and Conti-Tronconi, B. M. 1990. Immunodominant regions for T helper sensitization on the human nicotinic receptor α subunit in myasthenia gravis. *Proc. Natl. Acad. Sci. USA* 37:7792–7796.

Protti, M. P., Manfredi, A. A., Straub, C., Howard, J. F. Jr. and Conti-Tronconi, B. M. 1992. CD4$^+$ T cell response to the human acetylcholine receptor α subunit in severe myasthenia gravis. A study with synthetic peptides. *Neurology* 42:1092–1100.

Protti, M. P., Manfredi, A. A., Horton, B .M., Bellone, M. and Conti-Tronconi, B .M. 1993. Myasthenia Gravis: recognition of a human autoantigen at the molecular level. *Immunol. Today* 14:363–8.

Qian, A., Kazazian, H. Jr. and Hoyer, L. 1996. Inhibitor development and T cell response to human fVIII in murine hemophilia A. *Blood,* 88:656a.

Qian, A., Scott, D. and Hoyer, L. 1997. T cell response to human factor VIII in murine hemophilia. *Blood,* 90:599a.

Racke, M. K., Bonomo, A., Scott D. E., Cannella, B., Levine, B., Raine, C. S., Shevach, E. M. and Rocken, M. 1994. Cytokine-induced immune deviation as a therapy for inflammatory autoimmune disease. *J. Exp. Med.* 180:1961–1966.

Raju R., D. Navaneetham, D. Okita, B. Diethellm-Okita, D. McCormick, and B. Conti-Fine. 1995. Epitopes for human CD4+ cells on diphtheria-toxin: structural features of sequence segments forming epitopes recognized by most subjects. *Eur. J. Immunol.* 25:3207–3214.

Raju, R., B. Diethelem-Okita, B., D. K. Okita, and B. M. Conti-Fine. 1996. Epitope repertoire of human CD4+ lines propagated with tetanus toxoid or synthetic tetanus sequences. *J. Autoimmunity* 9:79–88.

Reece, J. C., Geysen, H. M. and Todda, S. J. 1993. Mapping the major human T helper epitopes of tetanus toxin. The emerging picture. *J. Immunol.,* 151:6175–84.

Reisner, H. M., Clar, A. and Levin, L. 1995. Immunogenetics of the human immune response to factor VIII. Inhibitors to Coagulation Factors, Aledort, L. M., ed., Plenum Press, N.Y., 65.

Romagnani, S. 1997. The Th1/Th2 paradigm. *Immunol Today* 18: 263–266.

Rudensky, A. Y., Preston-Hurburt, P., Hong, S. C., Barlow, A. and Janeway, C. A. Jr. 1991. Sequence analysis of peptide bound to MHC class II molecules. *Nature,* 353:622–627.

Scandella, D., Kessler, C., Esmon, P., Hurt, D., Courter, S., Gomperts, E., Felch, M. and Prescott, R. 1995. Epitope specificity and functional characterization of factor VIII inhibitors. In: Inhibitors to Coagulation Factors. Aledort, L. M., Hoyer, L. W., Lusher, J. M., Reisner, H. M. and White, G. C., eds., *Adv. Exp. Med. Biol.,* 386:47–63.

Scanella, D. 1996. Human anti-factor VIII antibodies: epitope localization and inhibitory function. *Vox Sang,* 70(suppl. 1):9–14.

Schmidt, J., and M. Raftery. 1973. A simple assay for the study of solubilized acetylcholine receptors. *Anal. Biochem.* 52:349–354.

Shaw, M. K., Lorens, J. B., Dhawan, A., Dal Canto, M., Tse, A. B., Tran, C., Bonpane, S. L., Eswaran, S., Brocke, N., Sarvetnick, L., steinman, G. P., Nolan, G. P. and Fatham, C. G. 1997. Local delivery of interleukin 4 by retrovirus-transduced T lymphocytes ameliorates experimental autoimmune encephalomyelitis. *J. Exp. Med.* 185: 1711–1714. Shenoy, M., M. Oshima, M. Atassi, and P. Christadoss. 1993. Suppression of experimental autoimmune myasthenia gravis by epitope-specific neonatal tolerance to synthetic region alpha 146–162 of acetylcholine receptor. *Clin. Immunol. Immunopathol.* 66:230–238.

Shenoy, M., E. Goluszko, and P. Christadoss. 1994. The pathogenic role of acetylcholine receptor a chain epitope within α146-162 in the development of experimental autoimmune myasthenia gravis in C57B1/6 mice. *Clin. ImmunoL Immunopathol.* 73:1–6.

Shenoy, M., Kaul, R. Goluszko, E., David, C., Christadoss, C. 1994. Effect of MHC class I and CD8$^+$ cell deficiency on experimental autoimmune myasthenia gravis pathogenesis. *J. Immunol.,* 153:5330–5335.

Shima, M., Nakai, H., Scandella, D. et al. 1995. Common inhibitory effects of human anti-C2 domain inhibitor alloantibodies on factor VIII binding to von Willebrand factor. *Brit. J. Haem.*, 91:714–721.

Stanley, J. R. 1995. Autoantibodies against Adhesion Molecules and Structures in Blistering Skin diseases. *J. Experimental Medicine* 181:1–4.

Stem, L. J., Brown, J. H., Jardetzky, T. S., et al. 1994. Crystal structure of the human class II MHC protein HLA-DR1 complexed with an influenza virus peptide. *Nature* 368:215–221.

Swain, S. L., Weinburg, A. D., English, M. and Huston, G. 1990. IL-4 dorects the development of different subsets of helper T cells. *J. Immunol.* 145: 3796:3806.

Texier, B., C. Bedin, H. Taiig, L. Camoin, C. Laurent-Winter and J. Charreire. 1992. Characterization and sequencing of a 40-arnino-acid peptide from human thyroglobulin inducing experimental autoimmune thyroiditis. *J. Immunol.* 148: 3405–3411.

Tian, J., Atkinson, M. A., Clare-Salzler, M., Herschenfeld, A., Forsthuber, T., Lehmann, P. V., and Kauflnan, D. L. 1996. Nasal administration of glutamate decarboxylase (GAD65) peptides induces Th2 responses and prevents murine insulin-dependent diabetes. *J. Exp. Med.* 183:1561–1567.

Tian, J., Lehmann, P. V. and Kaufinan, D. 1997. Determinant spreading of T helper Cell 2 (Th2) responses to pancreatic islet autoantigens. *J. Exp. Med.* 186: 2039–2043.

Wall, K. A., Hu, J-Y., Currier, P., Southwood, S., Sette, A. and Infante, A. J. 1994. A disease-related epitope of Torpedo acetylcholine receptor. Residues involved in I-Ab binding, self-nonself discrimination, and TCR antagonism. *J. Immunol*152: 4526–4646.

Wang, Z-Y., D. Okita, J. Howard Jr., and B. Conti-Fine. 1997. Th1 epitope repertoire on the alpha subunit of human muscle acetylcholine receptor in Myasthenia Gravis. *Neurology* 48:1643–1653.

Weetman, A. P. and A. M. McGregor. 1994. Autoimmune thyroid disease, Further developments in our understanding. *Endocrin. Rev.* 15: 788–830.

Weigle, W. O. and Romball, C. G. 1997. CD4+ T-cell subsets and cytokines involved in peripheral tolerance. *Immunol. Today* 18, 533–538.

Weiner, H., A. Friedman, A. Miller, S. J. Khoury, A. Al-Sabbagh, L. Santos, M. Sayegh, R. B. Nussenblatt, D. E. Trenthan, and A. D. Hafler. 1994. Oral tolerance: immunologic mechanisms and treatment of animal and human organ-specific autoimmune diseases by oral administration of autoantigens. *Ann. Rev. Immunol.* 12:809–837.

Vermeire, K., Heremans, H., Vandeputte, M., Huang, S., Billiau, A. and Matthys, P. 1997. Accelerated collagen-induced arthritis in IFN-γ receptor-deficient mice. *J. Immunol.* 158, 5507–5513.

Von Herrath, M. G. and Oldstone, M. 1997. Interferon-γ is essential for destruction of β cells and development of insulin-dependent diabetes mellitus. *J. Exp. Med.* 185: 531–539.

Willenborg, D. O., Fordhan, S., Bernard, C. A., Cowden, W. B. and Ramshaw, I. A. 1996, IFN-γ plays a critical down-regulatory role in the induction and effector phase of myelin oligodendrocyte glycoprotein-induced autoimmune encephalomyelitis. *J. Immunol.* 157, 3223–3227.

Wu, B., Deng, C., Goluszko, E. and Christadoss, P. 1997. Tolerance to a dominant T cell epitope in the acetylcholine receptor molecule induces epitope spread and suppresses murine myasthenia gravis. *J. Immunol.* 159: 3016–3023.

Yeh, T. M., and K. A. Krolick. 1990. T cells reactive with a small synthetic peptide of the acetylcholine receptor can provide help for a clonotypically heterogeneous antibody response and subsequently impaired muscle function. *J. Immunol.* 144:1654–1660.

Yu, M., J. Johnson, and V. Tuohy. 1996. A predictable sequential determinant spreading cascade invariably accompanies progression of experimental autoimmune encephalomyelitis: a basis for peptide-specific therapy after onset of clinical disease. *J. Exp. Med.* 183:1777–1788.

Yuen, M. H., K. Macklin and Bianca M. Conti-Fine. 1996. MHC class II presentation of human acetylcholine receptor in Myasthenia Gravis. Binding of synthetic gamma subunit sequences to purified DR molecules. *J. Autommunity*, 9:67–77.

Yuen, M-H, Protti, M. P., Diethelm-Okita, B., Moiola L., Howard, J. F. Jr., Conti-Fine, B. M. 1995. Immunoregulatory $CD8^+$ cells recognize antigen-activated $CD4^+$ cells in myasthenia gravis patients and in healthy controls. *J. Immunol*, 154:1508–1520.

Zhang, G-X, Ma, C-G, Xiao, B-G., Bakhiet, M., Link, H., Holsson, T. 1995. Depletion of CD8+ T cells suppresses the development of experimental autoimmune myasthenia gravis in Lewis rats. *Eur. J. Immuno.*, 25:1191–1198.

Zhang, G-X, Xiao, B-G, Bakhiet, M. et al. 1996. Both CD4- and CD8+ T cells are essential to induce experimental autoimmune myasthenia gravis. *J Exp. Med.*, 184:349–356.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A therapeutic method comprising administering to the respiratory tract of a mammal having hemophilia, and aberrant or pathological factor VIII or factor IX antibody production, and which mammal is subjected to an exogenous introduction of factor VIII or factor IX, an amount of at least one epitope peptide effective to suppress an immune response to the exogenously introduced factor VIII or factor IX, wherein the sequence of said epitope peptide comprises an immunodominant epitope sequence of factor VIII or factor IX, and wherein the sequence of said epitope peptide does not contain the full length sequence of factor VIII or factor IX.

2. A method to inhibit or treat an antibody-mediated pathological condition in a mammal having hemophilia, wherein the pathological condition is characterized by antibodies specific for factor VIII or factor IX, wherein said method comprises:

(a) administering to said mammal a dosage form comprising at least one epitope peptide effective to inhibit or treat at least one symptom of said pathological condition, wherein the sequence of said at least one epitope peptide comprises an immunodominant epitope sequence of factor VIII or factor IX and wherein the sequence of said epitope peptide does not contain the full length sequence of factor VIII or factor IX; and (b) subjecting said mammal to plasmaphoresis.

3. The method of claim 2 further comprising administering an agent that inhibits B cell activation.

4. The method of claim 1 or 2 wherein the at least one epitope peptide has an immunodominant epitope sequence of Factor VIII.

5. The method of claim 1 or 2 wherein a plurality of factor VIII or factor IX epitopes is administered.

6. The method of claim 5 wherein a plurality of Factor VIII epitope peptides is administered.

7. The method of claim 6 wherein the plurality of Factor VIII epitope peptides is from the A3 domain of Factor VIII.

8. The method of claim 4 wherein the at least one epitope peptide comprises an immunodominant epitope sequence in residues 1671–1690, 1711–1730, 1721–1740, 1771–1790, 1781–1800, 1801–1820, 1881–1900, 1891–1910, 1931–1950 or 1951–1970 of factor VIII.

9. The method of claim 6 wherein the plurality of Factor VIII epitope peptides is from the A2 domain of Factor VIII.

10. The method of claim 4 wherein the at least one epitope peptide comprises an immunodominant epitope sequence in residues 461–480, 471–490, 521–540, 571–590, 581–600, 611–630, 621–640, 631–650, 641–660, 651–670, 690–710 or 701–720 of factor VIII.

11. The method of claim 6 wherein the plurality of Factor VIII epitope peptides is from the C2 domain of Factor VIII.

12. The method of claim 4 wherein the at least one epitope peptide comprises an immunodominant epitope sequence in residues 2181–2200, 2191–2210, 2201–2220, 2231–2250, 2251–2270, 2261–2280, 2271–2290 or 2321–2333 of factor VIII.

13. The method of claim 6 wherein the plurality of Factor VIII epitope peptides is from the C1 domain of Factor VIII.

14. The method of claim 4, wherein the at least one epitope peptide comprises an immunodominant epitope sequence in residues 2051–2070, 2071–2090, 2091–2110, 2101–2120, 2111–2130, 2131–2150 or 2151–2170 of factor VIII.

15. The method of claim 1 or 2 wherein the mammal is a human.

16. The method of claim 1 or 2 wherein the mammal is a rodent.

17. The method of claim 1 or 2 wherein said administering does not increase the synthesis of pathogenic antibody to factor VIII or factor IX.

* * * * *

UNITED STATES PATENT AND TRADEMARK OFFICE
CERTIFICATE OF CORRECTION

PATENT NO. : 6,759,385 B1 Page 1 of 1
DATED : July 6, 2004
INVENTOR(S) : Conti-Fine It is certified that error appears in the above-identified patent and that said Letters Patent is hereby corrected as shown below:

Title page,
Item [56], References Cited, OTHER PUBLICATIONS, "Pruthi et a.," reference, delete "a." and insert -- al. --, therefor.
"Hetzel et al.," reference, after "Hetzel," insert -- C. --.

Signed and Sealed this

Fourteenth Day of September, 2004

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 1667
<212> TYPE: DNA
<213> ORGANISM: Homo sapiens
<220> FEATURE:
<221> NAME/KEY: CDS
<222> LOCATION: (49)...(1422)
```

```
<400> SEQUENCE: 1
aagcacaggc caccactctg ccctggtcca cacaagctcc ggtagccc atg gag ccc         57
                                                     Met Glu Pro
                                                      1 tgg cct ctc ctc ctg ctc ttt agc ctt tgc tca gct ggc ctc gtc ctg        105
Trp Pro Leu Leu Leu Leu Phe Ser Leu Cys Ser Ala Gly Leu Val Leu
     5                  10                  15 ggc tcc gaa cat gag acc cgt ctg gtg gca aag cta ttt aaa gac tac        153
Gly Ser Glu His Glu Thr Arg Leu Val Ala Lys Leu Phe Lys Asp Tyr
 20                  25                  30                  35 agc agc gtg gtt cgg cca gtg gaa gac cac cgc cag gtc gtg gag gtc        201
Ser Ser Val Val Arg Pro Val Glu Asp His Arg Gln Val Val Glu Val
                 40                  45                  50 acc gtg ggc ctg cag ctg ata cag ctc atc aat gtg gat gaa gta aat        249
Thr Val Gly Leu Gln Leu Ile Gln Leu Ile Asn Val Asp Glu Val Asn
             55                  60                  65 cag atc gtg aca acc aat gtg cgt ctg aaa cag caa tgg gtg gat tac        297
Gln Ile Val Thr Thr Asn Val Arg Leu Lys Gln Gln Trp Val Asp Tyr
         70                  75                  80 aac cta aaa tgg aat cca gat gac tat ggc ggt gtg aaa aaa att cac        345
Asn Leu Lys Trp Asn Pro Asp Asp Tyr Gly Gly Val Lys Lys Ile His
     85                  90                  95 att cct tca gaa aag atc tgg cgc cca gac ctt gtt ctc tat aac aat        393
Ile Pro Ser Glu Lys Ile Trp Arg Pro Asp Leu Val Leu Tyr Asn Asn
100                 105                 110                 115 gca gat ggt gac ttt gct att gtc aag ttc acc aaa gtg ctc ctg cag        441
Ala Asp Gly Asp Phe Ala Ile Val Lys Phe Thr Lys Val Leu Leu Gln
                 120                 125                 130 tac act ggc cac atc acg tgg aca cct cca gcc atc ttt aaa agc tac        489
Tyr Thr Gly His Ile Thr Trp Thr Pro Pro Ala Ile Phe Lys Ser Tyr
             135                 140                 145 tgt gag atc atc gtc acc cac ttt ccc ttt gat gaa cag aac tgc agc        537
Cys Glu Ile Ile Val Thr His Phe Pro Phe Asp Glu Gln Asn Cys Ser
         150                 155                 160 atg aag ctg ggc acc tgg acc tac gac ggc tct gtc gtg gcc atc aac        585
Met Lys Leu Gly Thr Trp Thr Tyr Asp Gly Ser Val Val Ala Ile Asn
     165                 170                 175 ccg gaa agc gac cag cca gac ctg agc aac ttc atg gag agc ggg gag        633
Pro Glu Ser Asp Gln Pro Asp Leu Ser Asn Phe Met Glu Ser Gly Glu
180                 185                 190                 195 tgg gtg atc aag gag tcc cgg ggc tgg aag cac tcc gtg acc tat tcc        681
Trp Val Ile Lys Glu Ser Arg Gly Trp Lys His Ser Val Thr Tyr Ser
                 200                 205                 210 tgc tgc ccc gac acc ccc tac ctg gac atc acc tac cac ttc gtc atg        729
Cys Cys Pro Asp Thr Pro Tyr Leu Asp Ile Thr Tyr His Phe Val Met
             215                 220                 225 cag cgc ctg ccc ctc tac ttc atc gtc aac gtc atc atc ccc tgc ctg        777
Gln Arg Leu Pro Leu Tyr Phe Ile Val Asn Val Ile Ile Pro Cys Leu
         230                 235                 240 ctc ttc tcc ttc tta act ggc ctg gta ttc tac ctg ccc aca gac tca        825
Leu Phe Ser Phe Leu Thr Gly Leu Val Phe Tyr Leu Pro Thr Asp Ser
     245                 250                 255 ggg gag aag atg act ctg agc atc tct gtc tta ctg tct ttg act gtg        873
Gly Glu Lys Met Thr Leu Ser Ile Ser Val Leu Leu Ser Leu Thr Val
260                 265                 270                 275 ttc ctt ctg gtc atc gtg gag ctg atc ccc tcc acg tcc agt gct gtg        921
Phe Leu Leu Val Ile Val Glu Leu Ile Pro Ser Thr Ser Ser Ala Val
                 280                 285                 290 ccc ttg att gga aaa tac atg ctg ttc acc atg gtg ttc gtc att gcc        969
```

```
Pro Leu Ile Gly Lys Tyr Met Leu Phe Thr Met Val Phe Val Ile Ala
            295                 300                 305 tcc atc atc atc act gtc atc gtc atc aac aca cac cac cgc tca ccc    1017
Ser Ile Ile Ile Thr Val Ile Val Ile Asn Thr His His Arg Ser Pro
        310                 315                 320 agc acc cat gtc atg ccc aac tgg gtg cgg aag gtt ttt atc gac act    1065
Ser Thr His Val Met Pro Asn Trp Val Arg Lys Val Phe Ile Asp Thr
    325                 330                 335 atc cca aat atc atg ttt ttc tcc aca atg aaa aga cca tcc aga gaa    1113
Ile Pro Asn Ile Met Phe Phe Ser Thr Met Lys Arg Pro Ser Arg Glu
340                 345                 350                 355 aag caa gac aaa aag att ttt aca gaa gac att gat atc tct gac att    1161
Lys Gln Asp Lys Lys Ile Phe Thr Glu Asp Ile Asp Ile Ser Asp Ile
                360                 365                 370 tct gga aag cca ggg cct cca ccc atg ggc ttc cac tct ccc ctg atc    1209
Ser Gly Lys Pro Gly Pro Pro Pro Met Gly Phe His Ser Pro Leu Ile
            375                 380                 385 aaa cac ccc gag gtg aaa agt gcc atc gag ggc atc aag tac atc gca    1257
Lys His Pro Glu Val Lys Ser Ala Ile Glu Gly Ile Lys Tyr Ile Ala
        390                 395                 400 gag acc atg aag tca gac cag gag tct aac aat gcg gcg gca gag tgg    1305
Glu Thr Met Lys Ser Asp Gln Glu Ser Asn Asn Ala Ala Ala Glu Trp
    405                 410                 415 aag tac gtt gca atg gtg atg gac cac ata ctc ctc gga gtc ttc atg    1353
Lys Tyr Val Ala Met Val Met Asp His Ile Leu Leu Gly Val Phe Met
420                 425                 430                 435 ctt gtt tgc atc atc gga acc cta gcc gtg ttt gca ggt cga ctc att    1401
Leu Val Cys Ile Ile Gly Thr Leu Ala Val Phe Ala Gly Arg Leu Ile
                440                 445                 450 gaa tta aat cag caa gga tga gcagaaaatg agctgagctt agctctgccc       1452
Glu Leu Asn Gln Gln Gly *
            455 tggaacctac cagagcagag aagggcagga gaggaagatt tgtctacttg ctccactcgc  1512 acttatcaaa cgtgttatat tccatactta ttattgatga taagatttac ctttatgtaa  1572 gtttatggcc ttgaagtgtt ttcatattgc ttctcccttt agttctgctg tctccctgaa  1632 gagtgaaccc tctttagtaa atgaaactaa tcact                             1667

<210> SEQ ID NO 2
<211> LENGTH: 457
<212> TYPE: PRT
<213> ORGANISM: Homo sapiens

<400> SEQUENCE: 2

Met Glu Pro Trp Pro Leu Leu Leu Phe Ser Leu Cys Ser Ala Gly
 1               5                  10                  15

Leu Val Leu Gly Ser Glu His Glu Thr Arg Leu Val Ala Lys Leu Phe
            20                  25                  30

Lys Asp Tyr Ser Ser Val Val Arg Pro Val Glu Asp His Arg Gln Val
        35                  40                  45

Val Glu Val Thr Val Gly Leu Gln Leu Ile Gln Leu Ile Asn Val Asp
    50                  55                  60

Glu Val Asn Gln Ile Val Thr Thr Asn Val Arg Leu Lys Gln Gln Trp
65                  70                  75                  80

Val Asp Tyr Asn Leu Lys Trp Asn Pro Asp Asp Tyr Gly Gly Val Lys
                85                  90                  95

Lys Ile His Ile Pro Ser Glu Lys Ile Trp Arg Pro Asp Leu Val Leu
            100                 105                 110
```

-continued

```
Tyr Asn Asn Ala Asp Gly Asp Phe Ala Ile Val Lys Phe Thr Lys Val
        115                 120                 125

Leu Leu Gln Tyr Thr Gly His Ile Thr Trp Thr Pro Pro Ala Ile Phe
        130                 135                 140

Lys Ser Tyr Cys Glu Ile Ile Val Thr His Phe Pro Phe Asp Glu Gln
145                 150                 155                 160

Asn Cys Ser Met Lys Leu Gly Thr Trp Thr Tyr Asp Gly Ser Val Val
                165                 170                 175

Ala Ile Asn Pro Glu Ser Asp Gln Pro Asp Leu Ser Asn Phe Met Glu
            180                 185                 190

Ser Gly Glu Trp Val Ile Lys Glu Ser Arg Gly Trp Lys His Ser Val
        195                 200                 205

Thr Tyr Ser Cys Cys Pro Asp Thr Pro Tyr Leu Asp Ile Thr Tyr His
        210                 215                 220

Phe Val Met Gln Arg Leu Pro Leu Tyr Phe Ile Val Asn Val Ile Ile
225                 230                 235                 240

Pro Cys Leu Leu Phe Ser Phe Leu Thr Gly Leu Val Phe Tyr Leu Pro
                245                 250                 255

Thr Asp Ser Gly Glu Lys Met Thr Leu Ser Ile Ser Val Leu Leu Ser
                260                 265                 270

Leu Thr Val Phe Leu Leu Val Ile Val Glu Leu Ile Pro Ser Thr Ser
            275                 280                 285

Ser Ala Val Pro Leu Ile Gly Lys Tyr Met Leu Phe Thr Met Val Phe
        290                 295                 300

Val Ile Ala Ser Ile Ile Ile Thr Val Ile Val Ile Asn Thr His His
305                 310                 315                 320

Arg Ser Pro Ser Thr His Val Met Pro Asn Trp Val Arg Lys Val Phe
                325                 330                 335

Ile Asp Thr Ile Pro Asn Ile Met Phe Phe Ser Thr Met Lys Arg Pro
            340                 345                 350

Ser Arg Glu Lys Gln Asp Lys Lys Ile Phe Thr Glu Asp Ile Asp Ile
        355                 360                 365

Ser Asp Ile Ser Gly Lys Pro Gly Pro Pro Met Gly Phe His Ser
    370                 375                 380

Pro Leu Ile Lys His Pro Glu Val Lys Ser Ala Ile Glu Gly Ile Lys
385                 390                 395                 400

Tyr Ile Ala Glu Thr Met Lys Ser Asp Gln Glu Ser Asn Asn Ala Ala
                405                 410                 415

Ala Glu Trp Lys Tyr Val Ala Met Val Met Asp His Ile Leu Leu Gly
            420                 425                 430

Val Phe Met Leu Val Cys Ile Ile Gly Thr Leu Ala Val Phe Ala Gly
        435                 440                 445

Arg Leu Ile Glu Leu Asn Gln Gln Gly
    450                 455
```